US010966984B2

(12) United States Patent
Strum et al.

(10) Patent No.: US 10,966,984 B2
(45) Date of Patent: *Apr. 6, 2021

(54) TRANSIENT PROTECTION OF NORMAL CELLS DURING CHEMOTHERAPY

(71) Applicant: G1 Therapeutics, Inc., Research Triangle Park, NC (US)

(72) Inventors: Jay Copeland Strum, Hillsborough, NC (US); John Emerson Bisi, Chapel Hill, NC (US); Patrick Joseph Roberts, Durham, NC (US); Francis Xavier Tavares, Durham, NC (US)

(73) Assignee: G1 Therapeutics, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/112,360

(22) Filed: Aug. 24, 2018

(65) Prior Publication Data

US 2018/0360840 A1  Dec. 20, 2018

Related U.S. Application Data

(63) Continuation of application No. 15/342,990, filed on Nov. 3, 2016, now Pat. No. 10,085,992, which is a continuation of application No. 14/212,430, filed on Mar. 14, 2014, now Pat. No. 9,487,530.

(60) Provisional application No. 61/949,786, filed on Mar. 7, 2014, provisional application No. 61/911,354, filed on Dec. 3, 2013, provisional application No. 61/861,374, filed on Aug. 1, 2013, provisional application No. 61/798,772, filed on Mar. 15, 2013.

(51) Int. Cl.

| | | |
|---|---|---|
| *A61K 31/527* | (2006.01) | |
| *C07D 487/14* | (2006.01) | |
| *A61K 45/06* | (2006.01) | |
| *A61K 31/519* | (2006.01) | |
| *A61K 31/5377* | (2006.01) | |
| *A61P 35/04* | (2006.01) | |
| *A61P 35/00* | (2006.01) | |
| *A61K 31/555* | (2006.01) | |
| *A61K 31/7048* | (2006.01) | |
| *A61K 9/00* | (2006.01) | |

(52) U.S. Cl.
CPC .......... *A61K 31/527* (2013.01); *A61K 9/0053* (2013.01); *A61K 31/519* (2013.01); *A61K 31/5377* (2013.01); *A61K 31/555* (2013.01); *A61K 31/7048* (2013.01); *A61K 45/06* (2013.01); *A61P 35/00* (2018.01); *A61P 35/04* (2018.01); *C07D 487/14* (2013.01)

(58) Field of Classification Search
CPC ................ A61K 31/527; A61K 9/0053; A61K 31/7048; A61K 31/555; A61K 31/5377; A61K 31/519; A61K 45/06; A61P 35/00; A61P 35/04; C07D 487/14
See application file for complete search history.

(56) References Cited

U.S. PATENT DOCUMENTS

| | | | |
|---|---|---|---|
| 5,591,855 A | 1/1997 | Hudkins et al. | |
| 5,628,984 A | 5/1997 | Boucher | |
| 6,291,504 B1 | 9/2001 | Nugiel et al. | |
| 6,369,086 B1 | 4/2002 | Davis et al. | |
| 6,610,684 B2 | 8/2003 | Zaharevitz et al. | |
| 6,667,346 B2 | 12/2003 | Reddy et al. | |
| 6,936,612 B2 | 8/2005 | Barvian et al. | |
| 6,962,993 B2 | 11/2005 | Blumenkopf et al. | |
| 6,982,277 B2 | 1/2006 | Gudkov et al. | |
| 7,208,489 B2 | 4/2007 | Barvain et al. | |
| 7,345,171 B2 | 3/2008 | Beylin et al. | |
| 7,482,354 B2 | 1/2009 | Traquandi et al. | |
| 7,855,211 B2 | 12/2010 | Coates et al. | |
| 7,977,347 B2 | 7/2011 | Qian et al. | |
| 8,598,186 B2 | 12/2013 | Tavares et al. | |
| 8,598,197 B2 | 12/2013 | Tavares et al. | |
| 8,691,830 B2 | 4/2014 | Tavares et al. | |
| 8,822,683 B2 | 9/2014 | Tavares et al. | |
| 8,829,012 B2 | 9/2014 | Tavares et al. | |
| 9,260,442 B2 | 2/2016 | Tavares | |

(Continued)

FOREIGN PATENT DOCUMENTS

| | | |
|---|---|---|
| CA | 2656290 | 1/2008 |
| CN | 1278794 | 1/2001 |

(Continued)

OTHER PUBLICATIONS

An, H. X. et al. "Gene amplification and overexpression of CDK4 in sporadic breast carcinomas is associated with high tumor cell proliferation" American Journal of Pathology, 1999; 154: 113-118.
Anderson, M. S. And J. A. Bluestone "The NOD mouse: a model of immune dysregulation" Annu Rev Immunol, 2005; 23: 447-485.
Barginear, M. F. and D. R. Budman "Trastuzumab-DM1: A review of the novel immuno-conjugate for HER2-overexpressing breast cancer" The Open Breast Cancer Journal, 2009; 1:25-30.

(Continued)

*Primary Examiner* — My-Chau T. Tran
(74) *Attorney, Agent, or Firm* — Knowles Intellectual Property Strategies, LLC

(57) ABSTRACT

This invention is in the area of improved compounds, compositions and methods of transiently protecting healthy cells, and in particular hematopoietic stem and progenitor cells (HSPC) as well as renal cells, from damage associated with DNA damaging chemotherapeutic agents. In one aspect, improved protection of healthy cells is disclosed using disclosed compounds that act as highly selective and short, transiently-acting cyclin-dependent kinase 4/6 (CDK 4/6) inhibitors when administered to subjects undergoing DNA damaging chemotherapeutic regimens for the treatment of proliferative disorders.

30 Claims, 62 Drawing Sheets

(56) References Cited

U.S. PATENT DOCUMENTS

| | | | |
|---|---|---|---|
| 9,487,530 B2* | 11/2016 | Strum | C07D 487/14 |
| 10,076,523 B2* | 9/2018 | Strum | A61P 35/00 |
| 10,085,992 B2* | 10/2018 | Strum | A61K 31/527 |
| 2002/0042412 A1 | 4/2002 | Zaharevitz et al. | |
| 2003/0069430 A1 | 4/2003 | Davis et al. | |
| 2003/0073668 A1 | 4/2003 | Booth et al. | |
| 2003/0224522 A1 | 12/2003 | de Jong et al. | |
| 2003/0229026 A1 | 12/2003 | Al-Awar et al. | |
| 2004/0006074 A1 | 1/2004 | Kelley et al. | |
| 2004/0048915 A1 | 3/2004 | Engler et al. | |
| 2004/0236084 A1 | 11/2004 | Biwersi et al. | |
| 2005/0222163 A1 | 10/2005 | Eck et al. | |
| 2005/0267073 A1 | 12/2005 | Dairi et al. | |
| 2007/0027147 A1 | 2/2007 | Hayama et al. | |
| 2007/0179118 A1 | 8/2007 | Barvian et al. | |
| 2007/0207143 A1 | 9/2007 | Dang et al. | |
| 2007/0212736 A1 | 9/2007 | Chen-Kiang et al. | |
| 2007/0270362 A1 | 11/2007 | Harlan et al. | |
| 2008/0085890 A1 | 4/2008 | Tsou et al. | |
| 2008/0161355 A1 | 7/2008 | Curry et al. | |
| 2008/0182853 A1 | 7/2008 | Kruman et al. | |
| 2011/0009353 A1 | 1/2011 | Chen-Kiang et al. | |
| 2011/0224221 A1 | 9/2011 | Sharpless et al. | |
| 2011/0224227 A1 | 9/2011 | Sharpless et al. | |
| 2011/0312909 A1 | 12/2011 | Ciomei et al. | |
| 2012/0100100 A1 | 4/2012 | Sharpless et al. | |
| 2013/0289031 A1 | 10/2013 | Arigon et al. | |
| 2014/0037622 A1 | 2/2014 | Boshoff et al. | |
| 2014/0080838 A1 | 3/2014 | Wendel et al. | |
| 2014/0271460 A1 | 9/2014 | Strum et al. | |
| 2014/0271466 A1 | 9/2014 | Strum et al. | |
| 2014/0274896 A1 | 9/2014 | Strum et al. | |
| 2014/0275066 A1 | 9/2014 | Strum et al. | |
| 2015/0031880 A1 | 1/2015 | Tavares et al. | |
| 2015/0210769 A1 | 7/2015 | Freeman et al. | |
| 2015/0246925 A1 | 9/2015 | Tavares et al. | |
| 2015/0246926 A1 | 9/2015 | Tavares et al. | |
| 2015/0297606 A1 | 10/2015 | Strum et al. | |
| 2015/0297607 A1 | 10/2015 | Strum et al. | |
| 2015/0297608 A1 | 10/2015 | Strum et al. | |
| 2015/0299212 A1 | 10/2015 | Strum et al. | |
| 2016/0045509 A1 | 2/2016 | Strum et al. | |
| 2016/0108054 A1 | 4/2016 | Tavares | |
| 2016/0220569 A1 | 8/2016 | Strum et al. | |
| 2016/0332989 A1 | 11/2016 | Wu et al. | |
| 2019/0321370 A1* | 10/2019 | Sorrentino | A61K 39/395 |

FOREIGN PATENT DOCUMENTS

| | | |
|---|---|---|
| CN | 1379668 | 11/2002 |
| JP | 2001-517652 | 10/2001 |
| JP | 2005-519909 | 7/2005 |
| JP | 2007-530425 | 11/2007 |
| JP | 2007-530654 | 11/2007 |
| WO | WO 1998/033798 | 8/1998 |
| WO | WO 1999/015500 | 4/1999 |
| WO | WO 2001/012188 | 2/2001 |
| WO | WO 2002/044174 | 6/2002 |
| WO | WO 2003/062236 A1 | 7/2003 |
| WO | WO 2005/005426 | 1/2005 |
| WO | WO 2005/040166 A1 | 5/2005 |
| WO | WO 2005/052147 | 6/2005 |
| WO | WO 2005/094830 | 10/2005 |
| WO | WO 2005/105213 A2 | 11/2005 |
| WO | WO 2006/074985 | 7/2006 |
| WO | WO 2006/127587 | 11/2006 |
| WO | WO 2007/025090 | 3/2007 |
| WO | WO 2007/048847 A2 | 5/2007 |
| WO | WO 2007/065820 | 6/2007 |
| WO | WO 2007/124252 A2 | 11/2007 |
| WO | WO 2008/005538 | 1/2008 |
| WO | WO 2008/079933 | 7/2008 |
| WO | WO 2009/003003 A2 | 12/2008 |
| WO | WO 2009/061345 | 5/2009 |
| WO | WO 2009/085185 A1 | 7/2009 |
| WO | WO 2010/012777 A1 | 2/2010 |
| WO | WO 2010/020675 A1 | 2/2010 |
| WO | WO 2010/039997 A2 | 4/2010 |
| WO | WO 2010/051127 A2 | 5/2010 |
| WO | WO 2010/132725 A2 | 11/2010 |
| WO | WO 2011/101409 | 8/2011 |
| WO | WO 2011/101417 | 8/2011 |
| WO | WO 2011/103485 A1 | 8/2011 |
| WO | WO 2012/061156 A1 | 5/2012 |
| WO | WO 2012/068381 A2 | 5/2012 |
| WO | WO 2012/129344 | 9/2012 |
| WO | WO 2013/006532 A1 | 1/2013 |
| WO | WO 2013/014448 A1 | 1/2013 |
| WO | WO 2013/148748 A1 | 10/2013 |
| WO | WO 2013/163239 A1 | 10/2013 |
| WO | WO 2014/085318 A1 | 6/2014 |
| WO | WO 2014/144326 A1 | 9/2014 |
| WO | WO 2014/144596 A2 | 9/2014 |
| WO | WO 2014/144740 A2 | 9/2014 |
| WO | WO 2014/144847 A2 | 9/2014 |
| WO | WO 2014/168975 A1 | 10/2014 |
| WO | WO 2015/061407 A1 | 4/2015 |
| WO | WO 2015/084892 A1 | 6/2015 |
| WO | WO 2015/161283 A1 | 10/2015 |
| WO | WO 2015/161285 A1 | 10/2015 |
| WO | WO 2015/161287 A1 | 10/2015 |
| WO | WO 2015/161288 A1 | 10/2015 |
| WO | WO 2016/040848 A1 | 3/2016 |
| WO | WO 2016/040858 A1 | 3/2016 |
| WO | WO 2016/126889 A1 | 8/2016 |

OTHER PUBLICATIONS

Baughn, L. B. et al. "A novel orally active small molecule potently induces G1 arrest in primary myeloma cells and prevents tumor growth by specific inhibition of cyclin-dependent kinase 4/6" Cancer Res, Aug. 1, 2006; 66(15): 7661-7667.

Berge et al. "Pharmaceutical Salts" J. Pharm. Sci., 1977; 66(1): 1-19.

Bernhard, E. J. et al. "Reducing the radiation-induced G2 delay causes HeLa cells to undergo apoptosis instead of mitotic death" Int J Radiat Biol., May 1996; 69(5): 575-584.

Blagosklonny, M. V. and A. B. Pardee "Exploiting cancer cell cycling for selective protection of normal cells" Cancer Res, Jun. 1, 2001; 61(11): 4301-4305.

Brookes et al. "INK4a-deficient human diploid fibroblasts are resistant to RAS-induced senescence" EMBO J., Jun. 17, 2002; 21(12): 2936-2945.

Bucher, N. and C. D. Britten "G2 checkpoint abrogation and checkpoint kinase-1 targeting in the treatment of cancer" Br J Cancer, Feb. 12, 2008; 98(3): 523-528.

Burdelya et al. "An agonist of toll-like receptor 5 has radioprotective activity in mouse and primate models" Science, Apr. 11, 2008; 320(5873): 226-230.

Casi, G. and D. Neri "Antibody-drug conjugates: basic concepts, examples and future perspectives" Journal of Controlled Release, 2012; 161(2): 422-428.

Chari, R.V. "Targeted cancer therapy: conferring specificity to cytotoxic drugs" Accounts of Chemical Research, 2008; 41(1): 98-107.

Chen, X. et al. "Protection of normal proliferating cells against chemotherapy by staurosporine-mediated, selective, and reversible G1 arrest" J Natl Cancer Inst., Dec. 20, 2000; 92(24): 1999-2008.

Chin et al. "Cooperative effects of INK4a and ras in melanoma susceptibility in vivo" Genes & Development, 1997; 11: 2822-2834.

Chu et al. "Discovery of [4-Amino-2-(1-methanesulfonylpiperidin-4-ylamino)pyrimidin-5-yl](2,3-difluoro-6-methoxyphenyl)methanone (R547), a potent and selective cyclin-dependent kinase inhibitor with significant in vivo antitumor activity" J Med Chem, Nov. 2, 2006; 49(22): 6549-6560.

Curtin et al. "Distinct Sets of Genetic Alterations in Melanoma" N Engl J Med 2005; 353: 2135-2147.

Daniotti et al. "BRAF alterations are associated with complex mutational profiles in malignant melanoma" Oncogene, 2004; 23: 5968-5977.

(56) References Cited

OTHER PUBLICATIONS

Davis, S. T. et al. "Prevention of chemotherapy-induced alopecia in rats by CDK inhibitors" Science, Jan. 5, 2001; 291(5501): 134-137.
Davis, S.T. et al. "Retraction" Science, Dec. 20, 2002; 298(5602): 2327.
Davis, T. A. et al. "Genistein induces radioprotection by hematopoietic stem cell quiescence" Int J Radiat Biol, Sep. 2008; 84(9): 713-726.
Decker et al. "Expression of Cyclin E in resting and activated B-chronic lymphocytic leukemia cells: cyclin E/cdk2 as protential therapeutic target" British Journal of Hematology, Jan. 13, 2004, 125, 141-148.
Deep, G. et al. "New Combination Therapies with Cell Cycle Agents" Current Opinion in Investigational Drugs, 2008; 9: 591-605.
Dickson, M. A. and G. K. Schwartz "Development of cell-cycle inhibitors for cancer therapy" Curr Oncol, Mar. 2009; 16(2): 36-43.
Dickson, Mark, et al. "Phase II Trial of the CDK4 Inhibitor PD0332991 in Patients With Advanced CDK4-Amplified Well-Differentiated or Dedifferentiated Liposarcoma." J Clin Oncol. Jun. 1, 2013; 31(16): 2024-2028.
Diehl, J. A. "Cycling to Cancer with Cyclin D1" Cancer Biology and Therapy, 2002; 1(3): 226-231.
El-Diery, W. S. "Meeting report: The international conference on tumor progression and therapeutic resistance" Cancer Res, Jun. 1, 2005; 65(11): 4475-4484.
Elkind, M.M. and H. Sutton "Radiation response of mammalian cells grown in culture. 1. Repair of x-ray damage in surviving Chinese hamster cells" Radiat Res., 1960; 13: 556-593.
Elkind, M.M. and H. Sutton "X-ray damage and recovery in mammalian cells in culture" Nature, 1959; 184: 1293-1295.
Engler et al. "Novel, potent and selective cyclin D1/CDK4 inhibitors: indolo[6,7-a]pyrrolo[3,4-c]carbazoles" Bioorg Med Chem Lett, Jul. 21, 2003; 13(14): 2261-2267.
Finn et al. "PD 0332991, a selective cyclin D kinase 4/6 inhibitor, preferentially inhibits proliferation of luminal estrogen receptor-positive human breast cancer cell lines in vitro" Breast Cancer Research, Oct. 29, 2009; 11(5): R77.
Finn et al. "Results of a randomized phase 2 study of PD 0332991, a cyclin-dependent kinase (CDK) 4/6 inhibitor, in combination with letrozole vs letrozole alone for first-line treatment of ER+/HER2− advanced breast cancer (BC)" Cancer Res, 2012; 72(24 Suppl): Abstract nr S1-6.
Firer, M. A. and G. J. Gellerman Targeted drug delivery for cancer therapy: the other side of antibodies, J. Hematol. Oncol., 2012; 5: 70. [retrieved from http://www.jhoonline.org/content/5/1/70 on Jul. 16, 2014].
Franken et al. "Clonogenic assay of cells in vitro" Nature Protocols, 2006; 1: 2315-2319.
Fry, D. W. et al. "Specific inhibition of cyclin-dependent kinase 4/6 by PD 0332991 and associated antitumor activity in human tumor xenografts" Mol Cancer Ther., Nov. 2004; 3(11): 1427-1438.
Goldberg et al. "Pyrazinoindolone inhibitors of MAPKAP-K2" Bioogranic & Medicinal Chemistry Letters, Dec. 23, 2007, 18, 938-941.
Guillard et al., "Synthesis and biological evaluations of new pyrrolo[2,3- b]pyrimidine as SDI analogs" Heterocyles, 2008, vol. 75(5), pp. 1163-1189.
Guo et al. "Staurosporine modulates radiosensitivity and radiation-induced apoptosis in U937 cells" Int J Radiat Biol., Feb. 2006; 82(2): 97-109.
Hallahan, D. E. et al. "Inhibition of protein kinases sensitizes human tumor cells to ionizing radiation" Radiat Res., Mar. 1992; 129(3): 345-350.
Hara, E. et al. "Regulation of p16CDKN2 expression and its implications for cell immortalization and senescence" Mol Cell Biol, Mar. 1996; 16(3): 859-867.
Herodin, F. et al. "Short-term injection of antiapoptotic cytokine combinations soon after lethal gamma-irradiation promotes survival" Blood, Apr. 1, 2003; 101(7): 2609-2616.

Hershman, D et al. "Acute myeloid leukemia or myelodysplastic syndrome following use of granulocyte colony-stimulating factors during breast cancer adjuvant chemotherapy" J Natl Cancer Inst, Feb. 7, 2007; 99(3): 196-205.
Hibbs, M. L. et al. "Multiple defects in the immune system of Lyn-deficient mice, culminating in autoimmune disease" Cell, Oct. 20, 1995; 83(2): 301-311.
Hirose, Y. et al. "Abrogation of the Chk1-mediated G(2) checkpoint pathway potentiates temozolomide-induced toxicity in a p53-independent manner in human glioblastoma cells" Cancer Res, Aug. 1, 2001; 61(15): 5843-5849.
Honma, T. et al. "A novel approach for the development of selective Cdk4 inhibitors: library design based on locations of Cdk4 specific amino acid residues" J Med Chem, Dec. 20, 2001; 44(26): 4628-4640.
Honma, T. et al. "Structure-based generation of a new class of potent Cdk4 inhibitors: new de novo design strategy and library design" J Med Chem, Dec. 20, 2001; 44(26): 4615-4627.
Humphreys, B.D. et al. "Intrinsic epithelial cells repair the kidney after injury" Cell Stem Cell, 2008; 2: 284-291.
Humphreys, B.D. et al. "Repair of injured proximal tubule does not involve specialized progenitors" Proc Natl Acad Sci USA, 2011; 108: 9226-9231.
Ikuta, M. et al. "Crystallographic approach to identification of cyclin-dependent kinase 4 (CDK4)-specific inhibitors by using CDK4 mimic CDK2 protein" J Biol Chem, Jul. 20, 2001; 276(29): 27548-27554.
Johnson, D. G. and C. L. Walker "Cyclins and Cell Cycle Checkpoints" Annual Review of Pharmacology and Toxicology, Apr. 1999; 39: 295-312.
Johnson, N. and G. Shapiro "Cyclin-dependent kinase 4/6 inhibition in cancer therapy" Cell Cycle, Nov. 1, 2012; 11(21): 3913-3918.
Johnson, S.M., et al. "Mitigation of hematologic radiation toxicity in mice through pharmacological quiescence induced by CDK4/6 inhibition" J Clin Invest, Jul. 2010; 120(7): 2528-2536.
Karaman, M. W. et al. "A quantitative analysis of kinase inhibitor selectivity" Nat Biotechnol., Jan. 2008; 26(1): 127-132.
Khuri, F. R. "Weighing the hazards of erythropoiesis stimulation in patients with cancer" N Engl J Med, Jun. 14, 2007; 356(24): 2445-2448.
Kiel et al. "SLAM Family Receptors Distinguish Hematopoietic Stem and Progenitor Cells and Reveal Endothelial Niches for Stem Cells" Cell, 2005; 121: 1109-1121.
Kim, S. et al. "Enhancement of radiation effects by flavopiridol in uterine cervix cancer cells" Cancer Res Treat, Jun. 2005; 37(3): 191-195.
Knockaert et al. "Pharmacological inhibitors of cyclin-dependent kinases" Trends Pharmacol Sci, Sep. 2002; 23(9): 417-425.
Konecny, Gottfried E., et al., Expression of p16 and Retinoblastoma Determines Response to CDK4/6 Inhibition in Ovarian Cancer, Clinical Cancer Research, 2011, vol. 17, No. 6, p. 1591-1602.
Kubinyi (3D QSAR in Drug Design: Ligand-Protein Interactions and Molecular Similarity, vol. 2-3, Springer, 1998, 800 pages). p. 243-44.
Kubo, et al. "The p16 status of tumor cell lines identifies small molecule inhibitors specific for cyclin-dependent kinase 4" Clin Cancer Res, 1999; 5: 4279-4286.
Lambert, J. M. Drug-conjugated antibodies for the treatment of cancer British Journal of Clinical Pharmacology, 2013; 76(2): 248-262.
Landis, M.W. et al. Cyclin D1-dependent kinase activity in murine development and mammary tumorigenesis. Cancer Cell, 2006; 9: 13-22.
Laredo, J. et al. "Effect of the protein kinase C inhibitor staurosporine on chemosensitivity to daunorubicin of normal and leukemic fresh myeloid cells" Blood, Jul. 1, 1994; 84(1): 229-237.
Le Deley et al. "Anthracyclines, Mitoxantrone, Radiotherapy, and Granulocyte Colony-Stimulating Factor: Risk Factors for Leukemia and Myelodysplastic Syndrome After Breast Cancer" J Clin Oncol, 2007; 25: 292-300.
Little, J.B. "Repair of sub-lethal and potentially lethal radiation damage in plateau phase cultures of human cells" Nature, 1969; 224(5221): 804-806.

(56) References Cited

OTHER PUBLICATIONS

Lohmann and Gallie "Retinoblastoma" Gene Reviews (2000), retrieved from http://www.ncbi.nlm.nih.gov/books/NBK1452/ on Jul. 10, 2014.
Lopus, M. Antibody-DM1 conjugates as cancer therapeutics, Cancer Letters, 2011; 307(2): 113-118.
Luo, Y. et al. "Blocking Chk1 expression induces apoptosis and abrogates the G2 checkpoint mechanism" Neoplasia, Sep.-Oct. 2001; 3(5): 411-419.
Malumbres, M. and M. Barbacid "Cell cycle, CDKs and cancer: a changing paradigm" Nature Reviews Cancer, Mar. 2009; 9(3): 153-166.
Malumbres, M. and M. Barbacid "Mammalian cyclin-dependent kinases" Trends Biochem. Sci., Nov. 2005; 30(11): 630-641.
McInnes, C. "Progress in the evaluation of CDK inhibitors as anti-tumor agents" Drug Discov Today, Oct. 2008; 13(19-20): 875-881.
Meng et al. "Ionizing Radiation and Busulfan Induce Premature Senescence in Murine Bone Marrow Hematopoietic Cells" Cancer Res, 2003; 63: 5414-5419.
Menu, E. et al. "A novel therapeutic combination using PD 0332991 and bortezomib: study in the 5T33MM myeloma model" Cancer Res, Jul. 15, 2008; 68(14): 5519-5523.
Michaud, Karine et al. "Pharmacologic inhibition of cdk4/6 arrests the growth of glioblastoma multiforme intracranial xenografts" Cancer Res, Apr. 15, 2011; 70: 3228-3238.
Morgan, D.O. "Cyclin-dependent Kinases: Engines, Clocks, and Microprocessors" Annual Review of Cell and Developmental Biology, 1997; 13: 261-291.
Na Nakorn et al. "Myeloerythroid-restricted progenitors are sufficient to confer radioprotection and provide the majority of day 8 CFU-S" J Clin Invest, 2002; 109: 1579-1585.
Newland, A. M. "Brentuximab vedotin: a CD30-directed antibody-cytotoxic drug conjugate" Pharmacotherapy, Jan. 2013; 33(1): 93-104.
O'Dwyer, et al. "A phase I dose escalation trial of a daily oral CDK 4/6 inhibitor PD-0332991" J Clin Oncol, 2007; 25(18S): 3550. [Abstract].
Ojeda, F. et al. "Role of protein kinase-C in thymocyte apoptosis induced by irradiation" Int J Radiat Biol., May 1992; 61(5): 663-667.
Park et al. "Toxicogenetics in drug development" Toxicology Letters, Mar. 31, 2001, 120, 281-291.
Parsam et al. "A comprehensive, sensitive and economical approach for the detection of mutations in the RB1 gene in retinoblastoma" Journal of Genetics, Dec. 2009; 88(4): 517-527.
Passegué et al. "Global analysis of proliferation and cell cycle gene expression in the regulation of hematopoietic stem and progenitor cell fates" J Exp Med, 2005; 202: 1599-1611.
Pawlik, T. M. and K. Keyomarsi "Role of cell cycle in mediating sensitivity to radiotherapy" Int J Radiat Oncol Biol Phys, Jul. 15, 2004; 59(4): 928-942.
Presser, Armin and Antje Hüfner "Trimethylsilyldiazomethane—A Mild and Efficient Reagent for the Methylation of Carboxylic Acids and Alcohols in Natural Products" Monatshefte für Chemie, 2004, 135(8): 1015-1022.
Ramsey, M. R. et al. "Expression of p16Ink4a compensates for p18Ink4c loss in cyclin-dependent kinase 4/6-dependent tumors and tissues" Cancer Res, May 15, 2007; 67(10): 4732-4741.
Reddy, H. K. et al. "Cyclin-dependent kinase 4 expression is essential for neu-induced breast tumorigenesis" Cancer Research, 2005; 65: 10174-10178.
Roberts et al. "Multiple Roles of Cyclin-Dependent Kinase 4/6 Inhibitors in Cancer Therapy" JNCI, 2012; 104(6):476-487.
Ruas et al. "CDK4 and CDK6 Delay Senescence by Kinase-Dependent and p16INK4a-Independent Mechanisms" Molecular and Cellular Biology, Jun. 2007; 27(12): 4273-4282.
Samady, L. et al. "Activation of CDK4 gene expression in human breast cancer cells by the Brn-3b POU family transcription factor" Cancer Biology & Therapy, 2004; 3: 317-323.

Sanchez-Martinez, C. et al. "Aryl[a]pyrrolo[3,4-c]carbazoles as selective cyclin D1-CDK4 inhibitors" Bioorg Med Chem Lett, Nov. 3, 2003; 13(21): 3835-3839.
Sanchez-Martinez, C. et al. "Studies on cyclin-dependent kinase inhibitors: indolo-[2,3-a]pyrrolo[3,4-c]carbazoles versus bis-indolylmaleimides" Bioorg Med Chem Lett, Nov. 3, 2003; 13(21): 3841-3846.
Sapra, P. and B. Shor "Monoclonal antibody-based therapies in cancer: advances and challenges" Pharmacology & Therapeutics, 2013; 138(3): 452-469.
Sarkar et al. "Nonsolvent Application of Ionic Liquids: Organo-Catalysis by 1-Alkyl-3-methylimidazolium Cation Based Room-Temperature Ionic Liquids for Chemoselective N-tert-Butyloxycarbonylation of Amines and the Influence of the C-2 Hydrogen on Catalytic Efficiency" Journal of Organic Chemistry, 2011; 76(17): 7132-7140.
Sawai, Catherine M., et al., "Therapeutic Targeting of the Cyclin D3:CDK4/6 Complex in T Cell Leukemia," Cancer Cell, Oct. 16, 2012, vol. 22, pp. 452-465.
Schliemann, C. and D. Neri "Antibody-based targeting of the tumor vasculature" Biochimica et Biophysica Acta, 2007; 1776(2): 175-192.
Schmidt, M. and Z. Fan "Protection against chemotherapy-induced cytotoxicity by cyclin-dependent kinase inhibitors (CKI) in CKI-responsive cells" Oncogene, Sep. 27, 2001; 20(43): 6164-6171.
Schönauer, K. and E. Zibral "Reactions with organophosphorus compounds, 50.: Trimethylsilylethoxymethylene triphenylphosphorane, a novel reagent for the homologation of carbonyl compounds." Tetrahedron Letters, 1983, 24: 573-576.
Schwartz, G.K. et al. "Phase I study of PD 0332991, a cyclin-dependent kinase inhibitor, administered in 3-week cycles (Schedule 2/1)" Br J Cancer, Jun. 7, 2011; 104(12): 1862-1868.
Seed, T. M. "Radiation protectants: current status and future prospects" Health Phys, Nov. 2005; 89(5): 531-545.
Sharma, P.S. et al. "Inhibitors of cyclin dependent kinases: useful targets for cancer treatment" Curr. Cancer Drug Targets, Feb. 2008; 8(1): 53-75.
Sharpless et al. "Both products of the mouse Ink4a/Arf locus suppress melanoma formation in vivo" Oncogene, Aug. 7, 2003; 22(32): 5055-5059.
Sherr, C. J., "Cancer Cell Cycles" Science, Dec. 6, 1996; 274(5293): 1672-1677.
Shields et al. "Lack of Extracellular Signal-Regulated Kinase Mitogen-Activated Protein Kinase Signaling Shows a New Type of Melanoma" Cancer Res, 2007; 67: 1502-1512.
Shimamura, T. et al. "Identification of potent 5-pyrimidinyl-2-aminothiazole CDK4, 6 inhibitors with significant selectivity over CDK1, 2, 5, 7, and 9" Bioorg Med Chem Lett., Jul. 15, 2006; 16(14): 3751-3754.
Sielecki et al "Quinazolines as cyclin dependent kinase inhibitors"Bioogranic & Medicinal Chemistry Letters, May 7, 2001, 11, 1157-1160.
Sinclair, W.K. and R.A. Morton "X-ray sensitivity during the cell generation cycle of cultured Chinese hamster cells" Radiat Res., Nov. 1966; 29(3): 450-474.
Soni, R. et al. "Selective in vivo and in vitro effects of a small molecule inhibitor of cyclin-dependent kinase 4" J Natl Cancer Inst, Mar. 21, 2001; 93(6): 436-446.
Stone, S. et al. "Reversible, p16-mediated cell cycle arrest as protection from chemotherapy" Cancer Research, Jul. 15, 1996; 56(14): 3199-3202.
Sun, Y. et al. "Antibody-drug conjugates as targeted cancer therapeutics" Acta Pharmaceutica Sinica, 2009; 44(9): 943-952.
Takano, Y. et al. Cyclin D1 overexpression in invasive breast cancers: correlation with cyclin-dependent kinase 4 and oestrogen receptor overexpression, and lack of correlation with mitotic activity Journal of Cancer Research and Clinical Oncology, 1999; 125: 505-512.
Teicher, B. A. and R. V. Chart "Antibody conjugate therapeutics: challenges and potential" Clinical Cancer Research, 2011; 17(20): 6389-6397.

(56) References Cited

OTHER PUBLICATIONS

Terasima, T. and Li Tolmach "X-ray sensitivity and DNA synthesis in synchronous populations of HeLa cells" Science, 1963, 140: 490-492.
Teyssier, F. et al. "Cell cycle regulation after exposure to ionizing radiation" Bull Cancer., Apr. 1999; 86(4): 345-357. [Abstract].
Toogood, P. L. et al. "Discovery of a potent and selective inhibitor of cyclin-dependent kinase 4/6" J Med Chem, Apr. 7, 2005; 48(7): 2388-2406.
Tsou, H. R. et al. "4-(Phenylaminomethylene)isoquinoline-1,3(2H,4H)-diones as potent and selective inhibitors of the cyclin-dependent kinase 4 (CDK4)" J Med Chem, Jun. 26, 2008; 51(12): 3507-3525.
Tsou, H. R. et al. "Discovery of 4-(benzylaminomethylene)isoquinoline-1,3-(2H,4H)-diones and 4-[(pyridylmethyl)aminomethylene]isoquinoline-1,3-(2H,4H)-diones as potent and selective inhibitors of the cyclin-dependent kinase 4" J Med Chem, Apr. 23, 2009; 52(8): 2289-2310.
Tu, S. et al. "New potential inhibitors of cyclin-dependent kinase 4: design and synthesis of pyrido[2,3-d]pyrimidine derivatives under microwave irradiation" Bioorg Med Chem Lett, Jul. 1, 2006; 16(13): 3578-3581.
Uckun, F. M. et al. "In vivo radioprotective effects of recombinant human granulocyte colony-stimulating factor in lethally irradiated mice" Blood, Feb. 1, 1990; 75(3): 638-645.
Vanderwel, S.N. et al. "Pyrido[2,3-d]pyrimidin-7-ones as specific inhibitors of cyclin-dependent kinase 4" J Med Chem., Apr. 7, 2005; 48(7): 2371-2387.
Vlachakis, D. and S. Kossida "Antibody Drug Conjugate bioinformatics: drug delivery through the letterbox" Comput. Math. Methods Med., 2013; 2013: 282398. Published online on Jun. 19, 2013. [retrieved from http://dx.doi.org/10.1155/2013/282398 on Jul. 16, 2014].
Walker et al. "Virtually 100% of melanoma cell lines harbor alterations at the DNA level within CDKN2A, CDKN2B, or one of their downstream targets" Genes Chromosomes & Cancer, 1998; 22: 157-163.
Wang et al. "Loss of p21 increases sensitivity to ionizing radiation and delays the onset of lymphoma in atm-deficient mice" Proc Natl Acad Sci, USA, 1997; 94: 14590-14595.
Wang, R. H. et al. "Protein kinase inhibitor staurosporine enhances cytotoxicity of antitumor drugs to cancer cells" Yao Xue Xue Bao, 1996; 31(6): 411-415. [Abstract].
Weiss and Landauer "History and development of radiation-protective agents" International Journal of Radiation Biology, Jul. 2009; 85: 539-573.
Wermuth, The Practice of Medicinal Chemistry, 2d ed. (2003), 768 pages. Chs. 9-10.
White, J.D. et al. "Transformations of Quinic Acid. Asymmetric Synthesis and Absolute Configuration of Mycosporin I and Mycosporingly" Journal of Organic Chemistry, 1995, 60(12): 3600-3611.
Wilson et al. "Hematopoietic Stem Cells Reversibly Switch from Dormancy to Self-Renewal during Homeostasis and Repair" Cell, 2008; 135: 1118-1129.
Yu, Q. et al. "Requirement for CDK4 kinase function in breast cancer" Cancer Cell, 2006; 9: 23-32.
Yu, Q. et al. "Specific protection against breast cancers by cyclin D1 ablation" Nature, 2001; 411: 1017-1021.
Zhang, W. et al. "Sensitization of C6 glioma cells to radiation by staurosporine, a potent protein kinase C inhibitor" J Neurooncol., Jan. 1993; 15(1): 1-7.
Zhu, G. et al. "Synthesis, structure-activity relationship, and biological studies of indolocarbazoles as potent cyclin D1-CDK4 inhibitors" J Med Chem., May 22, 2003; 46(11): 2027-2030.
Zhu, G. et al. "Synthesis of quinolinyl/isoquinolinyl[a]pyrrolo [3,4-c] carbazoles as cyclin D1/CDK4 inhibitors" Bioorg Med Chem Lett, Apr. 7, 2003; 13(7): 1231-1235.
US, 2018/0360841, A1, U.S. Appl. No. 16/112,362, Strum, et al., dated Dec. 20, 2018.
U.S. Appl. No. 16/432,244, Sorrentino, et al., filed Jun. 5, 2019.
U.S. Pat. No. 10,413,547, U.S. Appl. No. 16/142,574, Strum et al., dated Sep. 17, 2019.
US, 2019-0070185, A1, U.S. Appl. No. 16/178,419, Strum, et al., dated Mar. 7, 2019.
US, 2019-0119292, A1, U.S. Appl. No. 16/226,430, Tavares et al., dated Apr. 25, 2019.
US, 2019-0125752, A1, U.S. Appl. No. 16/228,308, Strum et al., dated May 2, 2019.
US, 2019-0151311, A1, U.S. Appl. No. 16/254,364, Strum, et al., dated May 23, 2019.
US, 2019-0374545, A1, U.S. Appl. No. 16/547,342, Sorrentino et al., dated Dec. 12, 2019.
US, 2020-0022983, A1, U.S. Appl. No. 16/572,418, Strum et al., dated Jan. 3, 2020.
Blachly et al., "Emerging Drug Profile: Cyclin-dependent kinase inhibitors", Leuk. Lymphoma, 2013, 54(10), 2133-2143.
Bose et al., "Cyclin-dependent kinase inhibitor therapy for hematologic malignancies", Expert Opin. Investig. Drugs, 2013, 22(6), 723-738.
Boss et al., "Safety, tolerability, pharmacokinetics and pharmacodynamics of the oral cyclin-dependent kinase inhibitor AZD5438 when administered at intermittent and continuous dosing schedules in patient with advanced solid tumors", Annals of Oncology, 2010, 21, 884-894.
Choi et al., "The requirement for cyclin D function in tumor maintenance", Cancer Cell, 2012 22(4), 438-451.
Choi et al., "Signaling through cyclin D-dependent kinase", Oncogene, 2014, 33, 1890-1903.
Giacinti et al., "RB and cell cycle progression", Oncogene, 2006, 25, 5220-5227.
Gojo et al., "Phase II study of the cyclin-dependent kinase (CDK) inhibitor Dinaciclib (SCH 727965) in patients with advanced acute leukemia", Blood, 2010, 116(21), 3287.
GTHX Corp Presentation, "Next Generation Cancer Therapies", Presented Jan. 2020.
Hamilton et al., "Synergistic anticancer activity of topotecan cyclin-dependent kinase inhibitor combinations against drug resistant small cell lug cancer (SCLC) cell lines", Journal of Cancer Therapy, 2013, 4, 47-53.
Hamilton et al., "Synergism of cyclin-dependent kinase inhibitors with camptothecin derivatives in small cell lung cancer cell lines", Molecules, 2014, 19, 2077-2088.
McClendon et al., "CDK4/6 inhibition antagonizes the cytotoxic response to anthracycline therapy", Cell Cycle, 2012, 11(14), 2747-2755.
McInnes Campbell, "Progress in the evaluation of CDK inhibitors as anti-tumor agents", Drug Discovery Today, 2008, 13, (19/20), 875-881.
Mita et al., "Randomized Phase II trial of the cyclin-dependent kinase inhibitors Dinaciclib (MK-7965) versus Capecitabine in patients with advanced breast cancer", Clinical Breast Cancer, 2014, 14(3), 169-176.
Rader et al., "Dual CDK4/CDK6 inhibition induces cell cycle arrest and senescence in neutroblastoma", Clinical Cancer Res., 2013, 19(22), 6173-6182.
Tan et al., "Trilaciclib plus chemotherapy versus chemotherapy alone in patients with metastatic triple-negative breast cancer: a multicenter, randomized, open-label, phase 2 trial", Lancet Oncol., 2019, 20, 1587-1601.
Tong et al., "Phase I and pharmacologic study of SNS-032, a potent and selective CDK2, 7 and 9 inhibitors in patients with advanced chronic lymphocytic leukemia and multiple myeloma", Journal of Clinical Oncology, 2010, 28(18), 3015-3022.
Weiss et al., "Myelopreservation with the CDK inhibitor trilaciclib in patients with small cell lung cancer receiving first-line chemotherapy: a phase Ib/randomized phase II trial", Annals of Oncology, 2019, 30, 1613-1621.
U.S. Appl. No. 16/886,309, Strum, et al., filed May 28, 2020.
U.S. Appl. No. 16/926,035, Strum, et al., filed Jul. 10, 2020.
Bisi et al., Preclinical Characterization of G1T28: A Novel CDK4/6 Inhibitor for Reduction of Chemotherapy-Induced Myelosuppression, Mol. Cancer Therap. (2016) (15)5: 783-793.

(56) References Cited

OTHER PUBLICATIONS

Bisi et al., Preclinical development of G1T38: A novel, potent and selective inhibitor of cyclin dependent kinases 4/6 for use as an oral antineoplastic in patients with CDK4/6 sensitive tumors, Oncotarget. Mar. 15, 2017: doi:10.18632/oncotarget.16216.

Deng et al., "New Strategies in the Treatment of Mantle Cell Lymphoma" Clinical Cancer Research, 2012; 18(13): 3499-3508.

Stice, James P. et al., "CDK4/6 Therapeutic Intervention and viable alternative to taxane in CRPC", Molecular Cancer Research, 2017, 15(6), 660-669, XP55457140.

He et al., "Transient CDK4/6 inhibition protects hematopoietic stem cells from chemotherapy-induced exhaustion", Science Translational Medicine, 2017, 9, eaal3986.

Johnson et al., Cyclin-dependent kinases (cdks) and the DNA damage response: rationale for cdk inhibitor-chemotherapy combinations as an anticancer strategy for solid tumors, Expert Opin Ther Targets. Nov. 2010; 14(11): 1199-1212.

Lima Caio Max S Rocha et al., "G1T28, a cyclin dependent kinase 4/6 inhibitor, in combination with etoposide and carboplatin for extensive stage small cell lung cancer (ES-SCLC): preliminary results", Cancer Research, 2016, 76(14), CT151, XP002799585; & 107th Annual Meeting of the American Association of Cancer Research (AACR), New Orleans, LA Apr. 16-20, 2016.

Matsui, K. et al., Phase II trial of carboplatin plus oral etoposide for elderly patients with small-cell lung cancer, British Journal of Cancer 77(11), pp. 1961-1965, 1998; abstract.

NCT02079636—A Study of Abemaciclib (LY2835219) in Combination with Another Anticancer Drug in Participants with Lung Cancer (NSCLC); Mar. 6, 2014.

Pommier et al., DNA topoisomerases and their poisoning by anticancer and antibacterial drugs, Chem. & Biol. Review 17 (2010) 421-433.

Sorrentino Jessica et al., "Trilaciclib (G1T28), a CDK 4/6 inhibitor, enhances the efficacy of combination therapy and immune checkpoint inhibitor treatment in preclinical models", Cancer Research, 2017, 77(13), Supplement 1, XP002799587.

Sorrentino Jessica et al., "G1T28, a novel CDK 4/6 inhibitor, protects murine hematopoietic stem and progenitor cells from cytotoxic chemotherapy", Cancer Research, 2015, 75(15), 941, XP002799586; & 106th Annual Meeting of the American Association for Cancer Research (AACR), Philadelphia, PA, Apr. 18-22, 2015.

* cited by examiner

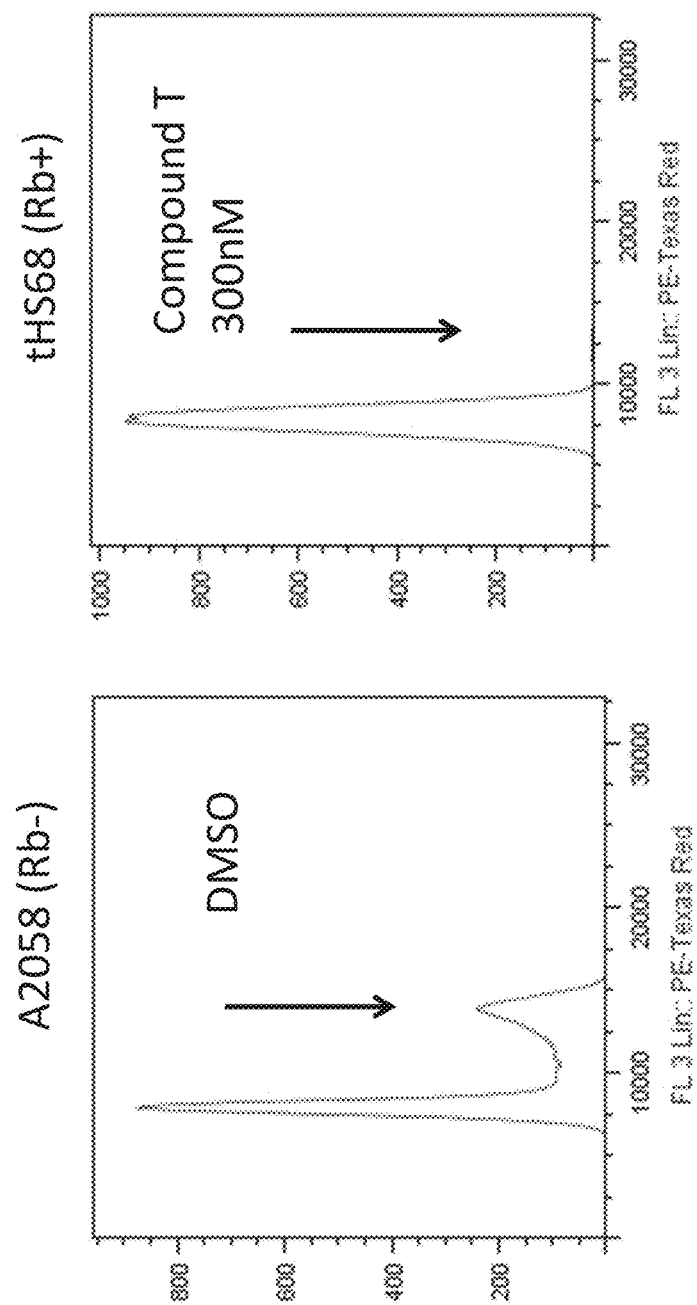

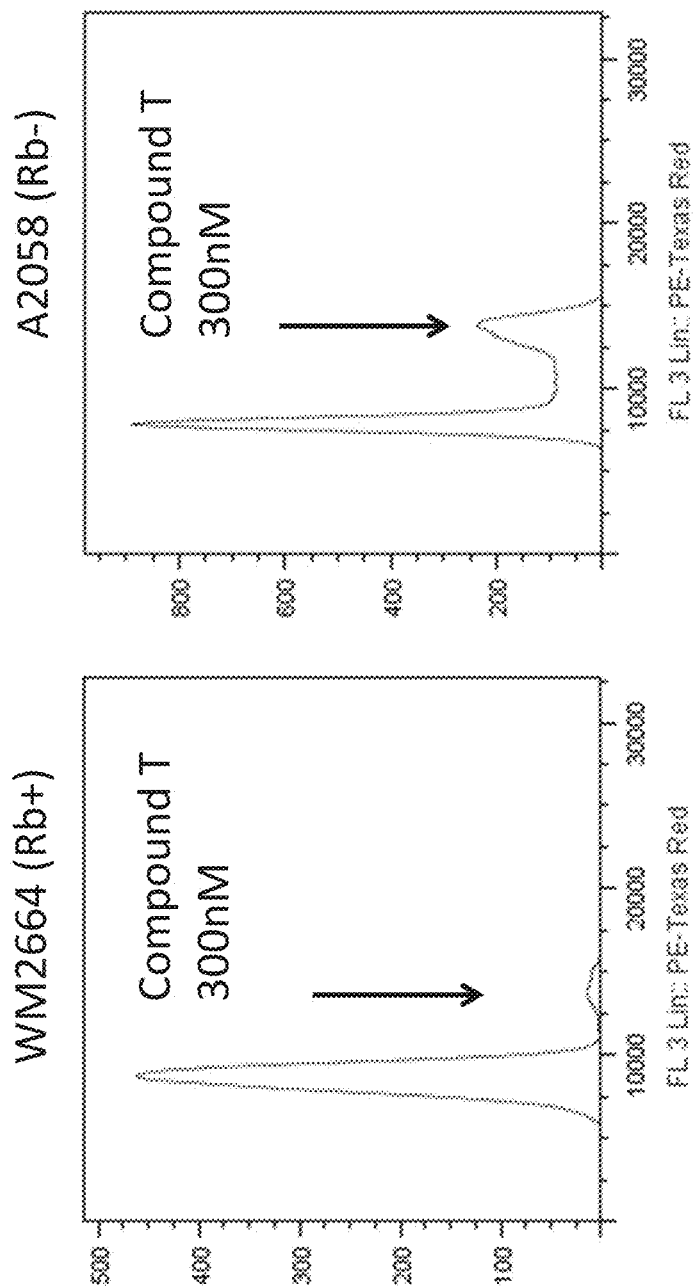

| Test Compound | Species | Half-Life (minutes) |
|---|---|---|
| Compound T | Human | >60 (66) |
| | Monkey | 30 |
| | Dog | 5 |
| | Rat | >60 (73) |
| | Mouse | 28 |
| PD0332991 | Human | >60 |
| | Monkey | >60 |
| | Dog | >60 |
| | Rat | >60 |
| | Mouse | >60 |

FIG. 10

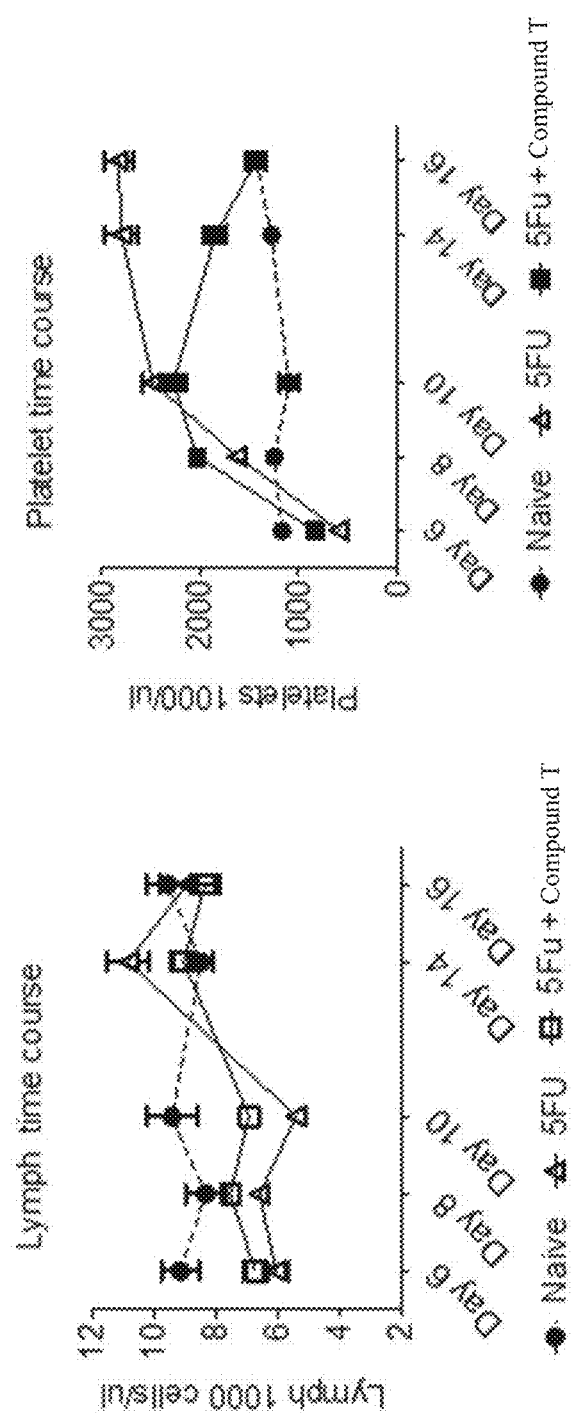

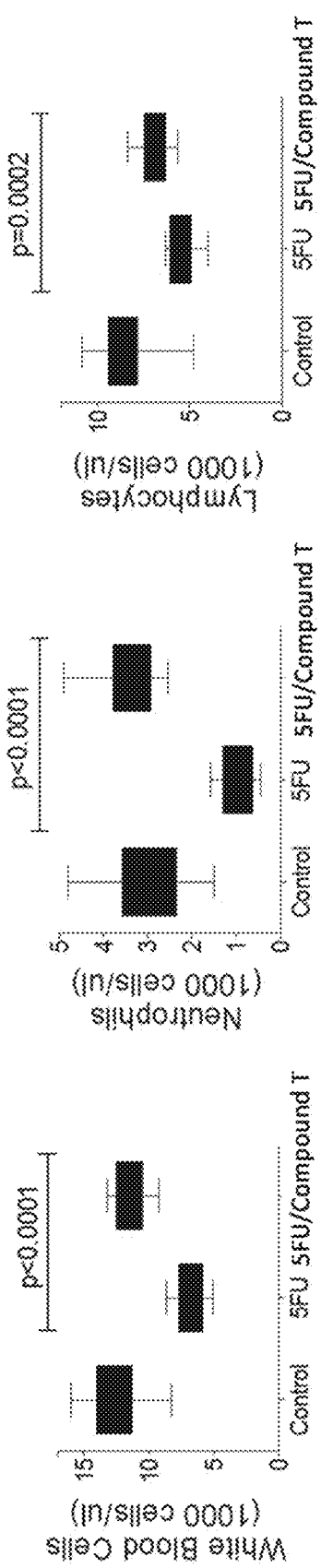
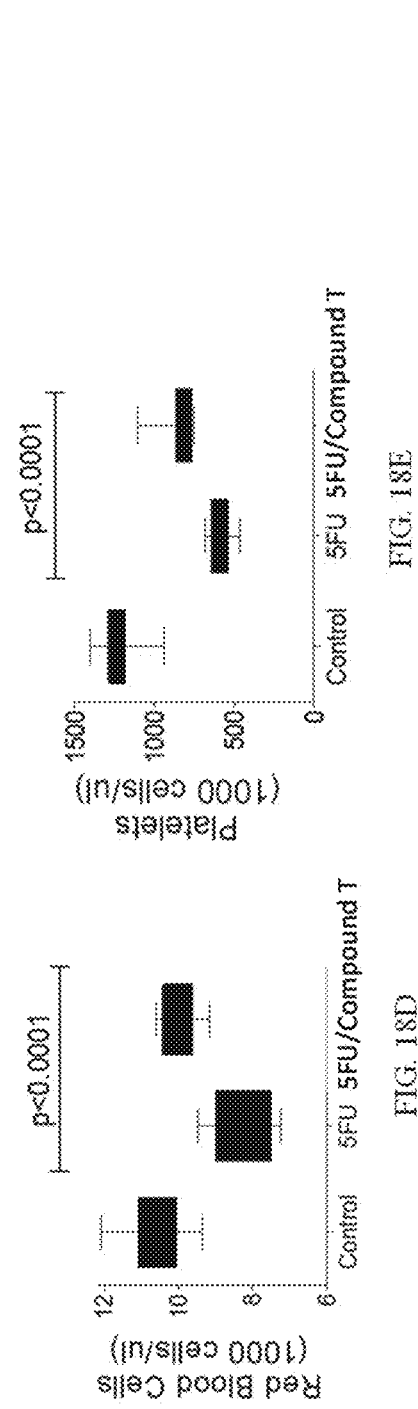
FIG. 18A, FIG. 18B, FIG. 18C, FIG. 18D, FIG. 18E

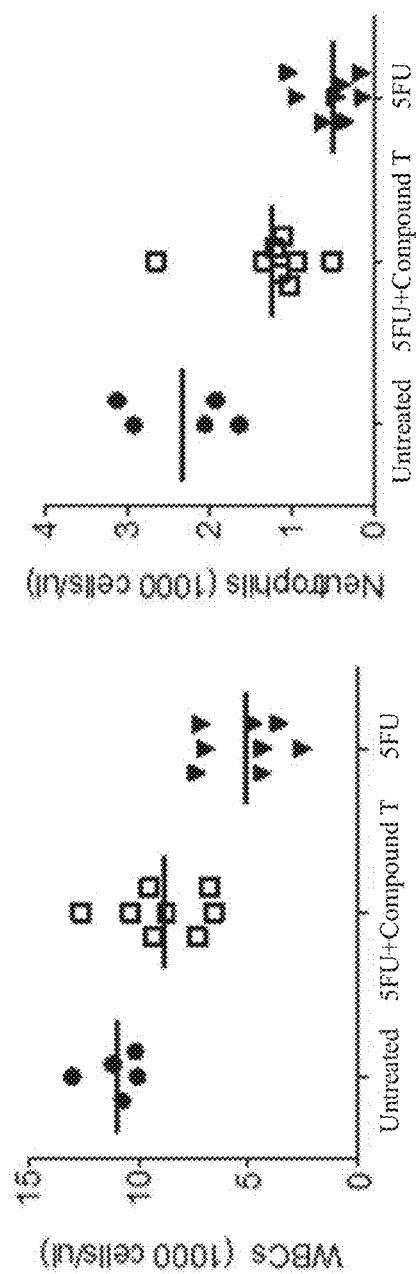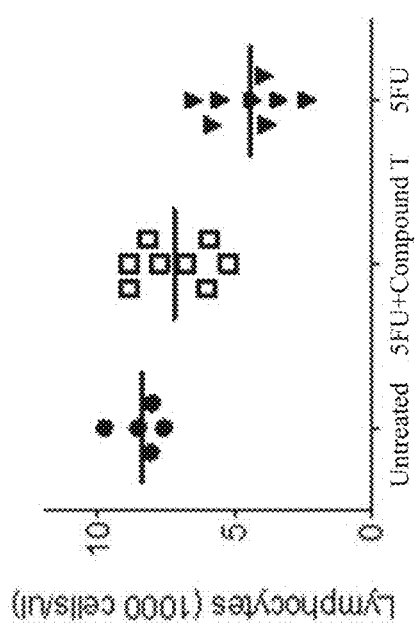
FIG. 19A
FIG. 19B
FIG. 19C

TRANSIENT PROTECTION OF NORMAL CELLS DURING CHEMOTHERAPY

CROSS-REFERENCE TO RELATED APPLICATIONS

This application is a continuation of U.S. patent application Ser. No. 15/342,990, filed Nov. 3, 2016, which is a continuation of U.S. patent application Ser. No. 14/212,430, filed Mar. 14, 2014, now U.S. Pat. No. 9,487,530, issued Nov. 8, 2016, which claims the benefit of U.S. Provisional Patent Application No. 61/798,772, filed Mar. 15, 2013, U.S. Provisional Patent Application No. 61/861,374, filed on Aug. 1, 2013, U.S. Provisional Patent Application No. 61/911,354, filed on Dec. 3, 2013, and U.S. Provisional Patent Application No. 61/949,786, filed on Mar. 7, 2014. The entirety of each of these applications is hereby incorporated by reference for all purposes.

GOVERNMENT INTEREST

The U.S. Government has rights in this invention by virtue of support under Grant No. 5R44AI084284 awarded by the National Institutes of Allergy and Infectious Disease.

FIELD OF THE INVENTION

This invention is in the area of improved compounds, compositions and methods of transiently protecting healthy cells, and in particular hematopoietic stem and progenitor cells (HSPC) as well as renal cells, from damage associated with DNA damaging chemotherapeutic agents. In one aspect, improved protection of healthy cells is disclosed using disclosed compounds that act as highly selective and short, transiently-acting cyclin-dependent kinase 4/6 (CDK 4/6) inhibitors when administered to subjects undergoing DNA damaging chemotherapeutic regimens for the treatment of proliferative disorders.

BACKGROUND

Chemotherapy refers to the use of cytotoxic (typically DNA damaging) drugs to treat a range of proliferative disorders, including cancer, tumors, psoriasis, arthritis, lupus and multiple sclerosis, among others. Chemotherapeutic compounds tend to be non-specific and, particularly at high doses, toxic to normal, rapidly dividing cells. This often leads to a variety of side effects in patients undergoing chemotherapy.

Bone marrow suppression, a severe reduction of blood cell production in bone marrow, is one such side effect. It is characterized by both myelosuppression (anemia, neutropenia, agranulocytosis, and thrombocytopenia) and lymphopenia. Neutropenia is characterized by a selective decrease in the number of circulating neutrophils and an enhanced susceptibility to bacterial infections. Anemia, a reduction in the number of red blood cells or erythrocytes, the quantity of hemoglobin, or the volume of packed red blood cells (characterized by a determination of the hematocrit) affects approximately 67% of cancer patients undergoing chemotherapy in the United States. See BioWorld Today, page 4, Jul. 23, 2002. Thrombocytopenia is a reduction in platelet number with increased susceptibility to bleeding. Lymphopenia is a common side-effect of chemotherapy characterized by a reduction in the number of circulating lymphocytes (also called T- and B-cells). Lymphopenic patients are predisposed to a number of types of infections.

Myelosuppression continues to represent the major dose-limiting toxicity of cancer chemotherapy, resulting in considerable morbidity along with the potential need to require a reduction in chemotherapy dose intensity, which may compromise disease control and survival. Considerable evidence from prospective and retrospective randomized clinical trials clearly shows that chemotherapy-induced myelosuppression compromises long-term disease control and survival (Lyman, G. H., Chemotherapy dose intensity and quality cancer care (Oncology (Williston Park), 2006. 20(14 Suppl 9): p. 16-25)). Furthermore, treatment regimens for, for example, lung, breast, and colorectal cancer recommended in the National Comprehensive Cancer Network guidelines are increasingly associated with significant myelosuppression yet are increasingly recommended for treating early-stage disease as well as advanced-stage or metastatic disease (Smith, R. E., Trends in recommendations for myelosuppressive chemotherapy for the treatment of solid tumors. J Natl Compr Canc Netw, 2006. 4(7): p. 649-58). This trend toward more intensive treatment of patients with cancer creates demand for improved measures to minimize the risk of myelosuppression and complications while optimizing the relative dose-intensity.

In addition to bone marrow suppression, chemotherapeutic agents can adversely affect other healthy cells such as renal epithelial cells, resulting potentially in the development of acute kidney injury due to the death of the tubular epithelia. Acute kidney injury can lead to chronic kidney disease, multi-organ failure, sepsis, and death.

One mechanism to minimize myelosuppression, nephrotoxicity, and other chemotherapeutic cytotoxicities is to reduce the planned dose intensity of chemotherapies. Dose reductions or cycle delays, however, diminish the effectiveness and ultimately compromise long-term disease control and survival.

Small molecules have been used to reduce some of the side effects of certain chemotherapeutic compounds. For example, leukovorin has been used to mitigate the effects of methotrexate on bone marrow cells and on gastrointestinal mucosa cells. Amifostine has been used to reduce the incidence of neutropenia-related fever and mucositis in patients receiving alkylating or platinum-containing chemotherapeutics. Also, dexrazoxane has been used to provide cardioprotection from anthracycline anti-cancer compounds. Unfortunately, there is concern that many chemoprotectants, such as dexrazoxane and amifostine, can decrease the efficacy of chemotherapy given concomitantly.

Additional chemoprotectant therapies, particularly with chemotherapy associated anemia and neutropenia, include the use of growth factors. Hematopoietic growth factors are available on the market as recombinant proteins. These proteins include granulocyte colony stimulating factor (G-CSF) and granulocyte-macrophage colony stimulating factor (GM-CSF) and their derivatives for the treatment of neutropenia, and erythropoietin (EPO) and its derivatives for the treatment of anemia. However, these recombinant proteins are expensive. Moreover, EPO has significant toxicity in cancer patients, leading to increased thrombosis, relapse and death in several large randomized trials. G-CSF and GM-CSF may increase the late (>2 years post-therapy) risk of secondary bone marrow disorders such as leukemia and myelodysplasia. Consequently, their use is restricted and not readily available any more to all patients in need. Further, while growth factors can hasten recovery of some blood cell lineages, no therapy exists to treat suppression of platelets, macrophages, T-cells or B-cells.

Roberts et al in 2012 reported that Pfizer compound PD-0332991 induced a transient cell cycle arrest in CDK4/6 dependent subsets of healthy cells such as HSPCs (see Roberts et al. Multiple Roles of Cyclin-Dependent Kinase 4/6 Inhibitors in Cancer Therapy. JNCI 2012; 104(6):476-487). This compound is currently being tested by Pfizer in clinical trials as an anti-neoplastic agent against estrogen-positive, HER2-negative breast cancer.

Hematopoietic stem cells give rise to progenitor cells which in turn give rise to all the differentiated components of blood as shown in FIG. 1 (e.g., lymphocytes, erythrocytes, platelets, granulocytes, monocytes). HSPCs require the activity of CDK4/6 for proliferation (see Roberts et al. Multiple Roles of Cyclin-Dependent Kinase 4/6 Inhibitors in Cancer Therapy. JNCI 2012; 104(6):476-487). In healthy kidneys, the renal epithelium infrequently enters the cell cycle (about 1% of epithelial cells). After a renal insult, however, a robust increase in epithelial proliferation occurs (see Humphreys, B. D. et al. Intrinsic epithelial cells repair the kidney after injury. Cell Stem Cell 2, 284-91 (2008)). Importantly, following renal injury, surviving renal epithelial cells replicate to repair damage to the kidney tubular epithelium (see Humphreys, B. D. et al. Repair of injured proximal tubule does not involve specialized progenitors. Proc Natl Acad Sci USA 108, 9226-31 (2011)). See also WO 2010132725 filed by Sharpless et al.

A number of CDK 4/6 inhibitors have been identified, including specific pyrido[2,3-d]pyrimidines, 2-anilinopyrimidines, diaryl ureas, benzoyl-2,4-diaminothiazoles, indolo[6,7-a]pyrrolo[3,4-c]carbazoles, and oxindoles (see P. S. Sharma, R. Sharma, R. Tyagi, Curr. Cancer Drug Targets 8 (2008) 53-75). WO 03/062236 identifies a series of 2-(pyridin-2-ylamino-pyrido[2,3]pyrimidin-7-ones for the treatment of Rb positive cancers that show selectivity for CDK4/6, including 6-acetyl-8-cyclopentyl-5-methyl-2-(5-piperazin-1-yl-pyridin-2-ylammino)-8H-pyrido-[2,3-d]-pyrimidin-7-one (PD0332991). The clinical trial studies have reported rates of Grade 3/4 neutropenia and leukopenia with the use of PD0332991, resulting in 71% of patients requiring a dose interruption and 35% requiring a dose reduction; and adverse events leading to 10% of the discontinuations (see Finn, Abstract S1-6, SABCS 2012).

VanderWel et al. describe an iodine-containing pyrido[2,3-d]pyrimidine-7-one (CKIA) as a potent and selective CDK4 inhibitor (see VanderWel et al., J. Med. Chem. 48 (2005) 2371-2387).

WO 99/15500 filed by Glaxo Group Ltd discloses protein kinase and serine/threonine kinase inhibitors.

WO 2010/020675 filed by Novartis AG describes pyrrolopyrimidine compounds as CDK inhibitors. WO 2011/101409 also filed by Novartis describes pyrrolopyrimidines with CDK 4/6 inhibitory activity.

WO 2005/052147 filed by Novartis and WO 2006/074985 filed by Janssen Pharma disclose addition CDK4 inhibitors.

US 2007/0179118 filed by Barvian et al. teaches the use of CDK4 inhibitors to treat inflammation.

WO 2012/061156 filed by Tavares and assigned to G1 Therapeutics describes CDK inhibitors. WO 2013/148748 filed by Tavares and assigned to G1 Therapeutics describes Lactam Kinase inhibitors.

U.S. Patent Publication 2011/0224227 to Sharpless et al. describes the use of certain CDK4/6 inhibitors, such as PD0332991 and 2BrIC (see Zhu, et al., J. Med. Chem., 46 (11) 2027-2030 (2003); PCT/US2009/059281) to reduce or prevent the effects of cytotoxic compounds on HSPCs in a subject undergoing chemotherapeutic treatments. See also U.S. Patent Publication 2012/0100100.

Stone, et al., Cancer Research 56, 3199-3202 (Jul. 1, 1996) describes reversible, p16-mediated cell cycle arrest as protection from chemotherapy.

Accordingly, it is an object of the present invention to provide new compounds, compositions and methods to treat patients during chemotherapy.

SUMMARY OF THE INVENTION

In one embodiment, improved compounds, methods, and compositions are provided to minimize the effect of chemotherapeutic agent toxicity on CDK4/6 replication dependent healthy cells, such as hematopoietic stem cells and hematopoietic progenitor cells (together referred to as HSPCs), and/or renal epithelial cells, in subjects, typically humans, that will be, are being, or have been exposed to the chemotherapeutic agent (typically a DNA-damaging agent).

Specifically, the invention includes administering an effective amount of a selected compound of Formula I, II, III, IV, or V, as described herein, a pharmaceutically acceptable composition, salt, isotopic analog, or prodrug thereof, which provides an optimal transient G1-arrest of healthy cells, for example HSPCs and/or renal epithelial cells, in a subject during or following the subject's exposure to a chemotherapeutic agent, such as a DNA-damaging chemotherapeutic agent:

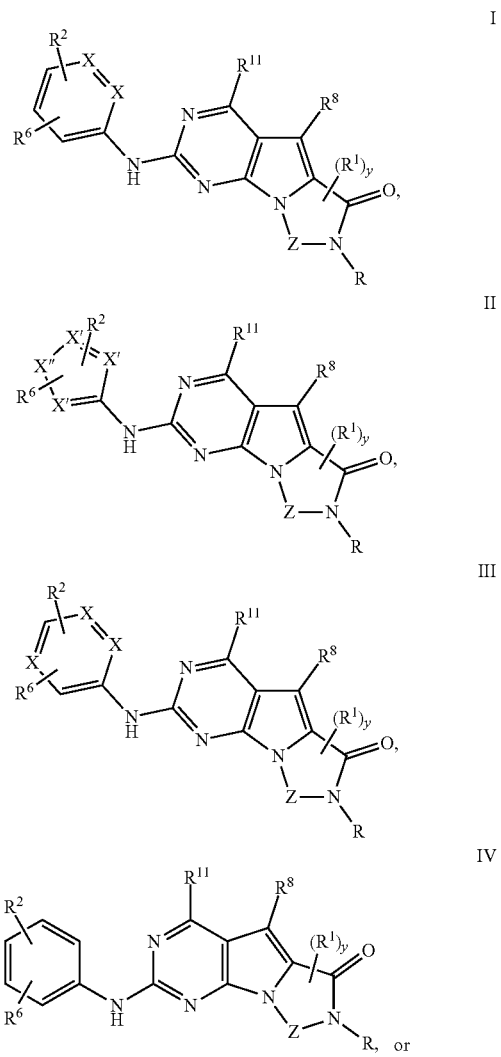

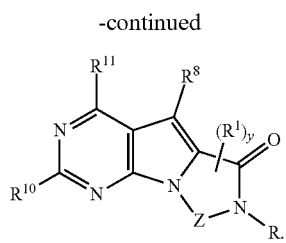

V

In one non-limiting example, a compound can be selected from the compounds of Table 1 below, or a pharmaceutically acceptable composition, salt, isotopic analog or prodrug thereof. In one non-limiting example, a compound can be selected from compounds T, Q, GG, U, or AAAA, described below, or a pharmaceutically acceptable composition, salt, isotopic analog or prodrug thereof.

The described compounds provide improved protection of CDK-replication dependent healthy cells during chemotherapeutic agent treatment due in part because they (i) exhibit a short, transient G1-arresting effect and (ii) display a rapid, synchronous reentry into the cell cycle by the cells following the cessation of the chemotherapeutic damaging effect. The use of these CDK4/6 specific, short, transient G1-arresting compounds as chemoprotectants allows for, for example, an accelerated cell lineage recovery, reduced cytotoxicity risk due to replication delay, and/or a minimization of chemotherapeutic agent induced cell death.

Despite reports using known CDK4/6 inhibitors such as 2BrIC and PD0332991 to demonstrate chemoprotection, it has been discovered that these inhibitors may not be the most ideal compounds for use in pharmacological quiescence (PQ) strategies. For example, the use of 2BrIC in vivo is limited by its restricted bioavailability, and despite the relative selectivity for CDK4/6 exhibited by PD0332991, the compound has a relatively long-acting intra-cellular effect (see Roberts et al. Multiple Roles of Cyclin-Dependent Kinase 4/6 Inhibitors in Cancer Therapy. JCNI 2012; 104(6):476-487 (FIG. 2A)), extending the transiency of G1 arrest beyond what may be necessary for sufficient protection from chemotherapeutic treatments. Such a long acting effect delays, for example, the proliferation of HSPC cell lineages necessary to reconstitute the hematological cell lines that are adversely affected by chemotherapeutic agents or are cycled out during their natural life-cycle. The long-acting G1 arrest provided by PD0332991 may limit its use as a potential chemoprotectant in subjects whose chemotherapeutic treatment regimen requires a rapid reentry into the cell cycle by HSPCs in order to reconstitute the erythroid, platelet, and myeloid cells (monocyte and granulocyte) adversely effected by chemotherapeutic agents or acute HSPC G1-arrest in order to limit myelosuppressive or hematologic toxicity effects. Furthermore, PD0332991 may be limited in its use as a chemoprotectant in subjects exposed to chemotherapeutic agents at regular and repeated intervals, for example, on regimens that are repeated every several days, as it may limit the ability of these subjects' HSPCs to reenter the cell-cycle quickly before it would be necessary to arrest them again prior to the subject's next chemotherapeutic cycle. With respect to other affected tissues, for example renal cells, the timely resumption of proliferation is critical to tissue repair, for example renal tubular epithelium repair, due to nephrotoxic agents, and therefore, an overly long period of PQ is undesirable.

Thus in an alternative embodiment, the invention includes administering a compound described herein in an effective amount to a host in need thereof, such compound displaying one or any combination of the following factors which provide an improved therapeutic effect (either alone or in any combination thereof, each of which is considered specifically and independently described): i) wherein a substantial portion of the CDK4/6-replication dependent healthy cells (e.g. at least 80% or greater) return to or approach pre-treatment baseline cell cycle activity (i.e., reenter the cell-cycle) in less than 24 hours, 30 hours or 36 hours from the last administration of the active compound in humans or for example, using a protocol described in the Examples below; ii) wherein a substantial portion of the healthy cells reenter the cell-cycle synchronously in less than 24 hours, 30 hours or 36 hours from the last administration of the active compound; (iii) wherein the dissipation of the active compound's CDK4/6 inhibitory effect occurs in less than 24 hours, 30 hours, or 36 hours from the administration of the inhibitor; (iv) wherein the active compound has an IC50 for CDK4 and/or CDK6 inhibition that is more than 1500 times less than its IC50 concentration for CDK2 inhibition; (v) wherein a substantial portion of the healthy cells return to or approach pre-treatment baseline cell cycle activity (i.e., reenter the cell-cycle) in less than 24 hours, 30 hours, or 36 hours from the dissipation of the active compound's CDK4/6 inhibitory effect; (vi) wherein the pre-treatment baseline cell cycle activity (i.e. reenter the cell-cycle) within less than about 24 hours, about 30 hours, or about 36 hours from the point in which the CDK4/6 inhibitor's concentration level in the subject's blood drops below a therapeutic effective concentration; or (vii) wherein a substantial portion of the healthy cells reenter the cell-cycle synchronously in less than 24 hours, 30 hours, or 36 hours from the last administration of the chemotherapeutic agent.

The compounds described herein can be administered to the subject prior to treatment with a chemotherapeutic agent, during treatment with a chemotherapeutic agent, after exposure to a chemotherapeutic agent, or a combination thereof. The compound described herein is typically administered in a manner that allows the drug facile access to the blood stream, for example via intravenous injection or sublingual, intraaortal, or other efficient blood-stream accessing route; however, oral, topical, transdermal, intranasal, intramuscular, or by inhalation such as by a solution, suspension, or emulsion, or other desired administrative routes can be used. In one embodiment, the compound is administered to the subject less than about 24 hours, 20 hours, 16 hours, 12 hours, 8 hours, or 4 hours, 2.5 hours, 2 hours, 1 hour, ½ hour or less prior to treatment with the chemotherapeutic agent. Typically, the active compound described herein is administered to the subject prior to treatment with the chemotherapeutic agent such that the compound reaches peak serum levels before or during treatment with the chemotherapeutic agent. In one embodiment, the active compound is administered concomitantly, or closely thereto, with the chemotherapeutic agent exposure. If desired, the active compound can be administered multiple times during the chemotherapeutic agent treatment to maximize inhibition, especially when the chemotherapeutic drug is administered over a long period or has a long half-life. The active compound described herein can be administered following exposure to the chemotherapeutic agent if desired to mitigate healthy cell damage associated with chemotherapeutic agent exposure. In certain embodiments, the active compound is administered up to about ½ hour, up to about 1 hour, up to about 2 hours, up to about 4 hours, up to about 8 hours, up to about 10 hours, up to about 12 hours, up to about 14 hours, up to about 16 hours, or up to about 20 hours or greater following the chemotherapeutic agent exposure. In a particular embodiment, the active compound is administered up to between about 12 hours and 20 hours following exposure to the chemotherapeutic agent.

The CDK4/6 inhibitors described herein show a marked selectivity for the inhibition of CDK4 and/or CDK6 in comparison to other CKD, for example CDK2. For example, CDK4/6 inhibitors described in the present invention provide for a dose-dependent G1-arresting effect on a subject's CDK4/6-replication dependent healthy cells, for example HSPCs or renal epithelial cells, and the methods provided for herein are sufficient to afford chemoprotection to targeted CDk4/6-replication dependent healthy cells during chemotherapeutic agent exposure, for example, during the time period that a DNA-damaging chemotherapeutic agent is capable of DNA-damaging effects on CDK4/6-replication dependent healthy cells in the subject, while allowing for the synchronous and rapid reentry into the cell-cycle by these cells shortly after the chemotherapeutic agent dissipates due to the time-limited CDK4/6 inhibitory effect provided by the compounds described herein compared to, for example, PD0332991. Likewise, CDK4/6 inhibitors useful in the present invention provide for a dose-dependent mitigating effect on CDK4/6-replication dependent healthy cells that have been exposed to toxic levels of chemotherapeutic agents, for example an accidental overdose, allowing for repair of DNA damage associated with chemotherapeutic agent exposure and synchronous, rapid reentry into the cell-cycle following dissipation of the CDK4/6 inhibitory effect compared to, for example, PD0332991. In one embodiment, the use of a CDK4/6 inhibitor described herein results in the G1-arresting effect on the subject's CDK4/6-replication dependent healthy cells dissipating following administration of the CDK4/6 inhibitor so that the subject's healthy cells return to or approach their pre-administration baseline cell-cycle activity within less than about 24 hours, 30 hours, 36 hours, or 40 hours, of administration. In one embodiment, the G1-arresting effect dissipates such that the subject's CDK4/6-replication dependent healthy cells return to their pre-administration baseline cell-cycle activity within less than about 24 hours, 30 hours, 36 hours, or 40 hours.

In one embodiment, the use of a CDK4/6 inhibitor described herein results in the G1-arresting effect dissipating such that the subject's CDk4/6-dependent healthy cells return to or approach their pre-administration baseline cell-cycle activity within less than about 24 hours, 30 hours, 36 hours, or 40 hours of the chemotherapeutic agent effect. In one embodiment, the G1-arresting effect dissipates such that the subject's CDK4/6-replication dependent cells return to their pre-administration baseline cell-cycle activity within less than about 24 hours, 30 hours, 36 hours, or 40 hours, or within about 48 hours of the cessation of the chemotherapeutic agent administration. In one embodiment, the CDK4/6-replication dependent healthy cells are HSPCs. In one embodiment, the CDK4/6-dependent healthy cells are renal epithelial cells.

In one embodiment, the use of a CDK4/6 inhibitor described herein results in the G1-arresting effect dissipating so that the subject's CDK4/6-replication dependent healthy cells return to or approach their pre-administration baseline cell-cycle activity within less than about 24 hours, 30 hours, 36 hours, 40 hours, or within less than about 48 hours from the point in which the CDK4/6 inhibitor's concentration level in the subject's blood drops below a therapeutic effective concentration.

In one embodiment, the CDK4/6 inhibitors described herein are used to protect renal epithelium cells during exposure to a chemotherapeutic agent, for example, a DNA damaging chemotherapeutic agent, wherein the renal epithelial cells are transiently prevented from entering S-phase in response to chemotherapeutic agent induced renal tubular epithelium damage for no more than about 24 hours, about 30 hours, about 36 hours, about 40 hours, or about 48 hours from the point in which the CDK4/6 inhibitor's concentration level in the subject's blood drops below a therapeutic effective concentration, from the cessation of the chemotherapeutic agent effect, or from administration of the CDK4/6 administration.

CDK4/6 inhibitors useful in the described methods may be synchronous in their off-effect, that is, upon dissipation of the G1 arresting effect, CDK4/6-replication dependent healthy cells exposed to a CDK4/6 inhibitor described herein reenter the cell-cycle in a similarly timed fashion. CDK4/6-replication dependent healthy cells that reenter the cell-cycle do so such that the normal proportion of cells in G1 and S are reestablished quickly and efficiently, within less than about 24 hours, 30 hours, 36 hours, 40 hours, or within about 48 hours of the from the point in which the CDK4/6 inhibitor's concentration level in the subject's blood drops below a therapeutic effective concentration.

This advantageously allows for a larger number of healthy cells to begin replicating upon dissipation of the G1 arrest compared with asynchronous CDK4/6 inhibitors such as PD0332991.

In addition, synchronous cell-cycle reentry following G1 arrest using a CDK4/6 inhibitor described herein provides for the ability to time the administration of hematopoietic growth factors to assist in the reconstitution of hematopoietic cell lines to maximize the growth factor effect. As such, in one embodiment, the use of the compounds or methods described herein is combined with the use of hematopoietic growth factors including, but not limited to, granulocyte colony stimulating factor (G-CSF), granulocyte-macrophage colony stimulating factor (GM-CSF), thrombopoietin, interleukin (IL)-12, steel factor, and erythropoietin (EPO), or their derivatives. In one embodiment, the CDK4/6 inhibitor is administered prior to administration of the hematopoietic growth factor. In one embodiment, the hematopoietic growth factor administration is timed so that the CDK4/6 inhibitor's effect on HSPCs has dissipated.

In one aspect, the use of a CDK4/6-inhibitor described herein allows for a chemo-protective regimen for use during standard chemotherapeutic dosing schedules or regimens common in many anti-cancer treatments. For example, the CDK4/6-inhibitor can be administered so that CDK4/6-replication dependent healthy cells are G1 arrested during chemotherapeutic agent exposure wherein, due to the rapid dissipation of the G1-arresting effect of the compounds, a significant number of healthy cells reenter the cell-cycle and are capable of replicating shortly after chemotherapeutic agent exposure, for example, within less than about 24, 30, 40, or 48 hours, and continue to replicate until administration of the CDK4/6-inhibitor in anticipation of the next chemotherapeutic treatment. In one embodiment, the CDK4/6-inhibitor is administered to allow for the cycling of the CDK4/6-replication dependent healthy cells between G1-arrest and reentry into the cell-cycle to accommodate a repeated-dosing chemotherapeutic treatment regimen, for example including but not limited to a treatment regimen wherein the chemotherapeutic agent is administered: on day 1-3 every 21 days; on days 1-3 every 28 days; on day 1 every 3 weeks; on day 1, day 8, and day 15 every 28 days, on day 1 and day 8 every 28 days; on days 1 and 8 every 21 days; on days 1-5 every 21 days; 1 day a week for 6-8 weeks; on days 1, 22, and 43; days 1 and 2 weekly; days 1-4 and 22-25; 1-4; 22-25, and 43-46; and similar type-regimens, wherein the CDK4/6-replication dependent cells are G1 arrested during chemotherapeutic agent exposure and a significant portion of the cells reenter the cell-cycle between chemotherapeutic agent exposure. In one embodiment, the CDK4/6-inhibitor can be administered so that the subject's CDK4/6-replication dependent cells are G1-arrested during daily chemotherapeutic agent exposure, for example a contiguous multi-day chemotherapeutic regimen, but a significant portion of CDK4/6-replication dependent cells reenter the cell-cycle and replicate between daily treatment. In one embodiment, the CDK4/6-inhibitors can be administered so that the subject's CDK4/6-replication dependent cells are G1-arrested during chemotherapeutic agent exposure, for example a contiguous multi-day regimen, but a significant portion of healthy cells reenter the cell-cycle and replicate during the off periods before the next chemotherapeutic agent exposure. In one embodiment, the CDK4/6 inhibitor is administered so that a subject's CDK4/6-replication dependent cells' G1-arrest is provided during a daily chemotherapeutic agent treatment regimen, for example, a contiguous multi-day treatment regimen, and the arrested cells are capable of reentering the cell-cycle shortly after the multi-day regimen ends. In one embodiment, the cancer is small cell lung cancer and the CDK4/6 inhibitor is administered on days 1, 2, and 3 during a 21-day treatment cycle wherein the administered DNA damaging agent is selected from the group consisting of carboplatin, cisplatin, and etoposide, or a combination thereof.

The subject treated according to the present invention may be undergoing therapeutic chemotherapy for the treatment of a proliferative disorder or disease such as cancer. The cancer can be characterized by one or a combination of increased activity of cyclin-dependent kinase 1 (CDK1), increased activity of cyclin-dependent kinase 2 (CDK2), loss, deficiency, or absence of retinoblastoma tumor suppressor protein (Rb)(Rb-null), high levels of MYC expression, increased cyclin E1, E2, and increased cyclin A. The cancer may be characterized by reduced expression of the retinoblastoma tumor suppressor protein or a retinoblastoma family member protein or proteins (such as, but not limited to p107 and p130). In one embodiment, the subject is undergoing chemotherapeutic treatment for the treatment of an Rb-null or Rb-deficient cancer, including but not limited to small cell lung cancer, triple-negative breast cancer, HPV-positive head and neck cancer, retinoblastoma, Rb-negative bladder cancer, Rb negative prostate cancer, osteosarcoma, or cervical cancer. In one embodiment, the cancer is a CDK4/6-independent cancer. Administration of the inhibitor compound may allow for a higher dose of a chemotherapeutic agent to be used to treat the disease than the standard dose that would be safely used in the absence of administration of the CDK4/6 inhibitor compound.

The host or subject, including a human, may be undergoing chemotherapeutic treatment of a non-malignant proliferative disorder, or other abnormal cellular proliferation, such as a tumor, multiple sclerosis, lupus, or arthritis.

The protected HSPCs include hematopoietic stem cells, such as long term hematopoietic stem cells (LT-HSCs) and short term hematopoietic stem cells (ST-HSCs), and hematopoietic progenitor cells, including multipotent progenitors (MPPs), common myeloid progenitors (CMPs), common lymphoid progenitors (CLPs), granulocyte-monocyte progenitors (GMPs) and megakaryocyte-erythroid progenitors (MEPs). Administration of the inhibitor compound provides temporary, transient pharmacologic quiescence of hematopoietic stem and/or hematopoietic progenitor cells in the subject.

Administration of a CDK4/6 inhibitor as described herein can result in reduced anemia, reduced lymphopenia, reduced thrombocytopenia, or reduced neutropenia compared to that typically expected after, common after, or associated with treatment with chemotherapeutic agents in the absence of administration of the CDK4/6 inhibitor. The use of the CDK4/6 inhibitor as described herein results in a faster recovery from bone marrow suppression associated with long-term use of CDK4/6 inhibitors, such as myelosuppression, anemia, lymphopenia, thrombocytopenia, or neutropenia, following the cessation of use of the CDK4/6 inhibitor. In some embodiments, the use of a CDK4/6 inhibitor as described herein results in reduced or limited bone marrow suppression associated with long-term use of CDK4/6 inhibitors, such as myelosuppression, anemia, lymphopenia, thrombocytopenia, or neutropenia.

In an alternative aspect, a CDK4/6 inhibitor described herein can be used for its anti-cancer, anti-tumor, or anti-proliferative effect in combination with a chemotherapeutic agent to treat an Rb-negative cancer or other Rb-negative abnormal proliferation. In one embodiment, the CDK4/6 inhibitor described herein provides an additive effect to or synergistic effect with the anti-cancer or anti-proliferative activity of the chemotherapeutic. Chemotherapeutics that can be combined with the CDK4/6 inhibitors described herein are any chemotherapeutics effective or useful to treat RB-null cancers or abnormal cellular proliferation. In one particular embodiment, the use of a compound described herein is combined in a therapeutic regime with at least one other chemotherapeutic agent, and can be one that does not rely on proliferation or advancement through the cell-cycle for anti-proliferative activity. Such agent may include, but is not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apopototic inducing compounds, AKT inhibitors, PD-1 inhibitors, or FLT-3 inhibitors, or combinations thereof. Examples of mTOR inhibitors include but are not limited to rapamycin and its analogs, everolimus (Afinitor), temsirolimus, ridaforolimus, sirolimus, and deforolimus. Examples of P13 kinase inhibitors include but are not limited to Wortmannin, demethoxyviridin, perifosine, idelalisib, PX-866, IPI-145 (Infinity), BAY 80-6946, BEZ235, RP6503, TGR 1202 (RP5264), MLN1117 (INK1117), Pictilisib, Buparlisib, SAR245408 (XL147), SAR245409 (XL765), Palomid 529, ZSTK474, PWT33597, RP6530, CUDC-907, and AEZS-136. Examples of MEK inhibitors include but are not limited to Tametinib, Selumetinib, MEK162, GDC-0973 (XL518), and PD0325901. Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol. The CDK4/6 inhibitor combined with the chemotherapeutic is selected from the group consisting of a compound or composition comprising Formula I, Formula II, Formula III, Formula IV, or Formula V described above, or a pharmaceutically acceptable composition, salt, isotopic analog or prodrug thereof. In one embodiment, the compound is selected from the compounds provided for in Table 1, or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof.

In certain embodiments, a compound described herein is administered to the subject prior to treatment with another chemotherapeutic agent, during treatment with another chemotherapeutic agent, after administration of another chemotherapeutic agent, or a combination thereof. In one embodiment, the CDK4/6 inhibitor is selected from a compound described in Table 1. In one embodiment, the compound is selected from compounds T, Q, GG, U, or AAAA.

In some embodiments, the subject or host is a mammal, including a human.

In summary, the present invention includes the following features:

A. Compounds of Formula I, II, III, IV, and V as described herein, and pharmaceutically acceptable compositions, salts, isotopic analogs, or prodrugs thereof, for use in the chemoprotection of CDK4/6-replication dependent healthy cells, for example HSPCs and/or renal epithelial cells, during a chemotherapeutic agent exposure. In one embodiment, the compound is selected from the compounds described in Table 1 or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof;

B. Compounds of Formula I, II, III, IV, and V as described herein, and pharmaceutically acceptable compositions, salts, isotopic analogs, and prodrugs thereof, for use in the chemoprotection of CDK4/6-replication dependent healthy cells, for example HSPCs and/or renal epithelial cells, during a chemotherapeutic regimen for the treatment of a proliferative disorder. In one embodiment, the compound is selected from the compounds described in Table 1 or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof;

C. Compounds of Formula I, II, III, IV, and V as described herein, and pharmaceutically acceptable compositions, salts, isotopic analogs, and prodrugs thereof, for use in the chemoprotection of CDK4/6-replication dependent healthy cells, for example HSPCs and/or renal epithelial cells, during a chemotherapeutic regimen for the treatment of a cancer. In one embodiment, the compound is selected from the compounds described in Table 1, or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof;

D. Compounds of Formula I, II, III, IV, and V as described herein, and pharmaceutically acceptable compositions, salts, isotopic analogs, and prodrugs thereof, for use in combination with hematopoietic growth factors in a subject that will be, is being, or has been exposed to chemotherapeutic agents. In one embodiment, the compound is selected from the compounds described in Table 1 or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof;

E. Use of compounds of Formula I, II, III, IV, and V as described herein, and pharmaceutically acceptable compositions, salts, isotopic analogs, and prodrugs thereof, in the manufacture of a medicament for use in the chemoprotection of CDK4/6-replication dependent healthy cells, for example HSPCs and/or renal epithelial cells. In one embodiment, the compound is selected from the compounds described in Table 1 or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof;

F. Use of compounds of Formula I, II, III, IV, and V as described herein, and pharmaceutically acceptable compositions, salts, isotopic analogs, and prodrugs thereof, in the manufacture of a medicament for use in the mitigation of DNA damage of CDK4/6-replication dependent healthy cells, for example HSPCs and/or renal epithelial cells, that have been exposed to chemotherapeutic agent exposure. In one embodiment, the compound is selected from the compounds described in Table 1 or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof;

G. A pharmaceutical formulation comprising an effective subject-treating amount of compounds of Formula I, II, III, IV, and V as described herein, or pharmaceutically acceptable compositions, salts, and prodrugs thereof for use in chemoprotection of healthy cells. In one embodiment, the compound is selected from the compounds described in Table 1 or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof;

H. A processes for the preparation of therapeutic products that contain an effective amount of compounds of Formula I, II, III, IV, and V as described herein. In one embodiment, the compound is selected from the compounds described in Table 1 or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof;

I. A method for manufacturing a medicament of Formula I, II, III, IV, and V intended for therapeutic use in the chemoprotection of CDK4/6-replication dependent healthy cells, for example HSPCs and/or renal epithelial cells. In one embodiment, the medicament is selected from the compounds described in Table 1 or a pharmaceutically acceptable composition, salt, isotopic analog or prodrug thereof. In one embodiment, the medicament is selected from compounds T, Q, GG, U, or AAAA, or a pharmaceutically acceptable composition, salt, isotopic analog or prodrug thereof;

J. A method for manufacturing a medicament of Formula I, II, III, IV, and V intended for therapeutic use in the mitigation of DNA damage of CDK4/6-replication dependent healthy cells, for example HSPCs and/or renal epithelial cells, that have been exposed to chemotherapeutic agents. In one embodiment, the medicament is selected from the compounds described in Table 1 or a pharmaceutically acceptable composition, salt, isotopic analog or prodrug thereof. In one embodiment, the medicament is selected from Compounds T, Q, GG, U, or AAAA, or a pharmaceutically acceptable composition, salt, isotopic analog or prodrug thereof;

K. A method of inhibiting the growth of an Rb-negative cancer or proliferative condition by administering a compound of Formula I, II, III, IV, or V, or pharmaceutically acceptable composition, salt, isotopic analog or prodrug thereof; in combination with a chemotherapeutic to provide an additive to or synergistic effect with a chemotherapeutic. In one embodiment, the compound is selected from the compounds described in Table 1 or a pharmaceutically acceptable composition, salt, isotopic analog or prodrug thereof. In one embodiment, the compound is selected from Compounds T, Q, GG, U, or AAAA, or a pharmaceutically acceptable composition, salt, isotopic analog or prodrug thereof. In one embodiment, the CDK4/6 inhibitors are combined with a chemotherapeutic selected from the group consisting of MEK inhibitors, PI3 kinase delta inhibitors, BCL-2 inhibitors, AKT inhibitors, apoptotic inducing compounds, AKT inhibitors, PD-1 inhibitors, FLT-3 inhibitors, HSP90 inhibitors, or mTOR inhibitors, or combinations thereof.

BRIEF DESCRIPTION OF THE DRAWINGS

FIG. 2D is a graph of the number of A2058 cells (CDK4/6-independent cell line) vs. the DNA content of the cells (as measured by propidium iodide). Cells were treated with DMSO for 24 hours, harvested, and analyzed for cell cycle distribution. FIG. 2E is a graph of the number of tHS68 cells (CDK4/6-dependent cell line) vs. the DNA content of the cells (as measured by propidium iodide) after treatment with Compound T. Cells were treated with Compound T (300 nM) for 24 hours, harvested, and analyzed for cell cycle distribution. As described in Example 152, treatment of tHS68 cells with Compound T causes a loss of the S-phase peak (indicated by arrow). FIG. 2F is a graph of the number of WM2664 cells (CDK4/6-dependent cell line) vs. the DNA content of the cells (as measured by propidium iodide) after treatment with Compound T. Cells were treated with Compound T (300 nM) for 24 hours, harvested, and analyzed for cell cycle distribution. As described in Example 152, treatment of WM2664 cells with Compound T causes a loss of the S-phase peak (indicated by arrow). FIG. 2G is a graph of the number of A2058 cells (CDK4/6-independent cell line) vs. the DNA content of the cells (as measured by propidium iodide) after treatment with Compound T. Cells were treated with Compound T (300 nM) for 24 hours, harvested, and analyzed for cell cycle distribution. As described in Example 152, treatment of A2058 cells with Compound T does not cause a loss of the S-phase peak (indicated by arrow).

FIG. 10 provides the half-life (minutes) of Compound T and PD0332991 in human and animal (monkey, dog, rat, and mouse) liver microsomes. As described in Example 158, PD0332991 has a half-life greater than 60 minutes in each of the species tested. Compound T was determined to have a shorter half-life than PD0332991 in each of the species tested.

FIG. 17C is a graph of lymphocyte cell counts vs. time (days) after administration of 5-fluoruracil (5FU) (triangles), 5FU plus Compound T (squares), or untreated control (circles). Experiments were conducted as described in FIG. 17A. As described in Example 166, lymphocytes recover more rapidly from chemotherapy (5FU) when pretreated with Compound T. FIG. 17D is a graph of platelet cell counts vs. time (days) after administration of 5-fluoruracil (5FU) (triangles), 5FU plus Compound T (squares), or untreated control (circles). Experiments were conducted as described in FIG. 17A. As described in Example 166, platelets recover more rapidly from chemotherapy (5FU) when pretreated with Compound T.

FIG. 18A is a graph of whole blood cell counts 14 days after administration of 5-fluoruracil (5FU), 5FU plus Compound T, or untreated control. FVB wild-type mice were treated with Compound T (150 mg/kg) or vehicle control by oral gavage thirty minutes prior to administration of 5-flurouracil (5FU) 150 mg/kg by intraperitoneal injection. Complete blood cell counts were measured on day 14. Boxes represent the 5%-95% distribution, whiskers represent minimum and maximum values, and the middle bar represents the median. Student's t test was done to calculate two-sided P values. As described in Example 166, whole blood cells recover more rapidly from chemotherapy (5FU) when pretreated with Compound T. FIG. 18B is a graph of neutrophil cell counts 14 days after administration of 5-fluoruracil (5FU), 5FU plus Compound T, or untreated control. Experiments were conducted as described in FIG. 18A. As described in Example 166, neutrophil cells recover more rapidly from chemotherapy (5FU) when pretreated with Compound T. FIG. 18C is a graph of lymphocyte cell counts 14 days after administration of 5-fluoruracil (5FU), 5FU plus Compound T, or untreated control. Experiments were conducted as described in FIG. 18A. As described in Example 166, lymphocyte cells recover more rapidly from chemotherapy (5FU) when pretreated with Compound T. FIG. 18D is a graph of red blood cell counts 14 days after administration of 5-fluoruracil (5FU), 5FU plus Compound T, or untreated control. Experiments were conducted as described in FIG. 18A. As described in Example 166, red blood cells recover more rapidly from chemotherapy (5FU) when pretreated with Compound T. FIG. 18E is a graph of platelet cell counts 14 days after administration of 5-fluoruracil (5FU), 5FU plus Compound T, or untreated control. Experiments were conducted as described in FIG. 18A. As described in Example 166, platelet cells recover more rapidly from chemotherapy (5FU) when pretreated with Compound T.

FIG. 19A is a graph of whole blood cells (1000 cells/ul) in untreated mice (circles), 5-fluoruracil (5FU) plus Compound T treated mice (squares), or 5-FU treated mice (triangles) at Cycle 3, Day 10 (Day 52). FVB wild-type mice were treated with Compound T (150 mg/kg) or vehicle control by oral gavage thirty minutes prior to administration of 5-fluoruracil (5FU) 150 mg/kg by intraperitoneal injection. Mice received 3 cycles of Compound T or vehicle control+5FU on Day 1 of a 21-day cycle. Complete blood cell counts were measured on Day 10 after the second dose (52 days after the first dose (Cycle 3 Day 10)). As described in Example 167, whole blood cells show an improved recovery from chemotherapy (5FU) when treated with several cycles of Compound T. FIG. 19B is a graph of neutrophils (1000 cells/ul) in untreated mice (circles), 5-fluoruracil (5FU) plus Compound T treated mice (squares), or 5-FU treated mice (triangles) at Cycle 3, Day 10 (Day 52). Experiments were conducted as described in FIG. 19A. As described in Example 167, neutrophils show an improved recovery from chemotherapy (5FU) when treated with several cycles of Compound T. FIG. 19C is a graph of lymphocytes (1000 cells/ul) in untreated mice (circles), 5-fluoruracil (5FU) plus Compound T treated mice (squares), or 5-FU treated mice (triangles) at Cycle 3, Day 10 (Day 52). Experiments were conducted as described in FIG. 19A. As described in Example 167, lymphocytes show an improved recovery from chemotherapy (5FU) when treated with several cycles of Compound T.

DETAILED DESCRIPTION OF THE INVENTION

Figure 1:
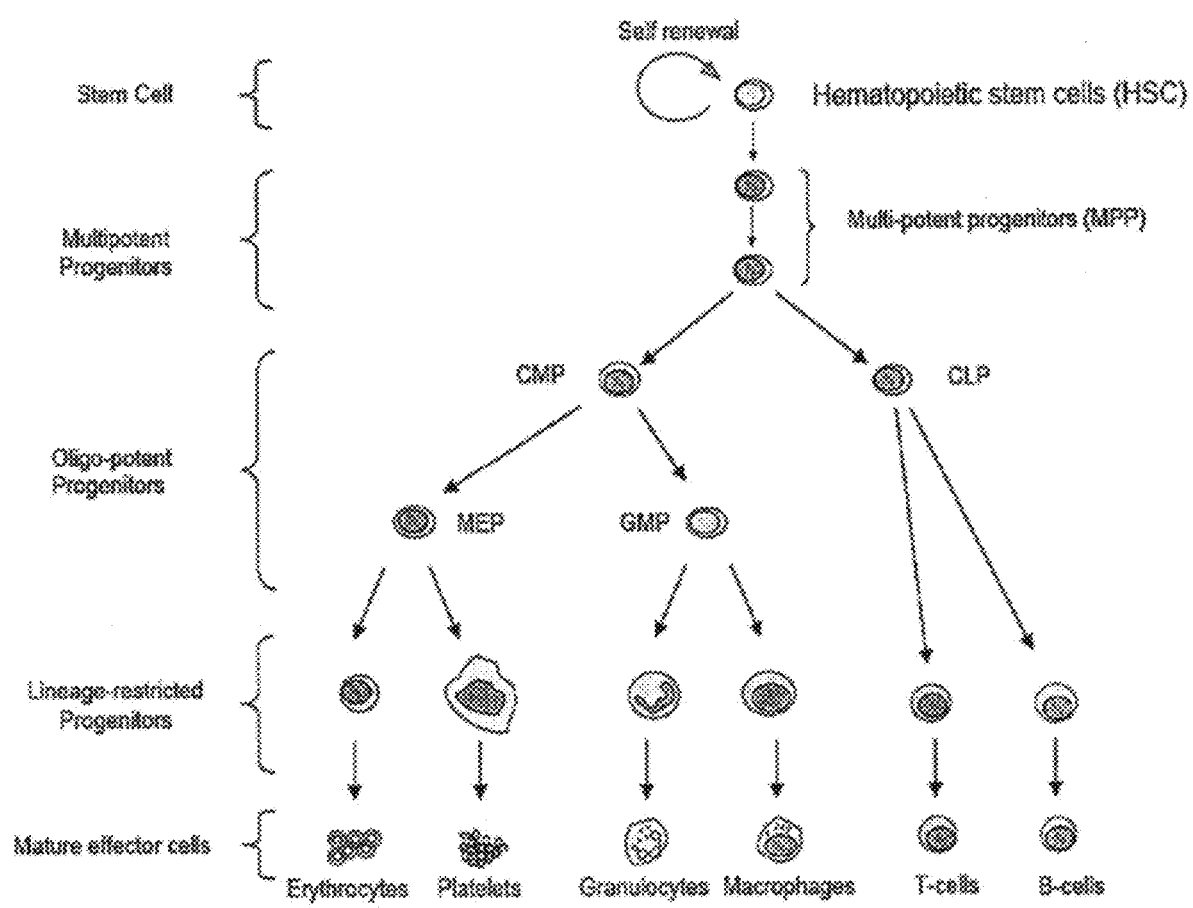
FIG. 1 is a schematic drawing of hematopoiesis showing the hierarchical proliferation of healthy hematopoietic stem cells (HSC) and healthy hematopoietic progenitor cells with increasing differentiation upon proliferation.

Improved compounds, methods, and compositions are provided to minimize the effect of chemotherapeutic agent toxicity on CDK4/6 replication dependent healthy cells, such as hematopoietic stem cells and/or hematopoietic progenitor cells (together referred to as HSPCs), and/or renal epithelial cells, in subjects, typically humans, that will be, are being or have been exposed to the chemotherapeutic agent (typically a DNA-damaging agent).

Definitions

Unless otherwise stated, the following terms used in this application, including the specification and claims, have the definitions given below. As used in the specification and the appended claims, the singular forms "a," "an" and "the" include plural referents unless the context clearly dictates otherwise. Definition of standard chemistry terms may be found in reference works, including Carey and Sundberg (2007) *Advanced Organic Chemistry 5th Ed.* Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology. Conventional methods of organic chemistry include those included in *March's Advanced Organic Chemistry: Reactions, Mechanisms, and Structure, 6th Edition*, M. B. Smith and J. March, John Wiley & Sons, Inc., Hoboken, N.J., 2007.

The term "alkyl," either alone or within other terms such as "haloalkyl" and "alkylamino," embraces linear or branched radicals having one to about twelve carbon atoms. "Lower alkyl" radicals have one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylene" embraces bridging divalent linear and branched alkyl radicals. Examples include methylene, ethylene, propylene, isopropylene and the like.

The term "alkenyl" embraces linear or branched radicals having at least one carbon-carbon double bond of two to about twelve carbon atoms. "Lower alkenyl" radicals having two to about six carbon atoms. Examples of alkenyl radicals include ethenyl, propenyl, allyl, propenyl, butenyl and 4-methylbutenyl. The terms "alkenyl" and "lower alkenyl," embrace radicals having "cis" and "trans" orientations, or alternatively, "E" and "Z" orientations.

The term "alkynyl" denotes linear or branched radicals having at least one carbon-carbon triple bond and having two to about twelve carbon atoms. "Lower alkynyl" radicals having two to about six carbon atoms. Examples of such radicals include propargyl, butynyl, and the like.

Alkyl, alkenyl, and alkynyl radicals may be optionally substituted with one or more functional groups such as halo, hydroxy, nitro, amino, cyano, haloalkyl, aryl, heteroaryl, heterocyclo and the like.

The term "alkylamino" embraces "N-alkylamino" and "N,N-dialkylamino" where amino groups are independently substituted with one alkyl radical and with two alkyl radicals, respectively. "Lower alkylamino" radicals have one or two alkyl radicals of one to six carbon atoms attached to a nitrogen atom. Suitable alkylamino radicals may be mono or dialkylamino such as N-methylamino, N-ethylamino, N.N-dimethylamino, N,N-diethylamino and the like.

The term "halo" means halogens such as fluorine, chlorine, bromine or iodine atoms.

The term "haloalkyl" embraces radicals wherein any one or more of the alkyl carbon atoms is substituted with one or more halo as defined above. Examples include monohaloalkyl, dihaloalkyl and polyhaloalkyl radicals including perhaloalkyl. A monohaloalkyl radical, for one example, may have an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means an alkyl radical having all hydrogen atoms replaced with fluoro atoms. Examples include trifluoromethyl and pentafluoroethyl.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 or more substituents such as lower alkyl, hydroxyl, halo, haloalkyl, nitro, cyano, alkoxy, lower alkylamino, and the like. An aryl group may be optionally substituted with one or more functional groups such as halo, hydroxy, nitro, amino, cyano, haloalkyl, aryl, heteroaryl, heterocyclo and the like.

The term "heterocyclyl" (or "heterocyclo") embraces saturated, and partially saturated heteroatom-containing ring radicals, where the heteroatoms may be selected from nitrogen, sulfur and oxygen. Heterocyclic rings comprise monocyclic 6-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like.

Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclo groups include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1V-benzo[d]isothiazol-6-yl, dihydropyranyl, dihydrofuryl and dihydrothiazolyl, and the like.

Heterocyclo groups also includes radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl].

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heteroarylalkyl" denotes alkyl radicals substituted with a heteroaryl group. Examples include pyridylmethyl and thienylethyl.

The term "sulfonyl", whether used alone or linked to other terms such as alkylsulfonyl, denotes respectively divalent radicals —$SO_2$—.

The terms "carboxy" or "carboxyl", whether used alone or with other terms, such as "carboxyalkyl", denotes —C(O)—OH.

The term "carbonyl", whether used alone or with other terms, such as "aminocarbonyl", denotes —C(O)—.

The term "aminocarbonyl" denotes an amide group of the Formula —C(O)—$NH_2$.

The terms "heterocycloalkyl" embrace heterocyclic-substituted alkyl radicals. Examples include piperidylmethyl and morpholinylethyl.

The term "arylalkyl" embraces aryl-substituted alkyl radicals. Examples include benzyl, diphenylmethyl and phenylethyl. The aryl in said aralkyl may be additionally substituted with halo, alkyl, alkoxy, halkoalkyl and haloalkoxy.

The term "cycloalkyl" includes saturated carbocyclic groups of 3 to 10 carbons. Lower cycloalkyl groups include $C_3$-$C_6$ rings. Examples include cyclopentyl, cyclopropyl, and cyclohexyl. Cycloalkyl groups may be optionally substituted with one or more functional groups such as halo, hydroxy, nitro, amino, cyano, haloalkyl, aryl, heteroaryl, heterocyclo and the like.

The term "cycloalkylalkyl" embraces cycloalkyl-substituted alkyl radicals. "Lower cycloalkylalkyl" radicals are cycloalkyl radicals attached to alkyl radicals having one to six carbon atoms. Examples of include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Examples include cyclopentenyl, cyclopentadienyl, cyclohexenyl and cycloheptadienyl.

The term "comprising" is meant to be open ended, including the indicated component but not excluding other elements.

The term "oxo" as used herein contemplates an oxygen atom attached with a double bond.

The term "nitro" as used herein contemplates —$NO_2$.

The term "cyano" as used herein contemplates —CN.

As used herein, the term "prodrug" means a compound which when administered to a host in vivo is converted into the parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

Throughout the specification and claims, a given chemical formula or name shall encompass all optical and stereoisomers, as well as racemic mixtures where such isomers and mixtures exist, unless otherwise noted.

In some embodiments, a CDK4/6-replication dependent healthy cell is a hematopoietic stem progenitor cell. Hematopoietic stem and progenitor cells include, but are not limited to, long term hematopoietic stem cells (LT-HSCs), short term hematopoietic stem cells (ST-HSCs), multipotent progenitors (MPPs), common myeloid progenitors (CMPs), common lymphoid progenitors (CLPs), granulocyte-monocyte progenitors (GMPs), and megakaryocyte-erythroid progenitors (MEPs). In some embodiments, the CDK4/6-replication dependent healthy cell may be a cell in a non-hematopoietic tissue, such as, but not limited to, the liver, kidney, pancreas, brain, lung, adrenals, intestine, gut, stomach, skin, auditory system, bone, bladder, ovaries, uterus, testicles, gallbladder, thyroid, heart, pancreatic islets, blood vessels, and the like. In some embodiments, the CDK4/6-replication dependent healthy cell is a renal cell, and in particular a renal epithelial cell, for example, a renal proximal tubule epithelial cells. In some embodiments, a CDK4/6-replication dependent healthy cell is a hematopoietic stem progenitor cell. In some embodiments, the CDK4/6-replication dependent healthy cell may be a cell in a non-hematopoietic tissue, such as, but not limited to, the liver, kidney, pancreas, brain, lung, adrenals, intestine, gut, stomach, skin, auditory system, bone, bladder, ovaries, uterus, testicles, gallbladder, thyroid, heart, pancreatic islets, blood vessels, and the like.

The term "selective CDK4/6 inhibitor" used in the context of the compounds described herein includes compounds that inhibit CDK4 activity, CDK6 activity, or both CDK4 and CDK6 activity at an $IC_{50}$ molar concentration at least about 500, or 1000, or 1500, or 1800, 2000, 5000 or 10,000 times less than the $IC_{50}$ molar concentration necessary to inhibit to the same degree of CDK2 activity in a standard phosphorylation assay.

By "induces G1-arrest" is meant that the inhibitor compound induces a quiescent state in a substantial portion of a cell population at the G1 phase of the cell cycle.

By "hematological deficiency" is meant reduced hematological cell lineage counts or the insufficient production of blood cells (i.e., myelodysplasia) and/or lymphocytes (i.e., lymphopenia, the reduction in the number of circulating lymphocytes, such as B- and T-cells). Hematological deficiency can be observed, for example, as myelosuppression in form of anemia, reduction in platelet count (i.e., thrombocytopenia), reduction in white blood cell count (i.e., leukopenia), or the reduction in granulocytes (e.g., neutropenia).

By "synchronous reentry into the cell cycle" is meant that CDK4/6-replication dependent healthy cells, for example HSPCs, in G1-arrest due to the effect of a CDK4/6 inhibitor compound reenter the cell-cycle within relatively the same collective timeframe or at relatively the same rate upon dissipation of the compound's effect. Comparatively, by "asynchronous reentry into the cell cycle" is meant that the healthy cells, for example HSPCs, in G1 arrest due to the effect of a CDK4/6 inhibitor compound within relatively different collective timeframes or at relatively different rates upon dissipation of the compound's effect such as PD0332991.

By "off-cycle" or "drug holiday" is meant a time period during which the subject is not administered or exposed to a chemotherapeutic. For example, in a treatment regime wherein the subject is administered the chemotherapeutic for 21 straight days and is not administered the chemotherapeutic for 7 days, and the regime is repeated a number of times, the 7 day period of non-administration is considered the "off-cycle" or "drug holiday." Off-target and drug holiday may also refer to an interruption in a treatment regime wherein the subject is not administered the chemotherapeutic for a time due to a deleterious side effect, for example, myelosuppression.

The subject treated is typically a human subject, although it is to be understood the methods described herein are effective with respect to other animals, such as mammals and vertebrate species. More particularly, the term subject can include animals used in assays such as those used in preclinical testing including but not limited to mice, rats, monkeys, dogs, pigs and rabbits; as well as domesticated swine (pigs and hogs), ruminants, equine, poultry, felines, bovines, murines, canines, and the like.

By "substantial portion" or "significant portion" is meant at least 80%. In alternative embodiments, the portion may be at least 85%, 90% or 95% or greater.

In some embodiments, the term "CDK4/6-replication independent cancer" refers to a cancer that does not significantly require the activity of CDK4/6 for replication. Cancers of such type are often, but not always, characterized by (e.g., that has cells that exhibit) an increased level of CDK2 activity or by reduced expression of retinoblastoma tumor suppressor protein or retinoblastoma family member protein (s), such as, but not limited to p107 and p130. The increased level of CDK2 activity or reduced or deficient expression of retinoblastoma tumor suppressor protein or retinoblastoma family member protein(s) can be increased or reduced, for example, compared to normal cells. In some embodiments, the increased level of CDK2 activity can be associated with (e.g., can result from or be observed along with) MYC proto-oncogene amplification or overexpression. In some embodiments, the increased level of CDK2 activity can be associated with overexpression of Cyclin E1, Cyclin E2, or Cyclin A.

As used herein the term "chemotherapy" or "chemotherapeutic agent" refers to treatment with a cytostatic or cytotoxic agent (i.e., a compound) to reduce or eliminate the growth or proliferation of undesirable cells, for example cancer cells. Thus, as used herein, "chemotherapy" or "chemotherapeutic agent" refers to a cytotoxic or cytostatic agent used to treat a proliferative disorder, for example cancer. The cytotoxic effect of the agent can be, but is not required to be, the result of one or more of nucleic acid intercalation or binding, DNA or RNA alkylation, inhibition of RNA or DNA synthesis, the inhibition of another nucleic acid-related activity (e.g., protein synthesis), or any other cytotoxic effect.

Thus, a "cytotoxic agent" can be any one or any combination of compounds also described as "antineoplastic" agents or "chemotherapeutic agents." Such compounds include, but are not limited to, DNA damaging compounds and other chemicals that can kill cells. "DNA damaging chemotherapeutic agents" include, but are not limited to, alkylating agents, DNA intercalators, protein synthesis inhibitors, inhibitors of DNA or RNA synthesis, DNA base analogs, topoisomerase inhibitors, and telomerase inhibitors or telomeric DNA binding compounds. For example, alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; and nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, include alkylating agents such as dimethyl sulfate, mitomycin C, nitrogen and sulfur mustards; intercalating agents, such as acridine dyes, actinomycins, adriamycin, anthracenes, benzopyrene, ethidium bromide, propidium diiodide-intertwining; and other agents, such as distamycin and netropsin. Topoisomerase inhibitors, such as coumermycin, nalidixic acid, novobiocin, and oxolinic acid; inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be used as the DNA damaging compound.

Current chemotherapeutic agents whose toxic effects can be mitigated by the presently disclosed selective CDK4/6 inhibitors include, but are not limited to, adrimycin, 5-fluorouracil (5FU), 6-mercaptopurine, gemcitabine, melphalan, chlorambucil, mitomycin, irinotecan, mitoxantrone, etoposide, camptothecin, actinomycin-D, mitomycin, cisplatin, hydrogen peroxide, carboplatin, procarbazine, mechlorethamine, cyclophosphamide, ifosfamide, melphalan, chlorambucil, busulfan, nitrosurea, dactinomycin, daunorubicin, doxorubicin, bleomycin, plicomycin, tamoxifen, taxol, transplatinum, vinblastine, vinblastin, carmustine, cytarabine, mechlorethamine, chlorambucil, streptozocin, lomustine, temozolomide, thiotepa, altretamine, oxaliplatin, campothecin, and methotrexate, and the like, and similar acting-type agents. In one embodiment, the DNA damaging chemotherapeutic agent is selected from the group consisting of cisplatin, carboplatin, campothecin, doxorubicin, and etoposide.

In certain alternative embodiments, the CDK4/6 inhibitors described herein are used for an anti-cancer or anti-proliferative effect in combination with a chemotherapeutic to treat a CDK4/6 replication independent, such as an Rb-negative, cancer or proliferative disorder. The CDK4/6 inhibitors described herein may provide an additive or synergistic effect to the chemotherapeutic, resulting in a greater anti-cancer effect than seen with the use of the chemotherapeutic alone. In one embodiment, the CDK4/6 inhibitors described herein can be combined with one or more of the chemotherapeutic compounds described above. In one embodiment, a CDK4/6 inhibitor described herein can be combined with a chemotherapeutic selected from, but not limited to, but not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apopototic inducing compounds, AKT inhibitors, including but not limited to, MK-2206, GSK690693, Perifosine, (KRX-0401), GDC-0068, Triciribine, AZD5363, Honokiol, PF-04691502, and Miltefosine, PD-1 inhibitors including but not limited to, Nivolumab, CT-011, MK-3475, BMS936558, and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of mTOR inhibitors include but are not limited to rapamycin and its analogs, everolimus (Afinitor), temsirolimus, ridaforolimus, sirolimus, and deforolimus. Examples of P13 kinase inhibitors include but are not limited to Wortmannin, demethoxyviridin, perifosine, idelalisib, PX-866, IPI-145 (Infinity), BAY 80-6946, BEZ235, RP6503, TGR 1202 (RP5264), MLN1117 (INK1117), Pictilisib, Buparlisib, SAR245408 (XL147), SAR245409 (XL765), Palomid 529, ZSTK474, PWT33597, RP6530, CUDC-907, and AEZS-136. Examples of MEK inhibitors include but are not limited to Tametinib, Selumetinib, MEK162, GDC-0973 (XL518), and PD0325901. Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol. In one embodiment, the CDK4/6 inhibitor combined with the chemotherapeutic is selected from the group consisting of a compound or composition comprising Formula I, Formula II, Formula III, Formula IV, or Formula V described above, or a pharmaceutically acceptable composition, salt, isotopic analog or prodrug thereof. In one embodiment, the compound is selected from the compounds provided for in Table 1, or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof.

In one embodiment, a CDK4/6 inhibitor described herein can be combined with a chemotherapeutic selected from, but are not limited to, Imatinib mesylate (Gleevac®), Dasatinib (Sprycel®), Nilotinib (Tasigna®), Bosutinib (Bosulif®), Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

By "long-term hematological toxicity" is meant hematological toxicity affecting a subject for a period lasting more than one or more weeks, months, or years following administration of a chemotherapeutic agent. Long-term hematological toxicity can result in bone marrow disorders that can cause the ineffective production of blood cells (i.e., myelodysplasia) and/or lymphocytes (i.e., lymphopenia, the reduction in the number of circulating lymphocytes, such as B- and T-cells). Hematological toxicity can be observed, for example, as anemia, reduction in platelet count (i.e., thrombocytopenia) or reduction in white blood cell count (i.e., neutropenia). In some cases, myelodysplasia can result in the development of leukemia. Long-term toxicity related to chemotherapeutic agents can also damage other self-renewing cells in a subject, in addition to hematological cells. Thus, long-term toxicity can also lead to graying and frailty.

Active Compounds

In one embodiment, the invention is directed to compounds or the use of such compounds of Formula I, II, III, IV, or V:

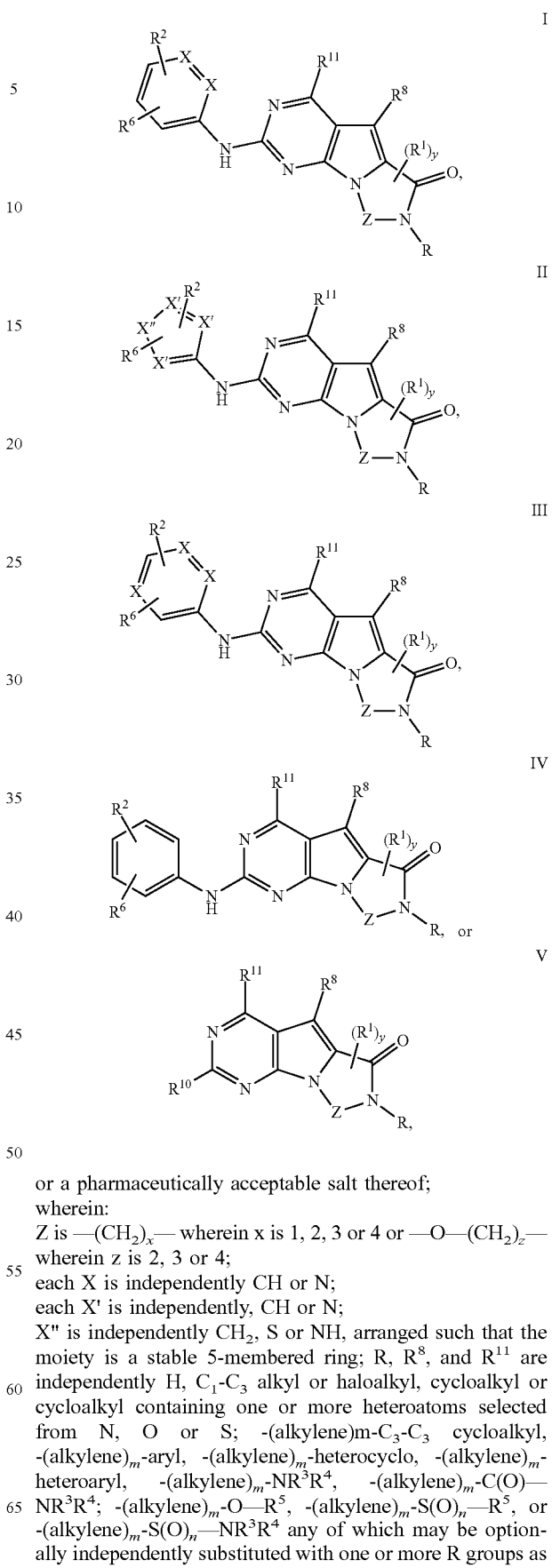

or a pharmaceutically acceptable salt thereof;
wherein:
Z is —(CH$_2$)$_x$— wherein x is 1, 2, 3 or 4 or —O—(CH$_2$)$_z$— wherein z is 2, 3 or 4;
each X is independently CH or N;
each X' is independently, CH or N;
X" is independently CH$_2$, S or NH, arranged such that the moiety is a stable 5-membered ring; R, R$^8$, and R$^{11}$ are independently H, C$_1$-C$_3$ alkyl or haloalkyl, cycloalkyl or cycloalkyl containing one or more heteroatoms selected from N, O or S; -(alkylene)m-C$_3$-C$_3$ cycloalkyl, -(alkylene)$_m$-aryl, -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R groups as allowed by valance, and wherein two $R^x$ groups bound to the same or adjacent atoms may optionally combine to form a ring;
each $R^1$ is independently aryl, alkyl, cycloalkyl or haloalkyl, wherein each of said alkyl, cycloalkyl and haloalkyl groups optionally includes O or N heteroatoms in place of a carbon in the chain and two $R^1$'s on adjacent ring atoms or on the same ring atom together with the ring atom(s) to which they are attached optionally form a 3-8-membered cycle;
y is 0, 1, 2, 3 or 4;
$R^2$ is -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-C(O)—O-alkyl; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more $R^x$ groups as allowed by valance, and wherein two $R^x$ groups bound to the same or adjacent atom may optionally combine to form a ring and wherein m is 0 or 1 and n is 0, 1 or 2;
$R^3$ and $R^4$ at each occurrence are independently:
  (i) hydrogen or
  (ii) alkyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance, and wherein two $R^x$ groups bound to the same or adjacent atom may optionally combine to form a ring; or $R^3$ and $R^4$ together with the nitrogen atom to which they are attached may combine to form a heterocyclo ring optionally independently substituted with one or more $R^x$ groups as allowed by valance, and wherein two $R^x$ groups bound to the same or adjacent atom may optionally combine to form a ring;
$R^5$ and $R^{5*}$ at each occurrence is:
  (i) hydrogen or
  (ii) alkyl, alkenyl, alkynyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance;
$R^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-OR$^5$, -(alkylene)$_m$-O-alkylene-OR$^5$, -(alkylene)$_m$-S(O)$_n$—R$^5$, -(alkylene)$_m$-NR$^3$R$^4$, -(alkylene)$_m$-CN, -(alkylene)$_m$-C(O)—R$^5$, -(alkylene)$_m$-C(S)—R$^5$, -(alkylene)$_m$-C(O)—OR$^5$, -(alkylene)$_m$-O—C(O)—R$^5$, -(alkylene)$_m$-C(S)—OR$^5$, -(alkylene)$_m$-C(O)-(alkylene)$_m$-NR$^3$R$^4$, -(alkylene)$_m$-C(S)—NR$^3$R$^4$, -(alkylene)$_m$-N(R$^3$)—C(O)—NR$^3$R$^4$, -(alkylene)$_m$-N(R$^3$)—C(S)—NR$^3$R$^4$, -(alkylene)$_m$-N(R$^3$)—C(O)—R$^5$, -(alkylene)$_m$-N(R$^3$)—C(S)—R$^5$, -(alkylene)$_m$-O—C(O)—NR$^3$R$^4$, -(alkylene)$_m$-O—C(S)—NR$^3$R$^4$, -(alkylene)$_m$-SO$_2$—NR$^3$R$^4$, -(alkylene)$_m$-N(R$^3$)—SO$_2$—R$^5$, -(alkylene)$_m$-N(R$^3$)—SO$_2$—NR$^3$R$^4$, -(alkylene)$_m$-N(R$^3$)—C(O)—OR$^5$ -(alkylene)$_m$-N(R$^3$)—C(S)—OR$^5$, or -(alkylene)$_m$-N(R$^3$)—SO$_2$—R$^5$; wherein:
  said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-CN, -(alkylene)$_m$-OR$^{5*}$, -(alkylene)$_m$-S(O)$_n$—R$^{5*}$, -(alkylene)$_m$-NR$^{3*}$R$^{4*}$, -(alkylene)$_m$-C(O)—R$^{5*}$, -(alkylene)$_m$-C(=S)R$^{5*}$, -(alkylene)$_m$-C(=O)O R$^{5*}$, -(alkylene)$_m$-OC(=O)R$^{5*}$, -(alkylene)$_m$-C(S)—OR$^{5*}$, -(alkylene)$_m$-C(O)—NR$^{3*}$R$^{4*}$, -(alkylene)$_m$-C(S)—NR$^{3*}$R$^{4*}$, -(alkylene)$_m$-N(R$^{3*}$)—C(O)—NR$^{3*}$R$^{4*}$, -(alkylene)$_m$-N(R$^{3*}$)—C(S)—NR$^{3*}$R$^{4*}$, -(alkylene)$_m$-N(R$^{3*}$)—C(O)—R$^{5*}$, -(alkylene)$_m$-N(R$^{3*}$)—C(S)—R$^{5*}$, -(alkylene)$_m$-O—C(O)—NR$^{3*}$R$^{4*}$, -(alkylene)$_m$-O—C(S)—NR$^{3*}$R$^{4*}$, -(alkylene)$_m$-SO$_2$—NR$^{3*}$R$^{4*}$, -(alkylene)$_m$-N(R$^{3*}$)—SO$_2$—R$^{5*}$, -(alkylene)$_m$-N(R$^{3*}$)—SO$_2$—NR$^{3*}$R$^{4*}$, -(alkylene)$_m$-N(R$^{3*}$)—C(O)—OR$^{5*}$, -(alkylene)$_m$-N(R$^{3*}$)—C(S)—OR$^{5*}$, or -(alkylene)$_m$-N(R$^{3*}$)—SO$_2$—R$^{5*}$,
n is 0, 1 or 2, and
m is 0 or 1;
$R^{3*}$ and $R^{4*}$ at each occurrence are independently:
  (i) hydrogen or
  (ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance; or $R^{3*}$ and $R^{4*}$ together with the nitrogen atom to which they are attached may combine to form a heterocyclo ring optionally independently substituted with one or more $R^x$ groups as allowed by valance; and
$R^6$ is H or lower alkyl, -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more $R^x$ groups as allowed by valance, and wherein two IV groups bound to the same or adjacent atoms may optionally combine to form a ring; and
$R^{10}$ is (i) NHR$^A$, wherein $R^A$ is unsubstituted or substituted $C_1$-$C_8$ alkyl, cycloalkylalkyl, or -TT-RR, $C_1$-$C_8$ cycloalkyl or cycloalkyl containing one or more heteroatoms selected from N, O, and S; TT is an unsubstituted or substituted $C_1$-$C_8$ alkyl or $C_3$-$C_8$ cycloalkyl linker; and RR is a hydroxyl, unsubstituted or substituted $C_1$-$C_6$ alkoxy, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising one or two 5- or 6-member rings and 1-4 heteroatoms selected from N, O and S, unsubstituted or substituted $C_3$-$C_{10}$ carbocycle, or unsubstituted or substituted heterocycle comprising one or two 5- or 6-member rings and 1-4 heteroatoms selected from N, O and S; or (ii) —C(O)—R$^{12}$ or —C(O)O—R$^{13}$, wherein R$^{12}$ is NHR$^A$ or R$^A$ and R$^{13}$ is R$^A$;

or a pharmaceutically acceptable salt, prodrug or isotopic variant, for example, partially or fully deuterated form thereof.

In some aspects, the compound is of Formula I or Formula II and $R^6$ is absent.

In some aspects, the compound is of Formula III:

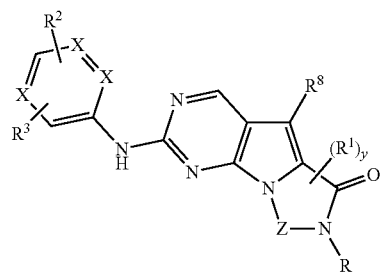

and the variables are as defined for compounds of Formulae I and II and pharmaceutically acceptable salts thereof.

In some aspects, $R^x$ is not further substituted.

In some aspects, $R^2$ is -(alkylene)$_m$-heterocyclo, -(alkylene)$_m$-heteroaryl, (alkylene)$_m$-NR$^3$R$^4$, -(alkylene)$_m$-C(O)—NR$^3$R$^4$; -(alkylene)$_m$-O—R$^5$, (alkylene)$_m$-S(O)$_n$—R$^5$, or -(alkylene)$_m$-S(O)$_n$—NR$^3$R$^4$ any of which may be optionally independently substituted with one or more IV groups as allowed by valance, and wherein two IV groups bound to the same or adjacent atom may optionally combine to form a ring and wherein m is 0 or 1 and n is 0, 1 or 2.

In some aspects, $R^8$ is hydrogen or $C_1$-$C_3$ alkyl.

In some aspects, R is hydrogen or $C_1$-$C_3$ alkyl.

In some aspects, $R^2$ is -(alkylene)$_m$-heterocyclo, -(alkylene)$_m$-NR$^3$R$^4$, (alkylene)$_m$-C(O)—NR$^3$R$^4$, -(alkylene)$_m$-C(O)—O-alkyl or -(alkylene)$_m$-OR$^5$ any of which may be optionally independently substituted with one or more IV groups as allowed by valance, and wherein two IV groups bound to the same or adjacent atom may optionally combine to form a ring.

In some aspects, $R^2$ is -(alkylene)$_m$-heterocyclo, -(alkylene)$_m$-NR$^3$R$^4$, (alkylene)$_m$-C(O)—NR$^3$R$^4$, -(alkylene)$_m$-C(O)—O-alkyl or -(alkylene)$_m$-OR$^5$ without further substitution.

In some aspects, m in $R^2$ is 1. In a further aspect, the alkylene in $R^2$ is methylene.

In some aspects, $R^2$ is

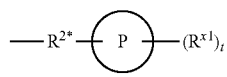

wherein:
$R^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- and -(alkylene)$_m$-NH-(alkylene)$_m$- wherein each m is independently 0 or 1;
P is a 4- to 8-membered mono- or bicyclic saturated heterocyclyl group;
each $R^{x1}$ is independently -(alkylene)$_m$-(C(O))$_m$-(alkylene)$_m$-(N(R$^N$))$_m$-(alkyl)$_m$ wherein each m is independently 0 or 1 provided at least one m is 1, —C(O))—O-alkyl, -(alkylene)$_m$-cycloalkyl wherein m is 0 or 1, —N(R$^N$)-cycloalkyl, —C(O)-cycloalkyl, -(alkylene)$_m$-heterocyclyl wherein m is 0 or 1, or —N(R$^N$)-heterocyclyl, —C(O)-heterocyclyl, —S(O)$_2$-(alkylene)$_m$ wherein m is 1 or 2,
wherein:
  $R^N$ is H, $C_1$ to $C_4$ alkyl or $C_1$ to $C_6$ heteroalkyl, and
  wherein two $R^{x1}$ can, together with the atoms to which they attach on P, which may be the same atom, form a ring; and
t is 0, 1 or 2.

In some aspects, each $R^{x1}$ is only optionally substituted by unsubstituted alkyl, halogen or hydroxy.

In some aspects, $R^{x1}$ is hydrogen or unsubstituted $C_1$-$C_4$ alkyl.

In some aspects, at least one $R^{x1}$ is -(alkylene)$_m$-heterocyclyl wherein m is 0 or 1.

In some aspects, $R^2$ is

wherein P* is a 4- to 8-membered mono- or bicyclic saturated heterocyclyl group.

In some aspects, $R^2$ is

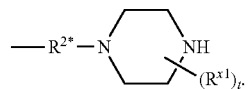

In some aspects, $R^2$ is

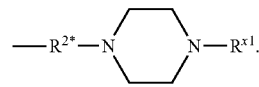

In some aspects, $R^2$ is

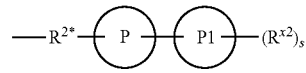

wherein:
$R^{2*}$ is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- and -(alkylene)$_m$-NH-(alkylene)$_m$- wherein each m is independently 0 or 1;
P is a 4- to 8-membered mono- or bicyclic saturated heterocyclyl group;
P1 is a 4- to 6-membered monocyclic saturated heterocyclyl group;
each $R^{x2}$ is independently hydrogen or alkyl; and
s is 0, 1 or 2.

In some aspects, $R^2$ is

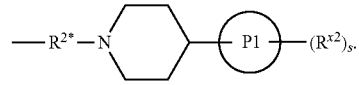

In some aspects, P1 includes at least one nitrogen.

In some aspects, any alkylene in $R^{2*}$ in any previous aspect is not further substituted.

Figure 24:
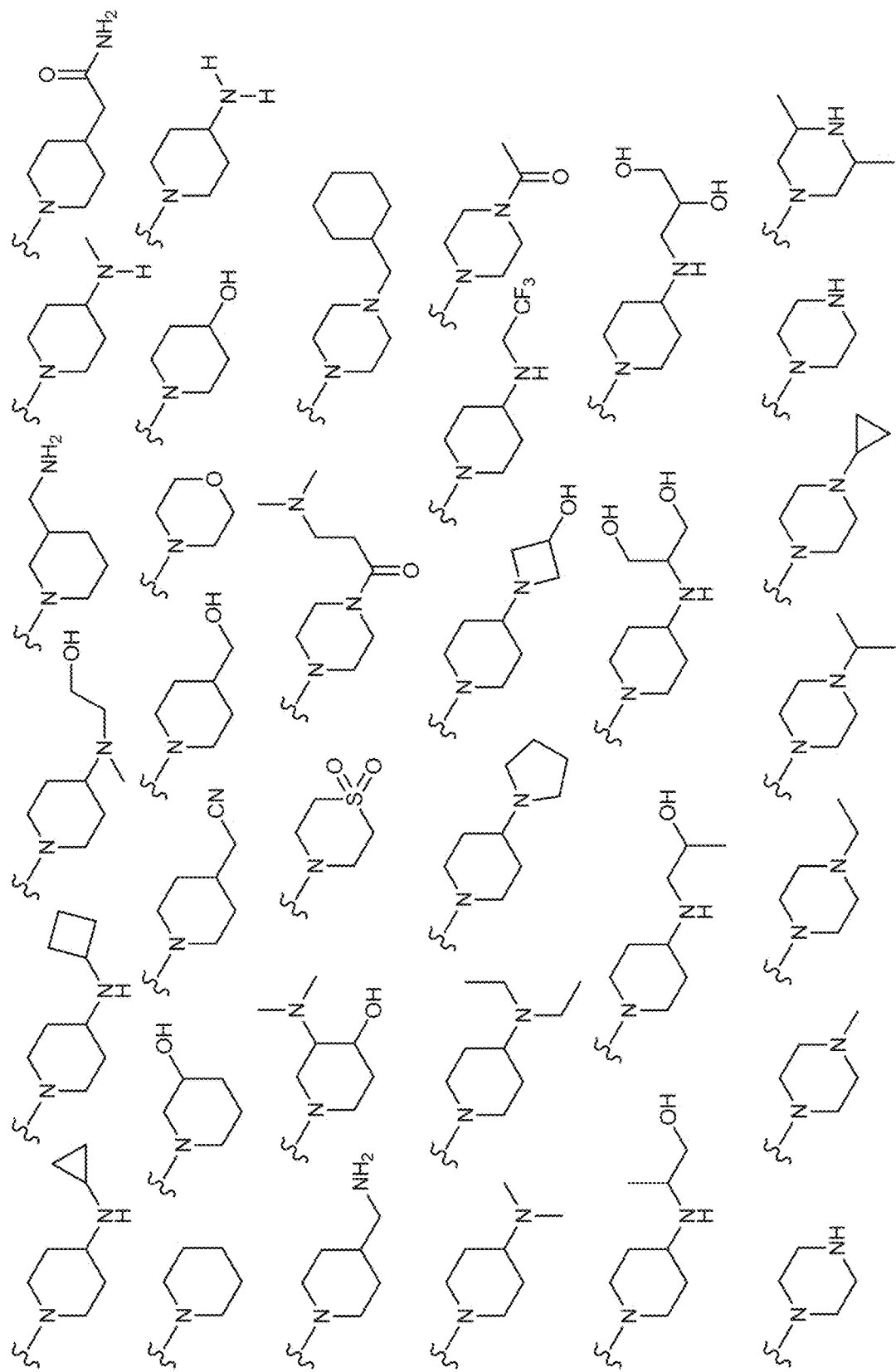
FIGS. 24-26 illustrate several exemplary embodiments of $R^2$ of the compounds of the invention.
Figure 25:
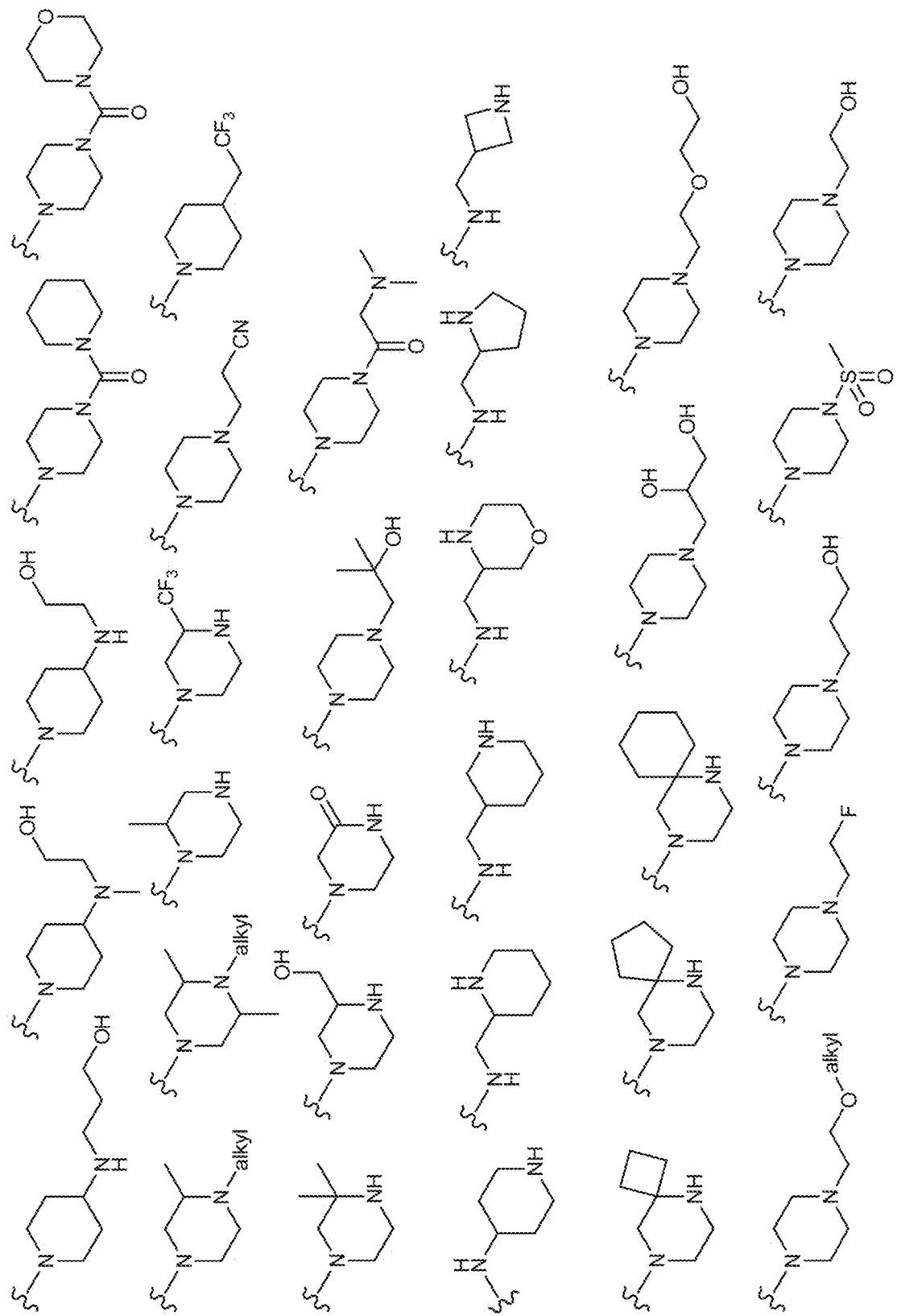
Figure 26:
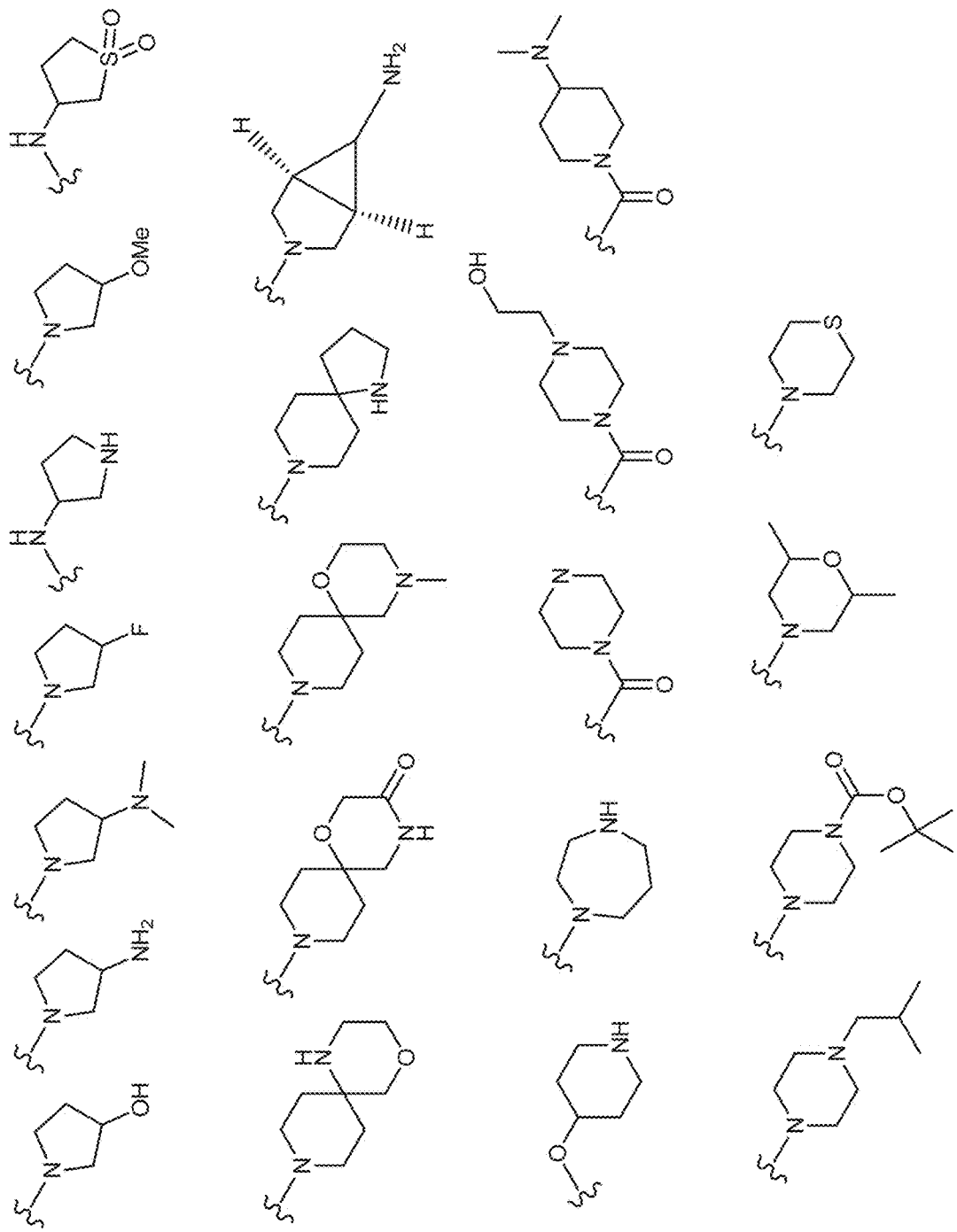
Figure 27A:
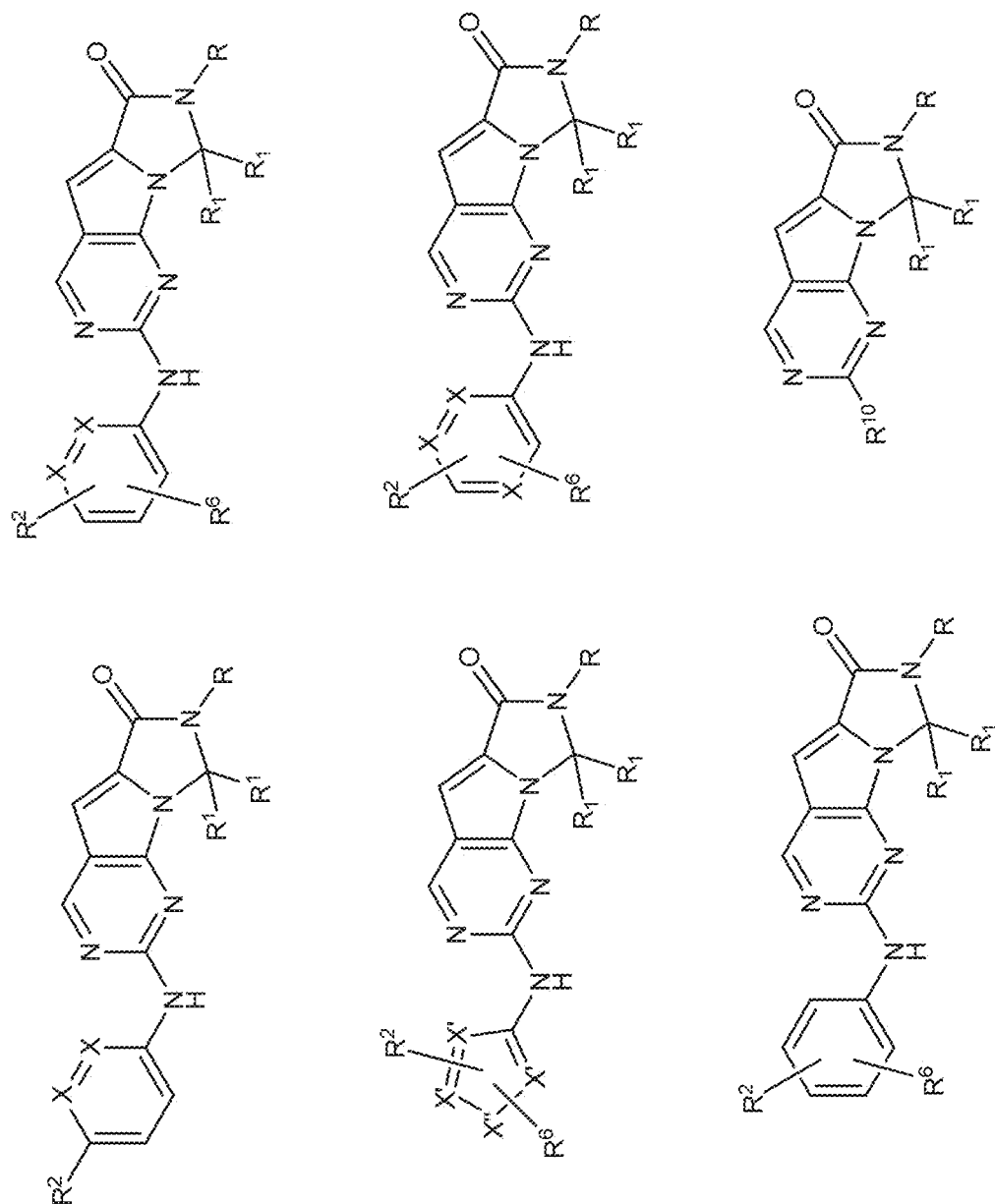
FIGS. 27A-27C, 28A-D, 29A-29C, 30A-30B, and 31A-31F illustrate exemplary embodiments of the core structure of the compounds of the invention.
Figure 27B:
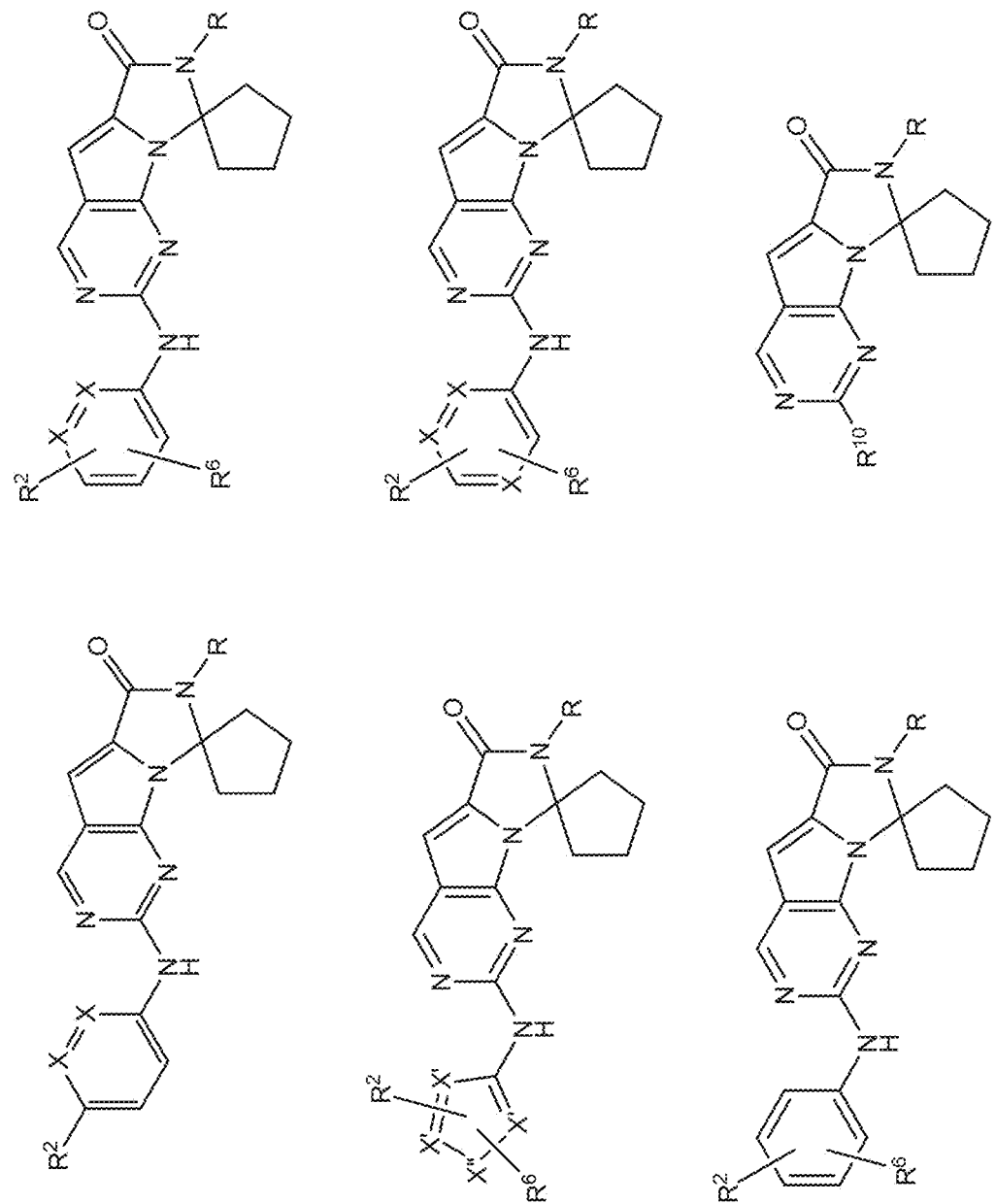
Figure 27C:
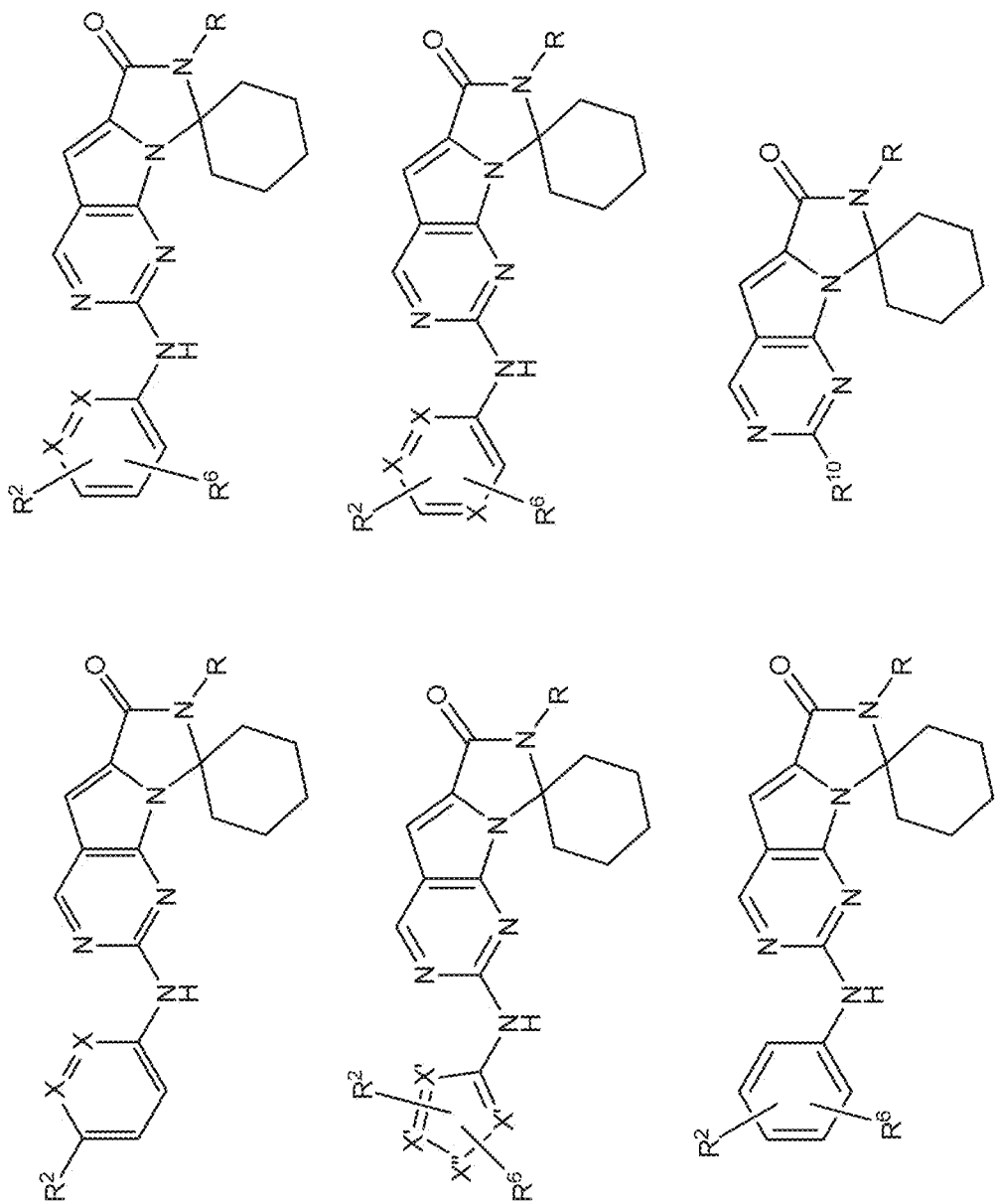
Figure 28A:
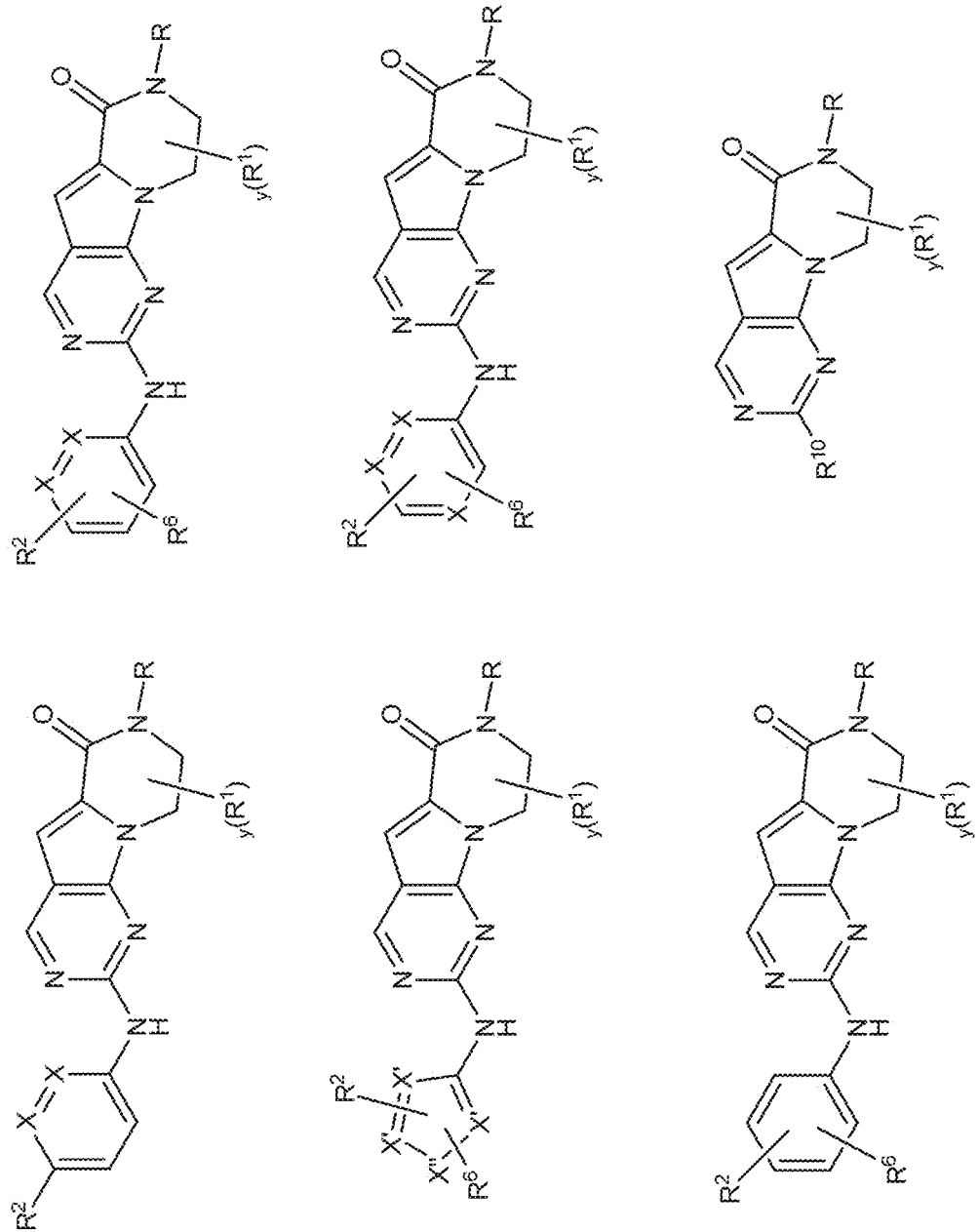
Figure 28B:
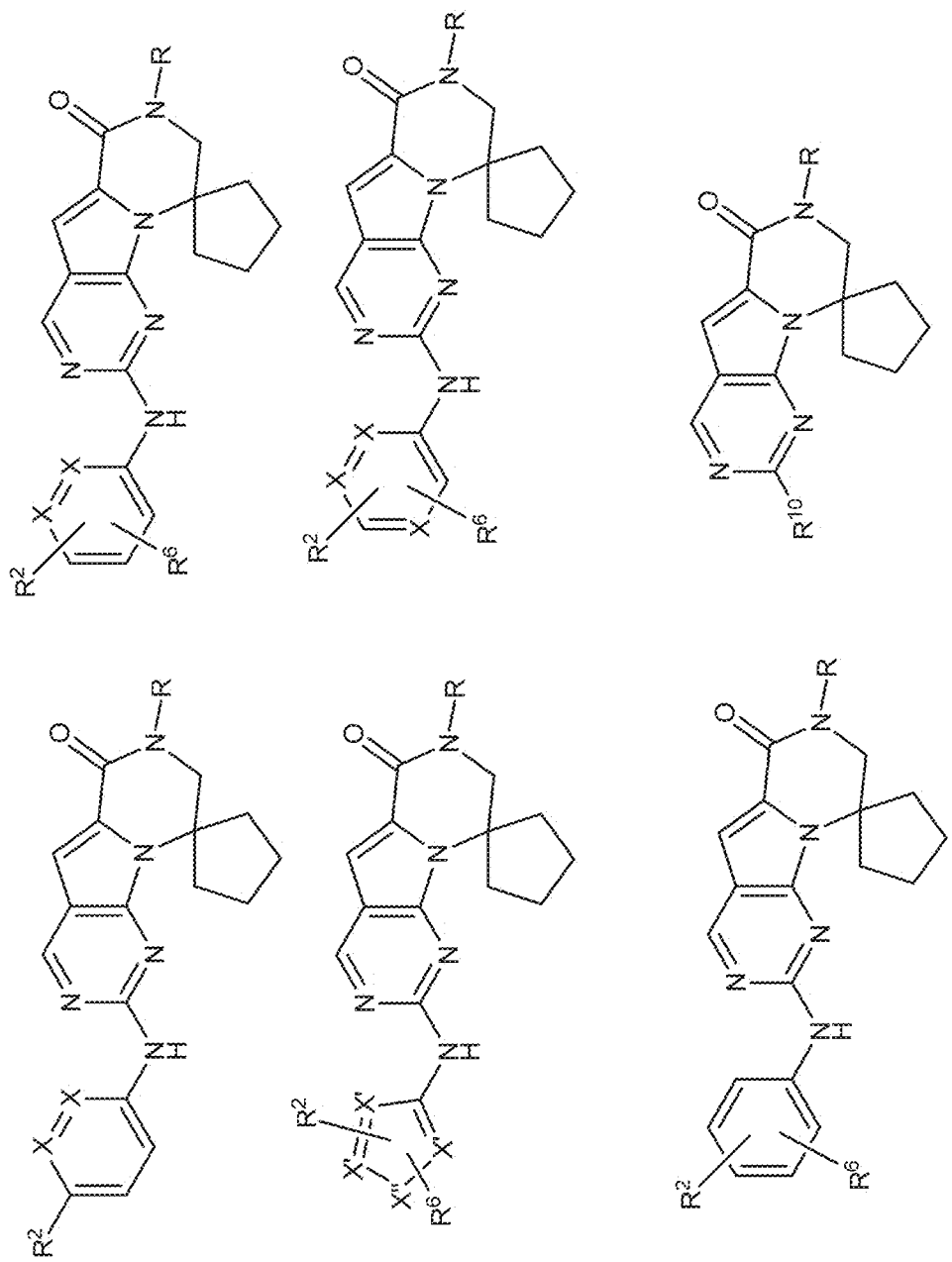
Figure 28C:
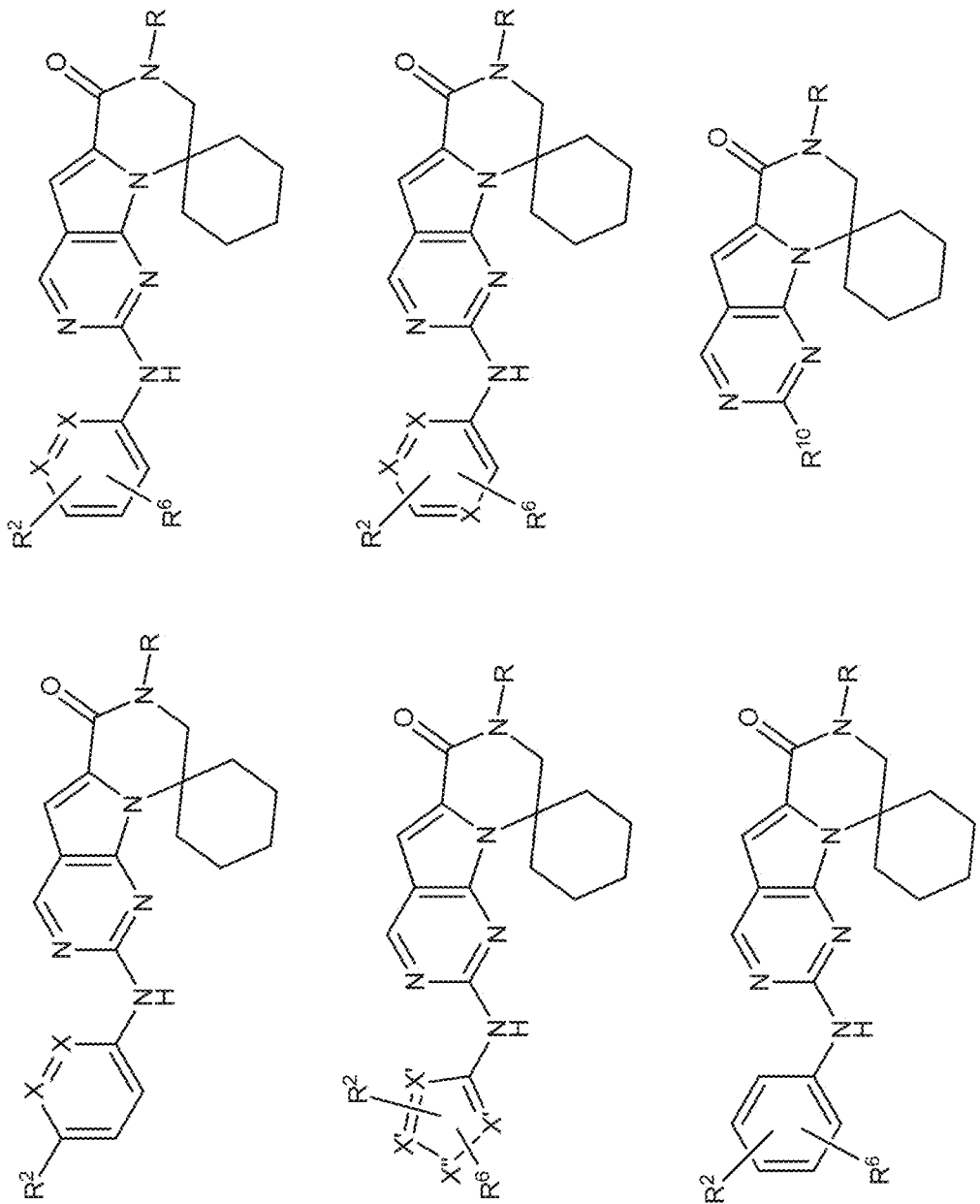
Figure 28D:
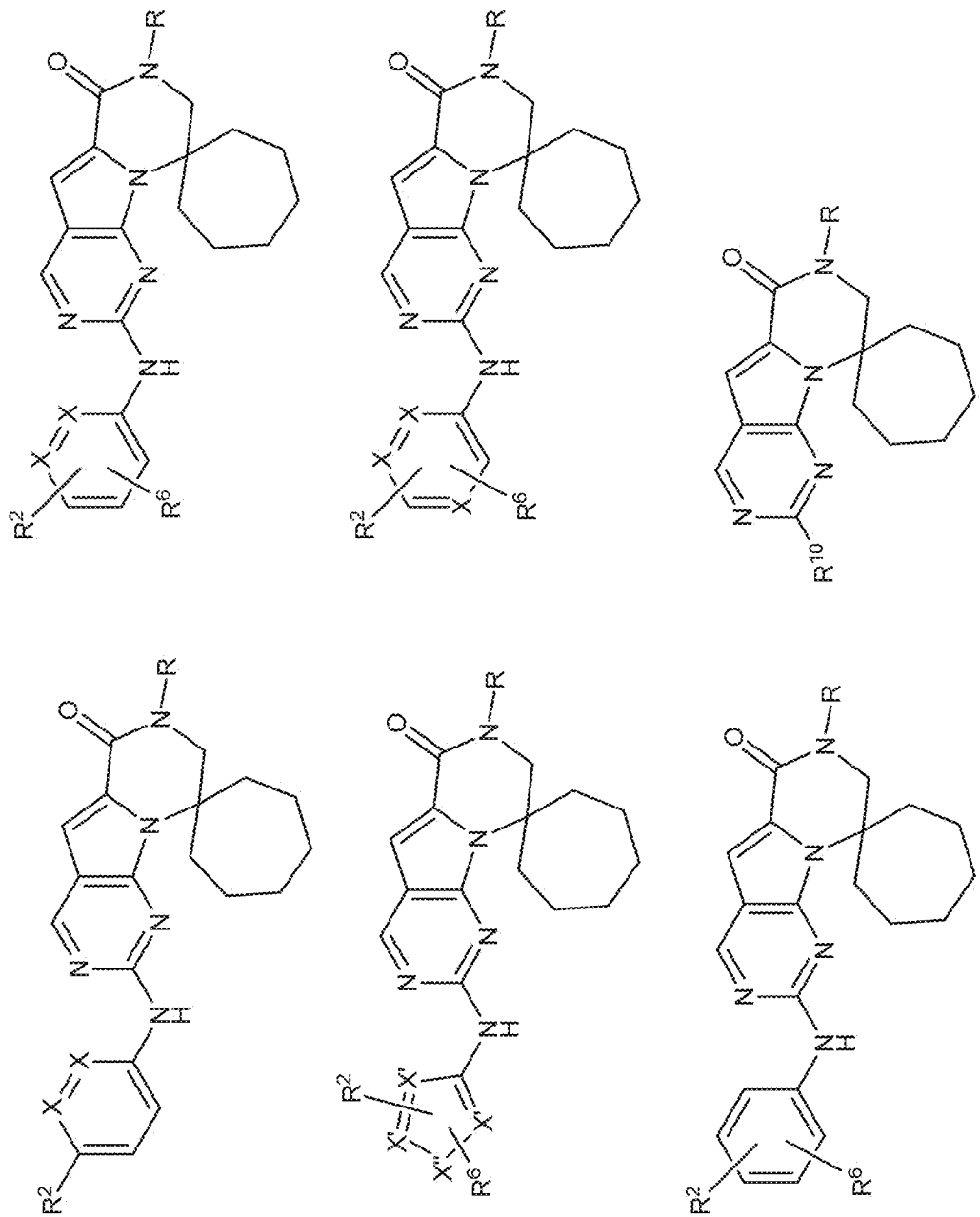
Figure 29A:
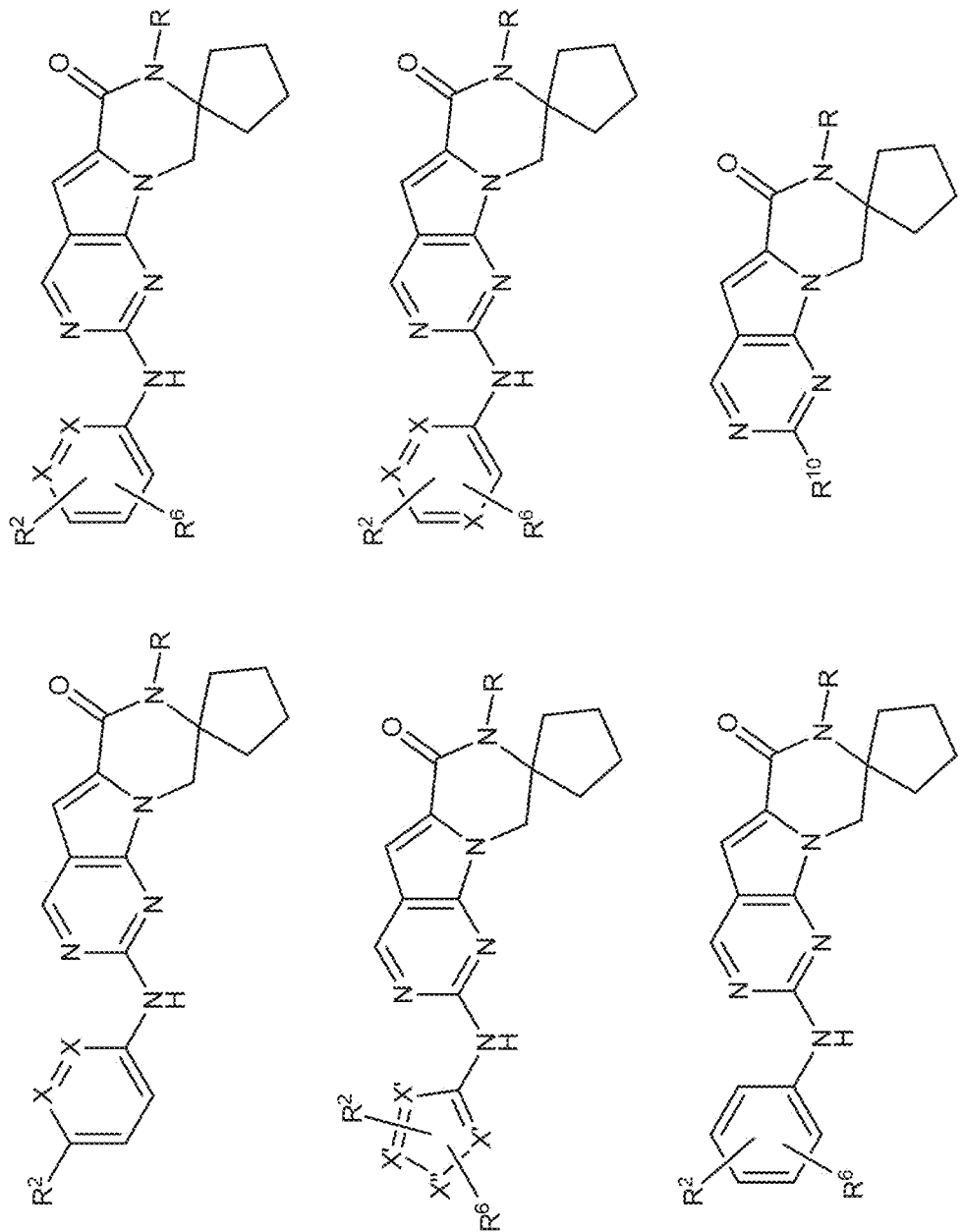
Figure 29B:
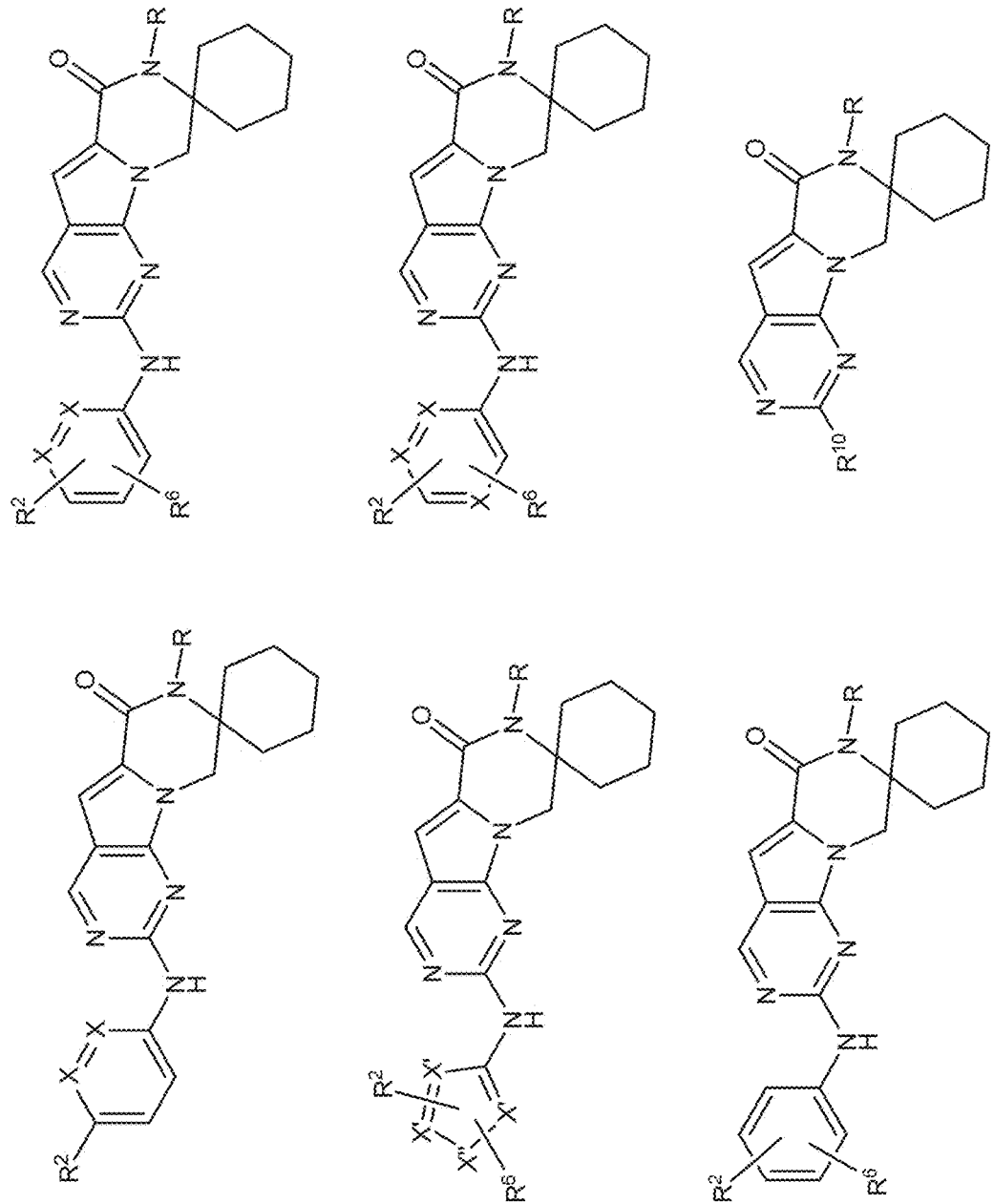
Figure 29C:
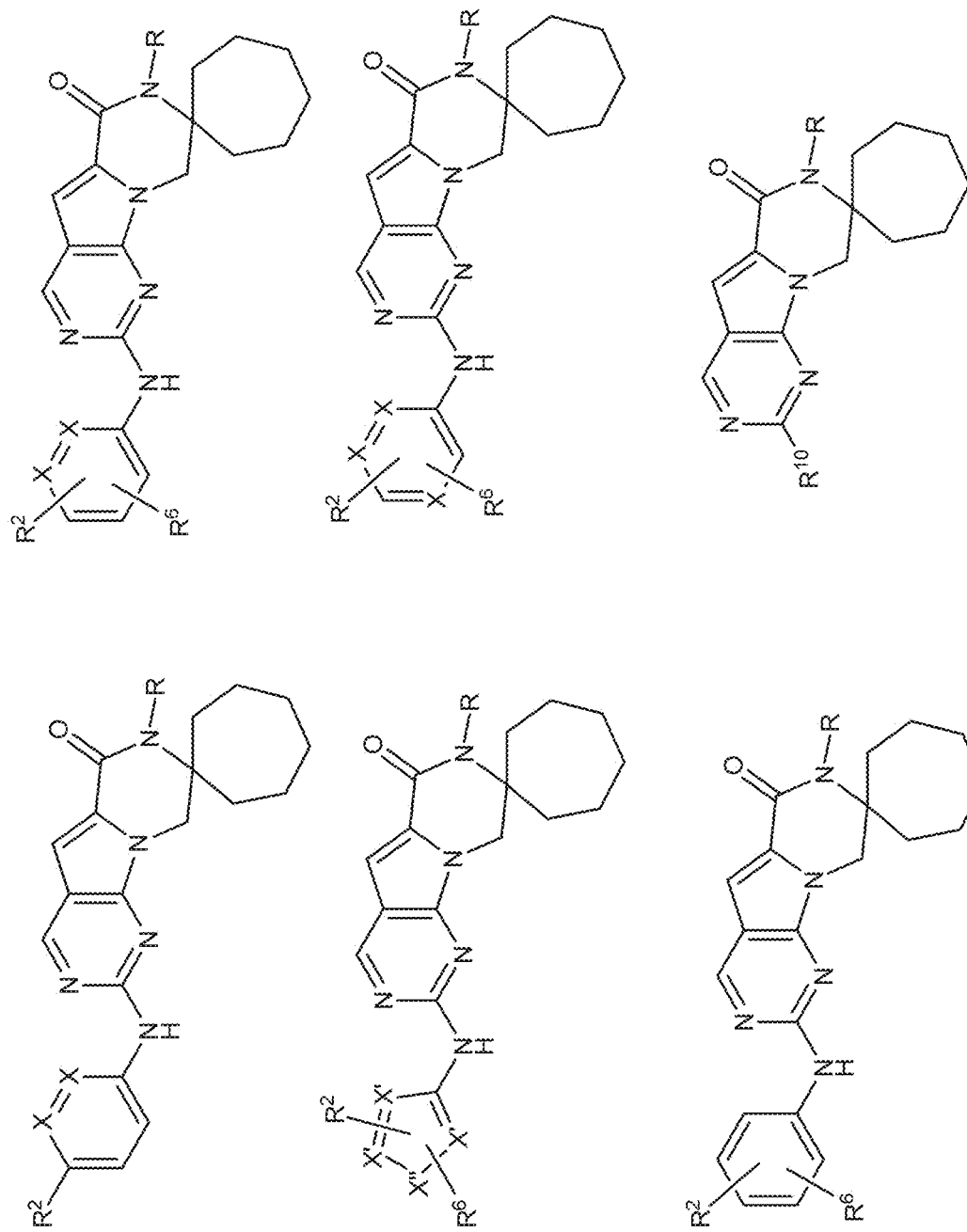
Figure 30A:
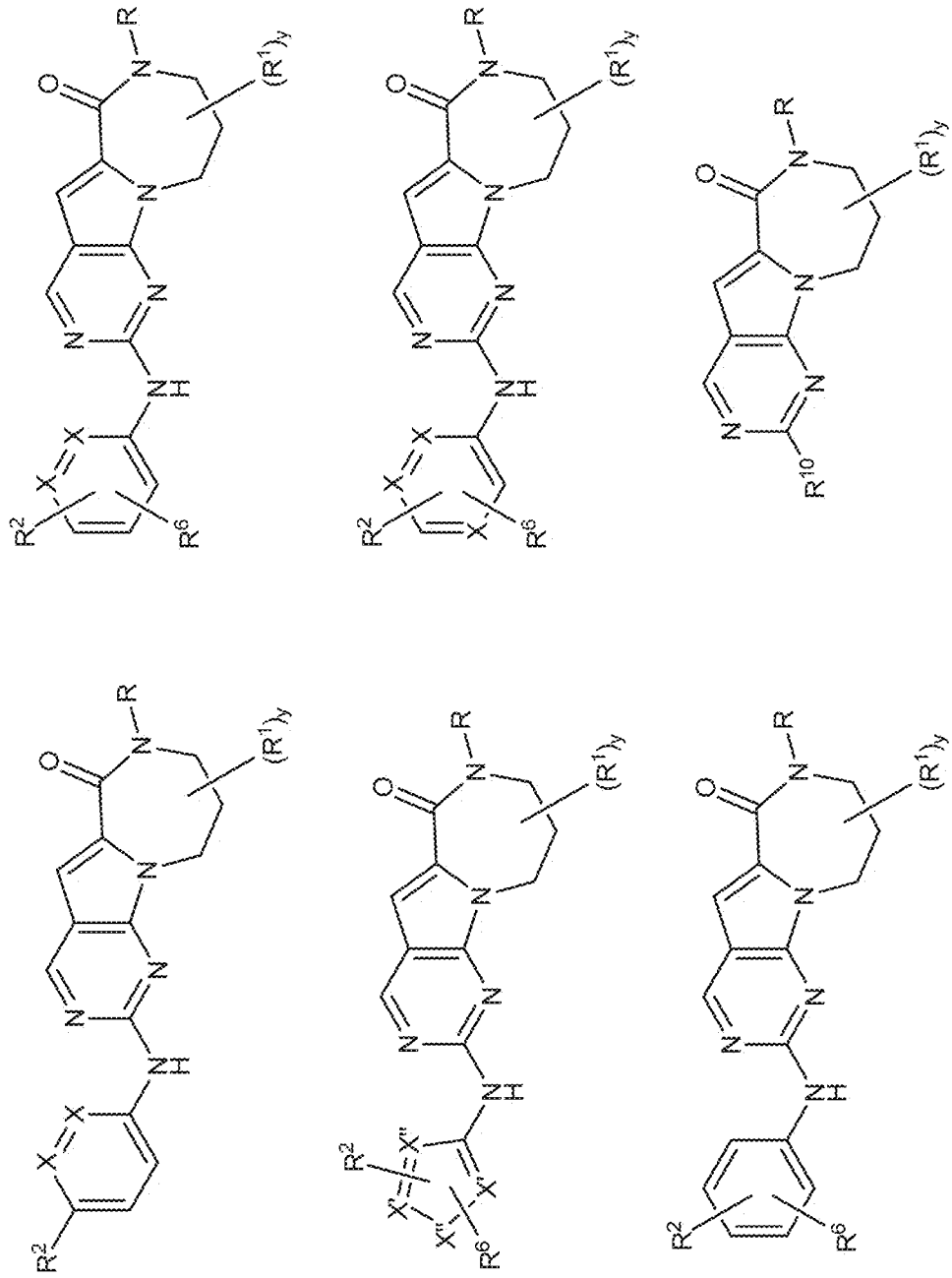
Figure 30B:
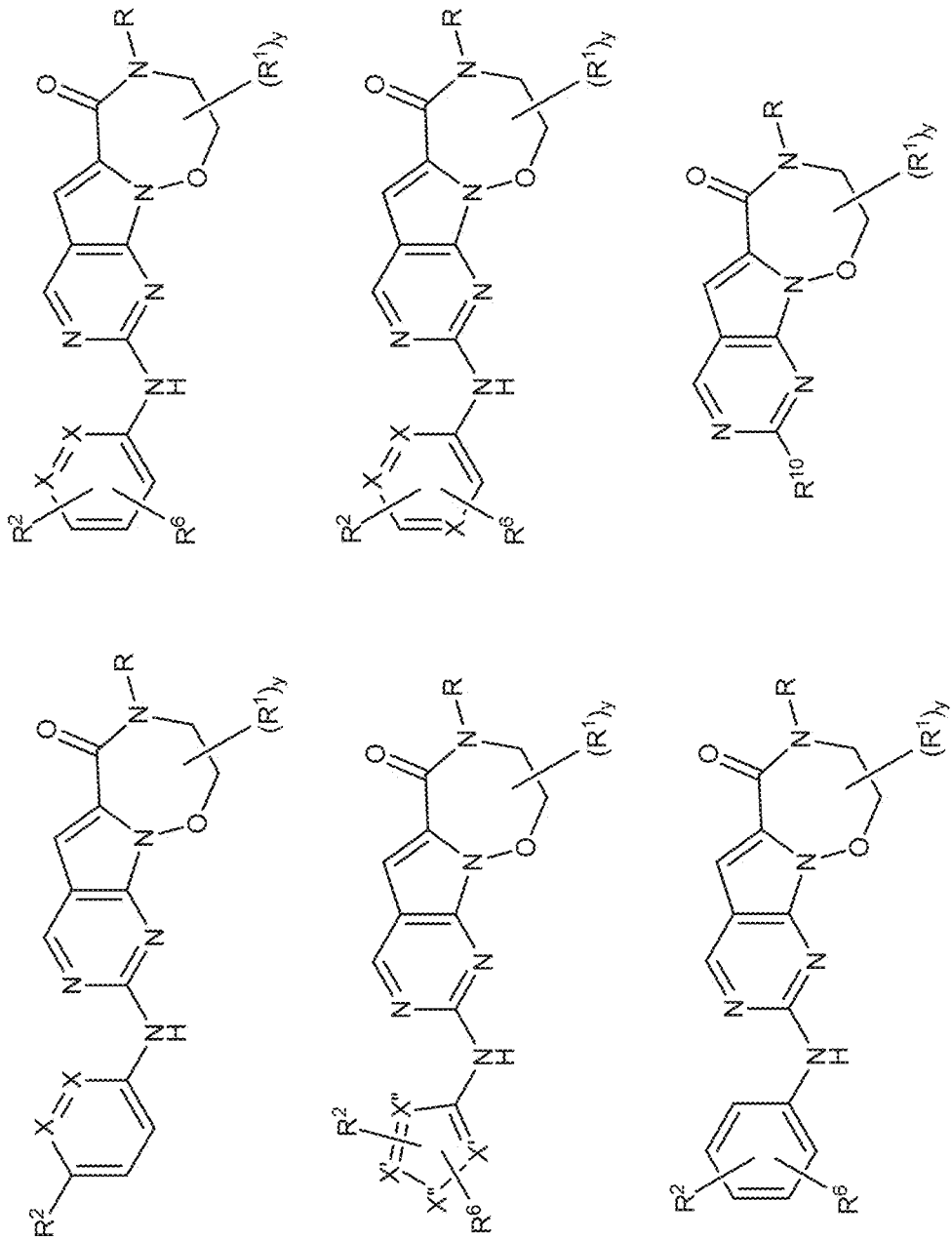
Figure 31A:
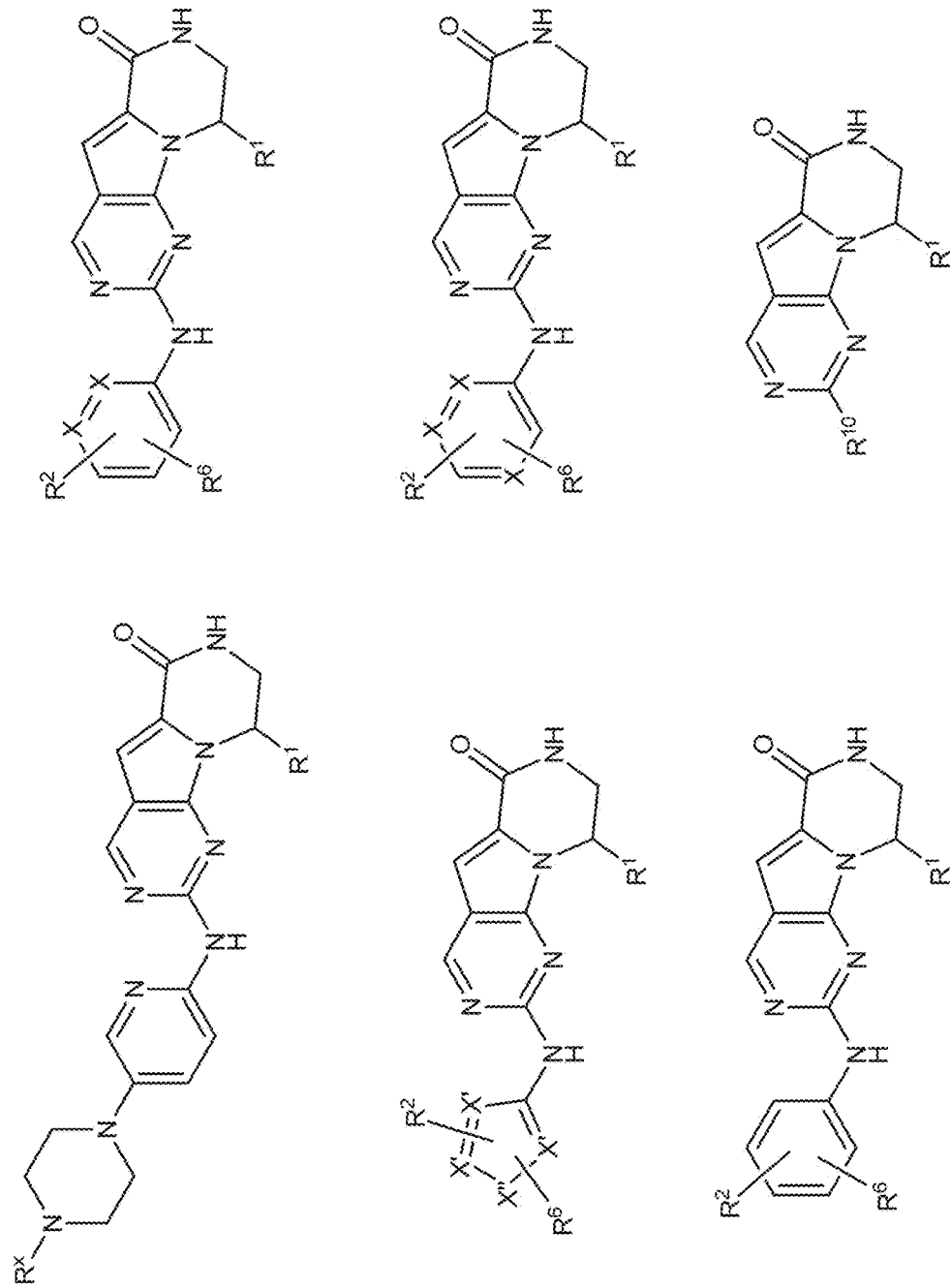
Figure 31B:
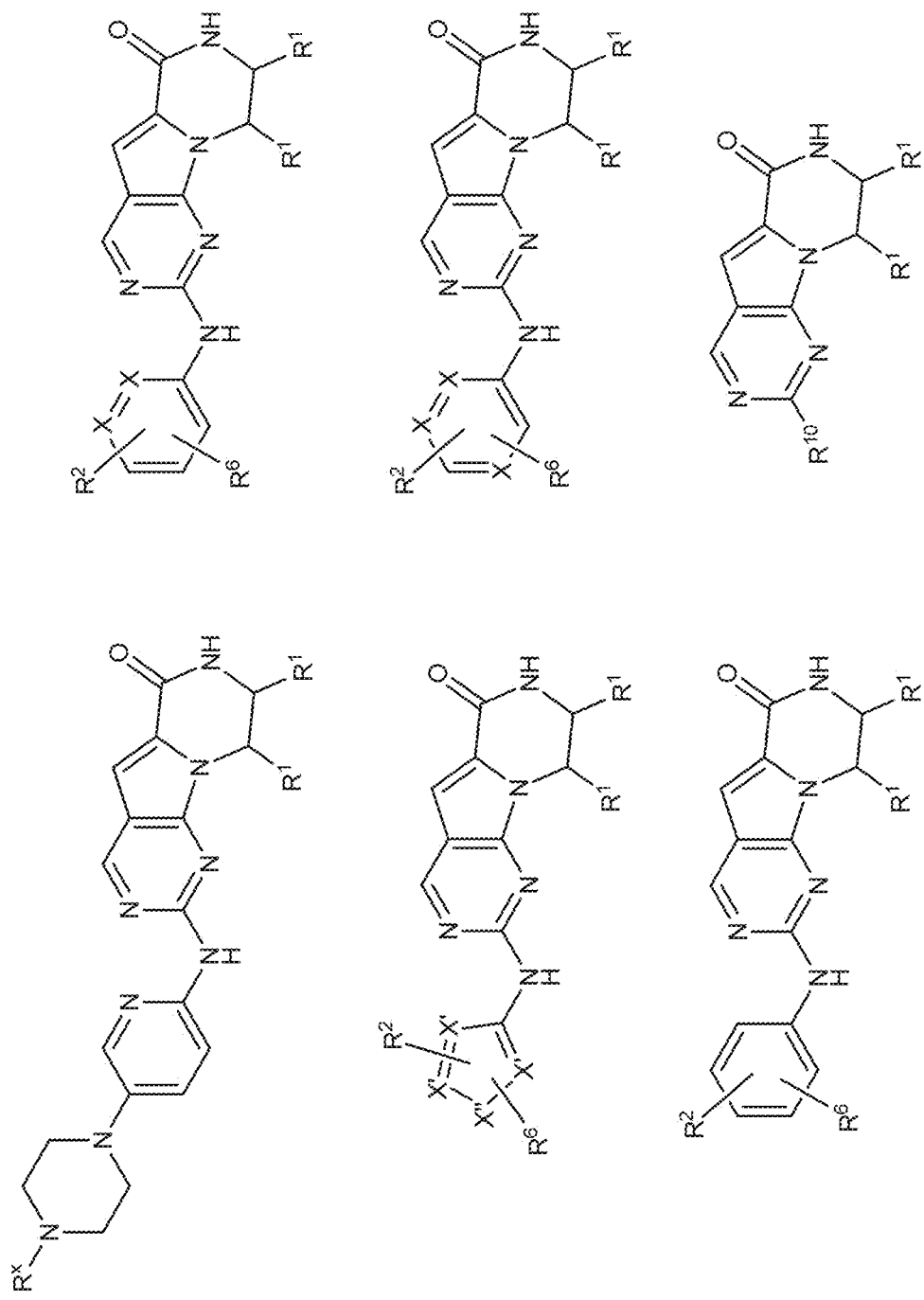
Figure 31C:
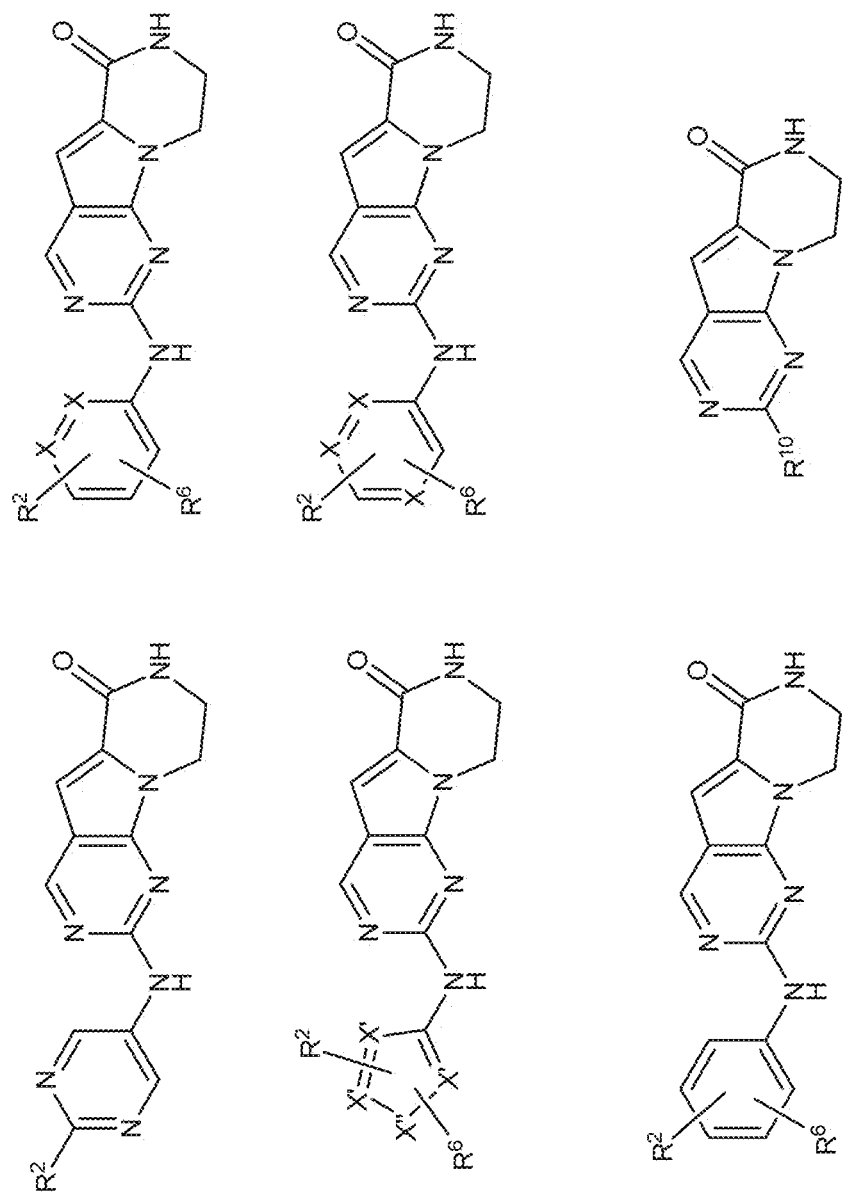
Figure 31D:
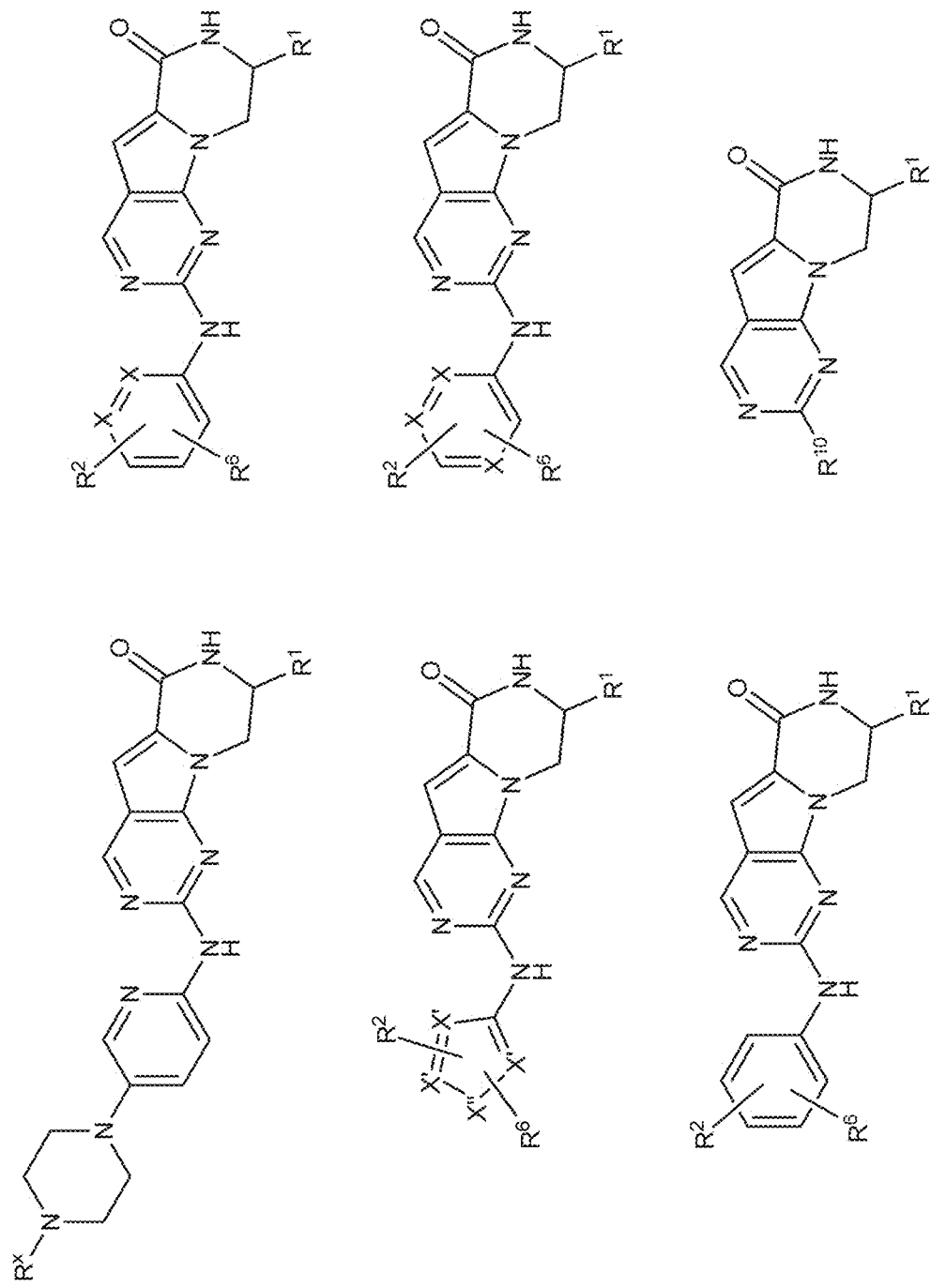
Figure 31E:
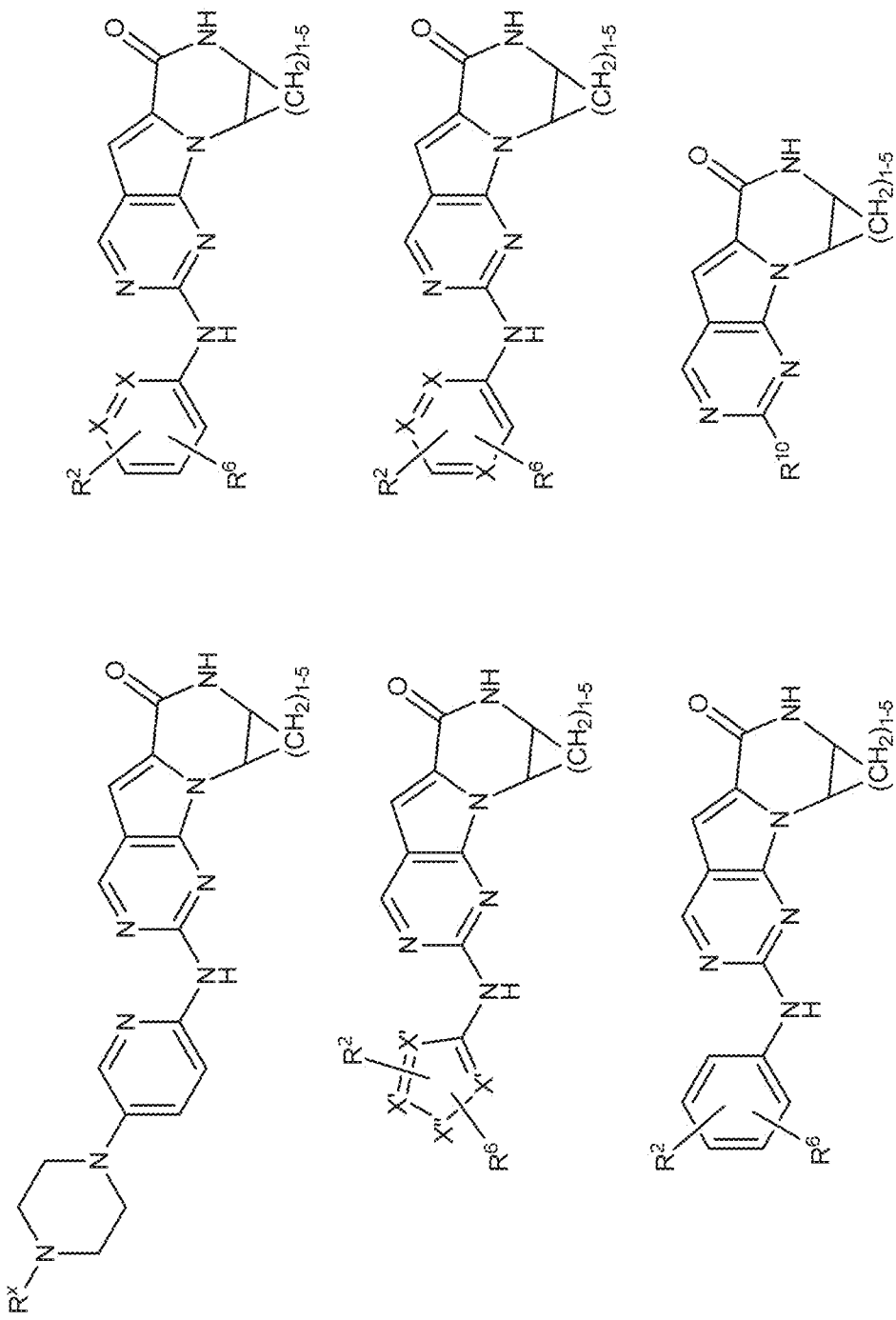
Figure 31F:
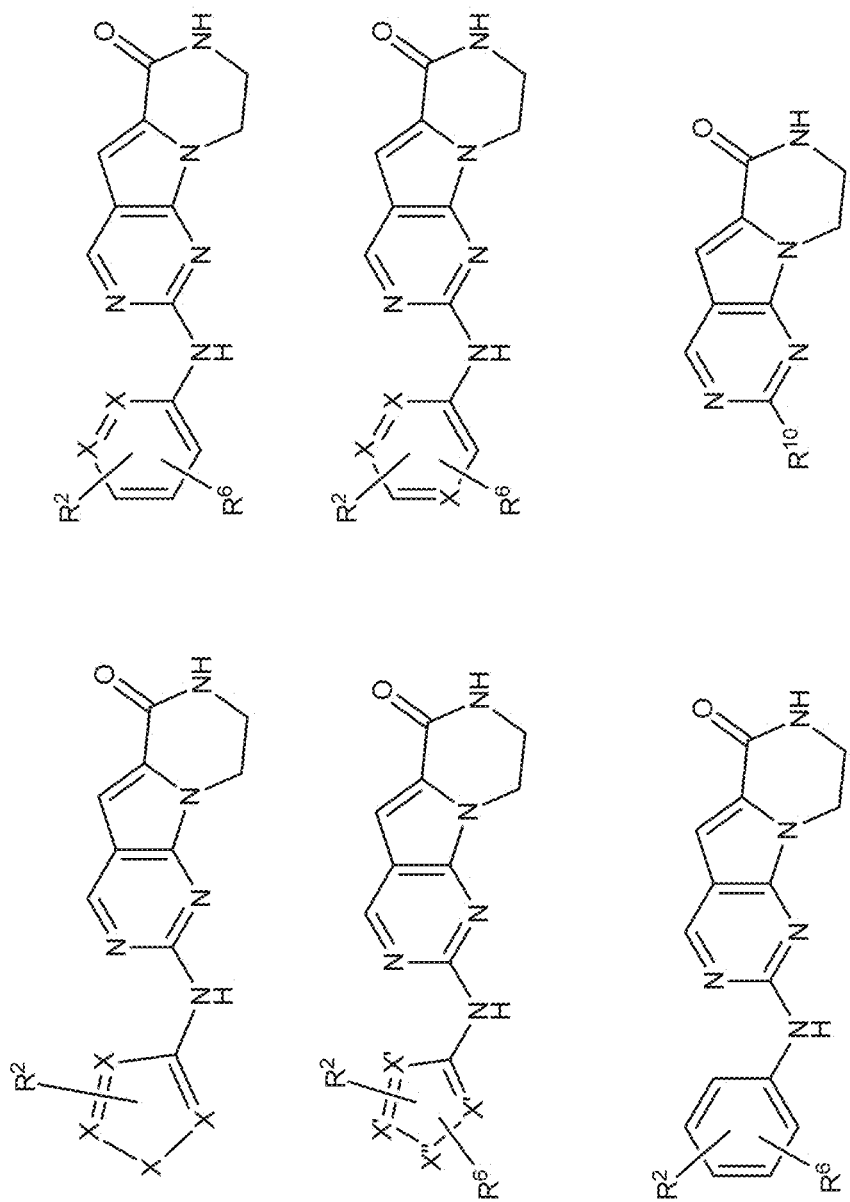

In some aspects, $R^2$ is selected from the structures depicted in FIGS. 24-26.

In some aspects, $R^2$ is

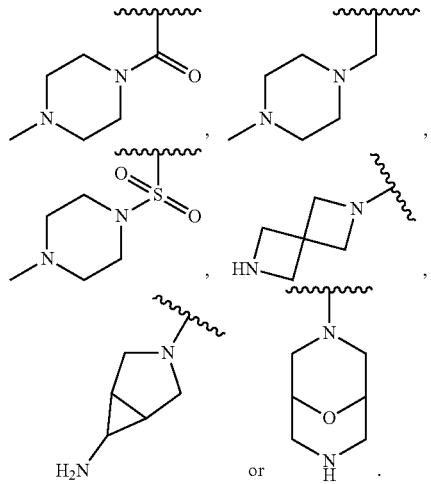

In some aspects, the compound has general Formula I and more specifically one of the general structures in FIGS. 27-31 wherein the variables are as previously defined.

In some aspects, the compound has general Formula Ia:

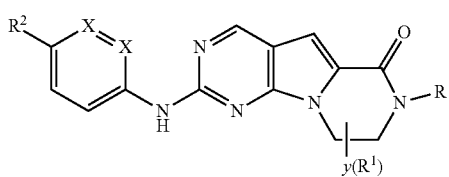

wherein $R^1$, $R^2$, R and y are as previously defined.

In some embodiments, the compound has Formula Ia and R is alkyl.

In some embodiments, the compound has Formula Ia and R is H.

In some embodiments, the compound has Formula Ia and $R^2$ is

wherein P* is a 4- to 8-membered mono- or bicyclic saturated heterocyclyl group and $R^{2*}$, $R^{x1}$ and t are as previously defined.

In some embodiments, the compound has Formula Ia and $R^2$ is

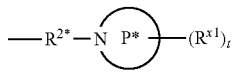

wherein P* is a 4- to 8-membered mono- or bicyclic saturated heterocyclyl group, $R^{x1}$ is hydrogen or unsubstituted $C_1$-$C_4$ alkyl and $R^{2*}$ is as previously defined.

In some embodiments, the compound has Formula Ib:

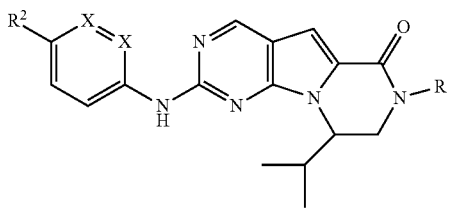

wherein $R^2$ and R are as previously defined.

In some embodiments, the compound has Formula Ib and R is alkyl.

In some embodiments, the compound has Formula Ib and R is H.

In some embodiments, the compound has Formula Ib and $R^2$ is

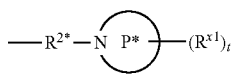

wherein P* is a 4- to 8-membered mono- or bicyclic saturated heterocyclyl group and $R^{2*}$, $R^{x1}$ and t are as previously defined.

In some embodiments, the compound has Formula Ib and $R^2$ is

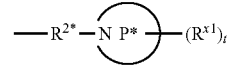

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ic:

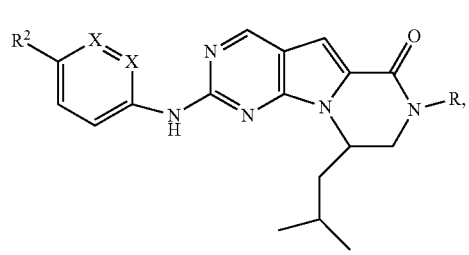

wherein $R^2$ and R are as previously defined.

In some embodiments, the compound has Formula Ic and R is alkyl.

In some embodiments, the compound has Formula Ic and R is H.

In some embodiments, the compound has Formula Ic and $R^2$ is

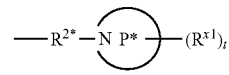

wherein P* is a 4- to 8-membered mono- or bicyclic saturated heterocyclyl group and $R^{2*}$, $R^{x1}$ and t are as previously defined.

In some embodiments, the compound has Formula Ic and $R^2$ is

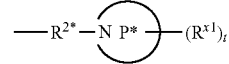

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Id:

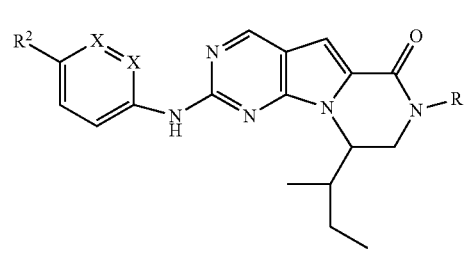

wherein $R^2$ and R are as previously defined.

In some embodiments, the compound has Formula Id and R is alkyl.

In some embodiments, the compound has Formula Id and R is H.

In some embodiments, the compound has Formula Id and $R^2$ is

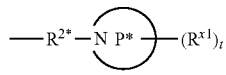

wherein P* is a 4- to 8-membered mono- or bicyclic saturated heterocyclyl group and $R^{2*}$, $R^{x1}$ and t are as previously defined.

In some embodiments, the compound has Formula Id and $R^2$ is

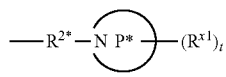

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ie:

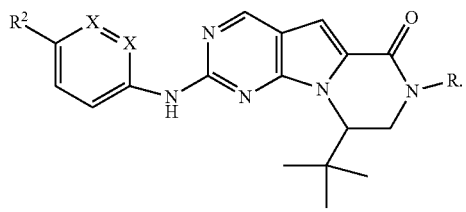

In some embodiments, the compound has Formula Ie and R is alkyl.

In some embodiments, the compound has Formula Ie and R is H.

In some embodiments, the compound has Formula Ie and $R^2$ is

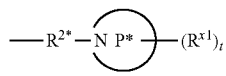

wherein P* is a 4- to 8-membered mono- or bicyclic saturated heterocyclyl group and $R^{2*}$, $R^x$ and t are as previously defined.

In some embodiments, the compound has Formula Ie and $R^2$ is

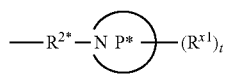

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula If:

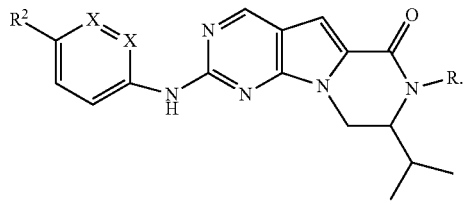

In some embodiments, the compound has Formula If and R is alkyl.

In some embodiments, the compound has Formula If and R is H.

In some embodiments, the compound has Formula If and $R^2$ is

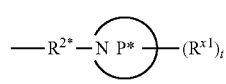

wherein P* is a 4- to 8-membered mono- or bicyclic saturated heterocyclyl group and $R^{2*}$, $R^{x1}$ and t are as previously defined.

In some embodiments, the compound has Formula If and $R^2$ is

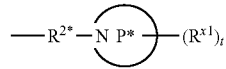

wherein P* is a 4- to 8-membered mono- or bicyclic saturated heterocyclyl group, $R^{x1}$ is hydrogen or $C_1$-$C_4$ alkyl and $R^{2*}$ is as previously defined.

In some embodiments, the compound has Formula Ig:

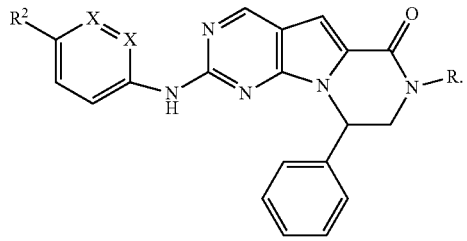

In some embodiments, the compound has Formula Ig and R is alkyl.

In some embodiments, the compound has Formula Ig and R is H.

In some embodiments, the compound has Formula Ig and $R^2$ is

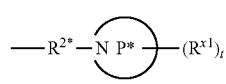

wherein P* is a 4- to 8-membered mono- or bicyclic saturated heterocyclyl group and $R^{2*}$, $R^{x1}$ and t are as previously defined.

In some embodiments, the compound has Formula Ig and R² is

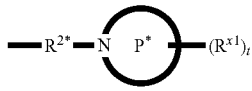

wherein P* is a 4- to 8-membered mono- or bicyclic saturated heterocyclyl group, R^{x1} is hydrogen or $C_1$-$C_4$ alkyl and R^{2*} is as previously defined.

In some embodiments, the compound has Formula Ih:

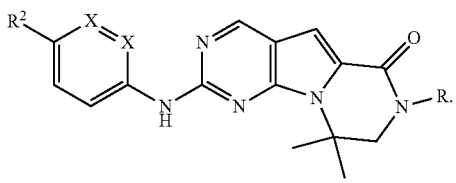

In some embodiments, the compound has Formula Ih and R is alkyl.

In some embodiments, the compound has Formula Ih and R is H.

In some embodiments, the compound has Formula Ih and R² is

wherein P* is a 4- to 8-membered mono- or bicyclic saturated heterocyclyl group and R^{2*}, R^{x1} and t are as previously defined.

In some embodiments, the compound has Formula Ih and R² is

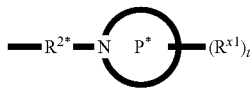

wherein P* is a 4- to 8-membered mono- or bicyclic saturated heterocyclyl group, R^{x1} is hydrogen or $C_1$-$C_4$ alkyl and R^{2*} is as previously defined.

In some embodiments, the compound has Formula Ii:

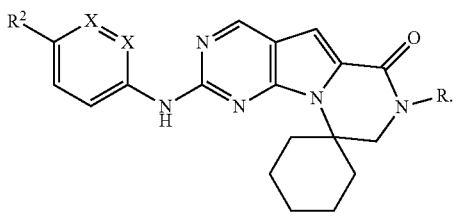

In some embodiments, the compound has Formula Ii and R is alkyl.

In some embodiments, the compound has Formula Ii and R is H.

In some embodiments, the compound has Formula Ii and R² is

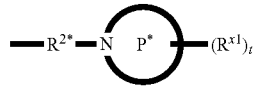

wherein P* is a 4- to 8-membered mono- or bicyclic saturated heterocyclyl group and R^{2*}, R^{x1} and t are as previously defined.

In some embodiments, the compound has Formula Ii and R² is

wherein P* is a 4- to 8-membered mono- or bicyclic saturated heterocyclyl group, R^{x1} is hydrogen or $C_1$-$C_4$ alkyl and R^{2*} is as previously defined.

In some embodiments, the compound has Formula Ij:

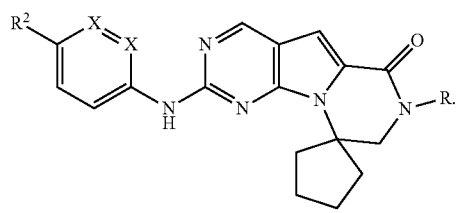

In some embodiments, the compound has Formula Ij and R is alkyl.

In some embodiments, the compound has Formula Ij and R is H.

In some embodiments, the compound has Formula Ij and R² is

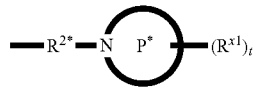

wherein P* is a 4- to 8-membered mono- or bicyclic saturated heterocyclyl group.

In some embodiments, the compound has Formula Ij and R² is

wherein P* is a 4- to 8-membered mono- or bicyclic saturated heterocyclyl group, R^{x1} is hydrogen or $C_1$-$C_4$ alkyl.

In some embodiments, the compound has Formula Ij and R is H, and both X are N.

In some embodiments, the compound has the structure:

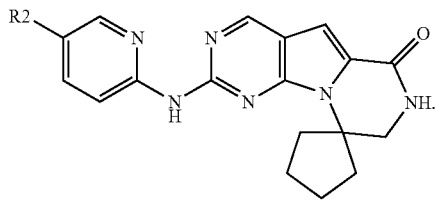

In some embodiments, the compound has Formula Ik and R² is

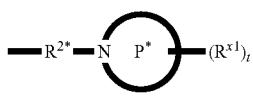

wherein P* is a 4- to 8-membered mono- or bicyclic saturated heterocyclyl group.

In some embodiments, the compound has Formula Ik and R² is

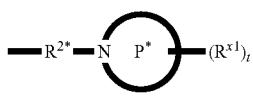

wherein P* is a 4- to 8-membered mono- or bicyclic saturated heterocyclyl group, $R^{x1}$ is hydrogen or $C_1$-$C_4$ alkyl.

In some embodiments, the compound has Formula Il:

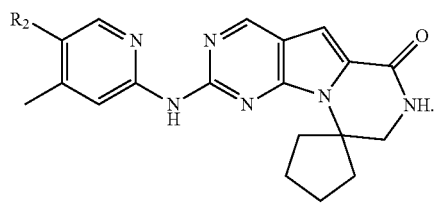

In some embodiments, the compound has Formula Il and R² is

wherein P* is a 4- to 8-membered mono- or bicyclic saturated heterocyclyl group.

In some embodiments, the compound has Formula Il and R² is

wherein P* is a 4- to 8-membered mono- or bicyclic saturated heterocyclyl group, $R^d$ is hydrogen or $C_1$-$C_4$ alkyl.

In some embodiments, the compound has Formula Im:

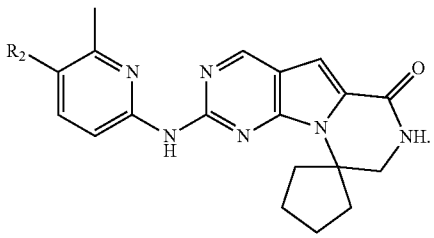

In some embodiments, the compound has Formula Im and R² is

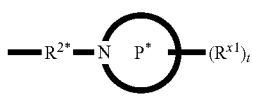

wherein P* is a 4- to 8-membered mono- or bicyclic saturated heterocyclyl group.

In some embodiments, the compound has Formula Im and R² is

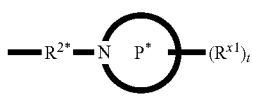

wherein P* is a 4- to 8-membered mono- or bicyclic saturated heterocyclyl group, $R^{x1}$ is hydrogen or $C_1$-$C_4$ alkyl.

In some embodiments, the compound has Formula IIa:

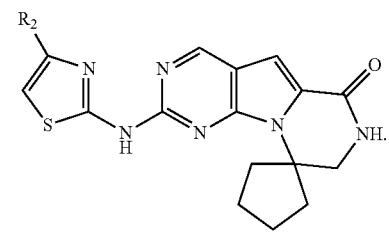

In some embodiments, the compound has Formula IIa and R² is

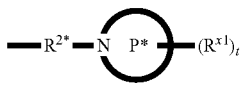

wherein P* is a 4- to 8-membered mono- or bicyclic saturated heterocyclyl group.

In some embodiments, the compound has Formula IIa and R² is

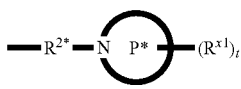

wherein P* is a 4- to 8-membered mono- or bicyclic saturated heterocyclyl group, R$^{x1}$ is hydrogen or C$_1$-C$_4$ alkyl.

In some embodiments, the compound has Formula IIb:

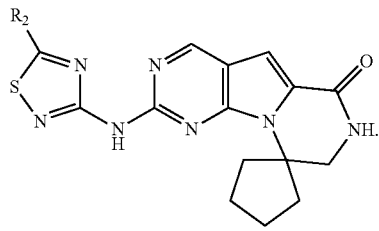

In some embodiments, the compound has Formula Im and R$^2$ is

wherein P* is a 4- to 8-membered mono- or bicyclic saturated heterocyclyl group.

In some embodiments, the compound has Formula Im and R$^2$ is

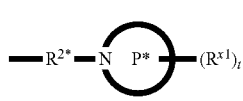

wherein P* is a 4- to 8-membered mono- or bicyclic saturated heterocyclyl group, R$^{x1}$ is hydrogen or C$_1$-C$_4$ alkyl.

In some aspects, the active compound is:

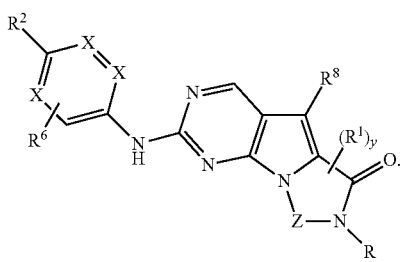

In certain embodiments, the compound is selected from:

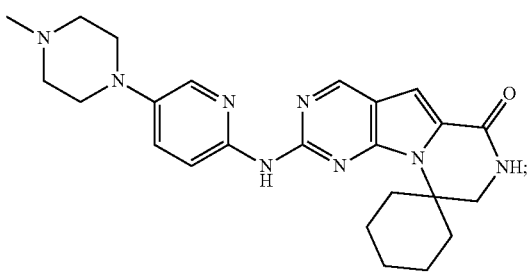
T

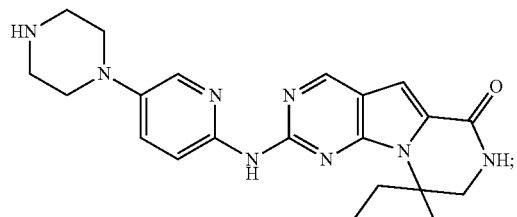
Q

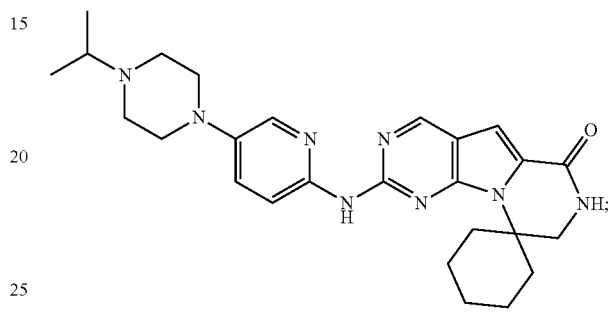
GG

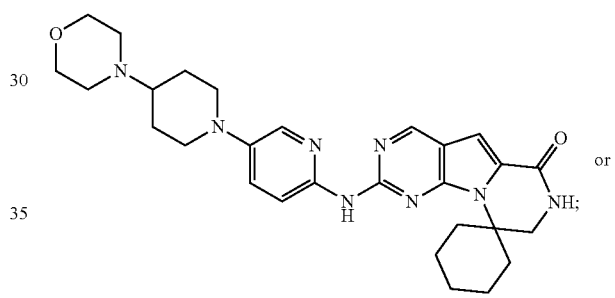
U

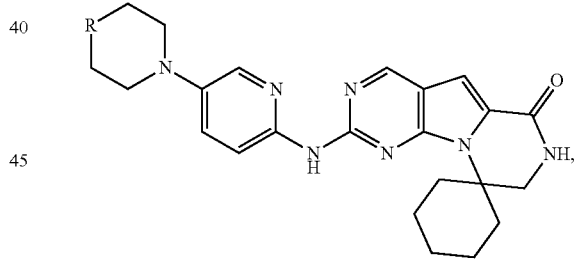
AAAA wherein R is C(H)X, NX, C(H)Y, or C(X)$_2$, where X is straight, branched or cyclic C$_1$ to C$_5$ alkyl group, including methyl, ethyl, propyl, cyclopropyl, isopropyl, butyl, sec-butyl, tert-butyl, isobutyl, cyclobutyl, pentyl, isopentyl, neopentyl, tert-pentyl, sec-pentyl, and cyclopentyl; and Y is NR$_1$R$_2$ wherein R$_1$ and R$_2$ are independently X, or wherein R$_1$ and R$_2$ are alkyl groups that together form a bridge that includes one or two heteroatoms (N, O, or S);

And wherein two X groups can together form an alkyl bridge or a bridge that includes one or two heteroatoms (N, S, or O) to form a spiro compound.

The IUPAC name for Formula T is 2'-((5-(4-methylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-

6'-one; for Formula Q is 2'-((5-(piperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one; for Formula GG is 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one; and for Formula U is 2'-((5-(4-morpholinopiperidin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one.

Further specific compounds that fall within the present invention and that can be used in the disclosed methods of treatment and compositions include the structures listed in Table 1 below.

TABLE 1

Structures of CDK4/6 Inhibitors

| Structure Reference | Structure |
|---|---|
| A | 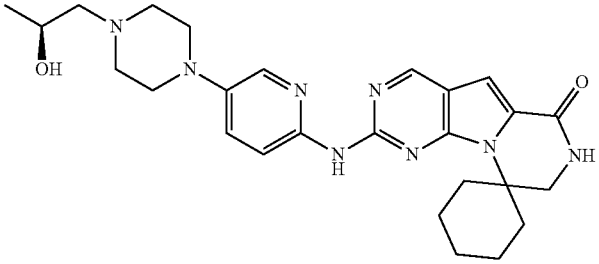 [SMILES: C[C@H](O)CN1CCN(c2ccc(Nc3ncc4cc5n(c4n3)C3(CCCCC3)CNC5=O)nc2)CC1] |
| B | 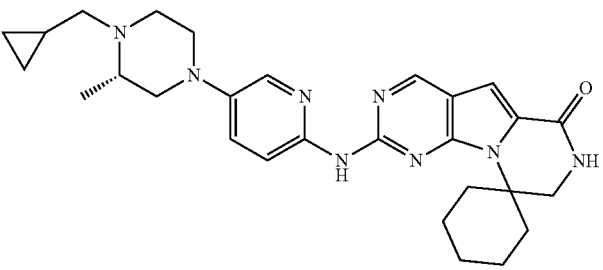 [SMILES: C[C@H]1CN(c2ccc(Nc3ncc4cc5n(c4n3)C3(CCCCC3)CNC5=O)nc2)CCN1CC1CC1] |
| C | 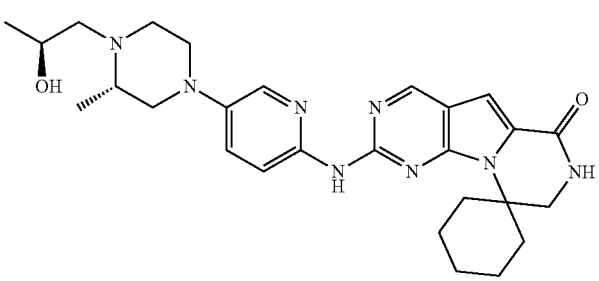 [SMILES: C[C@H](O)CN1CCN(c2ccc(Nc3ncc4cc5n(c4n3)C3(CCCCC3)CNC5=O)nc2)C[C@@H]1C] |
| D | 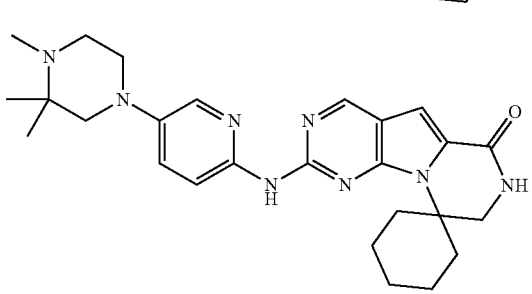 |
| E | 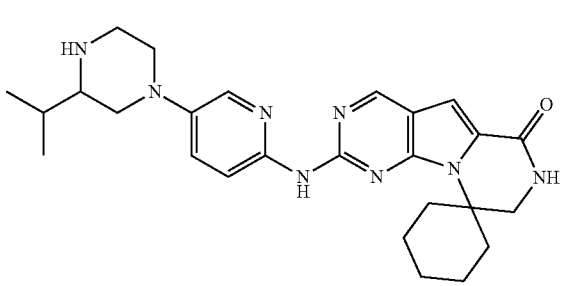 [SMILES: CC(C)C1CN(c2ccc(Nc3ncc4cc5n(c4n3)C3(CCCCC3)CNC5=O)nc2)CCN1] |

TABLE 1-continued
Structures of CDK4/6 Inhibitors
| Structure Reference | Structure |
|---|---|
| F | 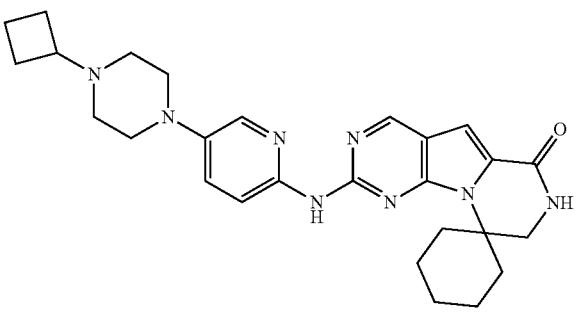 [SMILES: O=C1NCC2(CCCCC2)n2c1cc1cnc(Nc3ccc(N4CCN(C5CCC5)CC4)cn3)nc12] |
| G | 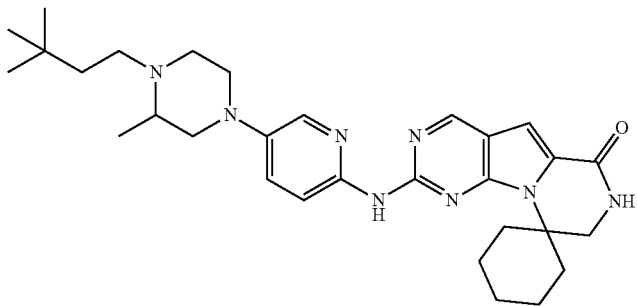 [SMILES: CC1CN(c2ccc(Nc3ncc4cc5n(c4n3)C3(CCCCC3)CNC5=O)nc2)CCN1CCC(C)(C)C] |
| H | 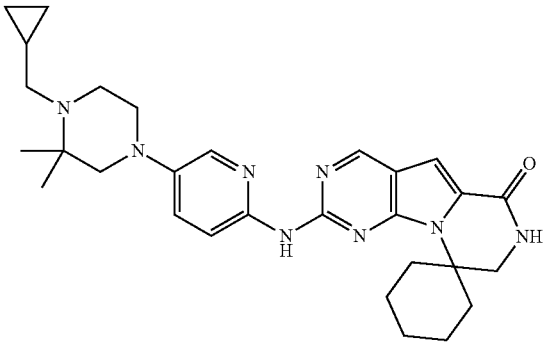 [SMILES: CC1(C)CN(c2ccc(Nc3ncc4cc5n(c4n3)C3(CCCCC3)CNC5=O)nc2)CCN1CC1CC1] |
| I | 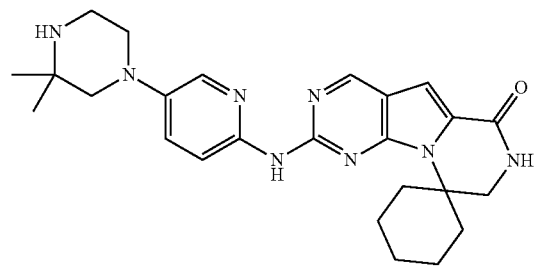 [SMILES: CC1(C)CN(c2ccc(Nc3ncc4cc5n(c4n3)C3(CCCCC3)CNC5=O)nc2)CCN1] |
| J | 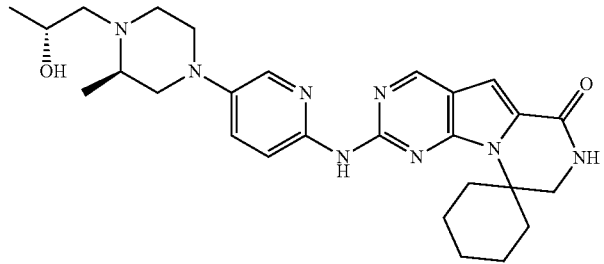 [SMILES: C[C@@H]1CN(c2ccc(Nc3ncc4cc5n(c4n3)C3(CCCCC3)CNC5=O)nc2)CCN1C[C@@H](C)O] |

TABLE 1-continued
Structures of CDK4/6 Inhibitors
| Structure Reference | Structure |
|---|---|
| K | 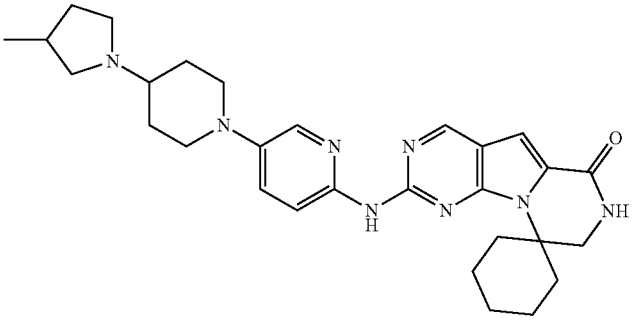 [SMILES: CC1CCN(C2CCN(c3ccc(Nc4ncc5cc6n(c5n4)C4(CCCCC4)CNC6=O)nc3)CC2)C1] |
| L | 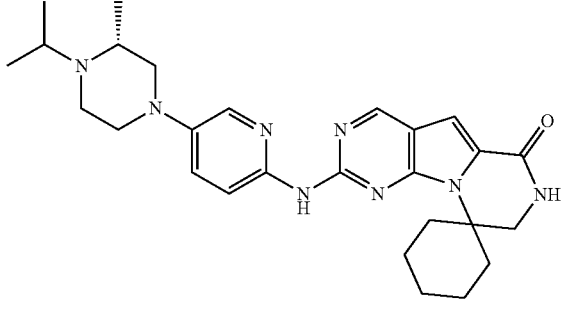 [SMILES: CC(C)N1CCN(c2ccc(Nc3ncc4cc5n(c4n3)C3(CCCCC3)CNC5=O)nc2)C[C@H]1C] |
| M | 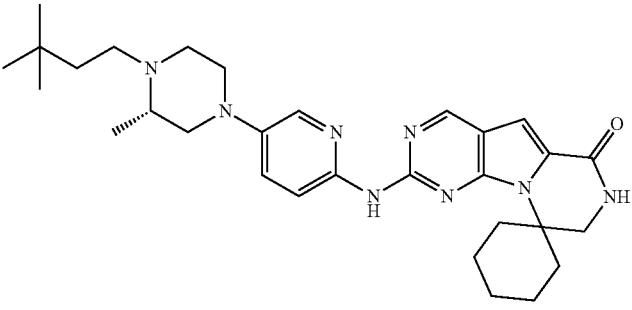 [SMILES: C[C@H]1CN(c2ccc(Nc3ncc4cc5n(c4n3)C3(CCCCC3)CNC5=O)nc2)CCN1CCC(C)(C)C] |
| N | 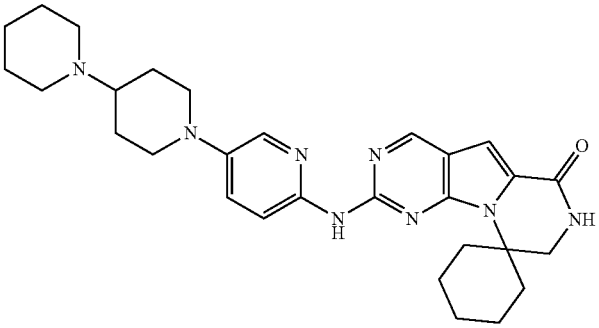 [SMILES: O=C1NCC2(CCCCC2)n2c1cc1cnc(Nc3ccc(N4CCC(N5CCCCC5)CC4)cn3)nc12] |

TABLE 1-continued
Structures of CDK4/6 Inhibitors
| Structure Reference | Structure |
|---|---|
| O | 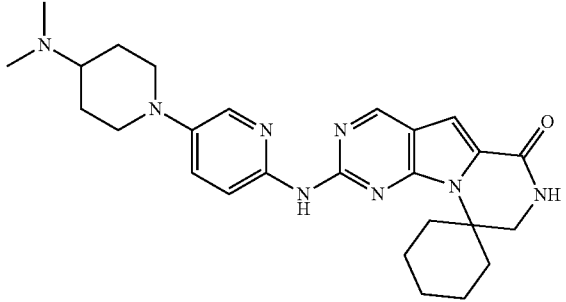 |
| P | 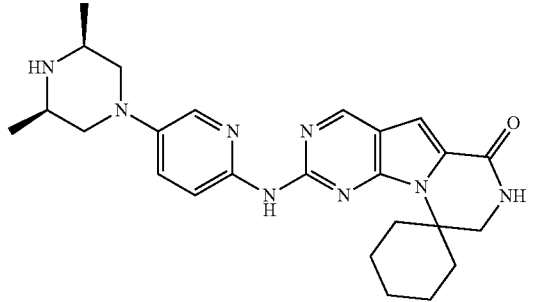 [SMILES: C[C@@H]1CN(c2ccc(Nc3ncc4cc5n(c4n3)C3(CCCCC3)CNC5=O)nc2)C[C@H](C)N1] |
| Q | 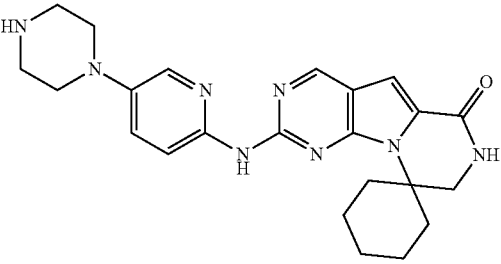 [SMILES: O=C1NCC2(CCCCC2)n2c1cc1cnc(Nc3ccc(N4CCNCC4)cn3)nc12] |
| R | 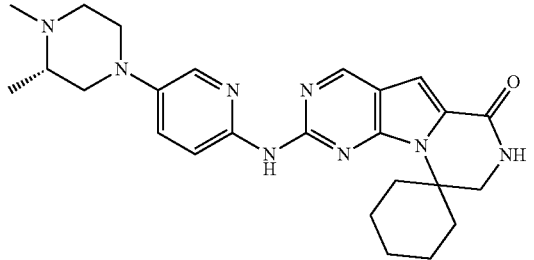 |
| S | 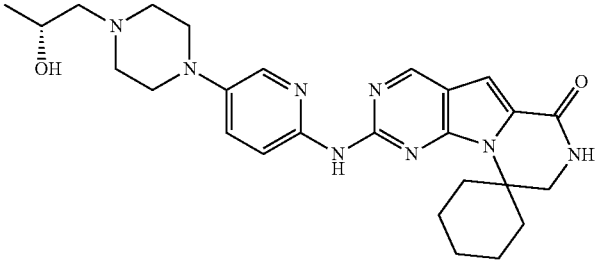 [SMILES: C[C@@H](O)CN1CCN(c2ccc(Nc3ncc4cc5n(c4n3)C3(CCCCC3)CNC5=O)nc2)CC1] |

TABLE 1-continued
Structures of CDK4/6 Inhibitors
| Structure Reference | Structure |
|---|---|
| T | 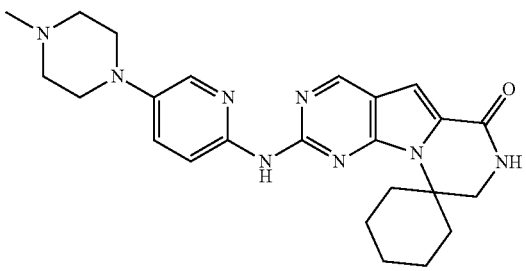 [SMILES: CN1CCN(c2ccc(Nc3ncc4cc5n(c4n3)C3(CCCCC3)CNC5=O)nc2)CC1] |
| U | 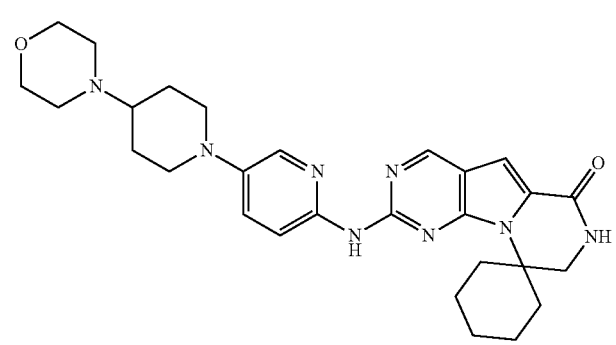 [SMILES: O=C1NCC2(CCCCC2)n2c1cc1cnc(Nc3ccc(N4CCC(N5CCOCC5)CC4)cn3)nc12] |
| V | 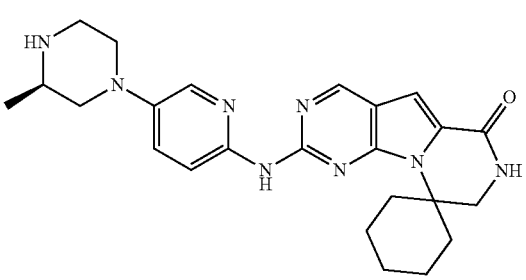 [SMILES: C[C@@H]1CN(c2ccc(Nc3ncc4cc5n(c4n3)C3(CCCCC3)CNC5=O)nc2)CCN1] |
| W | 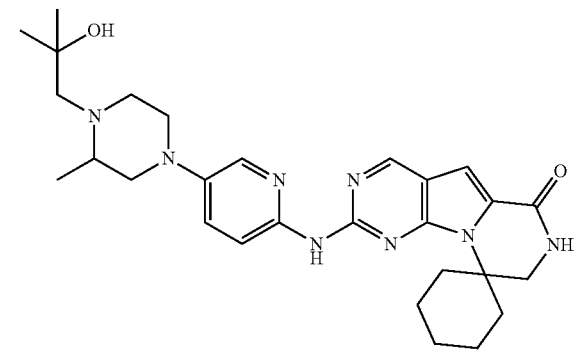 [SMILES: CC1CN(c2ccc(Nc3ncc4cc5n(c4n3)C3(CCCCC3)CNC5=O)nc2)CCN1CC(C)(C)O] |

TABLE 1-continued
Structures of CDK4/6 Inhibitors
| Structure Reference | Structure |
|---|---|
| X | 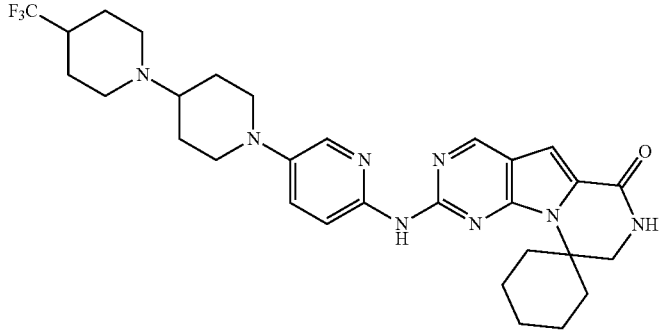 [SMILES: O=C1NCC2(CCCCC2)n2c1cc1cnc(Nc3ccc(N4CCC(N5CCC(C(F)(F)F)CC5)CC4)cn3)nc12] |
| Y | 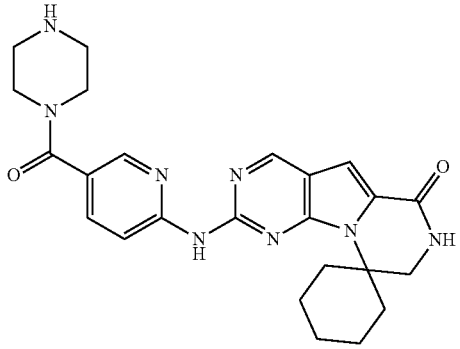 [SMILES: O=C1NCC2(CCCCC2)n2c1cc1cnc(Nc3ccc(C(=O)N4CCNCC4)cn3)nc12] |
| Z | 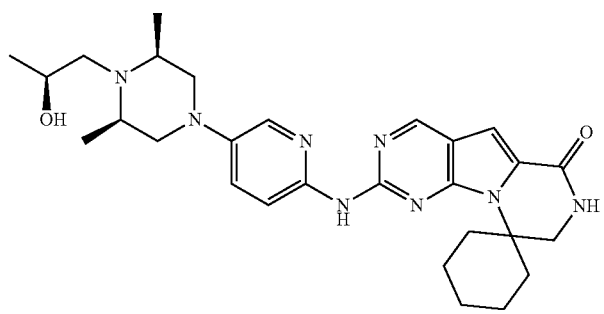 [SMILES: C[C@H](O)CN1[C@H](C)CN(c2ccc(Nc3ncc4cc5n(c4n3)C3(CCCCC3)CNC5=O)nc2)C[C@@H]1C] |
| AA | 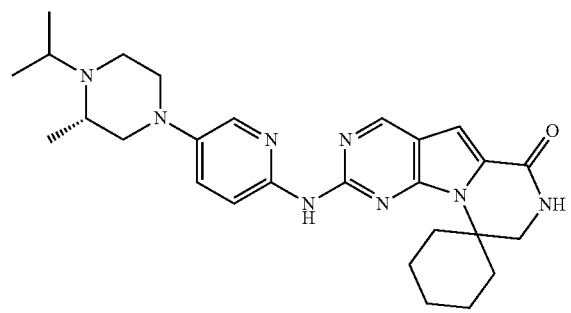 [SMILES: CC(C)N1CCN(c2ccc(Nc3ncc4cc5n(c4n3)C3(CCCCC3)CNC5=O)nc2)C[C@@H]1C] |

TABLE 1-continued

Structures of CDK4/6 Inhibitors

| Structure Reference | Structure |
|---|---|
| BB | 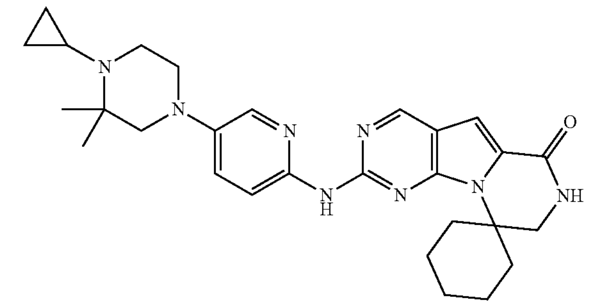 [SMILES: CC1(C)CN(c2ccc(Nc3ncc4cc5n(c4n3)C3(CCCCC3)CNC5=O)nc2)CCN1C1CC1] |
| CC | 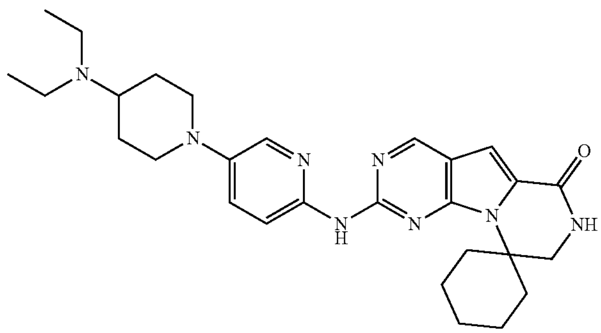 [SMILES: CCN(CC)C1CCN(c2ccc(Nc3ncc4cc5n(c4n3)C3(CCCCC3)CNC5=O)nc2)CC1] |
| DD | 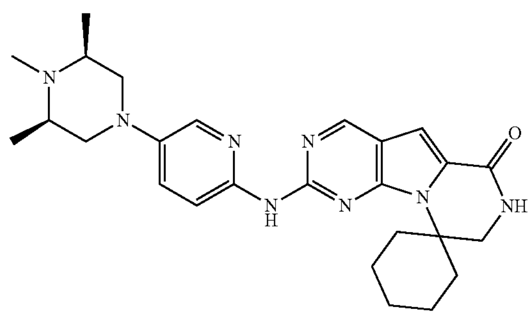 [SMILES: C[C@@H]1CN(c2ccc(Nc3ncc4cc5n(c4n3)C3(CCCCC3)CNC5=O)nc2)C[C@H](C)N1C] |
| EE | 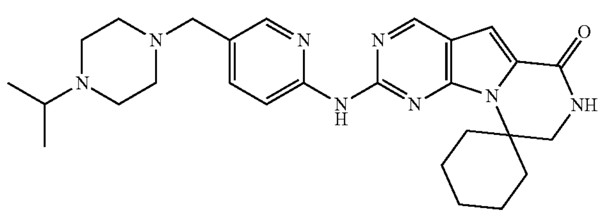 [SMILES: CC(C)N1CCN(Cc2ccc(Nc3ncc4cc5n(c4n3)C3(CCCCC3)CNC5=O)nc2)CC1] |
| FF | 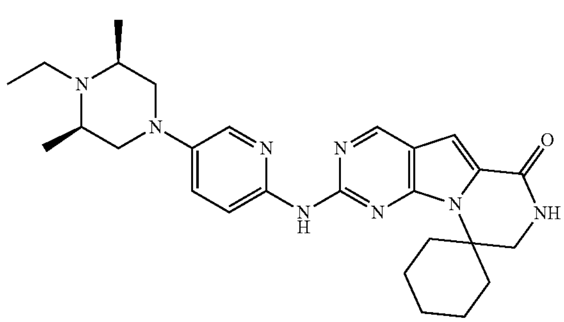 [SMILES: CCN1[C@H](C)CN(c2ccc(Nc3ncc4cc5n(c4n3)C3(CCCCC3)CNC5=O)nc2)C[C@@H]1C] |

TABLE 1-continued

Structures of CDK4/6 Inhibitors

| Structure Reference | Structure |
|---|---|
| GG | 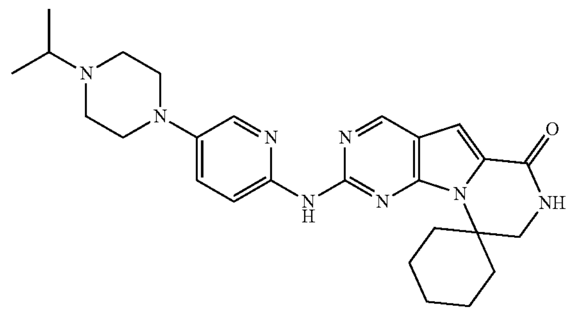 [SMILES: CC(C)N1CCN(c2ccc(Nc3ncc4cc5n(c4n3)C3(CCCCC3)CNC5=O)nc2)CC1] |
| HH | 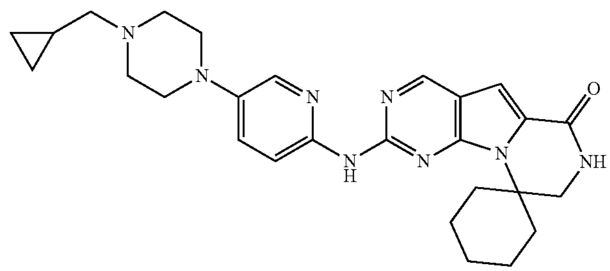 [SMILES: O=C1NCC2(CCCCC2)n2c1cc1cnc(Nc3ccc(N4CCN(CC5CC5)CC4)cn3)nc12] |
| II | 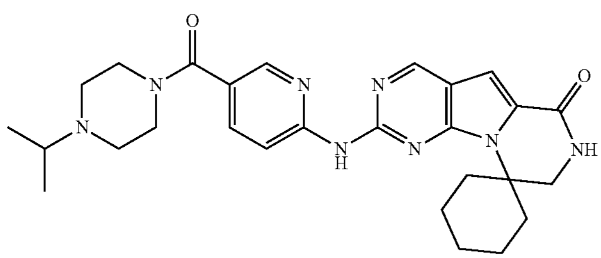 [SMILES: CC(C)N1CCN(C(=O)c2ccc(Nc3ncc4cc5n(c4n3)C3(CCCCC3)CNC5=O)nc2)CC1] |
| JJ | 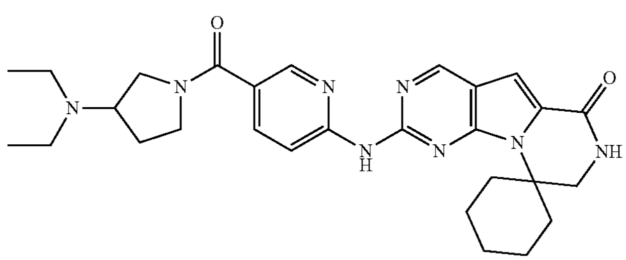 [SMILES: CCN(CC)C1CCN(C(=O)c2ccc(Nc3ncc4cc5n(c4n3)C3(CCCCC3)CNC5=O)nc2)C1] |
| KK | 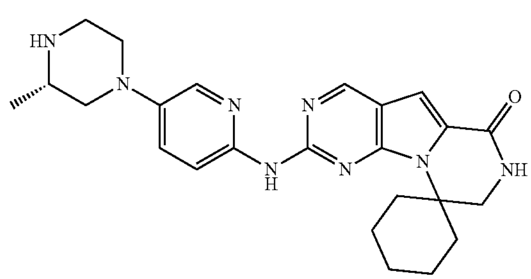 [SMILES: C[C@H]1CN(c2ccc(Nc3ncc4cc5n(c4n3)C3(CCCCC3)CNC5=O)nc2)CCN1] |

TABLE 1-continued
Structures of CDK4/6 Inhibitors
| Structure Reference | Structure |
|---|---|
| LL | 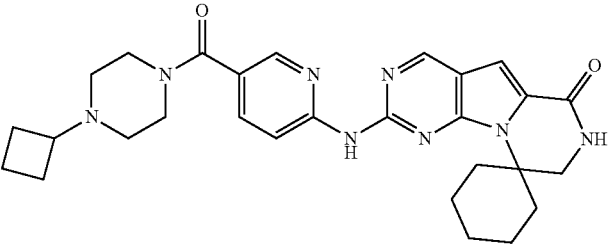 [SMILES: O=C1NCC2(CCCCC2)n2c1cc1cnc(Nc3ccc(C(=O)N4CCN(C5CCC5)CC4)cn3)nc12] |
| MM | 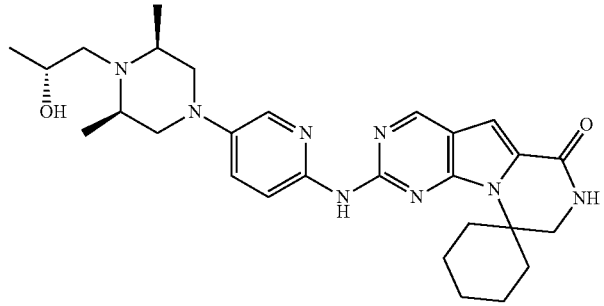 [SMILES: C[C@@H]1CN(c2ccc(Nc3ncc4cc5n(c4n3)C3(CCCCC3)CNC5=O)nc2)C[C@H](C)N1C[C@@H](C)O] |
| NN | 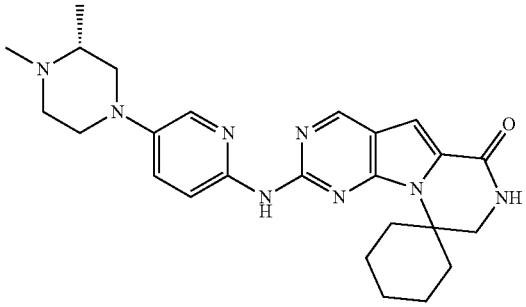 [SMILES: C[C@@H]1CN(c2ccc(Nc3ncc4cc5n(c4n3)C3(CCCCC3)CNC5=O)nc2)CCN1C] |
| OO | 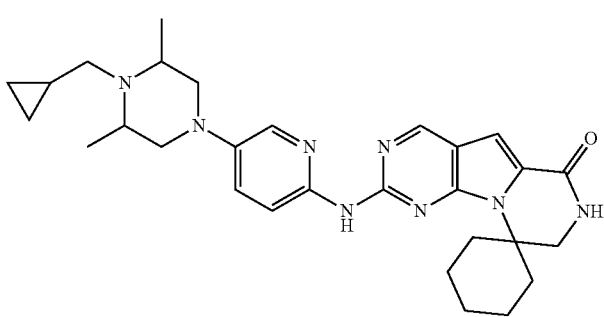 [SMILES: CC1CN(c2ccc(Nc3ncc4cc5n(c4n3)C3(CCCCC3)CNC5=O)nc2)CC(C)N1CC1CC1] |
| PP | 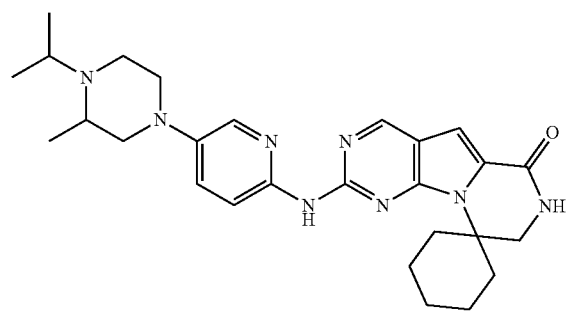 [SMILES: CC(C)N1CCN(c2ccc(Nc3ncc4cc5n(c4n3)C3(CCCCC3)CNC5=O)nc2)CC1C] |

TABLE 1-continued
Structures of CDK4/6 Inhibitors
| Structure Reference | Structure |
|---|---|
| QQ | 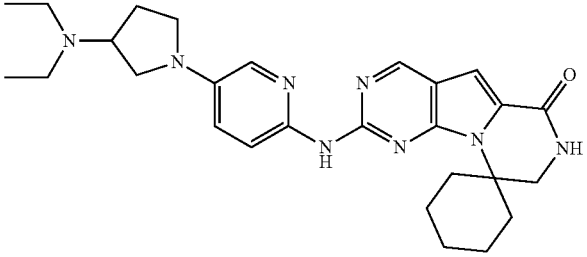 [SMILES: CCN(CC)C1CCN(c2ccc(Nc3ncc4cc5n(c4n3)C3(CCCCC3)CNC5=O)nc2)C1] |
| RR | 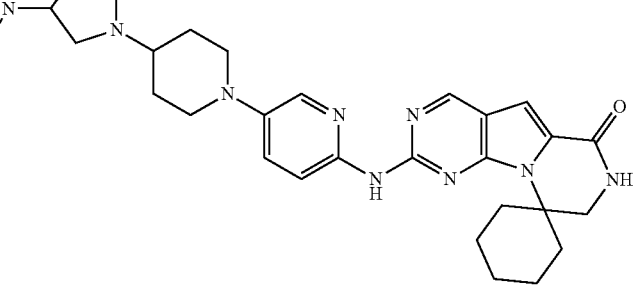 |
| SS | 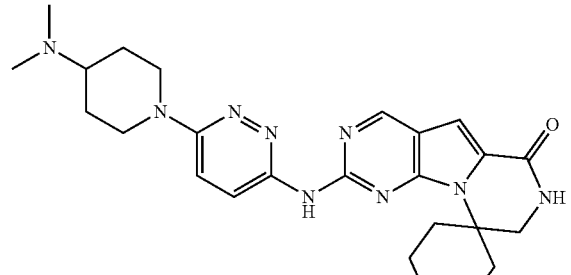 |
| TT | 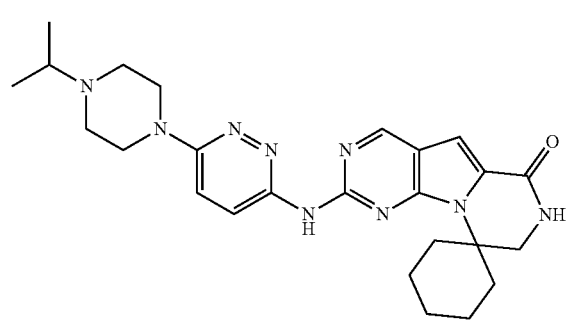 [SMILES: CN(C)C1CCN(c2ccc(Nc3ncc4cc5n(c4n3)C3(CCCCC3)CNC5=O)nn2)CC1] |
| UU | 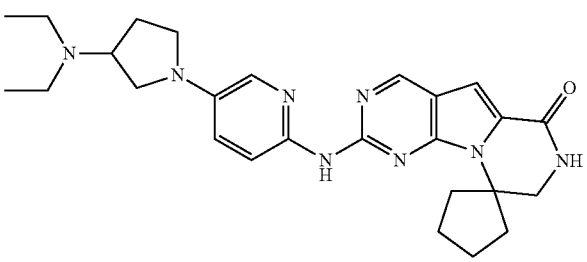 [SMILES: CCN(CC)C1CCN(c2ccc(Nc3ncc4cc5n(c4n3)C3(CCCC3)CNC5=O)nc2)C1] |

TABLE 1-continued

Structures of CDK4/6 Inhibitors

| Structure Reference | Structure |
|---|---|
| VV | *(chemical structure)* |
| WW | *(chemical structure)* |
| XX | *(chemical structure)* |
| YY | *(chemical structure)* |
| ZZ | *(chemical structure)* |

TABLE 1-continued
Structures of CDK4/6 Inhibitors
| Structure Reference | Structure |
|---|---|
| AAA | 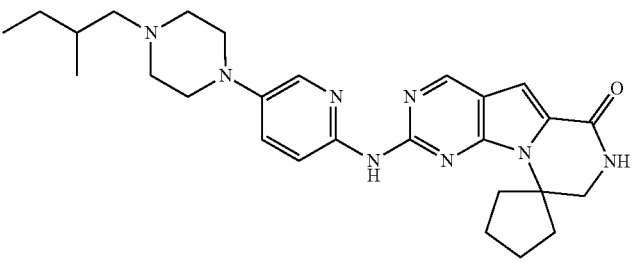 [SMILES: CCC(C)CN1CCN(c2ccc(Nc3ncc4cc5n(c4n3)C3(CCCC3)CNC5=O)nc2)CC1] |
| BBB | 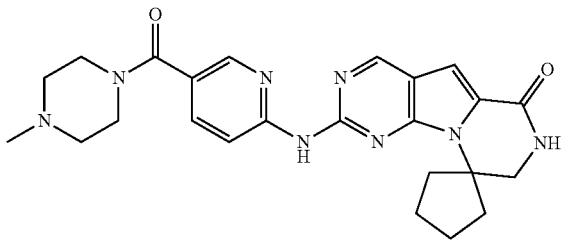 [SMILES: CN1CCN(C(=O)c2ccc(Nc3ncc4cc5n(c4n3)C3(CCCC3)CNC5=O)nc2)CC1] |
| CCC | 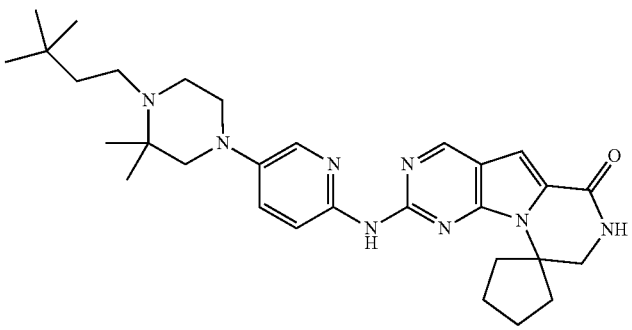 [SMILES: CC(C)(C)CCN1CCN(c2ccc(Nc3ncc4cc5n(c4n3)C3(CCCC3)CNC5=O)nc2)CC1(C)C] |
| DDD | 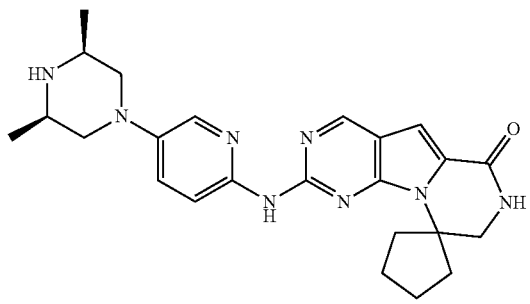 [SMILES: C[C@@H]1CN(c2ccc(Nc3ncc4cc5n(c4n3)C3(CCCC3)CNC5=O)nc2)C[C@H](C)N1] |
| EEE | 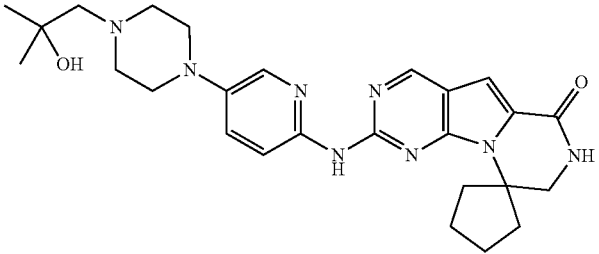 [SMILES: CC(C)(O)CN1CCN(c2ccc(Nc3ncc4cc5n(c4n3)C3(CCCC3)CNC5=O)nc2)CC1] |

TABLE 1-continued
Structures of CDK4/6 Inhibitors
| Structure Reference | Structure |
|---|---|
| FFF | 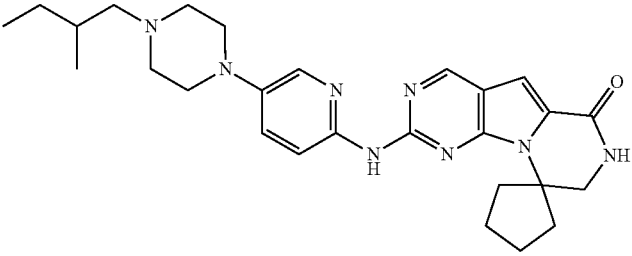 [SMILES: CCC(C)CN1CCN(c2ccc(Nc3ncc4cc5n(c4n3)C3(CCCC3)CNC5=O)nc2)CC1] |
| GGG | 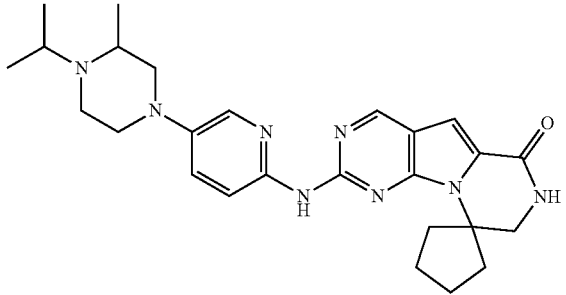 [SMILES: CC(C)N1CCN(c2ccc(Nc3ncc4cc5n(c4n3)C3(CCCC3)CNC5=O)nc2)CC1C] |
| HHH | 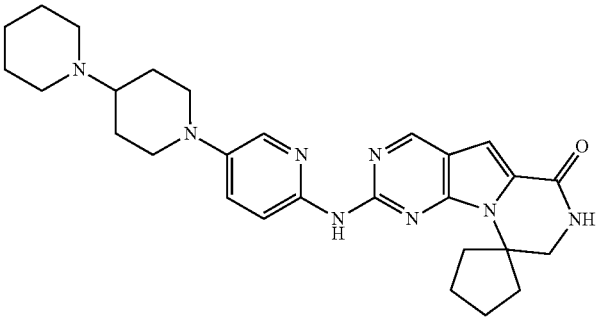 [SMILES: O=C1NCC2(CCCC2)n2c1cc1cnc(Nc3ccc(N4CCC(N5CCCCC5)CC4)cn3)nc12] |
| III | 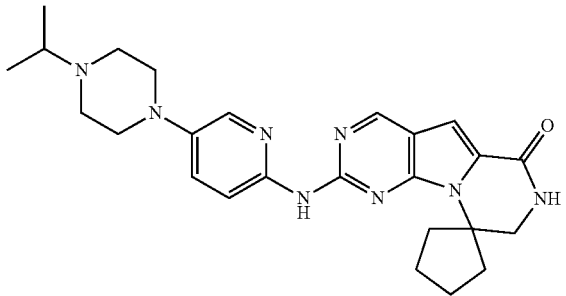 [SMILES: CC(C)N1CCN(c2ccc(Nc3ncc4cc5n(c4n3)C3(CCCC3)CNC5=O)nc2)CC1] |
| JJJ | 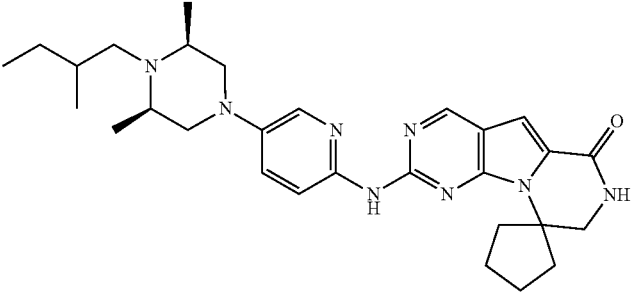 [SMILES: CCC(C)CN1[C@H](C)CN(c2ccc(Nc3ncc4cc5n(c4n3)C3(CCCC3)CNC5=O)nc2)C[C@@H]1C] |

TABLE 1-continued

Structures of CDK4/6 Inhibitors

| Structure Reference | Structure |
|---|---|
| KKK | 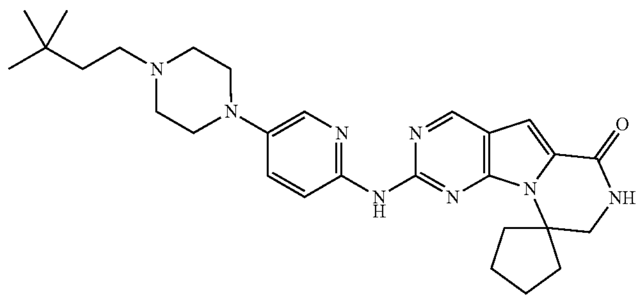 [SMILES: CC(C)(C)CCN1CCN(c2ccc(Nc3ncc4cc5n(c4n3)C3(CCCC3)CNC5=O)nc2)CC1] |
| LLL | 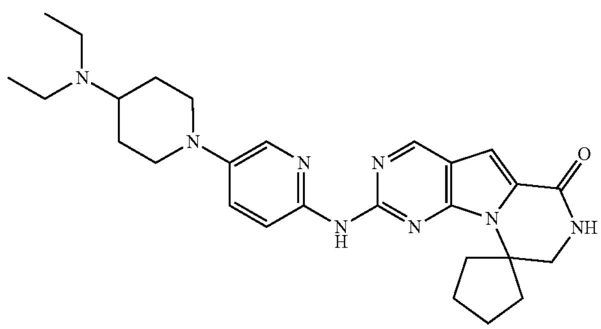 [SMILES: CCN(CC)C1CCN(c2ccc(Nc3ncc4cc5n(c4n3)C3(CCCC3)CNC5=O)nc2)CC1] |
| MMM | 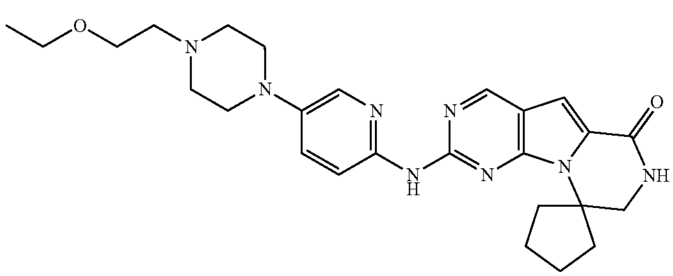 [SMILES: CCOCCN1CCN(c2ccc(Nc3ncc4cc5n(c4n3)C3(CCCC3)CNC5=O)nc2)CC1] |
| NNN | 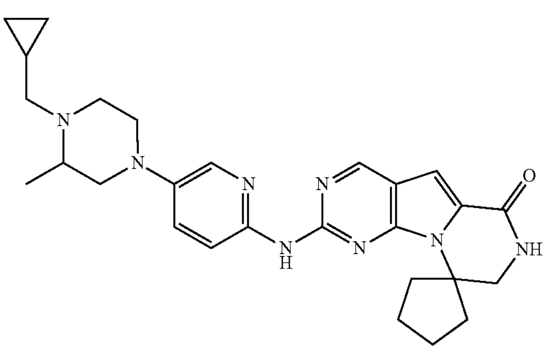 [SMILES: CC1CN(c2ccc(Nc3ncc4cc5n(c4n3)C3(CCCC3)CNC5=O)nc2)CCN1CC1CC1] |
| OOO | 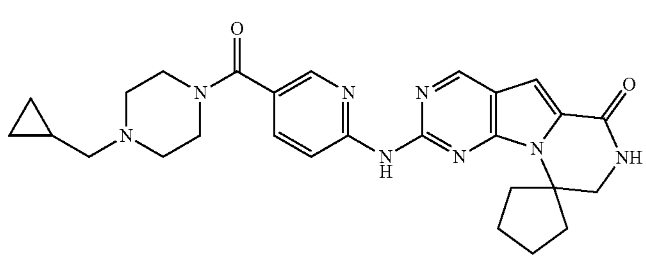 [SMILES: O=C1NCC2(CCCC2)n2c1cc1cnc(Nc3ccc(C(=O)N4CCN(CC5CC5)CC4)cn3)nc12] |

TABLE 1-continued
Structures of CDK4/6 Inhibitors
| Structure Reference | Structure |
|---|---|
| PPP | 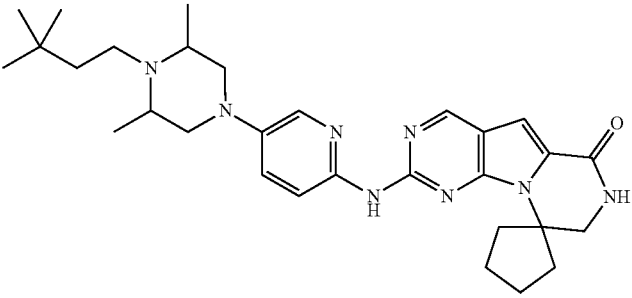 [SMILES: CC1CN(c2ccc(Nc3ncc4cc5n(c4n3)C3(CCCC3)CNC5=O)nc2)CC(C)N1CCC(C)(C)C] |
| QQQ | 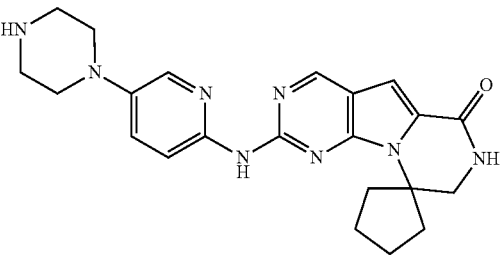 [SMILES: O=C1NCC2(CCCC2)n2c1cc1cnc(Nc3ccc(N4CCNCC4)cn3)nc12] |
| RRR | 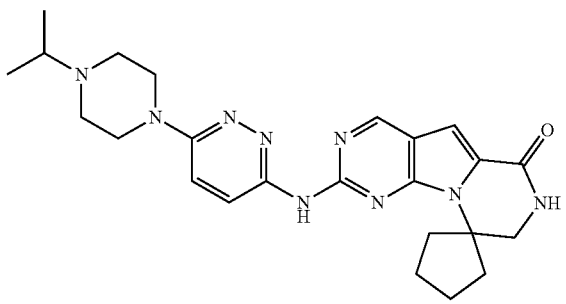 |
| SSS | 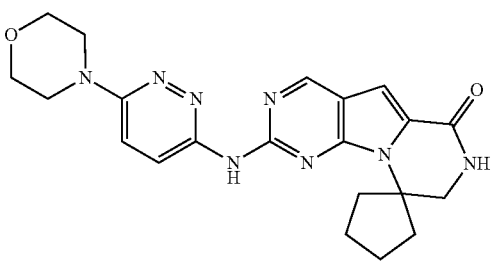 [SMILES: O=C1NCC2(CCCC2)n2c1cc1cnc(Nc3ccc(N4CCOCC4)nn3)nc12] |
| TTT | 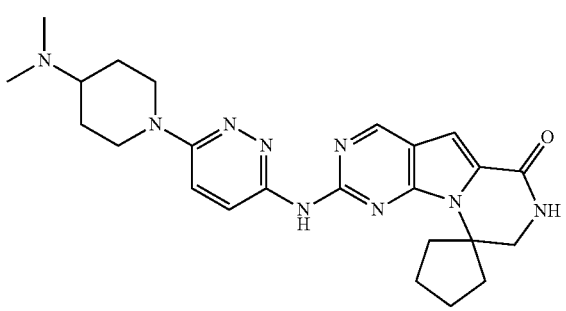 [SMILES: CN(C)C1CCN(c2ccc(Nc3ncc4cc5n(c4n3)C3(CCCC3)CNC5=O)nn2)CC1] |

TABLE 1-continued

Structures of CDK4/6 Inhibitors

| Structure Reference | Structure |
|---|---|
| UUU | 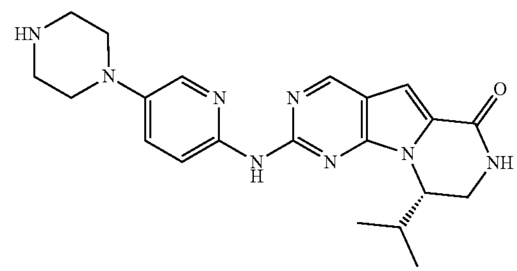 [SMILES: CC(C)[C@H]1CNC(=O)c2cc3cnc(Nc4ccc(N5CCNCC5)cn4)nc3n21] |
| VVV | 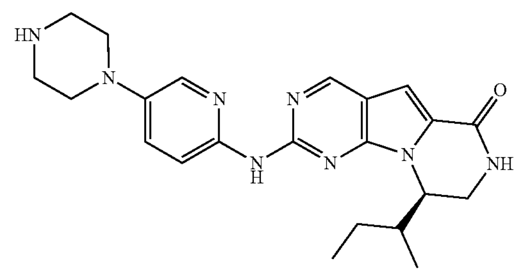 [SMILES: CCC(C)[C@@H]1CNC(=O)c2cc3cnc(Nc4ccc(N5CCNCC5)cn4)nc3n21] |
| WWW | 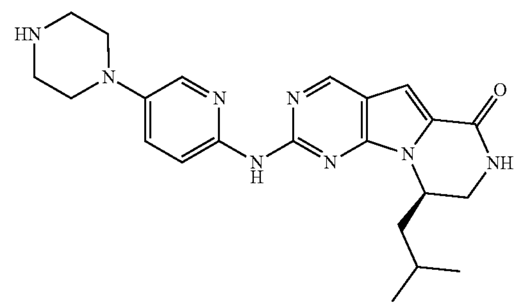 [SMILES: CC(C)C[C@@H]1CNC(=O)c2cc3cnc(Nc4ccc(N5CCNCC5)cn4)nc3n21] |
| XXX | 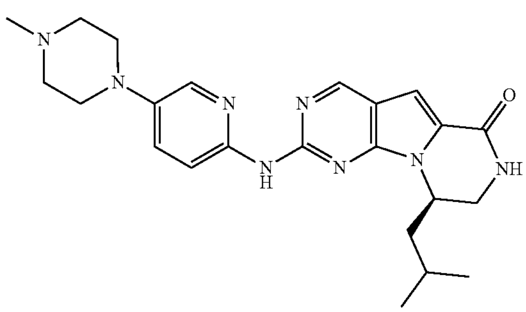 [SMILES: CC(C)C[C@@H]1CNC(=O)c2cc3cnc(Nc4ccc(N5CCN(C)CC5)cn4)nc3n21] |

Isotopic Substitution

The present invention includes compounds and the use of compounds with desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location.

CDK-Replication Dependent Cells and Cyclin-Dependent Kinase Inhibitors

Tissue-specific stem cells and subsets of other resident proliferating cells are capable of self-renewal, meaning that they are capable of replacing themselves throughout the adult mammalian lifespan through regulated replication. Additionally, stem cells divide asymmetrically to produce "progeny" or "progenitor" cells that in turn produce various components of a given organ. For example, in the hematopoietic system, the hematopoietic stem cells give rise to progenitor cells which in turn give rise to all the differentiated components of blood (e.g., white blood cells, red blood cells, and platelets). See FIG. 1.

Certain proliferating cells, such as HSPCs, require the enzymatic activity of the proliferative kinases cyclin-dependent kinase 4 (CDK4) and/or cyclin-dependent kinase 6 (CDK6) for cellular replication. In contrast, the majority of proliferating cells in adult mammals (e.g., the more differentiated blood-forming cells in the bone marrow) do not require the activity of CDK4 and/or CDK6 (i.e., CDK4/6). These differentiated cells can proliferate in the absence of CDK4/6 activity by using other proliferative kinases, such as cyclin-dependent kinase 2 (CDK2) or cyclin-dependent kinase 1 (CDK1).

The CDK4/6 inhibitor administered is selected from the group consisting of a compound or composition comprising Formula I, Formula II, Formula III, Formula IV, or Formula V, or a combination thereof. In one embodiment, the compound is selected from the compounds described in Table 1.

In certain embodiments, the CDK4/6 inhibitor is a CDK4/6 inhibitor of Formula I, II, III, IV, or V or a pharmaceutically acceptable composition, salt, isotopic analog, or prodrug thereof, wherein the protection afforded by the compound is short term and transient in nature, allowing a significant portion of the cells to synchronously renter the cell-cycle quickly following the cessation of the chemotherapeutic agent's effect, for example within less than about 24, 30, 36, or 40 hours. In one embodiment, the compound is selected from the compounds described in Table 1 or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof. Cells that are quiescent within the G1 phase of the cell cycle are more resistant to the damaging effect of chemotherapeutic agents than proliferating cells. CDK4/6 inhibitory compounds for use in the described methods are highly selective, potent CDK4/6 inhibitors, with minimal CDK2 inhibitory activity. In one embodiment, a CDK4/6 compound for use in the methods described herein has a CDK4/CycD1 IC$_{50}$ inhibitory concentration value that is >1500 times, >1800 times, >2000 times, >2200 times, >2500 times, >2700 times, >3000 times, >3200 times or greater lower than its respective IC$_{50}$ concentration value for CDK2/CycE inhibition. In one embodiment, a CDK4/6 inhibitor for use in the methods described herein has an IC$_{50}$ concentration value for CDK4/CycD1 inhibition that is about <1.50 nM, <1.25 nM, <1.0 nM, <0.90 nM, <0.85 nM, <0.80 nM, <0.75 nM, <0.70 nM, <0.65 nM, <0.60 nM, <0.55 nM, or less. In one embodiment, a CDK4/6 inhibitor for use in the methods described herein has an IC$_{50}$ concentration value for CDK2/CycE inhibition that is about >1.0 µM, >1.25 µM, >1.50 µm, >1.75 µM, >2.0 µM, >2.25 µM, >2.50 µM, >2.75 µM, >3.0 µM, >3.25 µM, >3.5 µM or greater. In one embodiment, a CDK4/6 inhibitor for use in the methods described herein has an IC$_{50}$ concentration value for CDK2/CycA IC$_{50}$ that is >0.80 µM, >0.85 µM, >0.90 µM, >0.95 µM, >0.1.0 µM, >1.25 µM, >1.50 µM, >1.75 µM, >2.0 µM, >2.25 µM, >2.50 µM, >2.75 uM, >3.0 µM or greater. In one embodiment, the CDK4/6 inhibitor for use in the methods described herein are selected from the group consisting of Formula I, Formula II, Formula III, Formula IV, or Formula V, or a pharmaceutically acceptable composition, salt, or prodrug, thereof. In one embodiment, the compound is selected from the compounds described in Table 1, or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof.

In one embodiment, the CDK4/6 inhibitors described herein are used in CDK4/6-replication dependent healthy cell cycling strategies wherein a subject is exposed to regular, repeated chemotherapeutic treatments, wherein the healthy cells are G1-arrested when chemotherapeutic agent exposed and allowed to reenter the cell-cycle before the subject's next chemotherapeutic treatment. Such cycling allows CDK4/6-replication dependent cells to regenerate damaged blood cell lineages between regular, repeated treatments, for example those associated with standard chemotherapeutic treatments for cancer, and reduces the risk associated with long term CDK4/6 inhibition. This cycling between a state of G1-arrest and a state of replication is not feasible in limited time-spaced, repeated chemotherapeutic agent exposures using longer acting CDK4/6 inhibitors such as PD0332991, as the lingering G1-arresting effects of the compound prohibit significant and meaningful reentry into the cell-cycle before the next chemotherapeutic agent exposure or delay the healthy cells from entering the cell cycle and reconstituting damaged tissues or cells following treatment cessation.

Proliferative disorders that are treated with chemotherapy include cancerous and non-cancer diseases. In a typical embodiment, the proliferative disorder is a CDK4/6-replication independent disorder. The compounds are effective in protecting healthy CDK4/6-replication dependent cells, for example HSPCs, during chemotherapeutic treatment of a broad range of tumor types, including but not limited to the following: breast, prostate, ovarian, skin, lung, colorectal, brain (i.e., glioma) and renal. Preferably, the selective CDK4/6 inhibitor should not compromise the efficacy of the chemotherapeutic agent or arrest G1 arrest the cancer cells. Many cancers do not depend on the activities of CDK4/6 for proliferation as they can use the proliferative kinases promiscuously (e.g., can use CDK 1/2/4/or 6) or lack the function of the retinoblastoma tumor suppressor protein (Rb), which is inactivated by the CDKs. The potential sensitivity of certain tumors to CDK4/6 inhibition can be deduced based on tumor type and molecular genetics using standard techniques. Cancers that are not typically affected by the inhibition of CDK4/6 are those that can be characterized by one or more of the group including, but not limited to, increased activity of CDK1 or CDK2, loss, deficiency, or absence of retinoblastoma tumor suppressor protein (Rb), high levels of MYC expression, increased cyclin E (e.g., E1 or E2) and increased cyclin A, or expression of a Rb-inactivating protein (such as HPV-encoded E7). Such cancers can include, but are not limited to, small cell lung cancer, retinoblastoma, HPV positive malignancies like cervical cancer and certain head and neck cancers, MYC amplified tumors such as Burkitts' Lymphoma, and triple negative breast cancer; certain classes of sarcoma, certain classes of non-small cell lung carcinoma, certain classes of melanoma, certain classes of pancreatic cancer, certain classes of leukemia, certain classes of lymphoma, certain classes of brain cancer, certain classes of colon cancer, certain classes of prostate cancer, certain classes of ovarian cancer, certain classes of uterine cancer, certain classes of thyroid and other endocrine tissue cancers, certain classes of salivary cancers, certain classes of thymic carcinomas, certain classes of kidney cancers, certain classes of bladder cancers, and certain classes of testicular cancers.

The loss or absence of retinoblastoma (Rb) tumor suppressor protein (Rb-null) can be determined through any of the standard assays known to one of ordinary skill in the art, including but not limited to Western Blot, ELISA (enzyme linked immunoadsorbent assay), IHC (immunohistochemistry), and FACS (fluorescent activated cell sorting). The selection of the assay will depend upon the tissue, cell line or surrogate tissue sample that is utilized e.g., for example Western Blot and ELISA may be used with any or all types of tissues, cell lines or surrogate tissues, whereas the IHC method would be more appropriate wherein the tissue utilized in the methods of the present invention was a tumor biopsy. FACs analysis would be most applicable to samples that were single cell suspensions such as cell lines and isolated peripheral blood mononuclear cells. See for example, US 20070212736 "Functional Immunohistochemical Cell Cycle Analysis as a Prognostic Indicator for Cancer".

Alternatively, molecular genetic testing may be used for determination of retinoblastoma gene status. Molecular genetic testing for retinoblastoma includes the following as described in Lohmann and Gallie "Retinoblastoma. Gene Reviews" (2010) http://www.ncbi.nlm.nih.gov/bookshelf/br.fcgi?book=gene&part=retinoblastoma or Parsam et al. "A comprehensive, sensitive and economical approach for the detection of mutations in the RB1 gene in retinoblastoma" Journal of Genetics, 88(4), 517-527 (2009).

Increased activity of CDK1 or CDK2, high levels of MYC expression, increased cyclin E and increased cyclin A can be determined through any of the standard assays known to one of ordinary skill in the art, including but not limited to Western Blot, ELISA (enzyme linked immunoadsorbent assay), IHC (immunohistochemistry), and FACS (fluorescent activated cell sorting). The selection of the assay will depend upon the tissue, cell line, or surrogate tissue sample that is utilized e.g., for example Western Blot and ELISA may be used with any or all types of tissues, cell lines, or surrogate tissues, whereas the IHC method would be more appropriate wherein the tissue utilized in the methods of the present invention was a tumor biopsy. FACs analysis would be most applicable to samples that were single cell suspensions such as cell lines and isolated peripheral blood mononuclear cells.

In some embodiments, the cancer is selected from a small cell lung cancer, retinoblastoma, and triple negative (ER/PR/Her2 negative) or "basal-like" breast cancer, which almost always inactivate the retinoblastoma tumor suppressor protein (Rb), and therefore do not require CDK4/6 activity to proliferate. Triple negative (basal-like) breast cancer is also almost always genetically or functionally Rb-null. Also, certain virally induced cancers (e.g. cervical cancer and subsets of Head and Neck cancer) express a viral protein (E7) which inactivates Rb making these tumors functionally Rb-null. Some lung cancers are also believed to be caused by HPV. In one particular embodiment, the cancer is small cell lung cancer, and the patient is treated with a DNA-damaging agent selected from the group consisting of etoposide, carboplatin, and cisplatin, or a combination thereof.

The selected CDK4/6 inhibitors described herein can also be used in protecting healthy CDK4/6-replication dependent cells during chemotherapeutic treatments of abnormal tissues in non-cancer proliferative diseases, including but not limited to: psoriasis, lupus, arthritis (notably rheumatoid arthritis), hemangiomatosis in infants, multiple sclerosis, myelodegenerative disease, neurofibromatosis, ganglioneuromatosis, keloid formation, Paget's Disease of the bone, fibrocystic disease of the breast, Peyronie's and Duputren's fibrosis, restenosis, and cirrhosis. Further, selective CDK4/6 inhibitors can be used to ameliorate the effects of chemotherapeutic agents in the event of accidental exposure or overdose (e.g., methotrexate overdose).

According to the present invention, the active compound can be administered to a subject on any chemotherapeutic treatment schedule and in any dose consistent with the prescribed course of treatment. The selective CDK4/6 inhibitor compound is administered prior to, during, or following the administration of the chemotherapeutic agent. In one embodiment, the CDK4/6 inhibitors described herein can be administered to the subject during the time period ranging from 24 hours prior to chemotherapeutic treatment until 24 hours following exposure. This time period, however, can be extended to time earlier that 24 hour prior to exposure to the agent (e.g., based upon the time it takes the chemotherapeutic agent used to achieve suitable plasma concentrations and/or the compound's plasma half-life). Further, the time period can be extended longer than 24 hours following exposure to the chemotherapeutic agent so long as later administration of the CDK4/6 inhibitor leads to at least some protective effect. Such post-exposure treatment can be especially useful in cases of accidental exposure or overdose.

In some embodiments, the selective CDK4/6 inhibitor can be administered to the subject at a time period prior to the administration of the chemotherapeutic agent, so that plasma levels of the selective CDK4/6 inhibitor are peaking at the time of administration of the chemotherapeutic agent. If convenient, the selective CDK4/6 inhibitor can be administered at the same time as the chemotherapeutic agent, in order to simplify the treatment regimen. In some embodiments, the chemoprotectant and chemotherapeutic can be provided in a single formulation.

In some embodiments, the selective CDK4/6 inhibitor can be administered to the subject such that the chemotherapeutic agent can be administered either at higher doses (increased chemotherapeutic dose intensity) or more frequently (increased chemotherapeutic dose density). Dose-dense chemotherapy is a chemotherapy treatment plan in which drugs are given with less time between treatments than in a standard chemotherapy treatment plan. Chemotherapy dose intensity represents unit dose of chemotherapy administered per unit time. Dose intensity can be increased or decreased through altering dose administered, time interval of administration, or both. Myelosuppression continues to represent the major dose-limiting toxicity of cancer chemotherapy, resulting in considerable morbidity and mortality along with frequent reductions in chemotherapy dose intensity, which may compromise disease control and survival. The compounds and their use as described herein represent a way of increasing chemotherapy dose density and/or dose intensity while mitigating adverse events such as, but not limited to, myelosuppression.

If desired, multiple doses of the selected CDK4/6 inhibitor compound can be administered to the subject. Alternatively, the subject can be given a single dose of the selected CDK4/6 inhibitor. For example, the CDK4/6-inhibitor can be administered so that CDK4/6-replication dependent healthy cells are G1 arrested during chemotherapeutic agent exposure wherein, due to the rapid dissipation of the G1-arresting effect of the compounds, a significant number of healthy cells reenter the cell-cycle and are capable of replicating shortly after chemotherapeutic agent exposure, for example, within about 24-48 hours or less, and continue to replicate until administration of the CDK4/6-inhibitor in anticipation of the next chemotherapeutic treatment. In one embodiment, the CDK4/6-inhibitor is administered to allow for the cycling of the CDK4/6-replication dependent healthy cells between G1-arrest and reentry into the cell-cycle to accommodate a repeated-dosing chemotherapeutic treatment regimen, for example, including but not limited to a treatment regimen wherein the chemotherapeutic agent is administered: on day 1-3 every 21 days; on days 1-3 every 28 days; on day 1 every 3 weeks; on day 1, day 8, and day 15 every 28 days, on day 1 and day 8 every 28 days; on days 1 and 8 every 21 days; on days 1-5 every 21 days; 1 day a week for 6-8 weeks; on days 1, 22, and 43; days 1 and 2 weekly; days 1-4 and 22-25; 1-4; 22-25, and 43-46; and similar type-regimens, wherein the CDK4/6-replication dependent cells are G1 arrested during chemotherapeutic agent exposure and a significant portion of the cells reenter the cell-cycle in between chemotherapeutic agent exposure.

In one embodiment, the CDK4/6 inhibitor described herein is used to provide chemoprotection to a subject's CDK4/6-replication dependent healthy cells during a CDK4/6-replication independent small cell lung cancer treatment protocol. In one embodiment, the CDK4/6 inhibitor is administered to provide chemoprotection in a small cell lung cancer therapy protocol such as, but not limited to: cisplatin 60 mg/m2 IV on day 1 plus etoposide 120 mg/m2 IV on days 1-3 every 21d for 4 cycles; cisplatin 80 mg/m2 IV on day 1 plus etoposide 100 mg/m2 IV on days 1-3 every 28d for 4 cycles; cisplatin 60-80 mg/m2 IV on day 1 plus etoposide 80-120 mg/m2 IV on days 1-3 every 21-28d (maximum of 4 cycles); carboplatin AUC 5-6 IV on day 1 plus etoposide 80-100 mg/m2 IV on days 1-3 every 28d (maximum of 4 cycles); Cisplatin 60-80 mg/m2 IV on day 1 plus etoposide 80-120 mg/m2 IV on days 1-3 every 21-28d; carboplatin AUC 5-6 IV on day 1 plus etoposide 80-100 mg/m2 IV on days 1-3 every 28d (maximum 6 cycles); cisplatin 60 mg/m2 IV on day 1 plus irinotecan 60 mg/m2 IV on days 1, 8, and 15 every 28d (maximum 6 cycles); cisplatin 30 mg/m2 IV on days 1 and 8 or 80 mg/m2 IV on day 1 plus irinotecan 65 mg/m2 IV on days 1 and 8 every 21d (maximum 6 cycles); carboplatin AUC 5 IV on day 1 plus irinotecan 50 mg/m2 IV on days 1, 8, and 15 every 28d (maximum 6 cycles); carboplatin AUC 4-5 IV on day 1 plus irinotecan 150-200 mg/m2 IV on day 1 every 21d (maximum 6 cycles); cyclophosphamide 800-1000 mg/m2 IV on day 1 plus doxorubicin 40-50 mg/m2 IV on day 1 plus vincristine 1-1.4 mg/m2 IV on day 1 every 21-28d (maximum 6 cycles); Etoposide 50 mg/m2 PO daily for 3 wk every 4 wk; topotecan 2.3 mg/m2 PO on days 1-5 every 21d; topotecan 1.5 mg/m2 IV on days 1-5 every 21d; carboplatin AUC 5 IV on day 1 plus irinotecan 50 mg/m2 IV on days 1, 8, and 15 every 28d; carboplatin AUC 4-5 IV on day 1 plus irinotecan 150-200 mg/m2 IV on day 1 every 21d; cisplatin 30 mg/m2 IV on days 1, 8, and 15 plus irinotecan 60 mg/m2 IV on days 1, 8, and 15 every 28d; cisplatin 60 mg/m2 IV on day 1 plus irinotecan 60 mg/m2 IV on days 1, 8, and 15 every 28d; cisplatin 30 mg/m2 IV on days 1 and 8 or 80 mg/m2 IV on day 1 plus irinotecan 65 mg/m2 IV on days 1 and 8 every 21d; paclitaxel 80 mg/m2 IV weekly for 6 wk every 8 wk; paclitaxel 175 mg/m2 IV on day 1 every 3 wk; etoposide 50 mg/m2 PO daily for 3 wk every 4 wk; topotecan 2.3 mg/m2 PO on days 1-5 every 21d; topotecan 1.5 mg/m2 IV on days 1-5 every 21d; carboplatin AUC 5 IV on day 1 plus irinotecan 50 mg/m2 IV on days 1, 8, and 15 every 28d; carboplatin AUC 4-5 IV on day 1 plus irinotecan 150-200 mg/m2 IV on day 1 every 21d; cisplatin 30 mg/m2 IV on days 1, 8, and 15 plus irinotecan 60 mg/m2 IV on days 1, 8, and 15 every 28d; cisplatin 60 mg/m2 IV on day 1 plus irinotecan 60 mg/m2 IV on days 1, 8, and 15 every 28d; cisplatin 30 mg/m2 IV on days 1 and 8 or 80 mg/m2 IV on day 1 plus irinotecan 65 mg/m2 IV on days 1 and 8 every 21d; paclitaxel 80 mg/m2 IV weekly for 6 wk every 8 wk; and paclitaxel 175 mg/m2 IV on day 1 every 3 wk.

In one embodiment, a CDK4/6 inhibitor described herein is administered to a subject with small cell lung cancer on days 1, 2, and 3 of a treatment protocol wherein the DNA damaging agent selected from the group consisting of carboplatin, etoposide, and cisplatin, or a combination thereof, is administered on days 1, 2, and 3 every 21 days.

In one embodiment, a CDK4/6 inhibitor described herein is used to provide chemoprotection to a subject's CDK4/6-replication dependent healthy cells during a CDK4/6-replication independent head and neck cancer treatment protocol. In one embodiment, the CDK4/6 inhibitor is administered to provide chemoprotection in a CDK4/6-replication independent head and neck cancer therapy protocol such as, but not limited to: cisplatin 100 mg/m2 IV on days 1, 22, and 43 or 40-50 mg/m2 IV weekly for 6-7 wk; cetuximab 400 mg/m2 IV loading dose 1 wk before the start of radiation therapy, then 250 mg/m2 weekly (premedicate with dexamethasone, diphenhydramine, and ranitidine); cisplatin 20 mg/m2 IV on day 2 weekly for up to 7 wk plus paclitaxel 30 mg/m2 IV on day 1 weekly for up to 7 wk; cisplatin 20 mg/m2/day IV on days 1-4 and 22-25 plus 5-FU 1000 mg/m2/day by continuous IV infusion on days 1-4 and 22-25; 5-FU 800 mg/m2 by continuous IV infusion on days 1-5 given on the days of radiation plus hydroxyurea 1 g PO q12h (11 doses per cycle); chemotherapy and radiation given every other week for a total of 13 wk; carboplatin 70 mg/m2/day IV on days 1-4, 22-25, and 43-46 plus 5-FU 600 mg/m2/day by continuous IV infusion on days 1-4, 22-25, and 43-46; carboplatin AUC 1.5 IV on day 1 weekly plus paclitaxel 45 mg/m2 IV on day 1 weekly; cisplatin 100 mg/m2 IV on days 1, 22, and 43 or 40-50 mg/m2 IV weekly for 6-7 wk; docetaxel 75 mg/m2 IV on day 1 plus cisplatin 100 mg/m2 IV on day 1 plus 5-FU 100 mg/m2/day by continuous IV infusion on days 1-4 every 3 wk for 3 cycles, then 3-8 wk later, carboplatin AUC 1.5 IV weekly for up to 7 wk during radiation therapy; docetaxel 75 mg/m2 IV on day 1 plus cisplatin 75 mg/m2 IV on day 1 plus 5-FU 750 mg/m2/day by continuous IV infusion on days 1-4 every 3 wk for 4 cycles; cisplatin 100 mg/m2 IV on day 1 every 3 wk for 6 cycles plus 5-FU 1000 mg/m2/day by continuous IV infusion on days 1-4 every 3 wk for 6 cycles plus cetuximab 400 mg/m2 IV loading dose on day 1, then 250 mg/m2 IV weekly until disease progression (premedicate with dexamethasone, diphenhydramine, and ranitidine); carboplatin AUC 5 IV on day 1 every 3 wk for 6 cycles plus 5-FU 1000 mg/m2/day by continuous IV infusion on days 1-4 every 3 wk for 6 cycles plus cetuximab 400 mg/m2 IV loading dose on day 1, then 250 mg/m2 IV weekly until disease progression (premedicate with dexamethasone, diphenhydramine, and ranitidine); cisplatin 75 mg/m2 IV on day 1 plus docetaxel 75 mg/m2 IV on day 1 every 3 wk; cisplatin 75 mg/m2 IV on day 1 plus paclitaxel 175 mg/m2 IV on day 1 every 3 wk; carboplatin AUC 6 IV on day 1 plus docetaxel 65 mg/m2 IV on day 1 every 3 wk; carboplatin AUC 6 IV on day 1 plus paclitaxel 200 mg/m2 IV on day 1 every 3 wk; cisplatin 75-100 mg/m2 IV on day 1 every 3-4 wk plus cetuximab 400 mg/m2 IV loading dose on day 1, then 250 mg/m2 IV weekly (premedicate with dexamethasone, diphenhydramine, and ranitidine); cisplatin 100 mg/m2 IV on day 1 plus 5-FU 1000 mg/m2/day by continuous IV infusion on days 1-4 every 3 wk; methotrexate 40 mg/m2 IV weekly (3 wk equals 1 cycle); paclitaxel 200 mg/m2 IV every 3 wk; docetaxel 75 mg/m2 IV every 3 wk; cetuximab 400 mg/m2 IV loading dose on day 1, then 250 mg/m2 IV weekly until disease progression (premedicate with dexamethasone, diphenhydramine, and ranitidine); cisplatin 100 mg/m2 IV on day 1 every 3 wk for 6 cycles plus 5-FU 1000 mg/m2/day by continuous IV infusion on days 1-4 every 3 wk for 6 cycles plus cetuximab 400 mg/m2 IV loading dose on day 1, then 250 mg/m2 IV weekly (premedicate with dexamethasone, diphenhydramine, and ranitidine); carboplatin AUC 5 IV on day 1 every 3 wk for 6 cycles plus 5-FU 1000 mg/m2/day by continuous IV infusion on days 1-4 every 3 wk for 6 cycles plus cetuximab 400 mg/m2 IV loading dose on day 1, then 250 mg/m2 IV weekly (premedicate with dexamethasone, diphenhydramine, and ranitidine); cisplatin 75 mg/m2 IV on day 1 plus docetaxel 75 mg/m2 IV on day 1 every 3 wk; cisplatin 75 mg/m2 IV on day 1 plus paclitaxel 175 mg/m2 IV on day 1 every 3 wk; carboplatin AUC 6 IV on day 1 plus docetaxel 65 mg/m2 IV on day 1 every 3 wk; carboplatin AUC 6 IV on day 1 plus paclitaxel 200 mg/m2 IV on day 1 every 3 wk; cisplatin 75-100 mg/m2 IV on day 1 every 3-4 wk plus cetuximab 400 mg/m2 IV loading dose on day 1, then 250 mg/m2 IV weekly (premedicate with dexamethasone, diphenhydramine, and ranitidine); cisplatin 100 mg/m2 IV on day 1 plus 5-FU 1000 mg/m2/day by continuous IV infusion on days 1-4 every 3 wk; methotrexate 40 mg/m2 IV weekly (3 wk equals 1 cycle); paclitaxel 200 mg/m2 IV every 3 wk; docetaxel 75 mg/m2 IV every 3 wk; cetuximab 400 mg/m2 IV loading dose on day 1, then 250 mg/m2 IV weekly until disease progression (premedicate with dexamethasone, diphenhydramine, and ranitidine); cisplatin 100 mg/m2 IV on days 1, 22, and 43 with radiation, then cisplatin 80 mg/m2 IV on day 1 plus 5-FU 1000 mg/m2/day by continuous IV infusion on days 1-4 every 4 wk for 3 cycles; cisplatin 75 mg/m2 IV on day 1 plus docetaxel 75 mg/m2 IV on day 1 every 3 wk; cisplatin 75 mg/m2 IV on day 1 plus paclitaxel 175 mg/m2 IV on day 1 every 3 wk; carboplatin AUC 6 IV on day 1 plus docetaxel 65 mg/m2 IV on day 1 every 3 wk; carboplatin AUC 6 IV on day 1 plus paclitaxel 200 mg/m2 IV on day 1 every 3 wk; cisplatin 100 mg/m2 IV on day 1 plus 5-FU 1000 mg/m2/day by continuous IV infusion on days 1-4 every 3 wk; cisplatin 50-70 mg/m2 IV on day 1 plus gemcitabine 1000 mg/m2 IV on days 1, 8, and 15 every 4 wk; gemcitabine 1000 mg/m2 IV on days 1, 8, and 15 every 4 wk or gemcitabine 1250 mg/m2 IV on days 1 and 8 every 3 wk; methotrexate 40 mg/m2 IV weekly (3 wk equals 1 cycle); paclitaxel 200 mg/m2 IV every 3 wk; docetaxel 75 mg/m2 IV every 3 wk; cisplatin 75 mg/m2 IV every 3 wk; cisplatin 75 mg/m2 IV on day 1 plus docetaxel 75 mg/m2 IV on day 1 every 3 wk; cisplatin 75 mg/m2 IV on day 1 plus paclitaxel 175 mg/m2 IV on day 1 every 3 wk; carboplatin AUC 6 IV on day 1 plus docetaxel 65 mg/m2 IV on day 1 every 3 wk; carboplatin AUC 6 IV on day 1 plus paclitaxel 200 mg/m2 IV on day 1 every 3 wk; cisplatin 100 mg/m2 IV on day 1 plus 5-FU 1000 mg/m2/day by continuous IV infusion on days 1-4 every 3 wk; cisplatin 50-70 mg/m2 IV on day 1 plus gemcitabine 1000 mg/m2 IV on days 1, 8, and 15 every 4 wk; gemcitabine 1000 mg/m2 IV on days 1, 8, and 15 every 4 wk or gemcitabine 1250 mg/m2 IV on days 1 and 8 every 3 wk; methotrexate 40 mg/m2 IV weekly (3 wk equals 1 cycle); paclitaxel 200 mg/m2 IV every 3 wk; and docetaxel 75 mg/m2 IV every 3 wk.

In one embodiment, the CDK4/6 inhibitor described herein is used to provide chemoprotection to a subject's CDK4/6-replication dependent healthy cells during a CDK4/6-replication independent triple negative breast cancer treatment protocol. In one embodiment, the CDK4/6 inhibitor is administered to provide chemoprotection in a CDK4/6-replication independent triple negative breast cancer therapy protocol such as, but not limited to: dose-dense doxorubicin (adriamycin) and cyclophosphamide (cytoxan) every two weeks for four cycles followed by dose-dense paclitaxel (Taxol) every two weeks for four cycles; adriamycin/paclitaxel/cyclophosphomide every three weeks for a total of four cycles; adriamycin/paclitaxel/cyclophosphomide every two weeks for a total of four cycles; adriamycin/cyclophosphomide followed by paclitaxel (Taxol) every three weeks for four cycles each; and adriamycin/cyclophosphomide followed by paclitaxel (Taxol) every two weeks for four cycles each.

Triple-negative breast cancer (TNBC) is defined as the absence of staining for estrogen receptor, progesterone receptor, and HER2/neu. TNBC is insensitive to some of the most effective therapies available for breast cancer treatment including HER2-directed therapy such as trastuzumab and endocrine therapies such as tamoxifen or the aromatase inhibitors. Combination cytotoxic chemotherapy administered in a dose-dense or metronomic schedule remains the standard therapy for early-stage TNBC. Platinum agents have recently emerged as drugs of interest for the treatment of TNBC with carboplatin added to paclitaxel and adriamycin plus cyclophosphamide chemotherapy in the neoadjuvant setting. The poly (ADP-ribose) polymerase (PARP) inhibitors are emerging as promising therapeutics for the treatment of TNBC. PARPs are a family of enzymes involved in multiple cellular processes, including DNA repair.

As a nonlimiting illustration, the subject is exposed to chemotherapeutic agent at least 5 times a week, at least 4 times a week, at least 3 times a week, at least 2 times a week, at least 1 time a week, at least 3 times a month, at least 2 times a month, or at least 1 time a month, wherein the subject's CDK4/6-replication dependent healthy cells are G1 arrested during treatment and allowed to cycle in between chemotherapeutic agent exposure, for example during a treatment break. In one embodiment, the subject is undergoing 5 times a week chemotherapeutic treatment, wherein the subject's CDK4/6-replication dependent healthy cells are G1 arrested during the chemotherapeutic agent exposure and allowed to reenter the cell-cycle during the 2 day break, for example, over the weekend.

In one embodiment, using a CDK4/6 inhibitor described herein, the subject's CDK4/6-replication dependent healthy cells are arrested during the entirety of the chemotherapeutic agent exposure time-period, for example, during a contiguous multi-day regimens, the cells are arrested over the time period that is required to complete the contiguous multi-day course, and then allowed to recycle at the end of the contiguous multi-day course. In one embodiment, using a CDK4/6 inhibitor described herein, the subject's CDK4/6-replication dependent healthy cells are arrested during the entirety of the chemotherapeutic regimen, for example, in a daily chemotherapeutic exposure for three weeks, and rapidly reenter the cell-cycle following the completion of the therapeutic regimen.

In one embodiment, the subject has been exposed to a chemotherapeutic agent, and, using a CDK4/6 inhibitor described herein, the subject's CDK4/6-replication dependent healthy cells are placed in G1 arrest following exposure in order to mitigate, for example, DNA damage. In one embodiment, the CDK4/6 inhibitor is administered at least 1/2 hour, at least 1 hour, at least 2 hours, at least 3 hours, at least 4 hours, at least 5 hours, at least 6 hours, at least 7 hours, at least 8 hours, at least 10 hours, at least 12 hours, at least 14 hours, at least 16 hours, at least 18 hours, at least 20 hours or more post chemotherapeutic agent exposure.

In some embodiments, the present invention provides methods for protection of mammals, particularly humans, from the acute and chronic toxic effects of chemotherapeutic agents by forcing CDK4/6-replication dependent healthy cells, for example hematopoietic stem and progenitor cells (HSPCs) and/or renal epithelial cells, into a quiescent state by transient (e.g., over a less than about 40, 36, 30, 24 hour or less period) treatment with a CDK4/6 inhibitor selected from the group consisting of Formula I, Formula II, Formula III, Formula IV, or Formula V or a pharmaceutically acceptable composition, salt, isotopic analog, or prodrug thereof. In one embodiment, the compound is selected from the compounds described in Table 1 or a pharmaceutically acceptable composition, salt, isotopic analog or prodrug thereof. In one embodiment, the compound is selected from compounds T, Q, GG, U, or AAAA, or a pharmaceutically acceptable composition, salt, isotopic analog or prodrug thereof. CDK4/6-replication dependent cells recover from this period of transient quiescence, and then function normally after treatment with the inhibitor is stopped, and its intra-cellular effect dissipates. During the period of quiescence, the CDK4/6-replication dependent cells are protected from the effects of chemotherapeutic agents.

In some embodiments, the CDK4/6-replication dependent healthy cells can be arrested for longer periods, for example, over a period of hours, days, and/or weeks, through multiple, time separated administrations of a CDK4/6 inhibitor described herein. Because of the rapid and synchronous reentry into the cell cycle by CDK4/6-replication dependent healthy cells, for example HSPCs, upon dissipation of the CDK4/6 inhibitors intra-cellular effects, the cells are capable of reconstituting the cell lineages faster than CDK4/6 inhibitors with longer G1 arresting profiles, for example PD0332991.

The reduction in chemotoxicity afforded by the selective CDK4/6 inhibitors can allow for dose intensification (e.g., more therapy can be given in a fixed period of time) in medically related chemotherapies, which will translate to better efficacy. Therefore, the presently disclosed methods can result in chemotherapy regimens that are less toxic and more effective. Also, in contrast to protective treatments with exogenous biological growth factors, the selective CDK4/6 inhibitors described herein are orally available small molecules, which can be formulated for administration via a number of different routes. When appropriate, the small molecules can be formulated for oral, topical, intranasal, inhalation, intravenous or any other desired form of administration.

A CDK4/6 inhibitor useful in the methods described herein is a selective CDK4/6 inhibitor compound that selectively inhibit at least one of CDK4 and CDK6, or whose predominant mode of action is through inhibition of CDK4 and/or CDK6. In one embodiment, the selective CDK4/6 inhibitors have an $IC_{50}$ for CDK4 as measured in a CDK4/CycD1 $IC_{50}$ phosphorylation assay that is at least 1500, 2000, 5000 or even 10,000 times or greater lower than the compound's $IC_{50}$s for CDK2 as measured in a CDK2/CycE $IC_{50}$ phosphorylation assay. In one embodiment, the CDK4/6 inhibitors are at least about 10 times or greater more potent (i.e., have an $IC_{50}$ in a CDK4/CycD1 phosphorylation assay that is at least 10 times or more lower) than PD0332991.

The use of a selected CDK4/6 inhibitor as described herein can induce selective G1 arrest in CDK4/6-dependent cells (e.g., as measured in a cell-based in vitro assay). In one embodiment, the CDK4/6 inhibitor is capable of increasing the percentage of CDK4/6-dependent cells in the G1 phase, while decreasing the percentage of CDK4/6-dependent cells in the G2/M phase and S phase. In one embodiment, the selective CDK4/6 inhibitor induces substantially pure (i.e., "clean") G1 cell cycle arrest in the CDK4/6-dependent cells (e.g., wherein treatment with the selective CDK4/6 inhibitor induces cell cycle arrest such that the majority of cells are arrested in G1 as defined by standard methods (e.g. propidium iodide (PI) staining or others) with the population of cells in the G2/M and S phases combined being less than about 30%, about 25%, about 20%, about 15%, about 10%, about 5%, about 3% or less of the total cell population. Methods of assessing the cell phase of a population of cells are known in the art (see, for example, in U.S. Patent Application Publication No. 2002/0224522) and include cytometric analysis, microscopic analysis, gradient centrifugation, elutriation, fluorescence techniques including immunofluorescence, and combinations thereof. Cytometric techniques include exposing the cell to a labeling agent or stain, such as DNA-binding dyes, e.g., PI, and analyzing cellular DNA content by flow cytometry. Immunofluorescence techniques include detection of specific cell cycle indicators such as, for example, thymidine analogs (e.g., 5-bromo-2-deoxyuridine (BrdU) or an iododeoxyuridine), with fluorescent antibodies.

In some embodiments, the use of a selective CDK4/6 inhibitor described herein result in reduced or substantially free of off-target effects, particularly related to inhibition of kinases other than CDK4 and or CDK6 such as CDK2, as the selective CDK4/6 inhibitors described herein are poor inhibitors (e.g., >1 uM $IC_{50}$) of CDK2. Furthermore, because of the high selectivity for CDK4/6, the use of the compounds described herein should not induce cell cycle arrest in CDK4/6-independent cells. In addition, because of the short transient nature of the G1-arrest effect, the CDK4/6-replication dependent cells more quickly reenter the cell-cycle than, comparatively, use of PD0332991 provides, resulting in the reduced risk of, in one embodiment, hematological toxicity development during long term treatment regimens due to the ability of HSPCs to replicate between chemotherapeutic treatments.

In some embodiments, the use of a selective CDK4/6 inhibitor described herein reduces the risk of undesirable off-target effects including, but not limited to, long term toxicity, anti-oxidant effects, and estrogenic effects. Anti-oxidant effects can be determined by standard assays known in the art. For example, a compound with no significant anti-oxidant effects is a compound that does not significantly scavenge free-radicals, such as oxygen radicals. The anti-oxidant effects of a compound can be compared to a compound with known anti-oxidant activity, such as genistein. Thus, a compound with no significant anti-oxidant activity can be one that has less than about 2, 3, 5, 10, 30, or 100 fold anti-oxidant activity relative to genistein. Estrogenic activities can also be determined via known assays. For instance, a non-estrogenic compound is one that does not significantly bind and activate the estrogen receptor. A compound that is substantially free of estrogenic effects can be one that has less than about 2, 3, 5, 10, 20, or 100 fold estrogenic activity relative to a compound with estrogenic activity, e.g., genistein.

Synthesis of Select CDK4/6 Inhibitors

CDK4/6 Inhibitors of the present invention can be synthesized by any means known to those of ordinary skill in the art, including for example, according to the generalized Schemes of 1 through 9 below. Specific syntheses can be found in, for instance, WO2012/061156 (5-(4-isopropylpiperazin-1-yl)pyridine-2-amine and 5-(4-morpholino-1-piperidyl)pyridine-2-amine respectively). Formula I and Formula II can be synthesized according to Scheme 1 using the corresponding substituted 2-aminopyrimidines or as described in WO2012/061156.

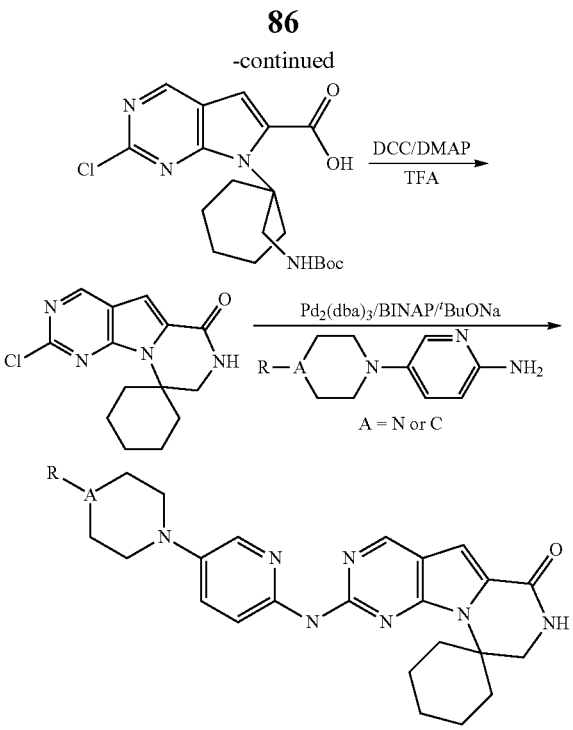

Scheme 1

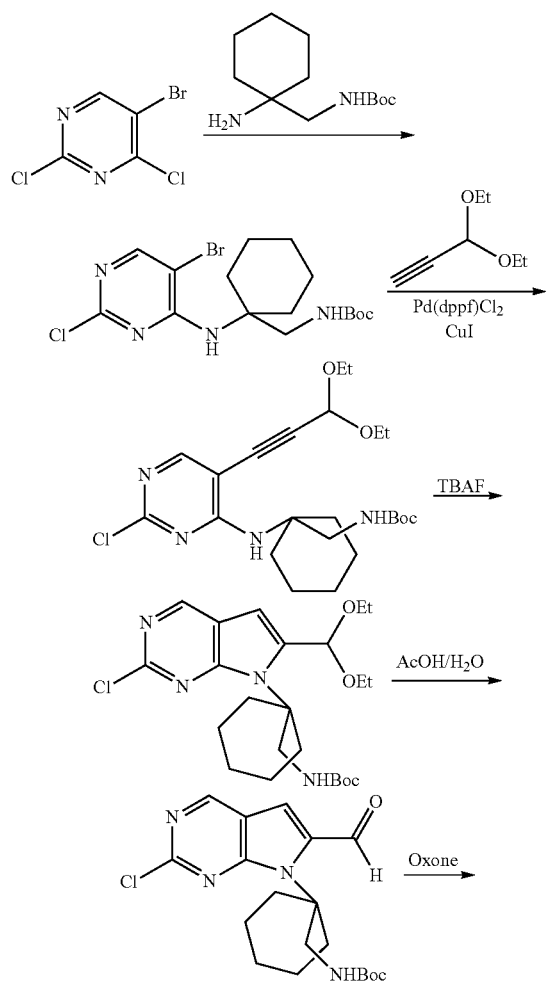

Scheme 2

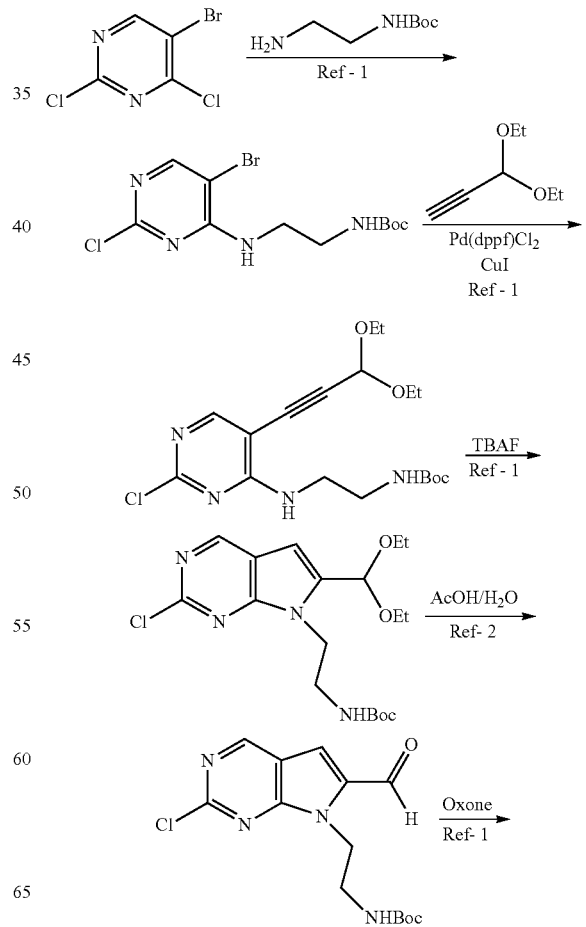

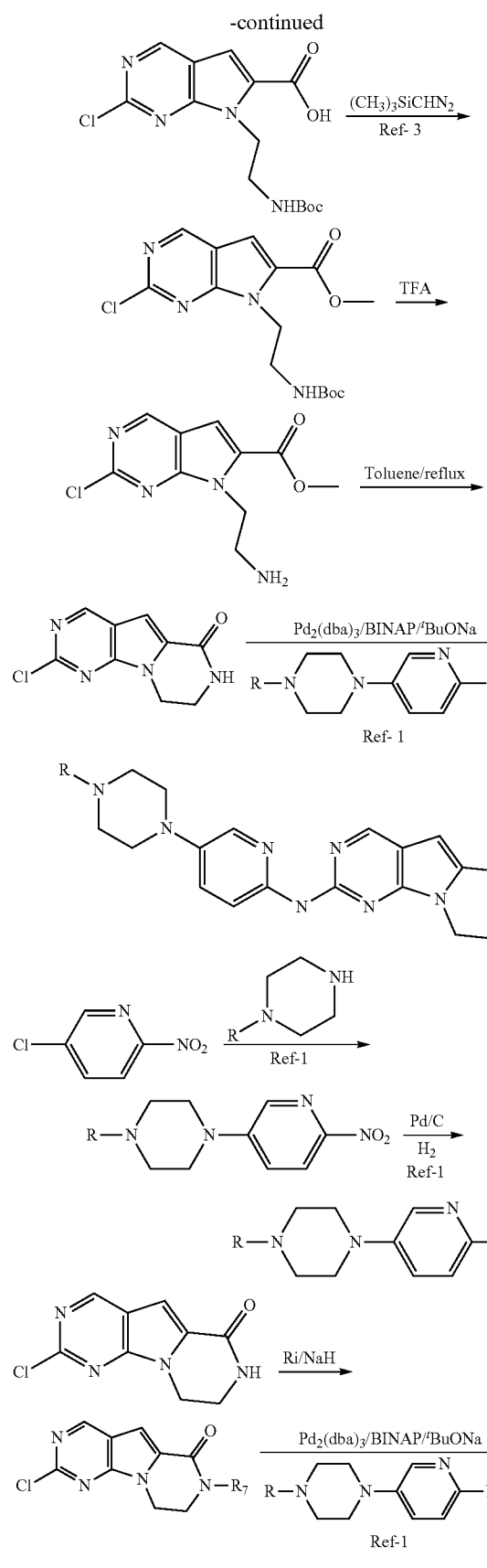
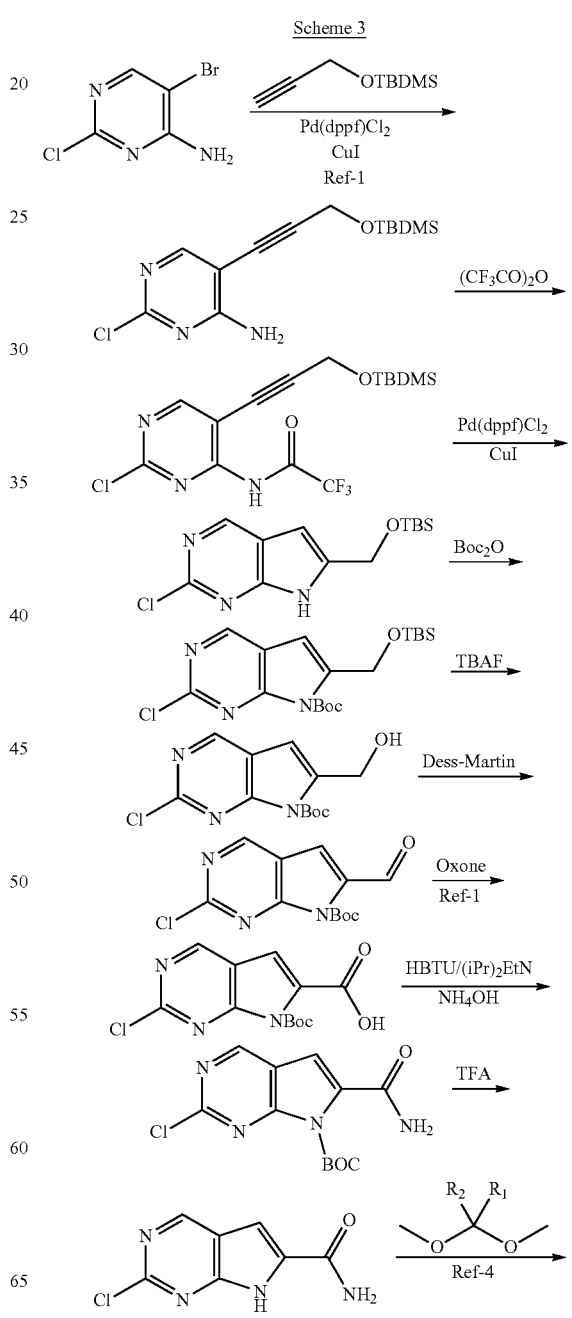
In Scheme 2, Ref-1 is WO 2010/020675 A1; Ref-2 is White, J. D.; et al. *J. Org. Chem.* 1995, 60, 3600; and Ref-3 Presser, A. and Hufner, A. *Monatshefte für Chemie* 2004, 135, 1015.
Scheme 3

89
90
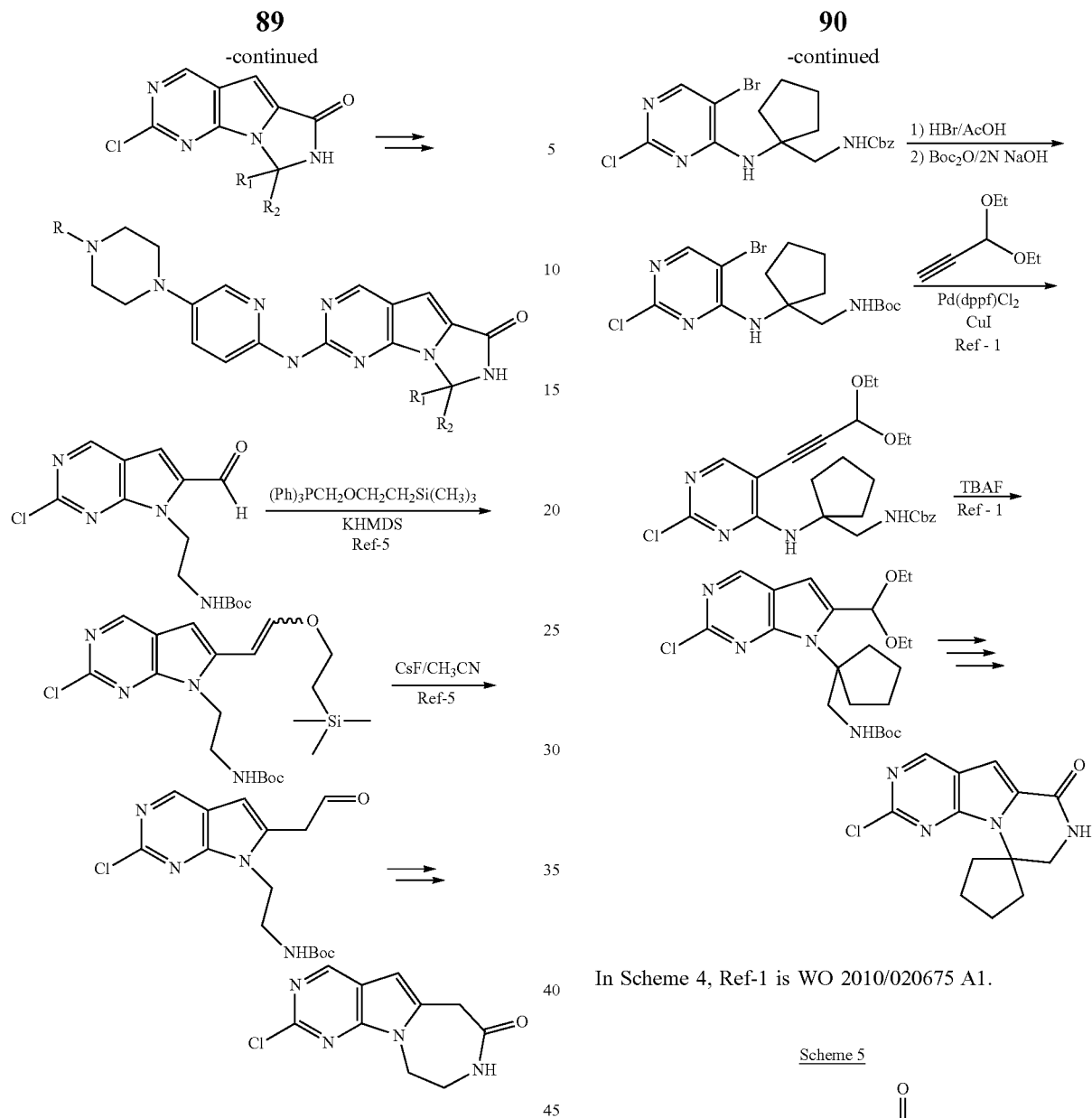
In Scheme 3, Ref-1 is WO 2010/020675 A1; Ref-4 is WO 2005/040166 A1; and Ref-5 is Schoenauer, K and Zbiral, E. *Tetrahedron Letters* 1983, 24, 573.
In Scheme 4, Ref-1 is WO 2010/020675 A1.
Scheme 4
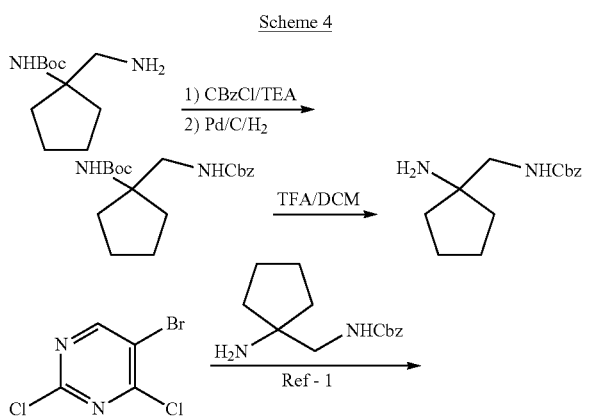
Scheme 5
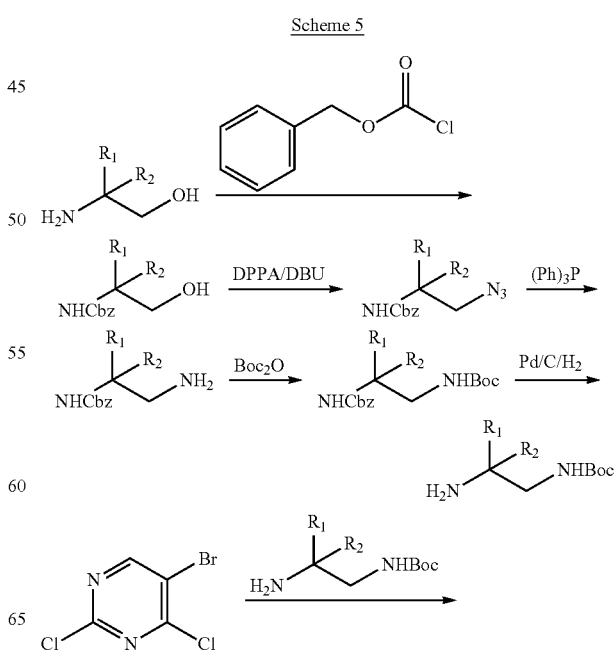

91
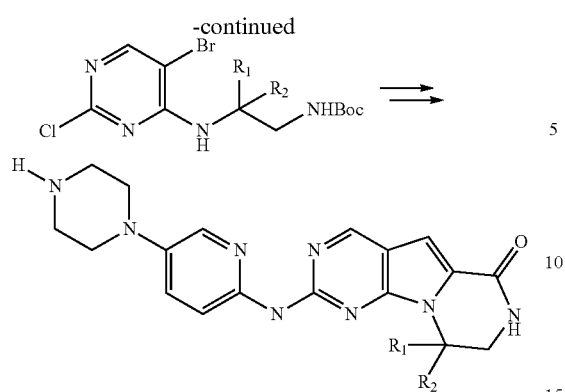
Scheme 6
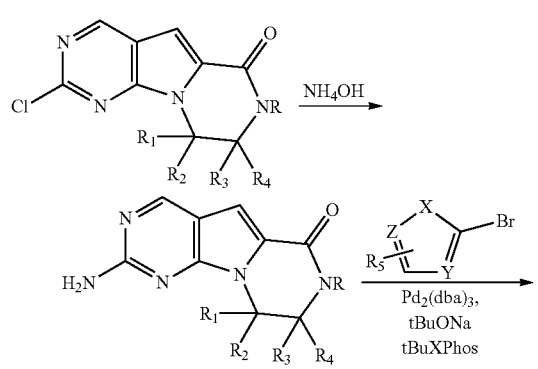
92
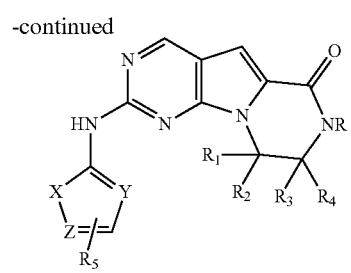
Scheme 7
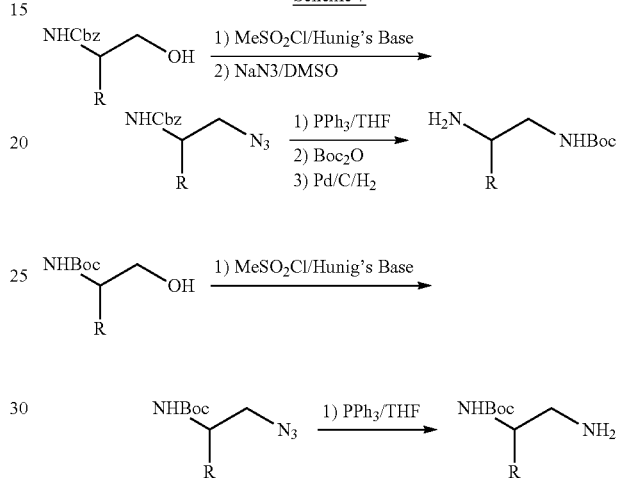
Scheme 8
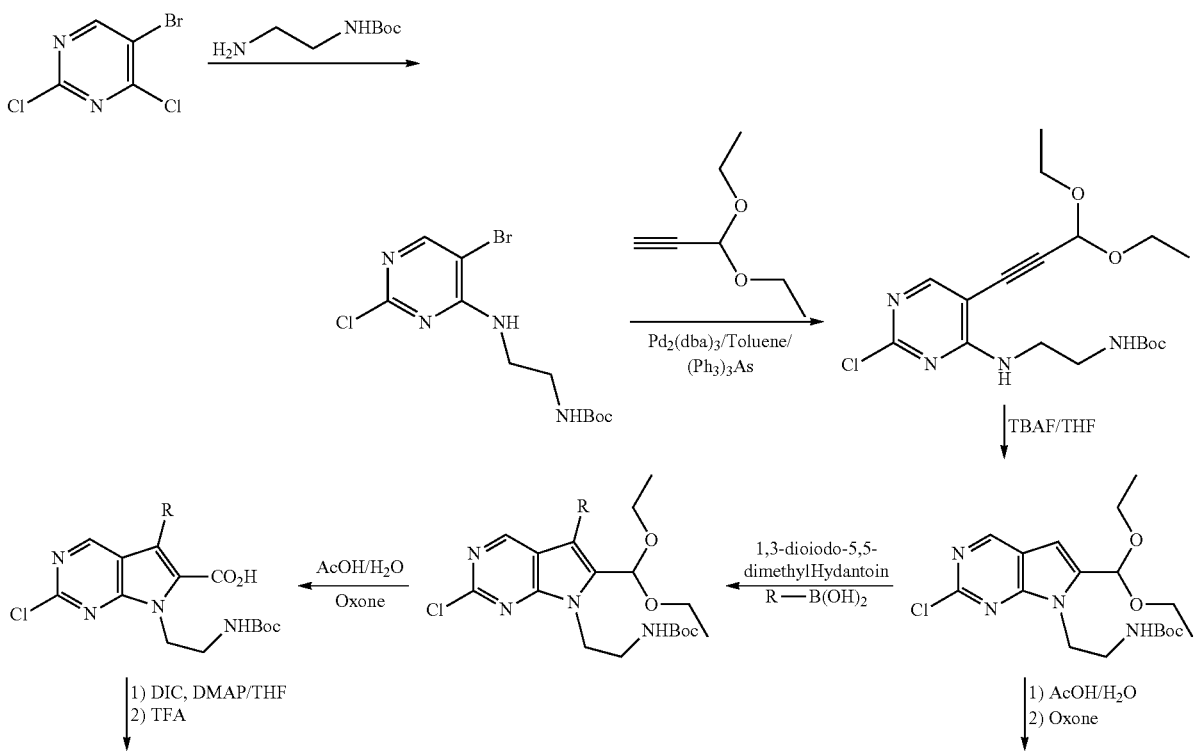

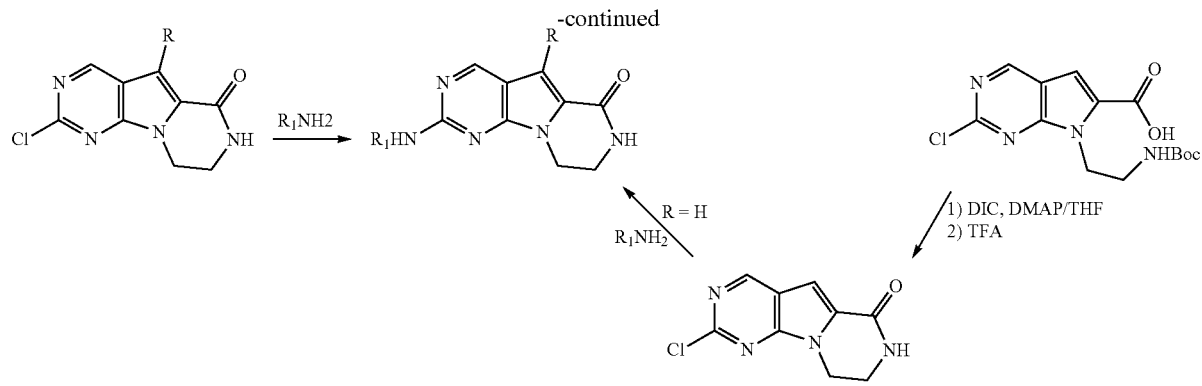
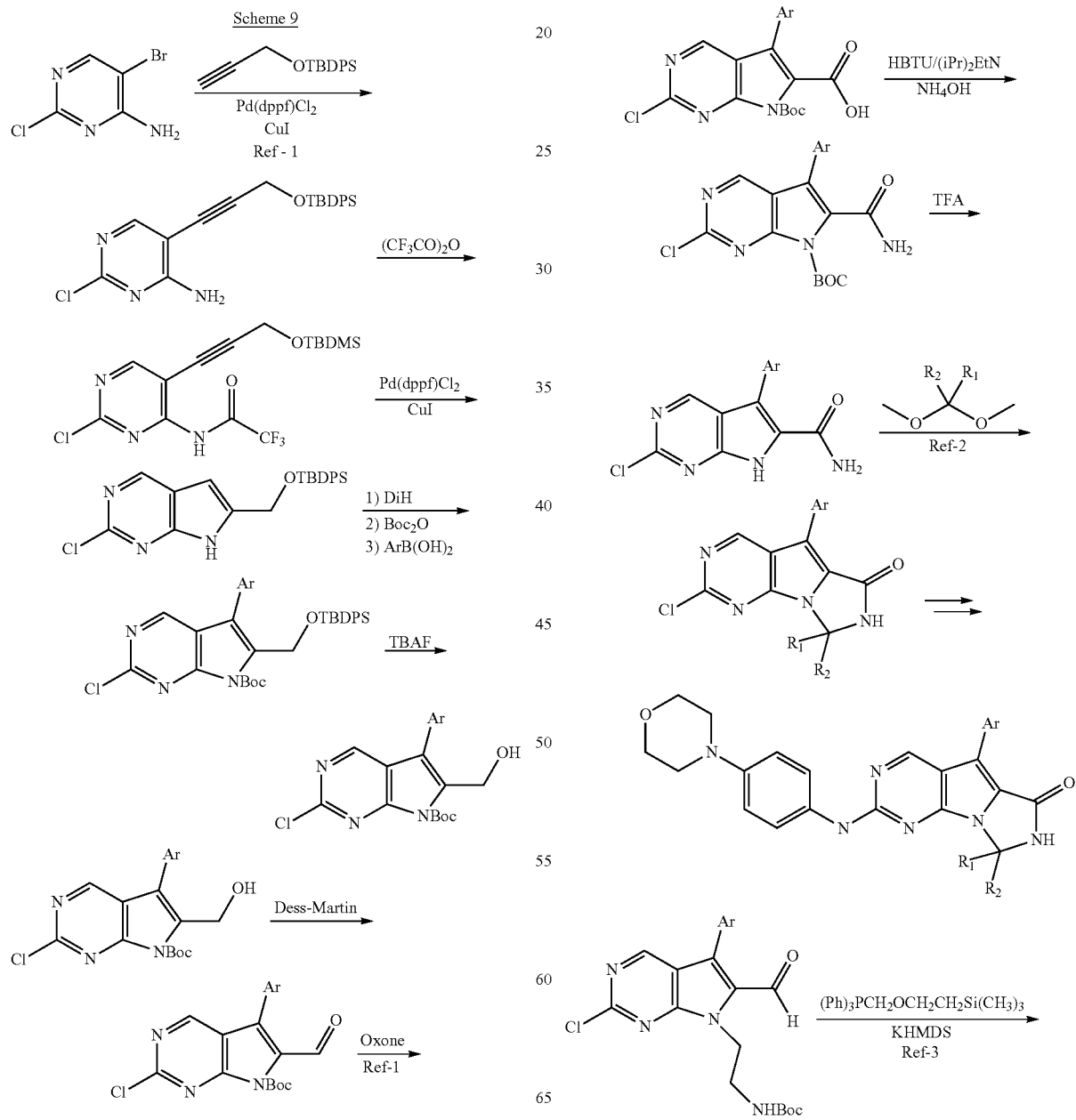

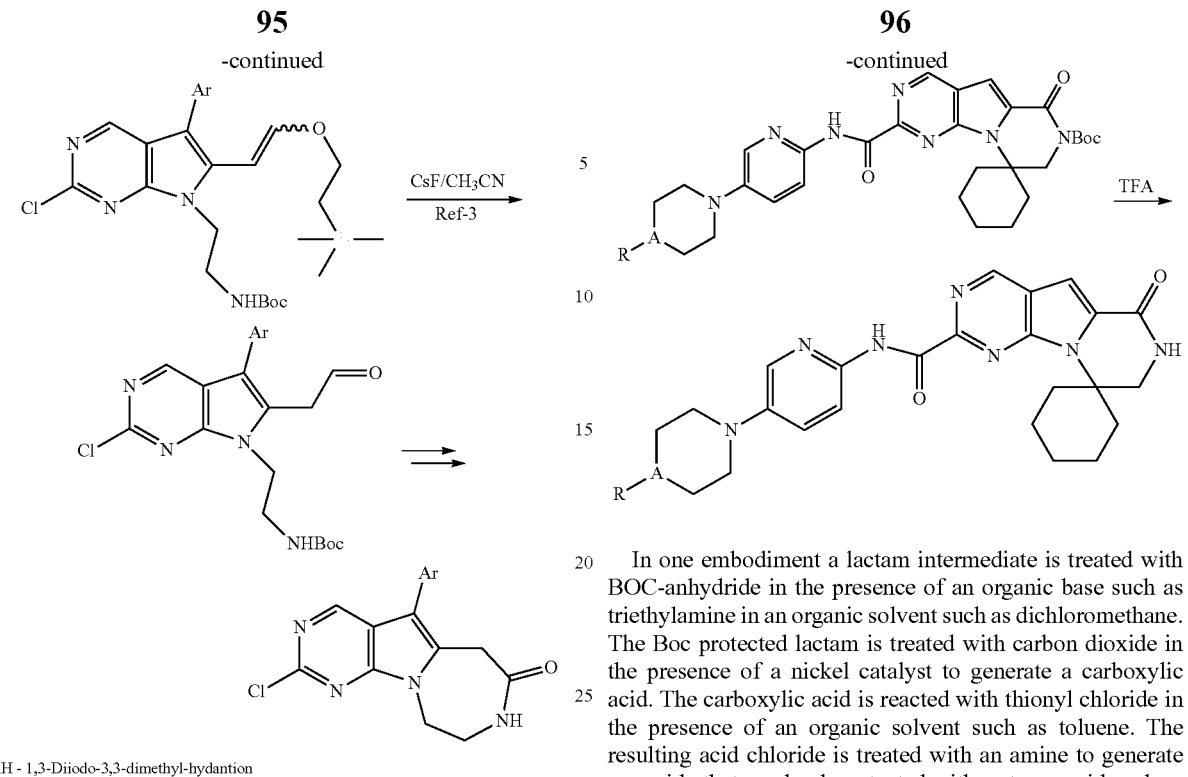

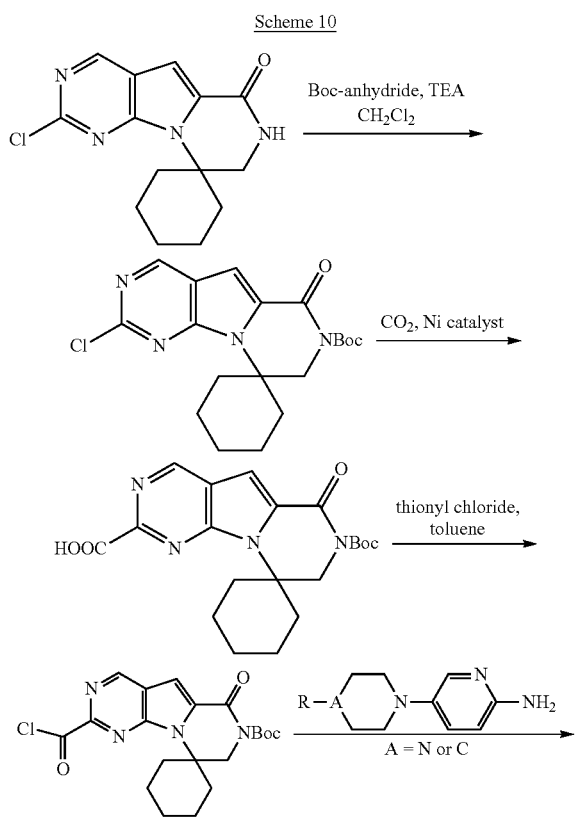

DiH - 1,3-Diiodo-3,3-dimethyl-hydantion

In Scheme 9, Ref-1 is WO 2010/020675 A1; Ref-2 is WO 2005/040166 A1; and Ref-3 is Schoenauer, K and Zbiral, E. *Tetrahedron Letters* 1983, 24, 573.

Scheme 10

In one embodiment a lactam intermediate is treated with BOC-anhydride in the presence of an organic base such as triethylamine in an organic solvent such as dichloromethane. The Boc protected lactam is treated with carbon dioxide in the presence of a nickel catalyst to generate a carboxylic acid. The carboxylic acid is reacted with thionyl chloride in the presence of an organic solvent such as toluene. The resulting acid chloride is treated with an amine to generate an amide that can be deprotected with a strong acid such as trifluoroacetic acid to generate the final target inhibitor compound.

Alternatively, the lactam can be generated by reacting the carboxylic acid with a protected amine in the presence of a strong acid and a dehydrating agent, which can be together in one moiety as a strong acid anhydride. Examples of strong acid anhydrides include, but are not limited to, trifluoroacetic acid anhydride, tribromoacetic acid anhydride, trichloroacetic acid anhydride, or mixed anhydrides. The dehydrating agent can be a carbodiimide based compound such as but not limited to DCC (N,N-dicyclohexylcarbodiimide), EDC (1-ethyl-3-(3-dimethylaminopropyl)carbodiimide or DIC (N,N-diisopropylcarbodiimide). An additional step may be necessary to take off the N-protecting group and the methodologies are known to those skilled in the art Alternatively, the halogen moiety bonded to the pyrimidine ring can be substituted with any leaving group that can be displaced by a primary amine, for example to create an intermediate for a final product such as Br, I, F, SMe, $SO_2Me$, SOalkyl, $SO_2$alkyl. See, for Example, PCT /US2013/037878 to Tavares.

Other amine intermediates and final amine compounds can be synthesized by those skilled in the art. It will be appreciated that the chemistry can employ reagents that comprise reactive functionalities that can be protected and de-protected and will be known to those skilled in the art at the time of the invention. See for example, Greene, T. W. and Wuts, P. G. M., Greene's Protective Groups in Organic Synthesis, $4^{th}$ edition, John Wiley and Sons.

Formulas T, Q, GG and U were prepared above were characterized by mass spectrometry and NMR as shown below:

Formula T 7.25 (s, 1H) 7.63 (br. s., 2H) 7.94 (br. s., 1H) 8.10 (br. s., 1H) 8.39 (br. s., 1H) 9.08 (br. s., 1H) 11.59 (br. s., 1H). LCMS ESI (M+H) 447.

Formula Q

1H NMR (600 MHz, DMSO-$d_6$) δ ppm 0.82 (d, J=7.32 Hz, 2H) 1.08-1.37 (m, 3H) 1.38-1.64 (m, 2H) 1.71 (br. s., 1H) 1.91 (br. s., 1H) 2.80 (br. s., 1H) 3.12 (s, 1H) 3.41 (br. s., 4H) 3.65 (br. s., 4H) 4.09 (br. s., 1H) 7.26 (s, 1H) 7.52-7.74 (m, 2H) 7.94 (br. s., 1H) 8.13 (br. s., 1H) 8.40 (br. s., 1H) 9.09 (br. s., 1H) 9.62 (br. s., 1H) 11.71 (br. s., 1H). LCMS ESI (M+) 433

Formula GG

1H NMR (600 MHz, DMSO-$d_6$) δ ppm 0.85 (br. s., 1H) 1.17-1.39 (m, 7H) 1.42-1.58 (m, 2H) 1.67-1.84 (m, 3H) 1.88-2.02 (m, 1H) 2.76-2.93 (m, 1H) 3.07-3.22 (m, 1H) 3.29-3.39 (m, 1H) 3.41-3.61 (m, 4H) 3.62-3.76 (m, 4H) 3.78-3.88 (m, 1H) 4.12 (br. s., 1H) 7.28 (s, 1H) 7.60-7.76 (m, 2H) 7.98 (s, 1H) 8.13 (br. s., 1H) 8.41 (s, 1H) 9.10 (br. s., 1H) 11.21 (br. s., 1H) 11.54 (s, 1H). LCMS ESI (M+H) 475

Formula U

1H NMR (600 MHz, DMSO-$d_6$) δ ppm 0.84 (t, J=7.61 Hz, 2H) 1.13-1.39 (m, 4H) 1.46 (d, J=14.05 Hz, 2H) 1.64-1.99 (m, 6H) 2.21 (br. s., 1H) 2.66-2.89 (m, 2H) 3.06 (br. s., 1H) 3.24-3.36 (m, 1H) 3.37-3.50 (m, 2H) 3.56-3.72 (m, 2H) 3.77-4.00 (m, 4H) 4.02-4.19 (m, 2H) 7.25 (s, 1H) 7.50-7.75 (m, 2H) 7.89 (d, J=2.93 Hz, 1H) 8.14 (d, J=7.32 Hz, 1H) 8.38 (br. s., 1H) 9.06 (s, 1H) 11.53 (br. s., 1H). LCMS ESI (M+H) 517

Active Compounds, Salts and Formulations

As used herein, the term "active compound" refers to the selective CDK 4/6 inhibitor compounds described herein or a pharmaceutically acceptable salt or isotopic analog thereof. The active compound can be administered to the subject through any suitable approach. The amount and timing of active compound administered can, of course, be dependent on the subject being treated, on the dosage of chemotherapy to which the subject is anticipated of being exposed to, on the time course of the chemotherapeutic agent exposure, on the manner of administration, on the pharmacokinetic properties of the particular active compound, and on the judgment of the prescribing physician. Thus, because of subject to subject variability, the dosages given below are a guideline and the physician can titrate doses of the compound to achieve the treatment that the physician considers appropriate for the subject. In considering the degree of treatment desired, the physician can balance a variety of factors such as age and weight of the subject, presence of preexisting disease, as well as presence of other diseases. Pharmaceutical formulations can be prepared for any desired route of administration including, but not limited to, oral, intravenous, or aerosol administration, as discussed in greater detail below.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In some embodiments, the dosage can be the amount of compound needed to provide a serum concentration of the active compound of up to between about 1 and 5, 10, 20, 30, or 40 μM. In some embodiments, a dosage from about 10 mg/kg to about 50 mg/kg can be employed for oral administration. Typically, a dosage from about 0.5 mg/kg to 5 mg/kg can be employed for intramuscular injection. In some embodiments, dosages can be from about 1 μmol/kg to about 50 μmol/kg, or, optionally, between about 22 μmol/kg and about 33 μmol/kg of the compound for intravenous or oral administration. An oral dosage form can include any appropriate amount of active material, including for example from 5 mg to, 50, 100, 200, or 500 mg per tablet or other solid dosage form.

In accordance with the presently disclosed methods, pharmaceutically active compounds as described herein can be administered orally as a solid or as a liquid, or can be administered intramuscularly, intravenously, or by inhalation as a solution, suspension, or emulsion. In some embodiments, the compounds or salts also can be administered by inhalation, intravenously, or intramuscularly as a liposomal suspension. When administered through inhalation the active compound or salt can be in the form of a plurality of solid particles or droplets having any desired particle size, and for example, from about 0.01, 0.1 or 0.5 to about 5, 10, 20 or more microns, and optionally from about 1 to about 2 microns. Compounds as disclosed in the present invention have demonstrated good pharmacokinetic and pharmacodynamics properties, for instance when administered by the oral or intravenous routes.

In one embodiment of the invention, these improved CDK4/6 inhibitors can be administered in a concerted regimen with a blood growth factor agent. As such, in one embodiment, the use of the compounds and methods described herein is combined with the use of hematopoietic growth factors including, but not limited to, granulocyte colony stimulating factor (G-CSF, for example, sold as Neupogen (filgrastin), Neulasta (peg-filgrastin), or lenograstin), granulocyte-macrophage colony stimulating factor (GM-CSF, for example sold as molgramostim and sargramostim (Leukine)), M-CSF (macrophage colony stimulating factor), thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbopoetin, Epocept, Nanokine, Epofit, Epogin, Eprex and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Reacrit) as well as for example Epocept, EPOTrust, Erypro Safe, Repoeitin, Vintor, Epofit, Erykine, Wepox, Espogen, Relipoeitin, Shanpoietin, Zyrop and EPIAO).

The pharmaceutical formulations can comprise an active compound described herein or a pharmaceutically acceptable salt thereof, in any pharmaceutically acceptable carrier. If a solution is desired, water may be the carrier of choice for water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulation is placed in a vial designed for multi-dose use. The pharmaceutical formulations described herein can be lyophilized using techniques well known in the art.

For oral administration a pharmaceutical composition can take the form of solutions, suspensions, tablets, pills, capsules, powders, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed subject matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the subject matter described herein, there is provided an injectable, stable, sterile formulation comprising an active compound as described herein, or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles may for example have a particle size in the range of about 0.5 to about 10 microns, and optionally from about 0.5 to about 5 microns. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation can comprise a water-soluble active compound in a carrier that comprises water. A surfactant can be present, which lowers the surface tension of the formulation sufficiently to result in the formation of droplets within the desired size range when subjected to nebulization.

The term "pharmaceutically acceptable salts" as used herein refers to those salts which are, within the scope of sound medical judgment, suitable for use in contact with subjects (e.g., human subjects) without undue toxicity, irritation, allergic response, and the like, commensurate with a reasonable benefit/risk ratio, and effective for their intended use, as well as the zwitterionic forms, where possible, of the compounds of the presently disclosed subject matter.

Thus, the term "salts" refers to the relatively non-toxic, inorganic and organic acid addition salts of compounds of the presently disclosed subject matter. These salts can be prepared in situ during the final isolation and purification of the compounds or by separately reacting the purified compound in its free base form with a suitable organic or inorganic acid and isolating the salt thus formed. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

EXAMPLES

Intermediates B, E, K, L, 1A, 1F and 1CA were synthesized according to U.S. Pat. No. 8,598,186 entitled CDK Inhibitors to Tavares, F. X. and Strum, J. C.

The patents WO 2013/148748 entitled Lactam Kinase Inhibitors to Tavares, F. X., WO 2013/163239 entitled Synthesis of Lactams to Tavares, F. X., and U.S. Pat. No. 8,598,186 entitled CDK Inhibitors to Tavares, F. X. and Strum, J. C. are incorporated by reference herein in their entirety.

Example 1

Synthesis of tert-butyl N-[2-[(5-bromo-2-chloro-pyrimidin-4yl)amino]ethyl]carbamate, Compound 1

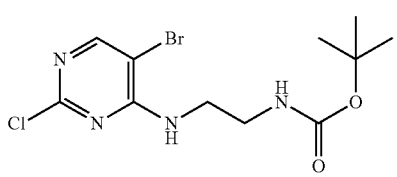 [SMILES: CC(C)(C)OC(=O)NCCNc1nc(Cl)ncc1Br]

To a solution of 5-bromo-2,4-dichloropyrimidine (3.2 g, 0.0135 mol) in ethanol (80 mL) was added Hunig's base (3.0 mL) followed by the addition of a solution of N-(tert-butoxycarbonyl)-1,2-diaminoethane (2.5 g, 0.0156 mole) in ethanol (20 mL). The contents were stirred overnight for 20 hrs. The solvent was evaporated under vacuum. Ethyl acetate (200 mL) and water (100 mL) were added and the layers separated. The organic layer was dried with magnesium sulfate and then concentrated under vacuum. Column chromatography on silica gel using hexane/ethyl acetate (0-60%) afforded tert-butyl N-[2-[(5-bromo-2-chloro-pyrimidin-4-yl)amino]ethyl]carbamate. $^1$HNMR (d6-DMSO) δ ppm 8.21 (s, 1H), 7.62 (brs, 1H), 7.27 (brs, 1H), 3.39 (m, 2H), 3.12 (m, 2H), 1.34 (s, 9H). LCMS (ESI) 351 (M+H).

Example 2

Synthesis of tert-butyl N-[2-[[2-chloro-5-(3,3-diethoxyprop-1-ynyl)pyrimidin-4-yl]amino]ethyl]carbamate, Compound 2

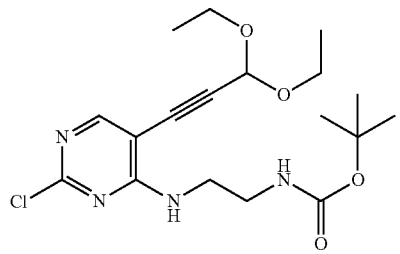 [SMILES: CCOC(C#Cc1cnc(Cl)nc1NCCNC(=O)OC(C)(C)C)OCC]

To tert-butyl N-[2-[(5-bromo-2-chloro-pyrimidin-4-yl)amino]ethyl]carbamate (1.265 g, 3.6 mmol) in THF (10 mL) was added the acetal (0.778 mL, 5.43 mmol), Pd(dppf)CH$_2$C$_{12}$ (148 mg), and triethylamine (0.757 mL, 5.43 mmol). The contents were degassed and then purged with nitrogen. To this was then added CuI (29 mg). The reaction mixture was heated at reflux for 48 hrs. After cooling, the contents were filtered over CELITE™ and concentrated. Column chromatography of the resulting residue using hexane/ethyl acetate (0-30%) afforded tert-butyl N-[2-[[2-chloro-5-(3,3-diethoxyprop-1-ynyl)pyrimidin-4-yl]amino]ethyl]carbamate. $^1$HNMR (d6-DMSO) δ ppm 8.18 (s, 1H), 7.63 (brs, 1H), 7.40 (brs, 1H), 5.55 (s, 1H), 3.70 (m, 2H), 3.60 (m, 2H), 3.42 (m, 2H), 3.15 (m, 2H), 1.19-1.16 (m, 15H). LCMS (ESI) 399 (M+H).

Example 3

Synthesis of tert-butyl N-[2-[2-chloro-6-(diethoxymethyl)pyrrolo[2,3-d]pyrimidin-7-yl]ethyl]carbamate, Compound 3

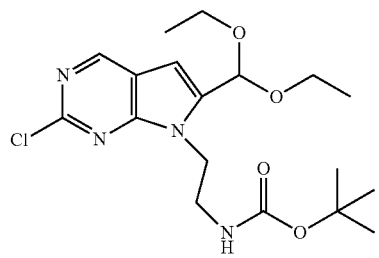 [SMILES: CCOC(OCC)c1cc2cnc(Cl)nc2n1CCNC(=O)OC(C)(C)C]

To a solution of the coupled product (2.1 g, 0.00526 mole) in THF (30 mL) was added TBAF solid (7.0 g). The contents were heated to and maintained at 65 degrees for 2 hrs. Concentration followed by column chromatography using ethyl acetate/hexane (0-50%) afforded tert-butyl N-[2-[2-chloro-6-(diethoxymethyl)pyrrolo[2,3-d]pyrimidin-7-yl]ethyl]carbamate as a pale brown liquid (1.1 g). $^1$HNMR (d6-DMSO) δ ppm 8.88 (s, 1H), 6.95 (brs, 1H), 6.69 (s, 1H), 5.79 (s, 1H), 4.29 (m, 2H), 3.59 (m, 4H), 3.34 (m, 1H), 3.18 (m, 1H), 1.19 (m, 9H), 1.17 (m, 6H). LCMS (ESI) 399 (M+H).

Example 4

Synthesis of tert-butyl N-[2-(2-chloro-6-formyl-pyrrolo[2,3-d]pyrimidin-7-yl)ethyl]carbamate, Compound 4

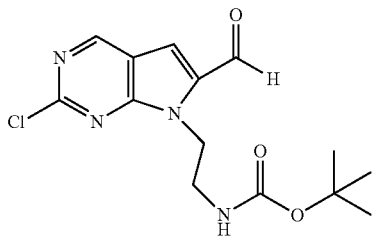 [SMILES: CC(C)(C)OC(=O)NCCn1c(C=O)cc2cnc(Cl)nc21]

To the acetal (900 mg) from the preceeding step was added AcOH (8.0 mL) and water (1.0 mL). The reaction was stirred at room temperature for 16 hrs. Conc. and column chromatography over silica gel using ethyl acetate/hexanes (0-60%) afforded tert-butyl N-[2-(2-chloro-6-formyl-pyrrolo[2,3-d]pyrimidin-7-yl)ethyl]carbamate as a foam (0.510 g). $^1$HNMR (d6-DMSO) δ ppm 9.98 (s, 1H), 9.18 (s, 1H), 7.66 (s, 1H), 6.80 (brs, 1H), 4.52 (m, 2H), 4.36 (m, 2H), 1.14 (s, 9H). LCMS (ESI) 325 (M+H).

Example 5

Synthesis of 7-[2-(tert-butoxycarbonylamino)ethyl]-2-chloro-pyrrolo[2,3-d]pyrimidine-6-carboxylic Acid, Compound 5

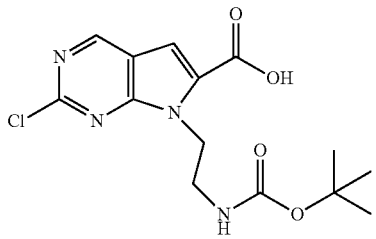 [SMILES: CC(C)(C)OC(=O)NCCn1c(C(=O)O)cc2cnc(Cl)nc21]

To the aldehyde (0.940 g) from the preceeding step in DMF (4 mL) was added oxone (1.95 g, 1.1 eq). The contents were stirred at room temp for 7 hrs. Silica gel column chromatography using hexane/ethyl acetate (0-100%) afforded 7-[2-(tert-butoxycarbonylamino)ethyl]-2-chloro-pyrrolo[2,3-d]pyrimidine-6-carboxylic acid (0.545 g). $^1$HNMR (d6-DMSO) δ ppm 9.11 (s, 1H), 7.39 (s, 1H), 4.38 (m, 2H), 4.15 (m, 2H), 1.48 (m, 9H). LCMS (ESI) 341 (M+H).

Example 6

Synthesis of methyl 7-[2-(tert-butoxycarbonylamino)ethyl]-2-chloro-pyrrolo[2,3-d]pyrimidine-6-carboxylate, Compound 6

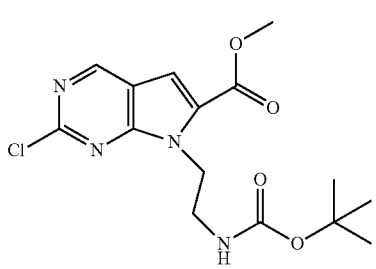 [SMILES: COC(=O)c1cc2cnc(Cl)nc2n1CCNC(=O)OC(C)(C)C]

To a solution of 2-chloro-7-propyl-pyrrolo[2,3-d]pyrimidine-6-carboxylic acid (0.545 g, 0.00156 mole) from the preceeding step in toluene (3.5 mL) and MeOH (1 mL) was added TMS-diazomethane (1.2 mL). After stirring overnight at room temperature, the excess of TMS-diazomethane was quenched with acetic acid (3 mL) and the reaction was concentrated under vacuum. The residue was purified by silica gel column chromatography with hexane/ethyl acetate (0-70%) to afford methyl 7-[2-(tert-butoxycarbonylamino)ethyl]-2-chloro-pyrrolo[2,3-d]pyrimidine-6-carboxylate as an off white solid (0.52 g). $^1$HNMR (d6-DMSO) δ ppm 9.10 (s, 1H), 7.45 (s, 1H), 6.81 (brs, 1H) 4.60 (m, 2H), 3.91 (s, 3H), 3.29 (m, 2H), 1.18 (m, 9H) LCMS (ESI) 355 (M+H).

Example 7

Synthesis of Chloro tricyclic amide, Compound 7

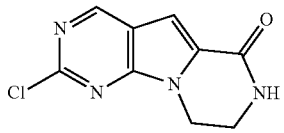 [SMILES: O=C1NCCn2c1cc1cnc(Cl)nc12]

To methyl 7-[2-(tert-butoxycarbonylamino)ethyl]-2-chloro-pyrrolo[2,3-d]pyrimidine-6-carboxylate (0.50 g, 0.0014 mole) from the preceeding step in dichloromethane (2.0 mL) was added TFA (0.830 mL). The contents were stirred at room temperature for 1 hr. Concentration under vacuum afforded the crude amino ester which was suspended in toluene (5 mL) and Hunig's base (0.5 mL). The contents were heated at reflux for 2 hrs. Concentration followed by silica gel column chromatography using hexane/ethyl acetate (0-50%) afforded the desired chloro tricyclic amide (0.260 g). $^1$HNMR (d6-DMSO) δ ppm 9.08 (s, 1H), 8.48 (brs, 1H), 7.21 (s, 1H) 4.33 (m, 2H), 3.64 (m, 2H). LCMS (ESI) 223 (M+H).

Example 8

Synthesis of chloro-N-methyltricyclic amide, Compound 8

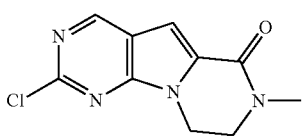 [SMILES: CN1CCn2c(cc3cnc(Cl)nc32)C1=O]

To a solution of the chloro tricycliclactam, Compound 7, (185 mg, 0.00083 mole) in DMF (2.0 mL) was added sodium hydride (55% dispersion in oil, 52 mg). After stirring for 15 mins, methyl iodide (62 μL, 1.2 eq). The contents were stirred at room temperature for 30 mins. After the addition of methanol (5 mL), sat NaHCO$_3$ was added followed by the addition of ethyl acetate. Separation of the organic layer followed by drying with magnesium sulfate and concentration under vacuum afforded the N-methylated amide in quantitative yield. $^1$HNMR (d6-DMSO) δ ppm 9.05 (s, 1H), 7.17 (s, 1H) 4.38 (m, 2H), 3.80 (m, 2H), 3.05 (s, 3H). LCMS (ESI) 237 (M+H).

105

Example 9

Synthesis of
1-methyl-4-(6-nitro-3-pyridyl)piperazine,
Compound 9

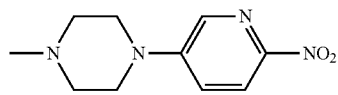

To 5-bromo-2-nitropyridine (4.93 g, 24.3 mmole) in DMF (20 mL) was added N-methylpiperazine (2.96 g, 1.1 eq) followed by the addition of DIPEA (4.65 mL, 26.7 mmole). The contents were heated at 90 degrees for 24 hrs. After addition of ethyl acetate (200 mL), water (100 mL) was added and the layers separated. Drying followed by concentration afforded the crude product which was purified by silica gel column chromatography using (0-10%) DCM/Methanol. $^1$HNMR (d6-DMSO) δ ppm 8.26 (s, 1H), 8.15 (1H, d, J=9.3 Hz), 7.49 (1H, d, J=9.4 Hz), 3.50 (m, 4H), 2.49 (m, 4H), 2.22 (s, 3H).

Example 10

Synthesis of
5-(4-methylpiperazin-1-yl)pyridin-2-amine,
Compound 10

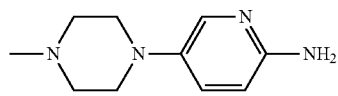

To 1-methyl-4-(6-nitro-3-pyridyl)piperazine (3.4 g) in ethyl acetate (100 mL) and ethanol (100 mL) was added 10% Pd/C (400 mg) and then the reaction was stirred under hydrogen (10 psi) overnight. After filtration through CELITE™, the solvents were evaporated and the crude product was purified by silica gel column chromatography using DCM/7N ammonia in MeOH (0-5%) to afford 5-(4-methylpiperazin-1-yl)pyridin-2-amine (2.2 g). $^1$HNMR (d6-DMSO) δ ppm 7.56 (1H, d, J=3 Hz), 7.13 (1H, m), 6.36 (1H, d, J=8.8 Hz), 5.33 (brs, 2H), 2.88 (m, 4H), 2.47 (m, 4H), 2.16 (s, 3H).

Example 11

Synthesis of tert-butyl
4-(6-amino-3-pyridyl)piperazine-1-carboxylate,
Compound 11

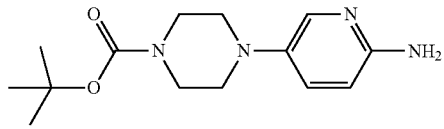 [SMILES: CC(C)(C)OC(=O)N1CCN(c2ccc(N)nc2)CC1]

This compound was prepared as described in WO 2010/020675 A1.

106

Example 12

Synthesis of tert-butyl N-[2-(benzyloxycarbonylamino)-3-methyl-butyl]carbamate, Compound 12

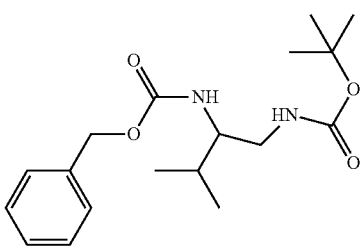 [SMILES: CC(C)C(CNC(=O)OC(C)(C)C)NC(=O)OCc1ccccc1]

To benzyl N-[1-(hydroxymethyl)-2-methyl-propyl]carbamate (11.0 g, 0.0464 mole) in dioxane (100 mL) cooled to 0° C. was added diphenylphosphoryl azide (10.99 mL, 1.1 eq) followed by the addition of DBU (8.32 mL, 1.2 eq). The contents were allowed to warm to room temperature and stirred for 16 hrs. After the addition of ethyl acetate (300 mL) and water (100 mL), the organic layer was separated and washed with satd. NaHCO$_3$ (100 mL). The organic layer was then dried (magnesium sulfate) and concentrated under vacuum. To this intermediate in DMSO (100 mL) was added sodium azide (7.54 g) and the contents then heated to 90 degrees for 2 hrs. After addition of ethyl acetate and water the layers were separated. The organic layer was dried with magnesium sulfate followed by concentration under vacuum to afford an oil that was purified by silica gel column chromatography using hexane/ethyl acetate (0-70%) to afford benzyl N-[1-(azidomethyl)-2-methyl-propyl]carbamate 6.9 g as a colorless oil.

To benzyl N-[1-(azidomethyl)-2-methyl-propyl]carbamate (6.9 g, 0.0263 mole) in THF (100 mL) was added triphenyl phosphine (7.59 g, 1.1 eq). The contents were stirred for 20 hrs. After addition of water (10 mL), and stirring for an additional 6 hrs, ethyl acetate was added and the layers separated. After drying with magnesium sulfate and concentration under vacuum, the crude product was purified by silica gel column chromatography using DCM/MeOH (0-10%) to afford benzyl N-[1-(aminomethyl)-2-methyl-propyl]carbamate as a yellow oil.

To benzyl N-[1-(aminomethyl)-2-methyl-propyl]carbamate (4.65 g, 0.019 mole) in THF (70 mL) was added 2N NaOH (20 mL) followed by the addition of di-tert-butyl dicarbonate (5.15 g, 1.2 eq). After stirring for 16 hrs, ethyl acetate was added and the layers were separated. After drying with magnesium sulfate and concentration under vacuum, the crude product was purified using hexane/ethyl acetate (0-40%) over a silica gel column to afford intermediate A, tert-butyl N-[2-(benzyloxycarbonylamino)-3-methyl-butyl]carbamate, (6.1 g). $^1$HNMR (600 MHz, CHLOROFORM-d) δ ppm 0.89 (d, J=6.73 Hz, 3H) 0.92 (d, J=6.73 Hz, 3H) 1.38 (s, 9H) 1.70-1.81 (m, 1H) 3.18 (d, J=5.56 Hz, 2H) 3.47-3.60 (m, 1H) 4.76 (s, 1H) 4.89 (d, J=7.90 Hz, 1H) 5.07 (s, 2H) 7.25-7.36 (m, 5H). LCMS (ESI) 337 (M+H).

Example 13

Synthesis of tert-butyl N-[2-(benzyloxycarbonylamino)-4-methyl-pentyl]carbamate, Compound 13

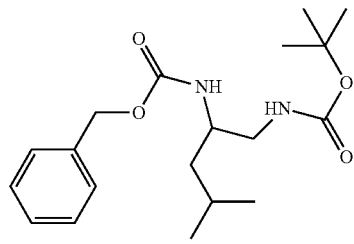 [SMILES: CC(C)CC(CNC(=O)OC(C)(C)C)NC(=O)OCc1ccccc1]

To a solution of benzyl N-[1-(hydroxymethyl)-3-methyl-butyl]carbamate (6.3 g, 0.025 mole) in DCM (100 mL) was added diisopropylethyl amine (5.25 mL, 1.2 eq) followed by the addition of methane sulfonylchloride (2.13 mL, 1.1 eq) at 0 degrees. After stirring for 3 hrs, water (100 mL) was added and the organic layer separated. After drying with magnesium sulfate and concentration under vacuum, the crude [2-(benzyloxycarbonylamino)-4-methyl-pentyl]methanesulfonate which was taken directly to the next step.

To the crude [2-(benzyloxycarbonylamino)-4-methyl-pentyl]methanesulfonate from the above reaction in DMF (50 mL), was added sodium azide 2.43 g. The reaction mixture was then heated to 85 degrees for 3 hrs. After cooling, ethyl acetate (300 mL) and water was added. The organic layer was separated, dried with magnesium sulfate and then concentrated under vacuum to afford the crude benzyl N-[1-(azidomethyl)-3-methyl-butyl]carbamate. To this crude intermediate was added THF (100 mL) followed by triphenylphosphine 7.21 g and stirred under nitrogen for 16 hrs. After addition of water (10 mL), and stirring for an additional 6 hrs, ethyl acetate was added and the layers separated. After drying with magnesium sulfate and concentration under vacuum, the crude product was columned using DCM/MeOH (0-10%) to afford benzyl N-[1-(aminomethyl)-3-methyl-butyl]carbamate (4.5 g).

To benzyl N-[1-(aminomethyl)-3-methyl-butyl]carbamate (4.5 g, 0.018 mole) in THF (60 mL) was added 2N NaOH (18 mL) followed by the addition of di-tert-butyl dicarbonate (4.19 g, 1.07 eq). After stirring for 16 hrs, ethyl acetate was added and the layers separated. After drying with magnesium sulfate and concentration under vacuum, the crude product was taken to the next step. $^1$HNMR (600 MHz, CHLOROFORM-d) δ ppm 0.89 (d, J=6.73 Hz, 6H) 1.25-1.34 (m, 1H) 1.39 (s, 9H) 1.57-1.71 (m, 2H) 3.04-3.26 (m, 2H) 3.68-3.80 (m, 1H) 4.72-4.89 (m, 2H) 5.06 (s, 2H) 7.25-7.38 (m, 5H). LCMS (ESI) 351 (M+H).

Example 14

Synthesis of tert-butyl N-[(2R)-2-(benzyloxycarbonylamino)-3-methyl-butyl]carbamate, Compound 14

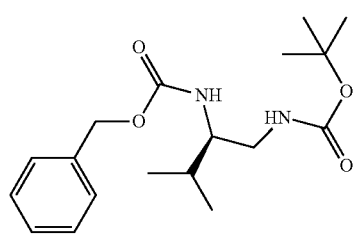 [SMILES: CC(C)[C@H](CNC(=O)OC(C)(C)C)NC(=O)OCc1ccccc1]

Compound 14 was synthesized from benzyl N-[(1R)-1-(hydroxymethyl)-2-methyl-propyl]carbamate using similar synthetic steps as that described for Compound 13. The analytical data (NMR and mass spec) was consistent with that for Compound 12.

Example 15

Synthesis of tert-butyl N-[(2S)-2-(benzyloxycarbonylamino)-3-methyl-butyl]carbamate, Compound 15

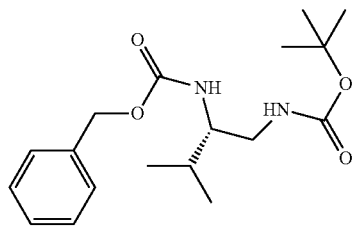 [SMILES: CC(C)[C@@H](CNC(=O)OC(C)(C)C)NC(=O)OCc1ccccc1]

Compound 15 was synthesized from benzyl N-[(1S)-1-(hydroxymethyl)-2-methyl-propyl]carbamate using similar synthetic steps as that described for Compound 13. The analytical data (NMR and mass spec) was consistent with that for Compound 12.

Example 16

Synthesis of tert-butyl N-[(1S)-1-(aminomethyl)-2-methyl-propyl]carbamate, Compound 16

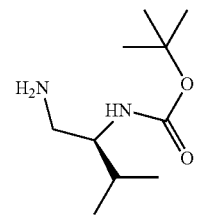

To a solution of tert-butyl N-[(1S)-1-(hydroxymethyl)-2-methyl-propyl]carbamate carbamate (6.3 g, 0.025 mole) in THF (100 mL) was added diisopropylethyl amine (5.25 mL, 1.2 eq) followed by the addition of methane sulfonylchloride (2.13 mL, 1.1 eq) at 0 degrees. After stirring for 3 hrs, water (100 mL) was added and the organic layer separated. After drying with magnesium sulfate and concentration under vacuum, the crude [(2S)-2-(tert-butoxycarbonylamino)-3-methyl-butyl]methanesulfonate was taken directly to the next step.

To the crude [(2S)-2-(tert-butoxycarbonylamino)-3-methyl-butyl]methanesulfonate from the above reaction in DMSO (50 mL), was added sodium azide (2.43 g). The reaction mixture was then heated to 85 degrees for 3 hrs. After cooling, ethyl acetate (300 mL) and water were added. The organic layer was separated, dried with magnesium sulfate and then concentrated under vacuum to afford the crude benzyl N-[1-(azidomethyl)-3-methyl-butyl]carbamate. To this crude intermediate was added THF (100 mL) followed by triphenylphosphine (7.21 g) and the reaction was stirred under nitrogen for 16 hrs. After addition of water (10 mL), and stirring for an additional 6 hrs, ethyl acetate was added and the layers separated. After drying with magnesium sulfate and concentration under vacuum, the crude product was purified by silica gel column chromatography using DCM/MeOH (0-10%) to afford benzyl N-[1-(aminomethyl)-3-methyl-butyl]carbamate (4.5 g). LCMS (ESI) 203 (M+H).

Example 17

Synthesis of tert-butyl N-[(1R)-1-(aminomethyl)-2-methyl-propyl]carbamate, Compound 17

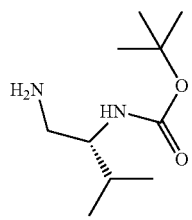

Compound 17 was synthesized from tert-butyl N-[(1R)-1-(hydroxymethyl)-2-methyl-propyl]carbamate using a similar synthetic sequence as described for Compound 16. The analytical data (NMR and mass spec) was consistent with Compound 16.

Example 18

Synthesis of tert-butyl N-[(2S)-2-(benzyloxycarbonylamino)-4-methyl-pentyl]carbamate, Compound 18

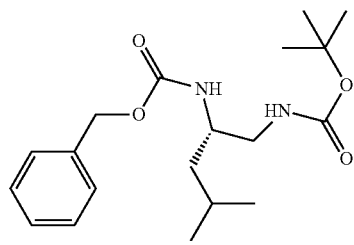 [SMILES: CC(C)C[C@@H](CNC(=O)OC(C)(C)C)NC(=O)OCc1ccccc1]

Compound 18 was synthesized from benzyl N-[(1S)-1-(hydroxymethyl)-3-methyl-butyl]carbamate using a similar synthetic sequence as described for Compound 13. The analytical data (NMR and mass spec) was consistent with Compound 13.

Example 19

Synthesis of tert-butyl N-[(2S)-2-(benzyloxycarbonylamino)-2-phenyl-ethyl]carbamate, Compound 19

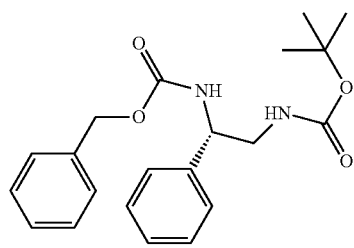 [SMILES: CC(C)(C)OC(=O)NC[C@@H](NC(=O)OCc1ccccc1)c1ccccc1]

Compound 19 was synthesized from benzyl N-[(1S)-2-hydroxy-1-phenyl-ethyl]carbamate using a similar synthetic sequence as described for Compound 13. ¹HNMR (600 MHz, DMSO-d$_6$) δ ppm 1.20-1.33 (m, 9H) 3.11 (t, J=6.29 Hz, 2H) 4.59-4.68 (m, 1H) 4.88-5.01 (m, 2H) 6.81 (t, J=5.42 Hz, 1H) 7.14-7.35 (m, 10H) 7.69 (d, J=8.49 Hz, 1H). LCMS (ESI) 371 (M+H).

Example 20

Synthesis of tert-butyl N-[(2S)-2-(benzyloxycarbonylamino)-3-methyl-pentyl]carbamate, Compound 20

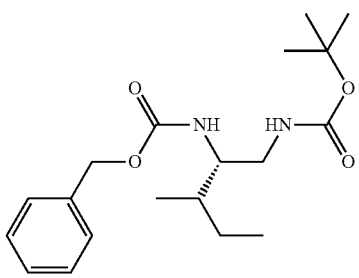 [SMILES: CCC(C)[C@@H](CNC(=O)OC(C)(C)C)NC(=O)OCc1ccccc1]

Compound 20 was synthesized from benzyl N-[(1S)-1-(hydroxymethyl)-2-methyl-butyl]carbamate using a similar synthetic sequence as described for Compound 13. ¹HNMR (600 MHz, CHLOROFORM-d) δ ppm 0.85-0.92 (m, 6H) 1.05-1.15 (m, 1H) 1.35-1.41 (m, 9H) 1.45-1.56 (m, 2H) 3.14-3.24 (m, 2H) 3.54-3.64 (m, 1H) 4.78 (s, 1H) 4.96 (d, J=7.91 Hz, 1H) 5.06 (s, 2H) 7.27-7.37 (m, 5H). LCMS (ESI) 351 (M+H).

Example 21

Synthesis of tert-butyl N-[(2S)-2-(benzyloxycarbonylamino)-3,3-dimethyl-butyl]carbamate, Compound 21

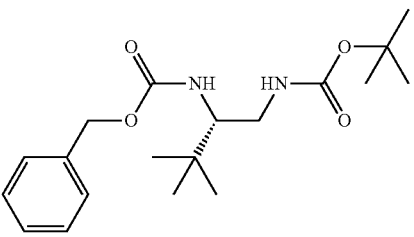 [SMILES: CC(C)(C)OC(=O)NC[C@@H](NC(=O)OCc1ccccc1)C(C)(C)C]

Compound 21 was synthesized from benzyl N-[(1S)-1-(hydroxymethyl)-2,2-dimethyl-propyl]carbamate using a similar synthetic sequence as described for Compound 13. LCMS (ESI) 351.

Example 22

Synthesis of tert-butyl N-[[1-(benzyloxycarbonylamino)cyclohexyl]methyl]carbamate, Compound 22

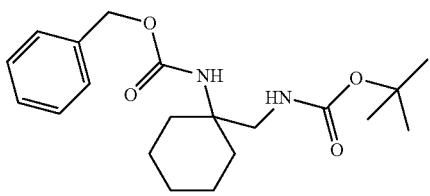 [SMILES: CC(C)(C)OC(=O)NCC1(NC(=O)OCc2ccccc2)CCCCC1]

To a solution of benzyl N-[1-(aminomethyl)cyclohexyl] carbamate (10.0 g, 0.0381 mole) in THF (150 mL) was added di-tert-butyl dicarbonate (9.15 g, 1.1 eq) and the contents were stirred at room temperature for 16 hrs. Ethyl acetate and water were then added. The organic layer was separated, dried over magnesium sulfate and then concentrated under vacuum to afford tert-butyl N-[[1-(benzyloxycarbonylamino)cyclohexyl]methyl]carbamate (13.1 g). $^1$HNMR (600 MHz, DMSO-$d_6$) δ ppm 0.92-1.54 (m, 17H) 1.76-2.06 (m, 2H) 3.09 (d, J=6.15 Hz, 2H) 4.92 (s, 2H) 6.63 (d, J=17.27 Hz, 1H) 7.16-7.49 (m, 6H). LCMS (ESI) 363 (M+H).

Example 23

Synthesis of tert-butyl N-[[1-(benzyloxycarbonylamino)cyclopentyl]methyl]carbamate, Compound 23

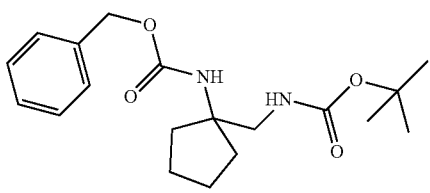 [SMILES: CC(C)(C)OC(=O)NCC1(NC(=O)OCc2ccccc2)CCCC1]

tert-butyl N-[[1-(benzyloxycarbonylamino)cyclopentyl]methyl]carbamate was synthesized in an analogous manner to tert-butyl N-[[1-(benzyloxycarbonylamino) cyclohexyl] methyl]carbamate. LCMS (ESI) 349 (M+H).

Example 24

Synthesis of 2-nitro-5-[4-(1-piperidyl)-1-piperidyl] pyridine, Compound 24

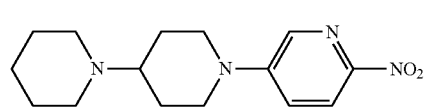

To 5-bromo-2-nitropyridine (1.2 g, 5.9 mmol) in DMSO (4 mL) was added 1-(4-piperidyl)piperidine (1.0 g, 5.9 mmole) and triethylamine (0.99 mL, 7.1 mmole). The contents were heated to 120° C. in a CEM Discovery microwave system for 3 hours. The crude reaction was then purified by silica gel column chromatography with DCM/methanol (0-20%) to afford 2-nitro-5-[4-(1-piperidyl)-1-piperidyl] pyridine as an oil (457 mg). $^1$HNMR (600 MHz, DMSO-$d_6$) δ ppm 1.26-1.36 (m, 2H) 1.43 (m, 6H) 1.76 (m, 2H) 2.37 (m, 5H) 2.94 (t, J=12.74 Hz, 2H) 4.06 (d, J=13.47 Hz, 2H) 7.41 (dd, J=9.37, 2.64 Hz, 1H) 8.08 (d, J=9.37 Hz, 1H) 8.20 (d, J=2.64 Hz, 1H).

Example 25

Synthesis of 5-[4-(1-piperidyl)-1-piperidyl]pyridin-2-amine, Compound 25

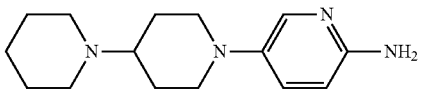 [SMILES: Nc1ccc(N2CCC(N3CCCCC3)CC2)cn1]

5-[4-(1-piperidyl)-1-piperidyl]pyridin-2-amine was prepared in a manner similar to that used in the synthesis of 5-(4-methylpiperazin-1-yl)pyridin-2-amine. $^1$HNMR (600 MHz, DMSO-$d_6$) δ ppm 1.13-1.37 (m, 6H) 1.40-1.63 (m, 6H) 1.71 (m, 2H), 2.24 (m, 1H) 2.43 (m, 2H) 3.33 (d, J=12.30 Hz, 2H) 5.31 (s, 2H) 6.33 (d, J=8.78 Hz, 1H) 7.10 (dd, J=8.78, 2.93 Hz, 1H) 7.55 (d, J=2.64 Hz, 1H). LCMS (ESI) 261 (M+H).

Example 26

Synthesis of 4-[1-(6-nitro-3-pyridyl)-4-piperidyl] morpholine, Compound 26

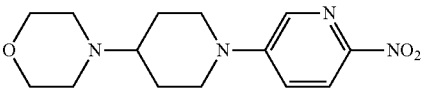

4-[1-(6-nitro-3-pyridyl)-4-piperidyl]morpholine was synthesized in a manner similar to that used in the synthesis of 2-nitro-5-[4-(1-piperidyl)-1-piperidyl]pyridine. $^1$HNMR (600 MHz, DMSO-$d_6$) δ ppm 1.41 (m, 2H) 1.82 (m, 2H) 2.42 (m, 5H) 2.98 (t, J=12.44 Hz, 2H) 3.52 (s, 4H) 4.04 (d, J=12.88 Hz, 2H) 7.42 (d, J=9.37 Hz, 1H) 8.08 (d, J=9.08 Hz, 1H) 8.21 (s, 1H).

Example 27

Synthesis of 5-(4-morpholino-1-piperidyl) pyridin-2-amine, Compound 27

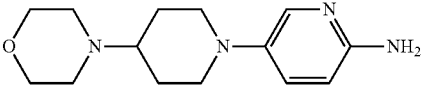

5-(4-morpholino-1-piperidyl)pyridin-2-amine was prepared in a manner similar to that used in the synthesis of 5-(4-methylpiperazin-1-yl)pyridin-2-amine. $^1$HNMR (600 MHz, DMSO-$d_6$) δ ppm 1.34-1.52 (m, 2H) 1.78 (m, 2H) 2.14 (m, 1H) 2.43 (m, 4H) 3.32 (d, J=12.30 Hz, 4H)

3.47-3.59 (m, 4H) 5.32 (s, 2H) 6.34 (d, J=8.78 Hz, 1H) 7.11 (dd, J=8.93, 2.78 Hz, 1H) 7.47-7.62 (m, 1H). LCMS (ESI) 263 (M+H).

Example 28

Synthesis of 4-[1-(6-nitro-3-pyridyl)-4-piperidyl] thiomorpholine, Compound 28

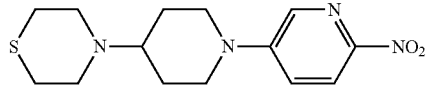

4-[1-(6-nitro-3-pyridyl)-4-piperidyl]thiomorpholine was synthesized in a manner similar to that used in the synthesis of 2-nitro-5-[4-(1-piperidyl)-1-piperidyl]pyridine. $^1$HNMR (600 MHz, DMSO-d$_6$) δ ppm 1.40-1.52 (m, 2H) 1.71 (m, 2H) 2.49-2.55 (m, 4H) 2.56-2.63 (m, 1H) 2.68-2.75 (m, 4H) 2.88-2.98 (m, 2H) 4.09 (d, J=13.18 Hz, 2H) 7.42 (dd, J=9.22, 3.07 Hz, 1H) 8.08 (d, J=9.37 Hz, 1H) 8.20 (d, J=3.22 Hz, 1H).

Example 29

Synthesis of 5-(4-thiomorpholino-1-piperidyl) pyridin-2-amine, Compound 29

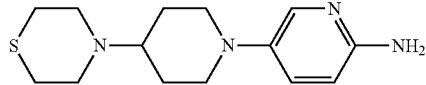

5-(4-thiomorpholino-1-piperidyl) pyridin-2-amine was prepared in a manner similar to that used in the synthesis of 5-(4-methylpiperazin-1-yl)pyridin-2-amine. $^1$HNMR (600 MHz, DMSO-d$_6$) δ ppm 1.47-1.59 (m, 2H) 1.65 (m, 2H) 2.22-2.38 (m, 1H) 2.50-2.59 (m, 6H) 2.68-2.82 (m, 4H) 3.33 (d, J=12.00 Hz, 2H) 5.31 (s, 2H) 6.33 (d, J=9.08 Hz, 1H) 7.10 (dd, J=8.78, 2.93 Hz, 1H) 7.55 (d, J=2.64 Hz, 1H). LCMS (ESI) 279 (M+H).

Example 30

Synthesis of 2-nitro-5-(1-piperidyl)pyridine, Compound 30

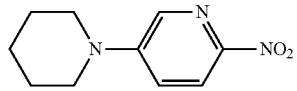 [SMILES: O=[N+]([O-])c1ccc(N2CCCCC2)cn1]

2-nitro-5-(1-piperidyl) pyridine was synthesized in a manner similar to that used in the synthesis of 2-nitro-5-[4-(1-piperidyl)-1-piperidyl]pyridine. $^1$HNMR (600 MHz, DMSO-d$_6$) δ ppm 1.56 (m, 6H) 3.49 (d, J=4.39 Hz, 4H) 7.30-7.47 (m, 1H) 8.02-8.12 (m, 1H) 8.15-8.26 (m, 1H).

Example 31

Synthesis of 5-(1-piperidyl)pyridin-2-amine, Compound 31

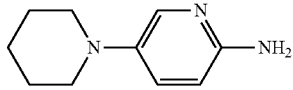 [SMILES: Nc1ccc(N2CCCCC2)cn1]

5-(1-piperidyl) pyridin-2-amine was prepared in a manner similar to that in the synthesis of 5-(4-methylpiperazin-1-yl)pyridin-2-amine. $^1$HNMR (600 MHz, DMSO-d$_6$) δ ppm 1.39-1.46 (m, 2H) 1.51-1.62 (m, 4H) 2.75-2.92 (m, 4H) 5.30 (s, 2H) 6.34 (d, J=8.78 Hz, 1H) 7.09 (dd, J=8.78, 2.93 Hz, 1H) 7.54 (d, J=2.93 Hz, 1H). LCMS (ESI) 178 (M+H).

Example 32

Synthesis of 4-(6-nitro-3-pyridyl) thiomorpholine, Compound 32

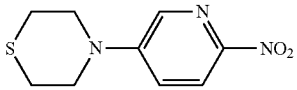 [SMILES: O=[N+]([O-])c1ccc(N2CCSCC2)cn1]

4-(6-nitro-3-pyridyl) thiomorpholine was synthesized in a manner similar to that used in the synthesis of 2-nitro-5-[4-(1-piperidyl)-1-piperidyl]pyridine. $^1$HNMR (600 MHz, DMSO-d$_6$) δ ppm 2.56-2.69 (m, 4H) 3.79-3.92 (m, 4H) 7.43 (dd, J=9.22, 3.07 Hz, 1H) 8.10 (d, J=9.37 Hz, 1H) 8.20 (d, J=2.93 Hz, 1H).

Example 33

Synthesis of 5-thiomorpholinopyridin-2-amine, Compound 33

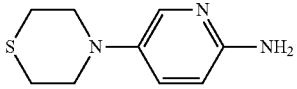

5-thiomorpholinopyridin-2-amine was prepared in a manner similar to that used in the synthesis of 5-(4-methylpiperazin-1-yl) pyridin-2-amine. $^1$HNMR (600 MHz, DMSO-d$_6$) δ ppm 2.59-2.73 (m, 4H) 3.04-3.20 (m, 4H) 5.41 (s, 2H) 6.35 (d, J=8.78 Hz, 1H) 7.10 (dd, J=8.78, 2.93 Hz, 1H) 7.57 (d, J=2.64 Hz, 1H). LCMS (ESI) 196 (M+H).

Example 34

Synthesis of tert-butyl (4R)-5-(6-nitro-3-pyridyl)-2,5-diazabicyclo[2.2.1]heptane-2-carboxylate, Compound 34

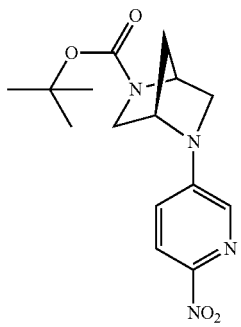 [SMILES: CC(C)(C)OC(=O)N1C[C@H]2CC1CN2c1ccc([N+](=O)[O-])nc1]

tert-butyl (4R)-5-(6-nitro-3-pyridyl)-2,5-diazabicyclo[2.2.1]heptane-2-carboxylate was synthesized in a manner similar to that used in the synthesis of 2-nitro-5-[4-(1-piperidyl)-1-piperidyl]pyridine. $^1$HNMR (600 MHz, DMSO-d$_6$) δ ppm 1.33 (d, J=32.21 Hz, 11H) 1.91 (m, 2H) 3.15 (d, J=10.25 Hz, 1H) 3.58 (m, 1H) 4.46 (m, 1H) 4.83 (s, 1H) 7.16 (s, 1H) 7.94 (s, 1H) 8.05-8.16 (m, 1H).

Example 35

Synthesis of tert-butyl (4R)-5-(6-amino-3-pyridyl)-2,5-diazabicyclo[2.2.1]heptane-2-carboxylate, Compound 35

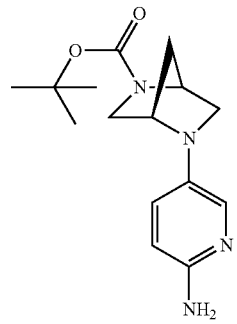 [SMILES: CC(C)(C)OC(=O)N1C[C@H]2CC1CN2c1ccc(N)nc1]

tert-butyl (4R)-5-(6-amino-3-pyridyl)-2,5-diazabicyclo[2.2.1]heptane-2-carboxylate was prepared in a manner similar to that used in the synthesis of 5-(4-methylpiperazin-1-yl)pyridin-2-amine. $^1$HNMR (600 MHz, DMSO-d$_6$) δ ppm 1.31 (d, J=31.91 Hz, 11H) 1.83 (m, 2H) 2.71-2.82 (m, 1H) 3.44 (m, 1H) 4.30 (d, 2H) 5.08 (s, 2H) 6.35 (d, J=8.78 Hz, 1H) 6.77-6.91 (m, 1H) 7.33 (s, 1H). LCMS (ESI) 291 (M+H).

Example 36

Synthesis of N,N-dimethyl-1-(6-nitro-3-pyridyl)piperidin-4-amine, Compound 36

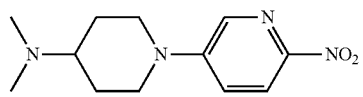 [SMILES: CN(C)C1CCN(c2ccc([N+](=O)[O-])nc2)CC1]

N,N-dimethyl-1-(6-nitro-3-pyridyl)piperidin-4-amine was synthesized in a manner similar to that used in the synthesis of 2-nitro-5-[4-(1-piperidyl)-1-piperidyl]pyridine. $^1$HNMR (600 MHz, DMSO-d$_6$) δ ppm 1.30-1.45 (m, 2H) 1.79 (m, 2H) 2.14 (s, 6H) 2.33 (m, 1H) 2.92-3.04 (m, 2H) 4.03 (d, J=13.76 Hz, 2H) 7.42 (dd, J=9.22, 3.07 Hz, 1H) 8.04-8.11 (m, 1H) 8.21 (d, J=2.93 Hz, 1H).

Example 37

Synthesis of 5-[4-(dimethylamino)-1-piperidyl]pyridin-2-amine, Compound 37

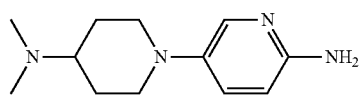

5-[4-(dimethylamino)-1-piperidyl]pyridin-2-amine was prepared in a manner similar to that used in the synthesis of 5-(4-methylpiperazin-1-yl)pyridin-2-amine. $^1$HNMR (600 MHz, DMSO-d$_6$) δ ppm 1.35-1.50 (m, 2H) 1.69-1.81 (m, 2H) 2.00-2.10 (m, 1H) 2.11-2.22 (s, 6H) 3.17-3.36 (m, 4H) 5.19-5.38 (s, 2H) 6.34 (d, J=8.78 Hz, 1H) 7.10 (dd, J=8.78, 2.93 Hz, 1H) 7.55 (d, J=2.63 Hz, 1H). LCMS (ESI) 221 (M+H).

Example 38

Synthesis of 4-(6-nitro-3-pyridyl) morpholine, Compound 38

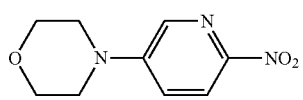 [SMILES: O=[N+]([O-])c1ccc(N2CCOCC2)cn1]

4-(6-nitro-3-pyridyl) morpholine was synthesized in a manner similar to that used in the synthesis of 2-nitro-5-[4-(1-piperidyl)-1-piperidyl]pyridine.

Example 39

Synthesis of 5-morpholinopyridin-2-amine, Compound 39

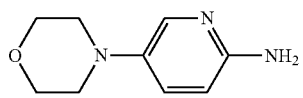 [SMILES: Nc1ccc(N2CCOCC2)cn1]

5-morpholinopyridin-2-amine was prepared in a manner similar to that used in the synthesis of 5-(4-methylpiperazin-1-yl) pyridin-2-amine. ¹HNMR (600 MHz, CHLOROFORM-d) δ ppm 2.91-3.00 (m, 4H) 3.76-3.84 (m, 4H) 4.19 (br. s., 2H) 6.45 (d, J=8.78 Hz, 1H) 7.12 (dd, J=8.78, 2.93 Hz, 1H) 7.72 (d, J=2.93 Hz, 1H).

Example 40

Synthesis of 5-(4-isobutylpiperazin-1-yl) pyridin-2-amine, Compound 40

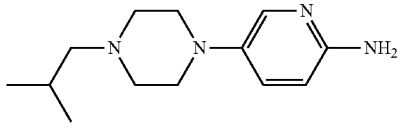 [SMILES: CC(C)CN1CCN(c2ccc(N)nc2)CC1]

1-isobutyl-4-(6-nitro-3-pyridyl)piperazine was synthesized in a manner similar to that used in the synthesis of 2-nitro-5-[4-(1-piperidyl)-1-piperidyl]pyridine which was then converted 5-(4-isobutylpiperazin-1-yl)pyridin-2-amine in a manner similar to that used in the synthesis of 5-(4-methylpiperazin-1-yl)pyridin-2-amine. ¹HNMR (600 MHz, CHLOROFORM-d) δ ppm 0.88 (d, J=6.73 Hz, 6H) 1.71-1.84 (m, 1H) 2.10 (d, J=7.32 Hz, 2H) 2.46-2.58 (m, 4H) 2.97-3.07 (m, 4H) 4.12 (s, 2H) 6.45 (d, J=8.78 Hz, 1H) 7.14 (dd, J=8.78, 2.93 Hz, 1H) 7.75 (d, J=2.93 Hz, 1H). LCMS (ESI) 235 (M+H).

Example 41

Synthesis of 5-(4-isopropylpiperazin-1-yl) pyridin-2-amine, Compound 41

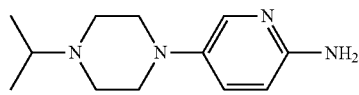 [SMILES: CC(C)N1CCN(c2ccc(N)nc2)CC1]

1-isopropyl-4-(6-nitro-3-pyridyl)piperazine was synthesized in a manner similar to that used in the synthesis of 2-nitro-5-[4-(1-piperidyl)-1-piperidyl]pyridine which was then converted to 5-(4-isopropylpiperazin-1-yl)pyridin-2-amine in a manner similar to that used in the synthesis of 5-(4-methylpiperazin-1-yl)pyridin-2-amine. ¹HNMR (600 MHz, CHLOROFORM-d) δ ppm 1.06 (d, J=6.44 Hz, 6H) 2.59-2.75 (m, 5H) 2.97-3.10 (m, 4H) 4.13 (s, 2H) 6.45 (d, J=8.78 Hz, 1H) 7.15 (dd, J=9.08, 2.93 Hz, 1H) 7.76 (d, J=2.93 Hz, 1H). LCMS (ESI) 221 (M+H).

Example 42

Synthesis of 5-[(2R,6S)-2,6-dimethylmorpholin-4-yl]pyridin-2-amine, Compound 42

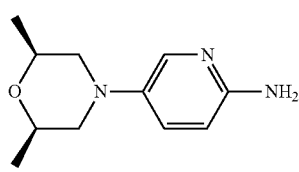

(2S,6R)-2,6-dimethyl-4-(6-nitro-3-pyridyl)morpholine was synthesized in a manner similar to that used in the synthesis of 2-nitro-5-[4-(1-piperidyl)-1-piperidyl]pyridine which was then converted to 5-[(2R,6S)-2,6-dimethylmorpholin-4-yl]pyridin-2-amine in a manner similar to that used in the synthesis of 5-(4-methylpiperazin-1-yl)pyridin-2-amine. ¹HNMR (600 MHz, CHLOROFORM-d) δ ppm 1.20 (d, J=6.44 Hz, 6H) 2.27-2.39 (m, 2H) 3.11-3.21 (m, 2H) 3.70-3.84 (m, 2H) 4.15 (s, 2H) 6.45 (d, J=8.78 Hz, 1H) 7.12 (dd, J=8.78, 2.93 Hz, 1H) 7.72 (d, J=2.63 Hz, 1H). LCMS (ESI) 208 (M+H).

Example 43

Synthesis of 5-[(3R,5S)-3,5-dimethylpiperazin-1-yl] pyridin-2-amine, Compound 43

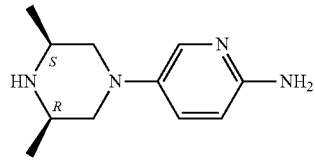

(3S,5R)-3,5-dimethyl-1-(6-nitro-3-pyridyl)piperazine was synthesized in a manner similar to that used in the synthesis of 2-nitro-5-[4-(1-piperidyl)-1-piperidyl]pyridine which was then converted to 5-[(3R,5S)-3,5-dimethylpiperazin-1-yl]pyridin-2-amine in a manner similar to that used in the synthesis of 5-(4-methylpiperazin-1-yl)pyridin-2-amine. ¹HNMR (600 MHz, CHLOROFORM-d) δ ppm 1.09 (d, J=6.44 Hz, 6H) 2.20 (t, J=10.83 Hz, 2H) 2.95-3.08 (m, 2H) 3.23 (dd, J=11.71, 2.05 Hz, 2H) 4.13 (s, 2H) 6.45 (d, J=8.78 Hz, 1H) 7.14 (dd, J=8.78, 2.93 Hz, 1H) 7.73 (d, J=2.63 Hz, 1H). LCMS (ESI) 207 (M+H).

Example 44

Synthesis of Compound 44

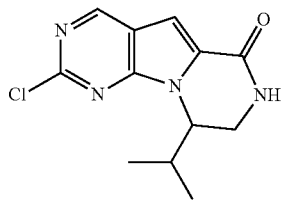 [SMILES: CC(C)C1CNC(=O)c2cc3cnc(Cl)nc3n21]

tert-butyl N-[2-[(5-bromo-2-chloro-pyrimidin-4-yl)amino]-3-methyl-butyl]carbamate

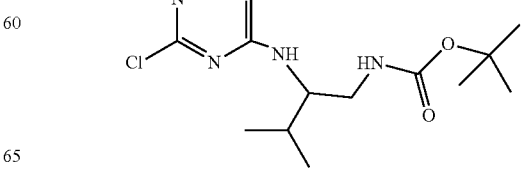

A solution of intermediate A in ethanol (100 mL) was hydrogenated under 30 psi of hydrogen using 10% Pd/C (0.7 g) in a pressure bomb for 7 hrs. After filtration of the reaction mixture through CELITE™, the organic layer was concentrated under vacuum to afford tert-butyl N-(2-amino-3-methyl-butyl) carbamate (3.8 g).

To a solution of 5-bromo-2,4-dichloro-pyrimidine (7.11 g, 0.0312 mole) in ethanol (100 mL) was added diisopropylethyl amine (5.45 mL, 1.0 eq) and tert-butyl N-(2-amino-3-methyl-butyl) carbamate (6.31 g, 0.0312 mole). The reaction mixture was stirred at room temperature for 20 hrs. After concentration under vacuum, ethyl acetate and water were added. The organic layer was separated, dried with magnesium sulfate and then concentrated under vacuum. The crude product was purified by silica gel column chromatography using hexane/ethyl acetate (0-30%) to afford tert-butyl N-[2-[(5-bromo-2-chloro-pyrimidin-4-yl)amino]-3-methyl-butyl] carbamate. $^1$HNMR (600 MHz, DMSO-$d_6$) δ ppm 0.77-0.85 (d, J=6.5 Hz, 3H) 0.87 (d, J=6.73 Hz, 3H) 1.31-1.39 (m, 9H) 1.82-1.93 (m, 1H) 2.94 (d, J=5.56 Hz, 1H) 3.08-3.22 (m, 2H) 3.98 (d, J=8.20 Hz, 1H) 6.96 (d, J=8.78 Hz, 1H) 8.21 (s, 1H). LCMS (ESI) 393 (M+H).

tert-butyl N-[2-[2-chloro-6-(diethoxymethyl)pyrrolo [2,3-d]pyrimidin-7-yl]-3-methyl-butyl]carbamate

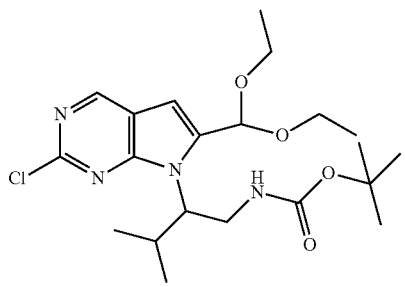 [SMILES: CCOC(OCC)c1cc2cnc(Cl)nc2n1C(CNC(=O)OC(C)(C)C)C(C)C]

tert-butyl N-[2-[2-chloro-6-(diethoxymethyl)pyrrolo[2,3-d]pyrimidin-7-yl]-3-methyl-butyl]carbamate was synthesized by hosting tert-butyl N-[2-[(5-bromo-2-chloro-pyrimidin-4-yl)amino]-3-methyl-butyl]carbamate to Sonogoshira conditions as described for tert-butyl N-[2-[[2-chloro-5-(3,3-diethoxyprop-1-ynyl)pyrimidin-4-yl]amino]ethyl]carbamate followed by subsequent treatment with TBAF as described in the synthesis of tert-butyl N-[2-[2-chloro-6-(diethoxymethyl)pyrrolo[2,3-d]pyrimidin-7-yl]ethyl]carbamate. $^1$HNMR (600 MHz, DMSO-$d_6$) δ ppm 1.11 (d, J=6.44 Hz, 3H) 1.18 (t, J=7.03 Hz, 6H) 1.21-1.26 (m, 12H) 2.88 (br. s., 1H) 3.43-3.78 (m, 6H) 3.97-4.08 (m, 1H) 5.61 (s, 1H) 6.65 (s, 1H) 6.71-6.78 (m, 1H) 8.87 (s, 1H). LCMS (ESI) 441 (M+H).

7-[1-[(tert-butoxycarbonylamino)methyl]-2-methyl-propyl]-2-chloro-pyrrolo[2,3-d]pyrimidine-6-carboxylic Acid

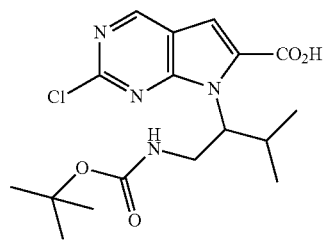 [SMILES: CC(C)C(CNC(=O)OC(C)(C)C)n1c(C(=O)O)cc2cnc(Cl)nc21]

To a solution tert-butyl N-[2-[[2-chloro-5-(3,3-diethoxyprop-1-ynyl)pyrimidin-4-yl]amino]ethyl]carbamate in THF was added TBAF and the contents were heated at reflux for 3 hrs. Ethyl acetate and water were then added and the organic layer separated, dried with magnesium sulfate and then concentrated under vacuum. To this crude reaction was added acetic acid/water (9:1) and the contents were stirred for 12 hrs at room temperature. After concentration under vacuum, sat NaHCO$_3$ and ethyl acetate were added. The organic layer was separated, dried and then concentrated under vacuum. The crude reaction product thus obtained was dissolved in DMF, oxone was then added and the contents stirred for 3 hrs. After addition of ethyl acetate, the reaction mixture was filtered through CELITE™ and concentrated under vacuum. Column chromatography of the crude product over silica gel using hexane/ethyl acetate (0-100%) afforded 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-$d_6$) δ ppm 0.85 (d, J=7.03 Hz, 3H) 0.97 (d, J=6.73 Hz, 3H) 1.52 (s, 9H) 1.99-2.23 (m, 1H) 3.98 (dd, J=14.05, 3.51 Hz, 1H) 4.47-4.71 (m, 2H) 7.47 (s, 1H) 9.17 (s, 1H). LCMS (ESI) 383 (M+H).

Compound 44

To 7-[1-[(tert-butoxycarbonylamino)methyl]-2-methyl-propyl]-2-chloro-pyrrolo[2,3-d]pyrimidine-6-carboxylic acid (0.050 g, 0.00013 mole) in DCM (1.5 mL) was added DIC (32.7 mg) and DMAP (10 mg). The contents were stirred for 2 hrs. Trifluoroacetic acid (0.4 mL) was then added and stirring continued for an additional 30 minutes. After addition of satd NaHCO$_3$ to neutralize the excess acid, ethyl acetate was added and the organic layer separated, dried using magnesium sulfate and then concentrated under vacuum. The crude product was purified by silica gel column chromatography using hexane/ethyl acetate (0-100%) to afford the product. $^1$HNMR (600 MHz, DMSO-$d_6$) δ ppm 0.72 (d, J=6.73 Hz, 3H) 0.97 (d, J=6.73 Hz, 3H) 2.09-2.22 (m, 1H) 3.57 (dd, J=13.18, 4.98 Hz, 1H) 3.72 (dd, J=13.61, 4.25 Hz, 1H) 4.53 (dd, J=8.05, 3.95 Hz, 1H) 7.20 (s, 1H) 8.34 (d, J=4.98 Hz, 1H) 9.08 (s, 1H). LCMS (ESI) 265 (M+H).

Example 45

Synthesis of Compound 45

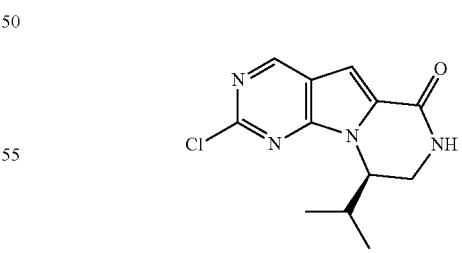

Compound 14 was hydrogenated with 10% Pd/C to afford the intermediate tert-butyl N-[(2R)-2-amino-3-methyl-butyl]carbamate, which was then treated with 5-bromo-2,4-dichloro-pyrimidine using analogous reaction conditions as described for Compound 44 to afford Compound 45 The analytical data is consistent with that reported for the racemate (Intermediate 1A).

Example 46

Synthesis of Compound 46

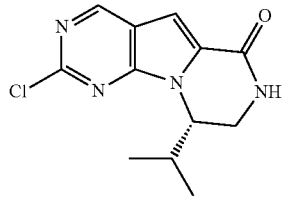 [SMILES: CC(C)[C@H]1CNC(=O)c2cc3cnc(Cl)nc3n21]

Compound 15 was hydrogenated with 10% Pd/C to afford the intermediate tert-butyl N-[(2S)-2-amino-3-methyl-butyl]carbamate, which was then treated with 5-bromo-2,4-dichloro-pyrimidine using analogous reaction conditions as described for Compound 44 to afford Compound 46. The analytical data (NMR and LCMS) was consistent with that reported for the racemate Compound 44.

Example 47

Synthesis of Compound 47

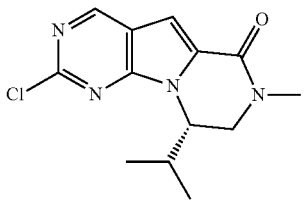 [SMILES: CC(C)[C@H]1CN(C)C(=O)c2cc3cnc(Cl)nc3n21]

To a solution of Compound 44 (80 mg, 0.00030 mole) in DMF (3 mL) was added a 60% dispersion of sodium hydride in oil (40 mg). After stirring for 15 minutes, methyl iodide (37 μL, 2 eq) was added. The contents were stirred at room temperature for 30 minutes. Saturated NaHCO$_3$ was then added followed by ethyl acetate. The organic layer was dried with magnesium sulfate and then concentrated under vacuum to afford the product. $^1$HNMR (600 MHz, DMSO-d$_6$) δ ppm 0.74 (d, J=6.73 Hz, 3H) 0.91 (d, J=6.73 Hz, 3H) 2.04-2.20 (m, 1H) 3.04 (s, 3H) 3.69 (dd, J=13.76, 1.17 Hz, 1H) 3.96 (dd, J=13.76, 4.68 Hz, 1H) 4.58 (dd, J=7.32, 3.51 Hz, 1H) 7.16 (s, 1H) 9.05 (s, 1H). LCMS (ESI) 279 (M+H).

Example 48

Synthesis of Compound 48

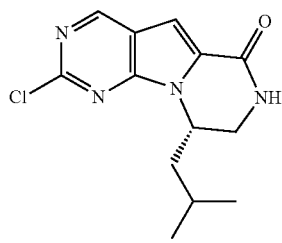 [SMILES: CC(C)C[C@H]1CNC(=O)c2cc3cnc(Cl)nc3n21]

tert-butyl N-[(2S)-2-[(5-bromo-2-chloro-pyrimidin-4-yl)amino]-4-methyl-pentyl]carbamate

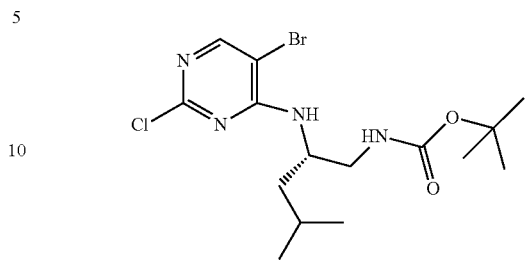

Compound 18 was hydrogenated with 10% Pd/C in ethanol under a blanket of hydrogen at 50 psi in a pressure bomb to afford tert-butyl N-[(2S)-2-amino-4-methyl-pentyl]carbamate which was then reacted with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-4-methyl-pentyl]carbamate. $^1$HNMR (600 MHz, CHLOROFORM-d) δ ppm 0.91 (d, J=6.44 Hz, 3H) 0.94 (d, J=6.44 Hz, 3H) 1.32-1.51 (m, 11H) 1.55-1.67 (m, 1H) 3.28 (t, J=5.86 Hz, 2H) 4.21-4.42 (m, 1H) 4.84 (s, 1H) 5.84 (d, J=7.32 Hz, 1H) 8.07 (s, 1H). LCMS (ESI) 407 (M+H).

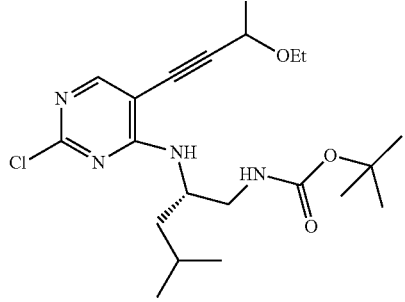

To a solution of tert-butyl N-[(2S)-2-[(5-bromo-2-chloro-pyrimidin-4-yl)amino]-4-methyl-pentyl]carbamate (5.0 g, 12.3 mmole) in toluene (36 mL) and triethylamine (7.2 mL) was added under nitrogen, 3,3-diethoxyprop-1-yne (2.8 mL, 19.7 mmole), Pd$_2$(dba)$_3$ (1.1 g, 1.23 mmole), and triphenylarsine (3.8 g, 12.3 mmole). The contents were heated to 70 degrees for 24 hrs. After cooling to room temperature, the reaction mixture was filtered through CELITE™ and then concentrated under vacuum. The crude product was purified by silica gel column chromatography using hexane/ethyl acetate (0-30%) to afford (2S)-N2-[2-chloro-5-(3,3-diethoxyprop-1-ynyl)pyrimidin-4-yl]-4-methyl-pentane-1,2-diamine. LCMS (ESI) 455 (M+H).

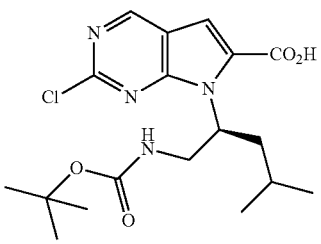 [SMILES: CC(C)C[C@@H](CNC(=O)OC(C)(C)C)n1c(C(=O)O)cc2cnc(Cl)nc21]

7-[(1 S)-1-[(tert-butoxycarbonylamino)methyl]-3-methyl-butyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. ¹HNMR (600 MHz, DMSO-d₆) δ ppm 0.88 (d, J=6.44 Hz, 3H) 0.97 (d, J=6.44 Hz, 3H) 1.47 (s, 9H) 1.49-1.54 (m, 1H) 1.56 (t, J=7.17 Hz, 2H) 3.98 (dd, J=13.91, 3.07 Hz, 1H) 3.76 (dd, J=13.31, 4.13 Hz, 1H) 4.38 (d, J=14.05 Hz, 1H) 4.90 (t, J=7.17 Hz, 1H) 7.41 (s, 1H) 9.11 (s, 1H). LCMS (M+H) 397.

Compound 48 was synthesized using an analogous synthetic sequence as that described for Compound 44. ¹HNMR (600 MHz, DMSO-d₆) δ ppm 0.82 (d, J=6.73 Hz, 3H) 0.97 (d, J=6.44 Hz, 3H) 1.34-1.46 (m, 1H) 1.48-1.65 (m, 2H) 3.40 (dd, J=13.32, 5.42 Hz, 1H) 3.76 (dd, J=13.47, 4.10 Hz, 1H) 4.76-4.92 (m, 1H) 7.17 (s, 1H) 8.34 (d, J=5.27 Hz, 1H) 9.04 (s, 1H). LCMS (ESI) 279 (M+H).

Example 49

Synthesis of Compound 49

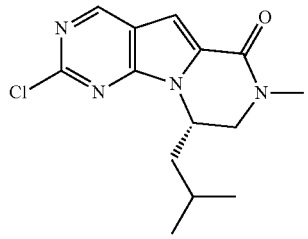 [SMILES: CC(C)C[C@H]1CN(C)C(=O)c2cc3cnc(Cl)nc3n21]

Compound 49 was synthesized in a manner similar to that described for Compound 47. ¹HNMR (600 MHz, DMSO-d₆) δ ppm 0.82 (d, J=6.44 Hz, 3H) 0.97 (d, J=6.44 Hz, 3H) 1.37-1.68 (m, 3H) 3.04 (s, 3H) 3.56 (d, J=13.47 Hz, 1H) 4.00 (dd, J=13.32, 4.25 Hz, 1H) 4.82-4.94 (m, 1H) 7.16 (s, 1H) 9.03 (s, 1H). LCMS (ESI) 293 (M+H).

Example 50

Synthesis of Compound 50

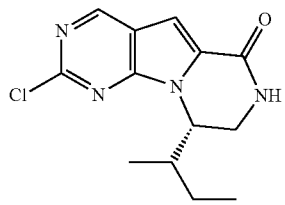 [SMILES: CCC(C)[C@H]1CNC(=O)c2cc3cnc(Cl)nc3n21]

tert-butyl N-[(2S)-2-[(5-bromo-2-chloro-pyrimidin-4-yl)amino]-3-methyl-pentyl]carbamate

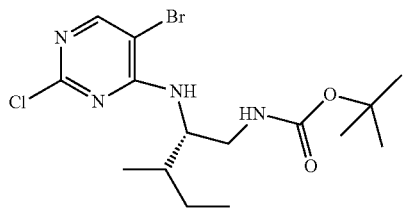 [SMILES: CCC(C)[C@@H](CNC(=O)OC(C)(C)C)Nc1nc(Cl)ncc1Br]

Compound 20 was hydrogenated using 10% Pd/C under hydrogen at 50 psi in a pressure vessel to afford tert-butyl N-[(2S)-2-amino-3-methyl-pentyl]carbamate which was reacted with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-3-methyl-pentyl]carbamate. ¹HNMR (600 MHz, CHLOROFORM-d) δ ppm 0.88-0.95 (m, 6H) 1.11-1.20 (m, 1H) 1.34 (s, 9H) 1.44-1.54 (m, 1H) 1.64-1.72 (m, 1H) 3.17-3.27 (m, 1H) 3.33-3.43 (m, 1H) 4.11-4.21 (m, 1H) 4.81 (s, 1H) 5.92 (d, J=8.20 Hz, 1H) 8.05 (s, 1H). LCMS (ESI) 407.

tert-butyl N-[(2S)-2-[[2-chloro-5-(3,3-diethoxyprop-1-ynyl)pyrimidin-4-yl]amino]-3-methyl-pentyl]carbamate

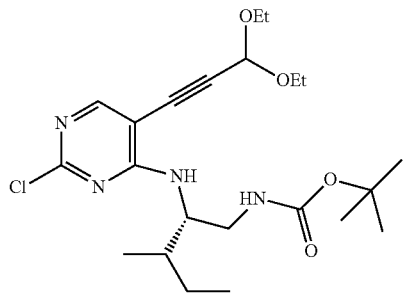 [SMILES: CCOC(C#Cc1cnc(Cl)nc1N[C@H](CNC(=O)OC(C)(C)C)C(C)CC)OCC]

tert-butyl N-[(2S)-2-[[2-chloro-5-(3,3-diethoxyprop-1-ynyl)pyrimidin-4-yl]amino]-3-methyl-pentyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. ¹HNMR (600 MHz, DMSO-d₆) δ ppm 0.76-0.89 (m, 6H) 1.03 (q, J=7.22 Hz, 3H) 1.10-1.17 (m, 3H) 1.25-1.42 (m, 11H) 1.59-1.73 (m, 1H) 3.35-3.47 (m, 4H) 3.51-3.73 (m, 2H) 3.99-4.11 (m, 1H) 5.52-5.56 (m, 1H) 6.76-7.03 (m, 2H) 8.12-8.23 (m, 1H). LCMS (ESI) 455 (M+H).

7-[(1S)-1-[(tert-butoxycarbonylamino)methyl]-2-methyl-butyl]-2-chloro-pyrrolo[2,3-d]pyrimidine-6-carboxylic Acid

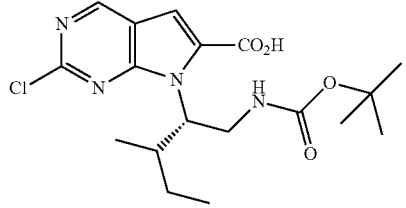 [SMILES: CCC(C)[C@@H](CNC(=O)OC(C)(C)C)n1c(C(=O)O)cc2cnc(Cl)nc21]

7-[(1 S)-1-[(tert-butoxycarbonylamino)methyl]-2-methyl-butyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. ¹HNMR (600 MHz, DMSO-d₆) δ ppm 0.80 (t, J=7.47 Hz, 3H) 0.86 (d, J=7.03 Hz, 3H) 1.06-1.30 (m, 2H) 1.48 (s, 9H) 1.79-1.96 (m, 1H)

3.95 (dd, J=14.05, 3.22 Hz, 1H) 4.52 (d, J=14.35 Hz, 1H) 4.61-4.73 (m, 1H) 7.43 (s, 1H) 9.13 (s, 1H). LCMS (ESI) 397 (M+H).

Compound 50 was synthesized using an analogous synthetic sequence as that described for Compound 44. ¹HNMR (600 MHz, DMSO-d₆) δ ppm 0.74 (t, J=7.32 Hz, 3H) 0.89 (d, J=6.73 Hz, 3H) 1.00-1.12 (m, 2H) 1.82-1.94 (m, 1H) 3.55 (dd, J=13.91, 4.83 Hz, 1H) 3.70 (dd, J=13.61, 4.25 Hz, 1H) 4.57 (dd, J=7.91, 4.10 Hz, 1H) 7.17 (s, 1H) 8.31 (d, J=5.27 Hz, 1H) 9.05 (s, 1H). LCMS (ESI) 279 (M+H).

Example 51

Synthesis of Compound 51

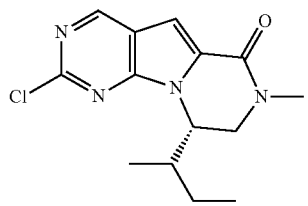 [SMILES: CCC(C)[C@H]1CN(C)C(=O)c2cc3cnc(Cl)nc3n21]

Compound 51 was synthesized in a manner similar to Compound 47. ¹HNMR (600 MHz, DMSO-d₆) δ ppm 0.77 (t, J=7.47 Hz, 3H) 0.84 (d, J=6.73 Hz, 3H) 1.07-1.16 (m, 2H) 1.82-1.95 (m, 1H) 3.03 (s, 3H) 3.68 (d, J=13.76 Hz, 1H) 3.96 (dd, J=13.76, 4.39 Hz, 1H) 4.59-4.70 (m, 1H) 7.16 (s, 1H) 9.04 (s, 1H). LCMS (ESI) 293 (M+H).

Example 52

Synthesis of Compound 52

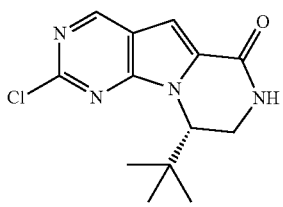 [SMILES: CC(C)(C)[C@H]1CNC(=O)c2cc3cnc(Cl)nc3n21]

tert-butyl N-[(2S)-2-[(5-bromo-2-chloro-pyrimidin-4-yl)amino]-3,3-dimethyl-butyl]carbamate

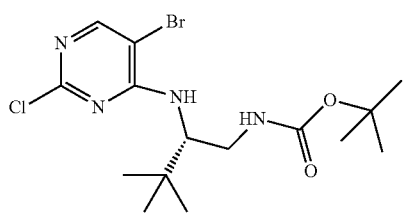 [SMILES: CC(C)(C)OC(=O)NC[C@@H](Nc1nc(Cl)ncc1Br)C(C)(C)C]

Compound 21 was hydrogenated using 10% Pd/C under hydrogen at 50 psi in a pressure vessel to afford tert-butyl N-[(2S)-2-amino-3,3-dimethyl-butyl]carbamate which was then reacted with 5-bromo-2,4-dichloro-pyrimidine using analogous reaction conditions as described using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-3,3-dimethyl-butyl]carbamate. LCMS (ESI) 407 (M+H).

tert-butyl N-[(2S)-2-[[2-chloro-5-(3,3-diethoxyprop-1-ynyl)pyrimidin-4-yl]amino]-3,3-dimethyl-butyl] carbamate

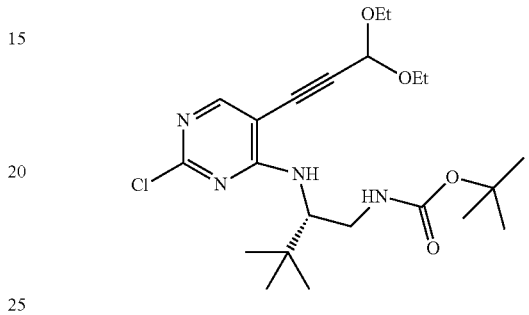

tert-butyl N-[(2S)-2-[[2-chloro-5-(3,3-diethoxyprop-1-ynyl)pyrimidin-4-yl]amino]-3,3-dimethyl-butyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. LCMS (ESI) 455 (M+H).

7-[(1S)-1-[(tert-butoxycarbonylamino)methyl]-2,2-dimethyl-propyl]-2-chloro-pyrrolo[2,3-d]pyrimidine-6-carboxylic Acid

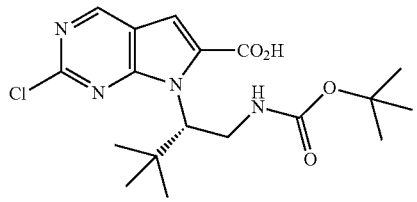 [SMILES: CC(C)(C)OC(=O)NC[C@@H](n1c(C(=O)O)cc2cnc(Cl)nc21)C(C)(C)C]

7-[(1 S)-1-[(tert-butoxycarbonylamino)methyl]-2,2-dimethyl-propyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. LCMS (ESI) 397 (M+H). Intermediate 1F was synthesized using an analogous synthetic sequence as that described for intermediate 1A. LCMS (ESI) 279 (M+H).

Example 53

Synthesis of Compound 53

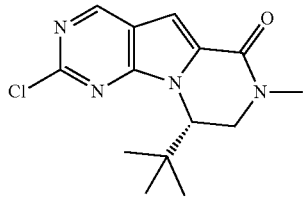 [SMILES: CN1C[C@H](C(C)(C)C)n2c(cc3cnc(Cl)nc32)C1=O]

Compound 53 was synthesized in a manner similar to that described for Intermediate 1CA. LCMS (ESI) 293 (M+H).

Example 54

Synthesis of Compound 54

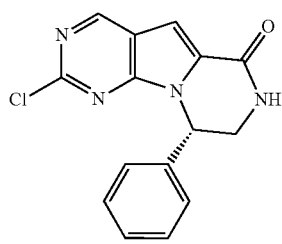 [SMILES: O=C1NC[C@H](c2ccccc2)n2c1cc1cnc(Cl)nc12]

tert-butyl N-[(2S)-2-[(5-bromo-2-chloro-pyrimidin-4-yl)amino]-2-phenyl-ethyl]carbamate

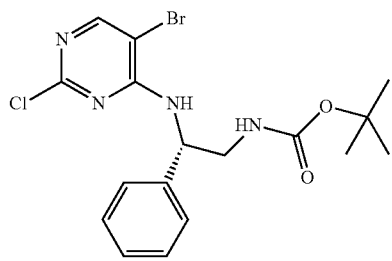 [SMILES: CC(C)(C)OC(=O)NC[C@@H](Nc1nc(Cl)ncc1Br)c1ccccc1]

Compound 21 was hydrogenated using 10% Pd/C under hydrogen at 50 psi in a pressure vessel to afford tert-butyl N-[(2S)-2-amino-2-phenyl-ethyl]carbamate which was then reacted with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate to afford tert-butyl N-[(2S)-2-[(5-bromo-2-chloro-pyrimidin-4-yl)amino]-2-phenyl-ethyl]carbamate.
$^1$HNMR (600 MHz, DMSO-d$_6$) δ ppm 1.32 (s, 9H) 3.29-3.50 (m, 2H) 5.12-5.24 (m, 1H) 7.10 (t, J=5.27 Hz, 1H) 7.21 (t, J=6.88 Hz, 1H) 7.26-7.34 (m, 4H) 7.89 (d, J=7.32 Hz, 1H) 8.24 (s, 1H). LCMS (ESI) 427 (M+H).

tert-butyl N-[(2S)-2-[[2-chloro-5-(3,3-diethoxyprop-1-ynyl)pyrimidin-4-yl]amino]-2-phenyl-ethyl]carbamate

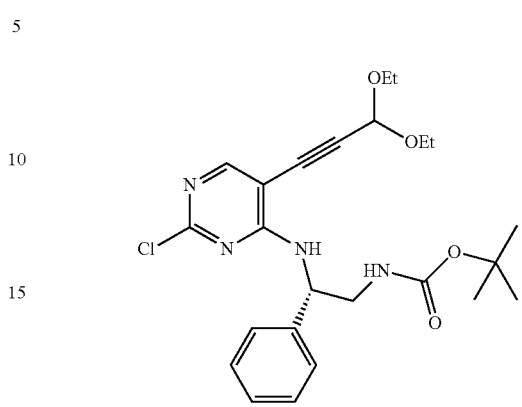

tert-butyl N-[(2S)-2-[[2-chloro-5-(3,3-diethoxyprop-1-ynyl)pyrimidin-4-yl]amino]-2-phenyl-ethyl]carbamate was synthesized using similar experimental conditions to those used in the synthesis of (2S)-N2-[2-chloro-5-(3,3-diethoxyprop-1-ynyl)pyrimidin-4-yl]-4-methyl-pentane-1,2-diamine. $^1$HNMR (600 MHz, DMSO-d$_6$) δ ppm 1.14 (t, J=7.03 Hz, 6H) 1.32 (s, 9H) 3.39 (s, 2H) 3.52-3.61 (m, 2H) 3.64-3.73 (m, 2H) 5.17-5.26 (m, 1H) 5.57 (s, 1H) 7.07-7.14 (m, 1H) 7.20-7.25 (m, 1H) 7.26-7.33 (m, 4H) 7.90 (d, J=7.61 Hz, 1H) 8.19 (s, 1H). LCMS (ESI) 475 (M+H).

7-[(1S)-2-(tert-butoxycarbonylamino)-1-phenyl-ethyl]-2-chloro-pyrrolo[2,3-d]pyrimidine-6-carboxylic Acid

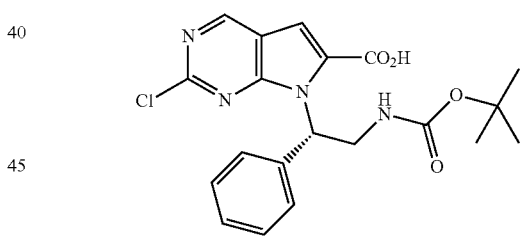

7-[(1S)-2-(tert-butoxycarbonylamino)-1-phenyl-ethyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. LCMS (ESI) 417 (M+H).

Compound 54

Compound 54 was synthesized using an analogous synthetic sequence as that described for Compound 44. $^1$HNMR (600 MHz, DMSO-d$_6$) δ ppm 3.58-3.69 (m, 1H) 4.13 (dd, J=13.47, 4.39 Hz, 1H) 6.07 (d, J=3.81 Hz, 1H) 6.85 (d, J=7.32 Hz, 2H) 7.19-7.31 (m, 3H) 7.34 (s, 1H) 8.27 (d, J=5.27 Hz, 1H) 9.13 (s, 1H). LCMS (ESI) 299 (M+H).

Example 55

Synthesis of Compound 55

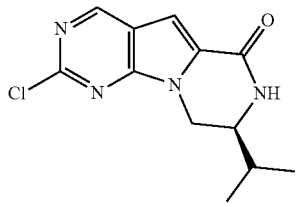 [SMILES: CC(C)[C@H]1Cn2c(cc3cnc(Cl)nc32)C(=O)N1]

tert-butyl N-[(1S)-1-[[(5-bromo-2-chloro-pyrimidin-4-yl)amino]methyl]-2-methyl-propyl]carbamate

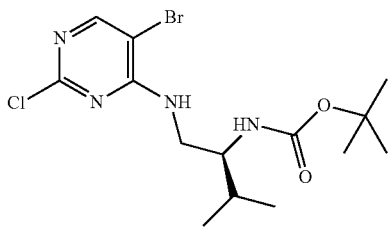 [SMILES: CC(C)[C@@H](CNc1nc(Cl)ncc1Br)NC(=O)OC(C)(C)C]

tert-butyl N-[(1S)-1-[[(5-bromo-2-chloro-pyrimidin-4-yl)amino]methyl]-2-methyl-propyl]carbamate was synthesized using 5-bromo-2,4-dichloro-pyrimidine and Intermediate E using analogous reaction conditions as described for tert-butyl N-[2-[(5-bromo-2-chloro-pyrimidin-4-yl)amino]-3-methyl-butyl]carbamate. $^1$HNMR (600 MHz, CHLOROFORM-d) δ ppm 0.95-1.02 (m, 6H) 1.35-1.45 (m, 9H) 1.75-1.90 (m, 1H) 3.35-3.48 (m, 1H) 3.52-3.61 (m, 1H) 3.64-3.76 (m, 1H) 4.56 (d, J=8.49 Hz, 1H) 6.47 (s, 1H) 8.07 (s, 1H). LCMS (ESI) 393 (M+H).

tert-butyl N-[(1S)-1-[[[2-chloro-5-(3,3-diethoxy-prop-1-ynyl)pyrimidin-4-yl]amino]methyl]-2-methyl-propyl]carbamate

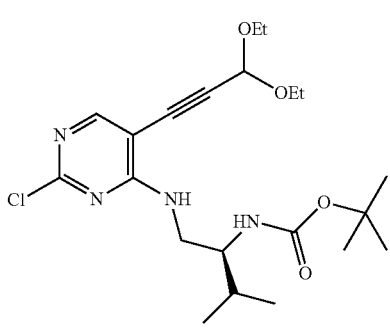 [SMILES: CCOC(C#Cc1cnc(Cl)nc1NC[C@@H](NC(=O)OC(C)(C)C)C(C)C)OCC]

tert-butyl N-[(1S)-1-[[[2-chloro-5-(3,3-diethoxyprop-1-ynyl)pyrimidin-4-yl]amino]methyl]-2-methyl-propyl]carbamate was synthesized using similar experimental conditions to those used in the synthesis (2S)-N2-[2-chloro-5-(3,3-diethoxyprop-1-ynyl)pyrimidin-4-yl]-4-methyl-pentane-1,2-diamine. $^1$HNMR (600 MHz, CHLOROFORM-d) δppm 0.90-1.00 (m, 6H) 1.18-1.25 (m, 6H) 1.34-1.36 (m, 9H) 1.69-1.90 (m, 1H) 3.34-3.82 (m, 6H) 4.53-4.77 (m, 1H) 5.45-5.55 (m, 1H) 6.37 (dd, J=15.37, 6.59 Hz, 1H) 6.56 (s, 1H) 8.05 (s, 1H). LCMS (ESI) 441 (M+H).

7-[(2S)-2-(tert-butoxycarbonylamino)-3-methyl-butyl]-2-chloro-pyrrolo[2,3-d]pyrimidine-6-carboxylic Acid

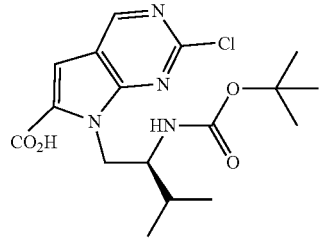 [SMILES: CC(C)[C@@H](Cn1c(C(=O)O)cc2cnc(Cl)nc21)NC(=O)OC(C)(C)C]

7-[(2 S)-2-(tert-butoxycarbonylamino)-3-methyl-butyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, CHLOROFORM-d) δ ppm 0.90 (d, J=6.73 Hz, 3H) 0.96 (d, J=7.03 Hz, 3H) 1.55-1.66 (m, 10H) 4.14 (dd, J=13.61, 3.95 Hz, 1H) 4.52-4.63 (m, 1H) 4.84 (dd, J=13.61, 1.32 Hz, 1H) 7.37 (s, 1H) 8.95 (s, 1H). LCMS (ESI) 383 (M+H).

Compound 55

Compound 55 was synthesized using an analogous synthetic sequence as that described for Compound 44. LCMS (ESI) 265 (M+H).

Example 56

Synthesis of Compound 56

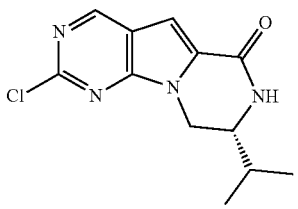 [SMILES: CC(C)[C@@H]1Cn2c(cc3cnc(Cl)nc32)C(=O)N1]

Compound 56 was synthesized using 5-bromo-2,4-dichloro-pyrimidine and Compound 17 as starting materials, and following a similar sequence of synthetic steps as for Compound 55. The analytical data was consistent with that described for its antipode (Compound 55). $^1$HNMR (600 MHz, DMSO-d$_6$) δ ppm 0.88 (d, J=6.44 Hz, 6H) 1.73-1.86 (m, 1H) 3.67-3.76 (m, 2H) 4.11-4.21 (m, 1H) 7.13-7.19 (m, 1H) 8.56 (s, 1H) 9.05 (s, 1H). LCMS (ESI) 265 (M+H).

Example 57

Synthesis of Compound 57

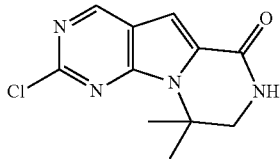 [SMILES: CC1(C)CNC(=O)c2cc3cnc(Cl)nc3n21]

tert-butyl N-[2-[(5-bromo-2-chloro-pyrimidin-4-yl)amino]-2-methyl-propyl]carbamate

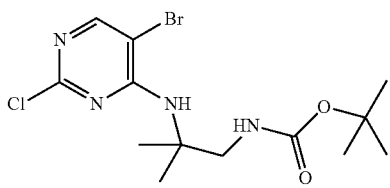 [SMILES: CC(C)(CNC(=O)OC(C)(C)C)Nc1nc(Cl)ncc1Br]

tert-butyl N-[2-[(5-bromo-2-chloro-pyrimidin-4-yl)amino]-2-methyl-propyl]carbamate was synthesized using 5-bromo-2,4-dichloro-pyrimidine and tert-butyl N-(2-amino-2-methyl-propyl)carbamate using analogous reaction conditions as described for tert-butyl N-[2-[(5-bromo-2-chloro-pyrimidin-4-yl)amino]-3-methyl-butyl]carbamate. LCMS (ESI) 379 (M+H).

tert-butyl N-[2-[[2-chloro-5-(3,3-diethoxyprop-1-ynyl)pyrimidin-4-yl]amino]-2-methyl-propyl]carbamate

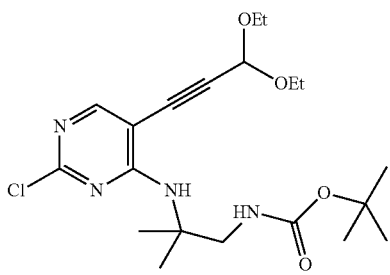 [SMILES: CCOC(C#Cc1cnc(Cl)nc1NC(C)(C)CNC(=O)OC(C)(C)C)OCC]

tert-butyl N-[2-[[2-chloro-5-(3,3-diethoxyprop-1-ynyl)pyrimidin-4-yl]amino]-2-methyl-propyl]carbamate was synthesized using similar experimental conditions to those used in the synthesis of (2S)-N2-[2-chloro-5-(3,3-diethoxyprop-1-ynyl)pyrimidin-4-yl]-4-methyl-pentane-1,2-diamine. $^1$HNMR (600 MHz, DMSO-$d_6$) δ ppm 1.11-1.22 (m, 6H) 1.31-1.45 (m, 15H) 3.10-3.24 (m, 2H) 3.51-3.76 (m, 4H) 5.60 (s, 1H) 6.94 (s, 1H) 7.33 (t, J=6.44 Hz, 1H) 8.18 (s, 1H). LCMS (ESI) 427 (M+H).

7-[2-(tert-butoxycarbonylamino)-1,1-dimethyl-ethyl]-2-chloro-pyrrolo[2,3-d]pyrimidine-6-carboxylic Acid

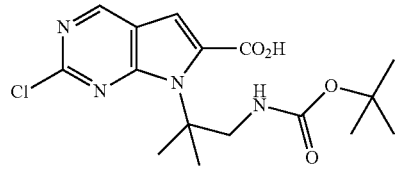 [SMILES: CC(C)(C)OC(=O)NCC(C)(C)n1c(C(=O)O)cc2cnc(Cl)nc21]

7-[2-(tert-butoxycarbonylamino)-1,1-dimethyl-ethyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-$d_6$) δ ppm 1.43 (s, 9H) 1.73 (s, 6H) 4.06 (s, 2H) 7.46 (s, 1H) 9.23 (s, 1H). LCMS (ESI) 369 (M+H).

Compound 57

Compound 57 was synthesized using an analogous synthetic sequence as that described for Compound 44. $^1$HNMR (600 MHz, DMSO-$d_6$) δ ppm 1.73 (s, 6H) 3.50 (d, J=2.93 Hz, 2H) 7.25 (s, 1H) 8.46-8.55 (m, 1H) 9.07 (s, 1H). LCMS (ESI) 251 (M+H).

Example 58

Synthesis of Compound 58

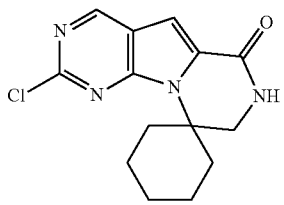 [SMILES: O=C1NCC2(CCCCC2)n2c1cc1cnc(Cl)nc12]

tert-butyl N-[[1-[(5-bromo-2-chloro-pyrimidin-4-yl)amino]cyclohexyl]methyl]carbamate

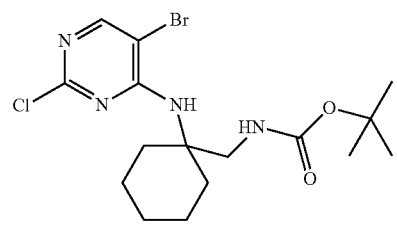 [SMILES: CC(C)(C)OC(=O)NCC1(Nc2nc(Cl)ncc2Br)CCCCC1]

tert-butyl N-[[1-[(5-bromo-2-chloro-pyrimidin-4-yl)amino]cyclohexyl]methyl]carbamate was synthesized using 5-bromo-2,4-dichloro-pyrimidine and Intermediate K using the analogous reaction conditions as described for tert-butyl N-[2-[(5-bromo-2-chloro-pyrimidin-4-yl)amino]-3-methyl-butyl]carbamate. $^1$HNMR (600 MHz, DMSO-$d_6$) δ ppm 1.18-1.54 (m, 17H) 2.23 (d, J=14.35 Hz, 2H) 3.36 (d, J=6.44 Hz, 2H) 5.82 (s, 1H) 6.93 (s, 1H) 8.22 (s, 1H). LCMS (ESI) 419 (M+H).

tert-butyl N-[[1-[[2-chloro-5-(3,3-diethoxyprop-1-ynyl)pyrimidin-4-yl]amino]cyclohexyl]methyl]carbamate

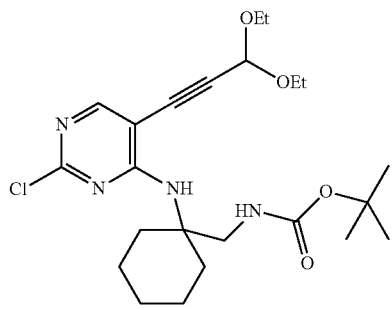 [SMILES: CCOC(C#Cc1cnc(Cl)nc1NC1(CNC(=O)OC(C)(C)C)CCCCC1)OCC]

tert-butyl N-[[1-[[2-chloro-5-(3,3-diethoxyprop-1-ynyl)pyrimidin-4-yl]amino]cyclohexyl]methyl]carbamate was synthesized using similar experimental conditions to those used in the synthesis of (2S)-N2-[2-chloro-5-(3,3-diethoxyprop-1-ynyl)pyrimidin-4-yl]-4-methyl-pentane-1,2-diamine. $^1$HNMR (600 MHz, DMSO-d$_6$) δ ppm 1.08-1.16 (m, 6H) 1.17-1.54 (m, 17H) 2.13 (br. s., 2H) 3.36 (d, J=6.73 Hz, 2H) 3.50-3.69 (m, 4H) 5.72 (s, 1H) 6.94 (s, 1H) 5.72 (br. s., 1H) 8.17 (s, 1H). LCMS (ESI) 467 (M+H).

7-[1-[(tert-butoxycarbonylamino)methyl]cyclohexyl]-2-chloro-pyrrolo[2,3-d]pyrimidine-6-carboxylic Acid

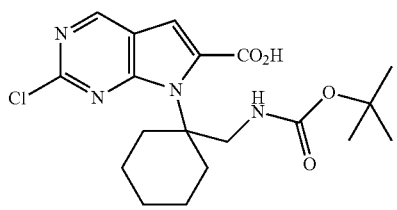 [SMILES: CC(C)(C)OC(=O)NCC1(n2c(C(=O)O)cc3cnc(Cl)nc32)CCCCC1]

7-[1-[(tert-butoxycarbonylamino)methyl]cyclohexyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-d$_6$) δ ppm 1.37-1.54 (m, 13H) 1.75 (br. s., 4H) 2.74 (br. s., 2H) 3.78-3.84 (m, 2H) 7.44-7.51 (m, 1H) 8.23 (s, 1H) 9.11 (s, 1H). LCMS (ESI) 409 (M+H).

Compound 58

Compound 58 was synthesized using an analogous synthetic sequence as that described for Compound 44. $^1$HNMR (600 MHz, DMSO-d$_6$) δ ppm 1.28 (br. s., 2H) 1.42 (br. s., 2H) 1.70 (br. s., 4H) 1.85-1.95 (m, 2H) 2.69 (m, 2H) 7.16-7.25 (m, 1H) 8.41 (br. s., 1H) 9.04 (s, 1H). LCMS 291 (M+H).

Example 59

Synthesis of Compound 59

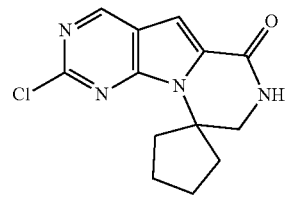 [SMILES: O=C1NCC2(CCCC2)n2c1cc1cnc(Cl)nc12]

tert-butyl N-[[1-[(5-bromo-2-chloro-pyrimidin-4-yl)amino]cyclopentyl]methyl]carbamate

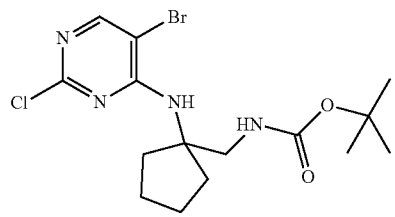 [SMILES: CC(C)(C)OC(=O)NCC1(Nc2nc(Cl)ncc2Br)CCCC1]

tert-butyl N-[[1-[(5-bromo-2-chloro-pyrimidin-4-yl)amino]cyclopentyl]methyl]carbamate was synthesized using 5-bromo-2,4-dichloro-pyrimidine and Intermediate L using analogous reaction conditions as described for tert-butyl N-[2-[(5-bromo-2-chloro-pyrimidin-4-yl)amino]-3-methyl-butyl]carbamate. $^1$HNMR (600 MHz, DMSO-d$_6$) δ ppm 1.34 (s, 9H) 1.50-1.58 (m, 2H) 1.63-1.78 (m, 4H) 1.96-2.06 (m, 2H) 3.25 (d, J=6.15 Hz, 2H) 6.71 (s, 1H) 7.18 (t, J=6.29 Hz, 1H) 8.20 (s, 1H). LCMS (ESI) 405 (M+H).

tert-butyl N-[[1-[[2-chloro-5-(3,3-diethoxyprop-1-ynyl)pyrimidin-4-yl]amino]cyclopentyl]methyl]carbamate

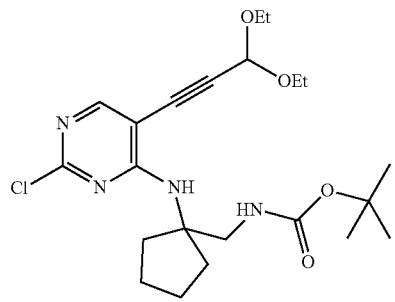 [SMILES: CCOC(C#Cc1cnc(Cl)nc1NC1(CNC(=O)OC(C)(C)C)CCCC1)OCC]

tert-butyl N-[[1-[[2-chloro-5-(3,3-diethoxyprop-1-ynyl)pyrimidin-4-yl]amino]cyclopentyl]methyl]carbamate was synthesized using similar experimental conditions to that used in the synthesis of (2S)-N2-[2-chloro-5-(3,3-diethoxyprop-1-ynyl)pyrimidin-4-yl]-4-methyl-pentane-1,2-diamine. LCMS (ESI) 453 (M+H).

7-[1-[(tert-butoxycarbonylamino)methyl]cyclopentyl]-2-chloro-pyrrolo[2,3-d]pyrimidine-6-carboxylic Acid

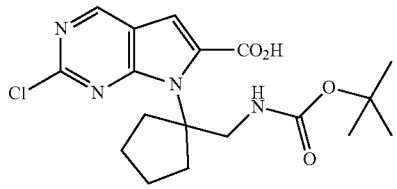 [SMILES: CC(C)(C)OC(=O)NCC1(n2c(C(=O)O)cc3cnc(Cl)nc32)CCCC1]

7-[1-[(tert-butoxycarbonylamino)methyl]cyclopentyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-$d_6$) δ ppm 1.47 (s, 9H) 1.74 (br. s., 2H) 1.88 (br. s., 2H) 2.04 (br. s., 2H) 2.41-2.45 (m, 2H) 4.06 (s, 2H) 7.45 (s, 1H) 9.11 (s, 1H). LCMS (ESI) 395 (M+H).

Compound 59

Compound 59 was synthesized using an analogous synthetic sequence as that described for Compound 44. $^1$HNMR (600 MHz, DMSO-$d_6$) δ ppm 1.72 (br. s., 2H) 1.86-1.93 (m, 2H) 1.99 (d, J=3.81 Hz, 2H) 2.40 (br. s., 2H) 3.48 (d, J=2.34 Hz, 2H) 7.22 (s, 1H) 8.53 (br. s., 1H) 9.05 (s, 1H). LCMS (ESI) 277 (M+H).

Example 60

Synthesis of Compound 60

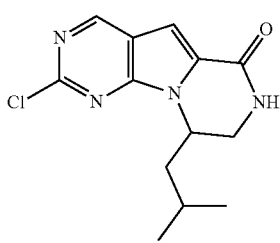 [SMILES: CC(C)CC1CNC(=O)c2cc3cnc(Cl)nc3n21]

tert-butyl N-[2-[(5-bromo-2-chloro-pyrimidin-4-yl)amino]-4-methyl-pentyl]carbamate

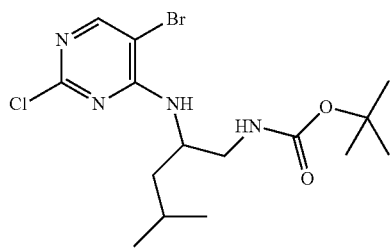 [SMILES: CC(C)CC(CNC(=O)OC(C)(C)C)Nc1nc(Cl)ncc1Br]

tert-butyl N-[2-[(5-bromo-2-chloro-pyrimidin-4-yl)amino]-4-methyl-pentyl]carbamate was synthesized using 5-bromo-2,4-dichloro-pyrimidine and Intermediate B using analogous reaction conditions as described for tert-butyl N-[2-[(5-bromo-2-chloro-pyrimidin-4-yl)amino]-3-methyl-butyl]carbamate. The analytical data is consistent with that described for the L-enantiomer.

tert-butyl N-[2-[[2-chloro-5-(3,3-diethoxyprop-1-ynyl)pyrimidin-4-yl]amino]-4-methyl-pentyl]carbamate

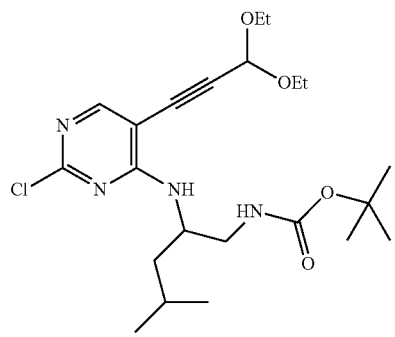 [SMILES: CCOC(C#Cc1cnc(Cl)nc1NC(CNC(=O)OC(C)(C)C)CC(C)C)OCC]

tert-butyl N-[2-[[2-chloro-5-(3,3-diethoxyprop-1-ynyl)pyrimidin-4-yl]amino]-4-methyl-pentyl]carbamate was synthesized using similar experimental conditions to that used in the synthesis of tert-butyl N-[2-[[2-chloro-5-(3,3-diethoxyprop-1-ynyl)pyrimidin-4-yl]amino]ethyl]carbamate. $^1$HNMR (600 MHz, CHLOROFORM-d) δ ppm 1.21-1.31 (m, 12H) 1.38-1.46 (m, 11H) 1.70 (m, 1H) 3.24 (m, 2H) 3.65-3.82 (m, 4H) 4.86 (br s., 1H), 5.65 (s, 1H) 5.85 (br s., 1H) 6.94 (s, 1H) 8.21 (s, 1H). LCMS (ESI) 455 (M+H).

7-[1-[(tert-butoxycarbonylamino)methyl]-3-methyl-butyl]-2-chloro-pyrrolo[2,3-d]pyrimidine-6-carboxylic Acid

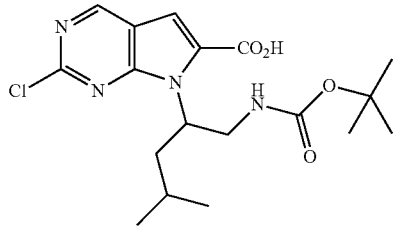 [SMILES: CC(C)CC(CNC(=O)OC(C)(C)C)n1c(C(=O)O)cc2cnc(Cl)nc21]

7-[1-[(tert-butoxycarbonylamino)methyl]-3-methyl-butyl]-2-chloro-pyrrolo[2,3-d]pyrimidine-6-carboxylic acid was synthesized using analogous synthetic sequence as that described for 7-[1-[(tert-butoxycarbonylamino)methyl]-2-methyl-propyl]-2-chloro-pyrrolo[2,3-d]pyrimidine-6-carboxylic acid. The analytical data was consistent with that described for the L-isomer.

Compound 60

Compound 60 was synthesized using an analogous synthetic sequence as that described for Compound 44. The analytical data was consistent with that described for the L-isomer.

Example 61

Synthesis of Compound 61

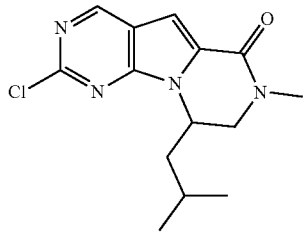 [SMILES: CC(C)CC1CN(C)C(=O)c2cc3cnc(Cl)nc3n21]

To a solution of Compound 60 (100 mg, 0.00024 mole) in DMF (3.0 mL) was added sodium hydride (60% dispersion in oil), (27.6 mg, 3 eq). After stirring for 15 mins, methyl iodide (30, 2 eq) was added. The contents were stirred at room temperature for 30 mins. After the addition of sat NaHCO$_3$, ethyl acetate was added. Separation of the organic layer followed by drying with magnesium sulfate and concentration under vacuum afforded the product. Analytical data was similar to the Compound 49.

Example 62

Synthesis of Compound 62

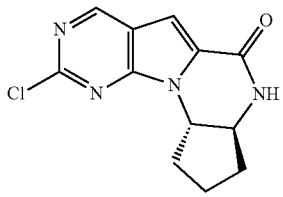 [SMILES: O=C1N[C@H]2CCC[C@@H]2n2c1cc1cnc(Cl)nc12]

tert-butyl N-[(1S,2S)-2-[(5-bromo-2-chloro-pyrimidin-4-yl)amino]cyclopentyl]carbamate

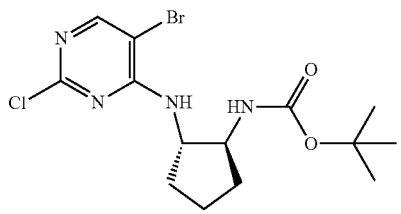 [SMILES: CC(C)(C)OC(=O)N[C@H]1CCC[C@@H]1Nc1nc(Cl)ncc1Br]

tert-butyl N-[(1S,2S)-2-[(5-bromo-2-chloro-pyrimidin-4-yl)amino]cyclopentyl]carbamate was synthesized by treating tert-butyl N-[(1S,2S)-2-aminocyclopentyl]carbamate with 5-bromo-2,4-dichloro-pyrimidine using analogous reaction conditions as described for tert-butyl N-[2-[(5-bromo-2-chloro-pyrimidin-4-yl)amino]-3-methyl-butyl]carbamate. $^1$HNMR (600 MHz, DMSO-d$_6$) δ ppm 1.27 (s, 9H) 1.42-1.54 (m, 2H) 1.56-1.65 (m, 2H) 1.80-1.88 (m, 1H) 1.96-2.01 (m, 1H) 3.88-3.96 (m, 1H) 4.03-4.09 (m, 1H) 6.91 (d, J=8.20 Hz, 1H) 7.41 (d, J=7.32 Hz, 1H) 8.18 (s, 1H). LCMS (ESI) 391 (M+H).

tert-butyl N-[(1S,2S)-2-[[2-chloro-5-(3,3-diethoxy-prop-1-ynyl)pyrimidin-4-yl]amino]cyclopentyl]carbamate

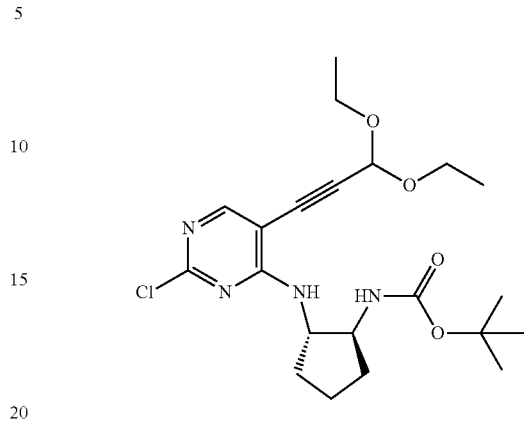

tert-butyl N-[(1S,2S)-2-[[2-chloro-5-(3,3-diethoxyprop-1-ynyl)pyrimidin-4-yl]amino]cyclopentyl]carbamate was synthesized using similar experimental conditions to that used in the synthesis of (2S)-N2-[2-chloro-5-(3,3-diethoxy-prop-1-ynyl)pyrimidin-4-yl]-4-methyl-pentane-1,2-diamine. $^1$HNMR (600 MHz, DMSO-d$_6$) δ ppm 1.13 (t, 6H) 1.28 (s, 9H) 1.42-1.52 (m, 2H) 1.58-1.65 (m, 2H) 1.81-1.90 (m, 1H) 1.99-2.08 (m, 1H) 3.49-3.60 (m, 2H) 3.63-3.71 (m, 2H) 3.84-3.93 (m, 1H) 3.96-4.04 (m, 1H) 5.53 (s, 1H) 6.96 (d, J=7.90 Hz, 1H) 7.34 (d, J=7.03 Hz, 1H) 8.14 (s, 1H). LCMS (ESI) 439 (M+H).

7-[(1S,2S)-2-(tert-butoxycarbonylamino)cyclopentyl]-2-chloro-pyrrolo[2,3-d]pyrimidine-6-carboxylic Acid

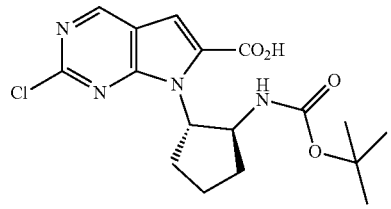 [SMILES: CC(C)(C)OC(=O)N[C@H]1CCC[C@@H]1n1c(C(=O)O)cc2cnc(Cl)nc21]

7-[(1 S,2 S)-2-(tert-butoxycarbonylamino)cyclopentyl]-2-chloro-pyrrolo[2,3-d]pyrimidine-6-carboxylic acid was synthesized using the analogous synthetic sequence as that described for 7-[1-[(tert-butoxycarbonylamino)methyl]-2-methyl-propyl]-2-chloro-pyrrolo[2,3-d]pyrimidine-6-carboxylic acid. $^1$HNMR (600 MHz, DMSO-d$_6$) δ ppm 1.41-1.52 (m, 9H) 1.55-1.68 (m, 1H) 1.88-2.00 (m, 2H) 2.05-2.15 (m, 1H) 2.26-2.35 (m, 1H) 2.71-2.89 (m, 1H) 4.01-4.16 (m, 1H) 4.28-4.45 (m, 1H) 7.41 (s, 1H) 9.11 (s, 1H). LCMS (ESI) 381 (M+H).

Compound 62

Compound 62 was synthesized using an analogous synthetic sequence as that described for Compound 44. $^1$HNMR (600 MHz, DMSO-d$_6$) δ ppm 1.48-1.60 (m, 1H) 1.88-1.98 (m, 3H) 1.99-2.08 (m, 1H) 2.66-2.75 (m, 1H) 3.63-3.74 (m, 1H) 3.99-4.12 (m, 1H) 7.21 (s, 1H) 8.89 (s, 1H) 9.04 (s, 1H). LCMS (ESI) 263 (M+H).

Example 63

Synthesis of Compound 63

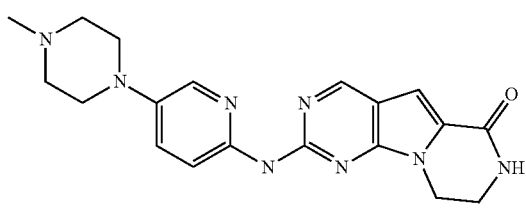 [SMILES: CN1CCN(c2ccc(Nc3ncc4cc5n(c4n3)CCNC5=O)nc2)CC1]

To chloro tricycliclactam (0.050 g, 0.225 mmole) in dioxane (2.0 mL) under nitrogen was added 5-(4-methylpiperazin-1-yl)pyridin-2-amine (0.052 g, 1.2 eq, 0.270 mmole) followed by the addition of $Pd_2(dba)_3$ (18.5 mg), BINAP (25 mg) and sodium-tert-butoxide (31 mg, 0.324 mmole). The contents of the flask are degassed for 10 minutes and then heated to 100 degrees for 12 hours. The crude reaction was loaded on a silica gel column and eluted with DCM/MeOH (0-15%) to afford the desired product (26 mg). To this compound dissolved in DCM/MeOH (10%) was added 3N HCl in iso-propanol (2 eq) and the reaction was stirred overnight. Concentration under vacuum afforded the hydrochloride salt. $^1$HNMR (d6-DMSO) δ ppm 11.13 (brs, 1H), 9.07 (s, 1H), 8.42 (s, 1H), 8.03 (br m 1H), 7.99 (s, 1H), 7.67 (brm, 1H), 7.18 (s, 1H), 4.33 (m, 2H), 3.79 (m, 2H), 3.64 (m, 2H), 3.50 (m, 2H), 3.16 (m, 4H), 2.79 (s, 3H). LCMS (ESI) 379 (M+H).

Example 64

Synthesis of Compound 64

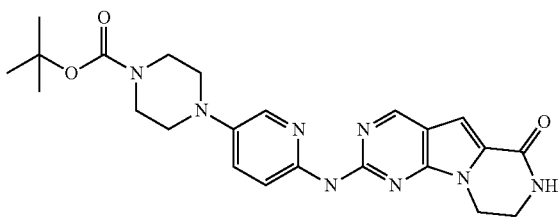 [SMILES: CC(C)(C)OC(=O)N1CCN(c2ccc(Nc3ncc4cc5n(c4n3)CCNC5=O)nc2)CC1]

To chloro tricycliclactam (0.075 g, 0.338 mmole) in dioxane (3.5 mL) under nitrogen was added tert-butyl 4-(6-amino-3-pyridyl)piperazine-1-carboxylate (0.098 g, 1.05 eq) followed by the addition of $Pd_2(dba)_3$ (27 mg), BINAP (36 mg) and sodium-tert-butoxide (45 mg). The contents were heated at reflux for 11 hrs. The crude reaction was loaded onto a silica gel column and eluted with DCM/MeOH (0-10%) to afford the desired product (32 mg). $^1$HNMR (d6-DMSO) δ ppm 9.48 (s, 1H), 8.84 (s, 1H), 8.29 (s, 1H), 8.18 (s, 1H), 7.99 (s, 1H), 7.42 (m, 1H), 6.98 (s, 1H), 4.23 (m, 2H), 3.59 (m, 2H), 3.45 (m, 4H), 3.50 (m, 2H), 3.05 (m, 4H). LCMS (ESI) 465 (M+H).

Example 65

Synthesis of Compound 65

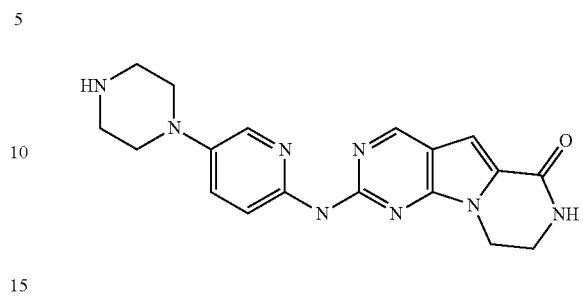

To a solution of Compound 64 (23 mg) in 10% DCM/MeOH was added 10 mL of a 3M solution of HCl in iso-propanol. The contents were stirred for 16 hrs. Concentration of the reaction mixture afforded the hydrochloride salt. $^1$HNMR (d6-DMSO) δ ppm 9.01 (s, 1H), 7.94 (m, 1H), 7.86 (m, 1H), 7.23 (s, 1H), 4.30 (m, 2H), 3.64 (m, 2H), 3.36 (m, 4H), 3.25 (m, 4H). LCMS (ESI) 465 (M+H).

Example 66

Synthesis of Compound 66

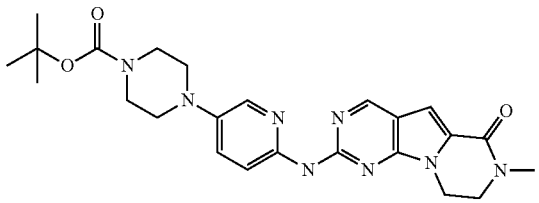 [SMILES: CN1CCn2c(cc3cnc(Nc4ccc(N5CCN(C(=O)OC(C)(C)C)CC5)cn4)nc32)C1=O]

To chloro-N-methyltricyclic amide (0.080 g, 0.338 mmole) in dioxane (3.5 mL) under nitrogen was added tert-butyl 4-(6-amino-3-pyridyl)piperazine-1-carboxylate 0.102 g (1.1 eq) followed by the addition of $Pd_2(dba)_3$ (27 mg), BINAP (36 mg) and sodium-tert-butoxide (45 mg). The contents were heated at reflux for 11 hrs. The crude product was purified using silica gel column chromatography with an eluent of dichloromethane/methanol (0-5%) to afford the desired product (44 mg). $^1$HNMR (d6-DMSO) δ ppm 9.49 (s, 1H), 8.85 (s, 1H), 8.32 (m, 1H), 8.02 (s, 1H), 7.44 (m, 1H), 7.00 (s, 1H), 4.33 (m, 2H), 3.80 (m, 2H), 3.48 (m, 4H), 3.07 (m, 4H), 3.05 (s, 3H), 1.42 (s, 9H). LCMS (ESI) 479 (M+H).

Example 67

Synthesis of Compound 67

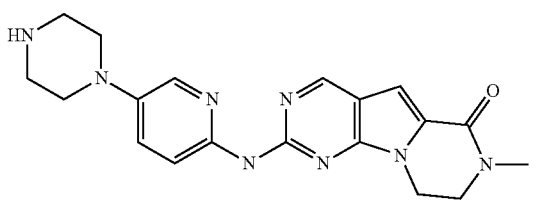 [SMILES: CN1CCn2c(cc3cnc(Nc4ccc(N5CCNCC5)cn4)nc32)C1=O]

To Compound 66 (32 mg) was added 3N HCL (10 mL) in isopropanol and the contents were stirred at room temperature overnight for 16 hrs. Concentration afforded the hydrochloride salt. ¹HNMR (d6-DMSO) δ ppm 9.13 (m, 2H), 8.11 (m, 1H), 8.10 (s, 1H), 7.62 (m, 1H), 7.21 (s, 1H), 4.43 (m, 2H), 3.85 (m, 2H), 3.41 (m, 4H), 3.28 (m, 4H), 3.08 (s, 3H). LCMS (ESI) 379 (M+H).

Example 68

Synthesis of Compound 68

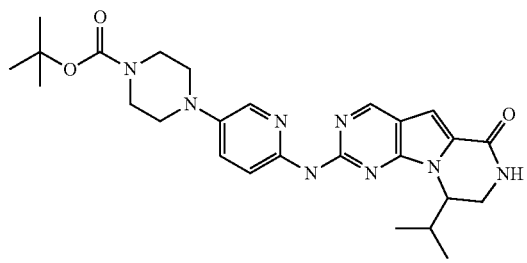 [SMILES: CC(C)C1CNC(=O)c2cc3cnc(Nc4ccc(N5CCN(C(=O)OC(C)(C)C)CC5)cn4)nc3n21]

Compound 68 was synthesized using similar experimental conditions to that described for compound 64. ¹HNMR (600 MHz, DMSO-d₆) δ ppm 0.79 (d, J=7.03 Hz, 3H) 1.01 (d, J=6.73 Hz, 3H) 1.35-1.48 (m, 9H) 2.16 (dd, J=14.64, 6.73 Hz, 1H) 3.00-3.14 (m, 4H) 3.40-3.51 (m, 4H) 3.51-3.60 (m, 1H) 3.63-3.74 (m, 1H) 4.44 (dd, J=7.90, 3.81 Hz, 1H) 6.99 (s, 1H) 7.46 (dd, J=8.93, 2.78 Hz, 1H) 7.94-8.09 (m, 2H) 8.31 (dd, J=9.08, 1.46 Hz, 1H) 8.85 (s, 1H) 9.46 (s, 1H). LCMS (ESI) 507 (M+H).

Example 69

Synthesis of Compound 69

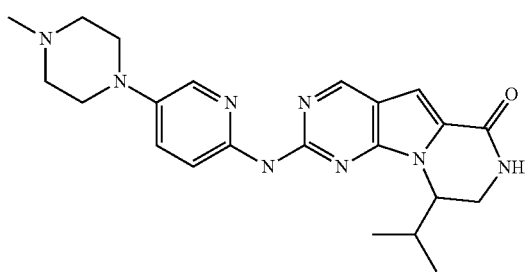 [SMILES: CC(C)C1CNC(=O)c2cc3cnc(Nc4ccc(N5CCN(C)CC5)cn4)nc3n21]

Compound 69 was synthesized using similar experimental conditions to those described for compound 63 and was recovered as an HCl salt. ¹HNMR (600 MHz, DMSO-d₆) δ ppm 0.77-0.86 (m, 3H) 0.96 (d, J=7.03 Hz, 3H) 2.10-2.24 (m, 1H) 3.07 (s, 3H) 3.37-3.79 (m, 8H) 4.00 (dd, J=13.61, 4.54 Hz, 2H) 4.63-4.73 (m, 1H) 7.20 (s, 1H) 7.58-7.71 (m, 1H) 7.99 (d, J=2.34 Hz, 1H) 8.12 (d, J=9.37 Hz, 1H) 9.11 (s, 1H) 9.41 (br. s., 2H) 11.76 (br. s., 1H). LCMS (ESI) 421 (M+H).

Example 70

Synthesis of Compound 70

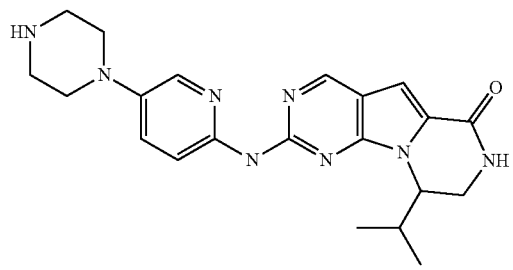 [SMILES: CC(C)C1CNC(=O)c2cc3cnc(Nc4ccc(N5CCNCC5)cn4)nc3n21]

Compound 70 was synthesized using similar experimental conditions to those described for compounds 64 and 65 and was recovered as an HCl salt. The characterization data (NMR and LCMS) was consistent with that reported for compound 71.

Example 71

Synthesis of Compound 71

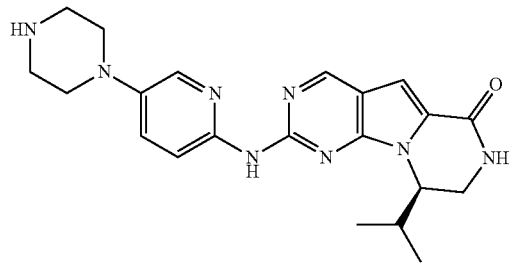

Compound 71 was synthesized using similar experimental conditions to those described for compounds 64 and 65 and was recovered as an HCl salt. ¹HNMR (600 MHz, DMSO-d₆) δ ppm 0.79 (d, J=6.73 Hz, 3H) 1.01 (d, J=6.73 Hz, 3H) 2.18 (dd, J=14.49, 7.17 Hz, 1H) 3.18-3.84 (m, 10H) 4.53-4.71 (m, 1H) 7.24 (s, 1H) 7.65 (d, J=9.37 Hz, 1H) 8.01 (d, J=2.64 Hz, 1H) 8.14 (d, J=1.46 Hz, 1H) 8.35 (d, J=5.27 Hz, 1H) 9.14 (s, 1H) 9.46 (s, 2H) 11.80 (s, 1H) LCMS (ESI) 407 (M+H).

Example 72

Synthesis of Compound 72 (Compound UUU)

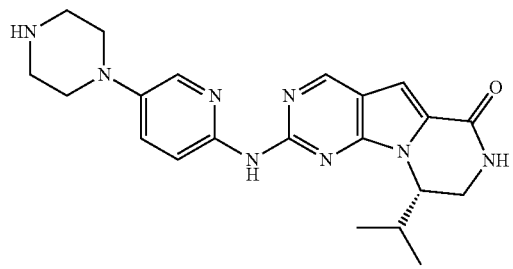 [SMILES: CC(C)[C@H]1CNC(=O)c2cc3cnc(Nc4ccc(N5CCNCC5)cn4)nc3n21]

Compound 72 was synthesized using similar experimental conditions to that described for compounds 64 and 65 and was recovered as an HCl salt. ¹HNMR (600 MHz, DMSO-d₆) δ ppm 0.77 (d, J=7.03 Hz, 3H) 0.99 (d, J=6.73 Hz, 3H) 2.10-2.24 (m, 1H) 3.18-3.81 (m, 10H) 4.54-4.69 (m, 1H) 7.22 (s, 1H) 7.63 (d, J=9.08 Hz, 1H) 7.99 (d, J=2.63 Hz, 1H) 8.11 (s, 1H) 8.33 (d, J=5.27 Hz, 1H) 9.12 (s, 1H) 9.43 (s, 2H) 11.77 (s, 1H). LCMS (ESI) 407 (M+H).

Example 73

Synthesis of Compound 73

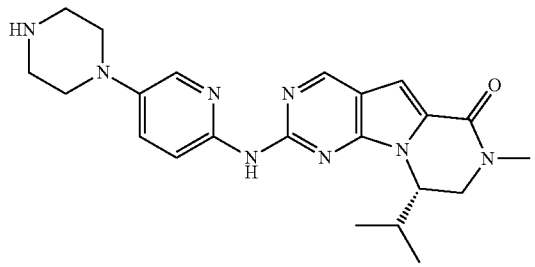 [SMILES: CC(C)[C@H]1CN(C)C(=O)c2cc3cnc(Nc4ccc(N5CCNCC5)cn4)nc3n21]

Compound 73 was synthesized using similar experimental conditions to those described for compounds 64 and 65 and was recovered as an HCl salt. ¹H NMR (600 MHz, DMSO-d₆) δ ppm 0.84 (d, J=6.73 Hz, 3H) 0.98 (d, J=6.73 Hz, 3H) 2.12-2.26 (m, 1H) 3.09 (s, 3H) 3.22-3.81 (m, 8H) 4.01 (dd, J=13.61, 4.25 Hz, 2H) 4.59-4.72 (m, 1H) 7.19 (s, 1H) 7.74 (s, 1H) 7.96-8.10 (m, 2H) 9.08 (s, 1H) 9.22 (s, 2H). LCMS (ESI) 421 (M+H).

Example 74

Synthesis of Compound 74

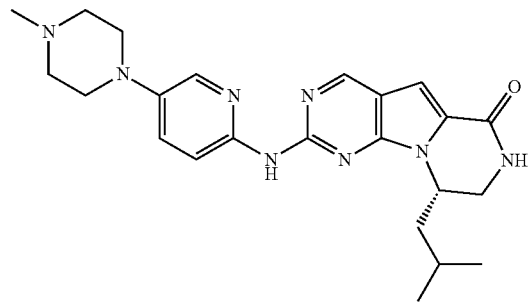 [SMILES: CC(C)C[C@H]1CNC(=O)c2cc3cnc(Nc4ccc(N5CCN(C)CC5)cn4)nc3n21]

Compound 74 was synthesized using similar experimental conditions to those described for compound 63 and was recovered as an HCl salt. ¹HNMR (600 MHz, DMSO-d₆) δ ppm 0.85 (d, J=4.98 Hz, 3H) 0.95 (d, J=4.98 Hz, 3H) 1.42-1.70 (m, 3H) 2.77 (d, J=2.93 Hz, 3H) 3.07-4.14 (m, 10H) 4.95 (s, 1H) 7.20 (s, 1H) 7.66 (d, J=9.66 Hz, 1H) 7.94 (s, 1H) 8.08-8.16 (m, 1H) 8.33 (d, J=4.68 Hz, 1H) 9.09 (s, 1H) 11.38 (s, 1H) 11.71 (s, 1H). LCMS (ESI) 435 (M+H).

Example 75

Synthesis of Compound 75

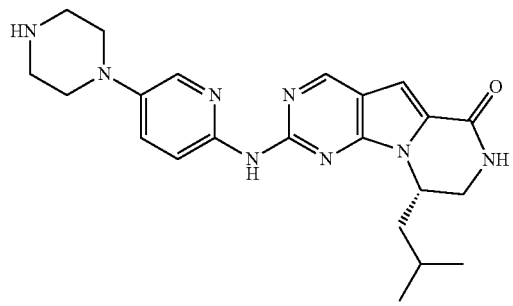 [SMILES: CC(C)C[C@H]1CNC(=O)c2cc3cnc(Nc4ccc(N5CCNCC5)cn4)nc3n21]

Compound 75 was synthesized using similar experimental conditions to those described for compounds 64 and 65 and was recovered as an HCl salt. ¹H NMR (600 MHz, DMSO-d₆) δ ppm 0.87 (d, J=6.15 Hz, 3H) 0.94 (d, J=6.15 Hz, 3H) 1.57 (d, J=84.61 Hz, 3H) 3.05 (s, 3H) 3.13-3.55 (m, 8H) 3.69 (d, J=78.17 Hz, 2H) 4.90 (s, 1H) 7.15 (s, 1H) 7.63-7.85 (m, 1H) 7.93 (s, 1H) 8.26 (s, 1H) 9.03 (s, 1H) 9.20 (s, 2H). LCMS (ESI) 421 (M+H).

Example 76

Synthesis of Compound 76

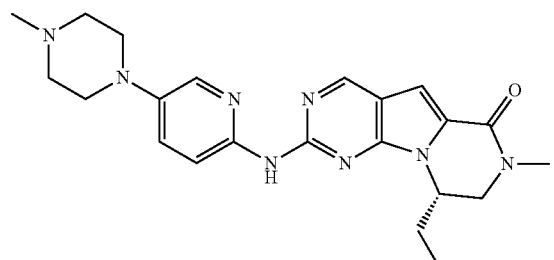

Compound 76 was synthesized using similar experimental conditions to those described for compound 63 and was recovered as an HCl salt. ¹HNMR (600 MHz, DMSO-d₆) δ ppm 0.85 (d, J=6.44 Hz, 3H) 0.95 (d, J=6.44 Hz, 3H) 1.43-1.70 (m, 3H) 2.78 (d, J=2.93 Hz, 3H) 3.05 (s, 3H) 3.24-3.84 (m, 8H) 4.01 (d, J=9.66 Hz, 2H) 4.89-5.01 (m, 1H) 7.15 (s, 1H) 7.77 (s, 1H) 7.91-8.05 (m, 2H) 9.03 (s, 1H) 10.96-11.55 (m, 2H). LCMS (ESI) 449 (M+H).

Example 77

Synthesis of Compound 77

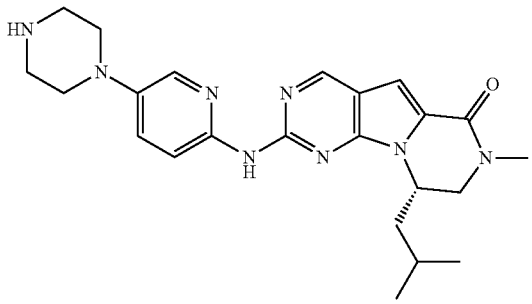 [SMILES: CC(C)C[C@H]1CN(C)C(=O)c2cc3cnc(Nc4ccc(N5CCNCC5)cn4)nc3n21]

Compound 77 was synthesized using similar experimental conditions to those described for compounds 64 and 65 and was recovered as an HCl salt. $^1$H NMR (600 MHz, DMSO-d$_6$) δ ppm 0.83-0.88 (d, J=6.15 Hz, 3H) 0.95 (d, J=6.15 Hz, 3H) 1.40-1.71 (m, 3H) 3.28-3.83 (m, 8H) 4.00 (d, J=3.22 Hz, 2H) 4.91-5.08 (m, 1H) 7.17 (s, 1H) 7.68 (d, J=9.66 Hz, 1H) 7.93 (s, 1H) 8.07 (s, 1H) 9.06 (s, 1H) 9.40 (s, 2H) 11.59 (s, 1H). LCMS (ESI) 435 (M+H).

Example 78

Synthesis of Compound 78

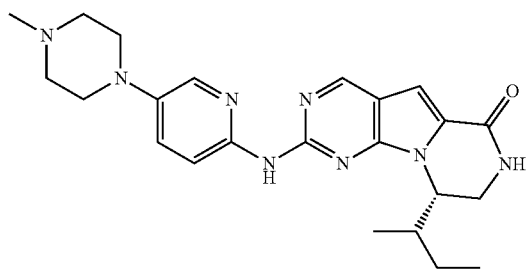 [SMILES: CCC(C)[C@H]1CNC(=O)c2cc3cnc(Nc4ccc(N5CCN(C)CC5)cn4)nc3n21]

To Compound 50 0.060 g (0.205 mmole) was added 5-(4-methylpiperazin-1-yl)pyridin-2-amine (35.42 mg, 0.9 eq) followed by the addition of 1,4-dioxane (3 mL). After degassing with nitrogen, Pd$_2$dba$_3$ (12 mg), BINAP (16 mg) and sodium tert-butoxide (24 mg) were added. The contents were then heated at 90 degrees in a CEM Discovery microwave for 3 hrs. The reaction was then loaded onto a silica gel column and purified by eluting with DCM/MeOH (0-15%). $^1$HNMR (600 MHz, DMSO-d$_6$) δ ppm 0.75 (t, J=7.47 Hz, 3H) 0.91 (d, J=6.73 Hz, 3H) 1.04-1.20 (m, 2H) 1.80-1.98 (m, 1H) 2.77 (d, J=3.81 Hz, 3H) 2.94-3.90 (m, 10H) 4.54-4.68 (m, 1H) 7.06-7.23 (m, 2H) 7.56-7.75 (m, 1H) 7.90-8.12 (m, 2H) 8.29 (s, 1H) 9.07 (s, 1H) 10.98-11.74 (m, 2H). LCMS (ESI) 435 (M+H).

Example 79

Synthesis of Compound 79

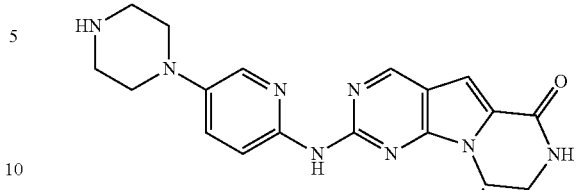

Compound 79 was synthesized in a similar manner to that described for compound 78 followed by the deblocking step described for compound 65 and was converted to an HCl salt. $^1$HNMR (600 MHz, DMSO-d$_6$) δ ppm 0.75 (t, J=7.32 Hz, 3H) 0.90 (d, J=6.73 Hz, 3H) 1.07-1.15 (m, 2H) 1.85-1.94 (m, 1H) 3.17-3.75 (m, 10H) 4.58-4.67 (m, 1H) 7.17 (s, 1H) 7.71 (s, 1H) 7.96 (s, 1H) 7.98-8.05 (m, 1H) 8.28 (d, J=4.10 Hz, 1H) 9.06 (s, 1H) 9.39 (s, 2H). LCMS (ESI) 421 (M+H).

Example 80

Synthesis of Compound 80

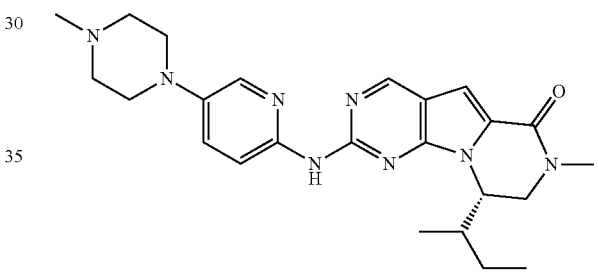

Compound 80 was synthesized in a similar manner to that described for compound 78. $^1$HNMR (600 MHz, DMSO-d$_6$) δ ppm 0.78 (t, J=7.32 Hz, 3H) 0.86 (d, J=6.73 Hz, 3H) 1.13-1.21 (m, 2H) 1.84-1.96 (m, 1H) 2.77 (d, J=4.39 Hz, 3H) 3.04 (s, 3H) 3.11-3.84 (m, 8H) 3.98 (dd, J=13.61, 4.25 Hz, 2H) 4.66-4.74 (m, 1H) 7.17 (s, 1H) 7.64 (s, 1H) 7.96 (d, J=2.34 Hz, 1H) 8.03-8.13 (m, 1H) 9.08 (s, 1H) 11.26 (s, 1H) 11.66 (s, 1H). LCMS (ESI) 449 (M+H).

Example 81

Synthesis of Compound 81

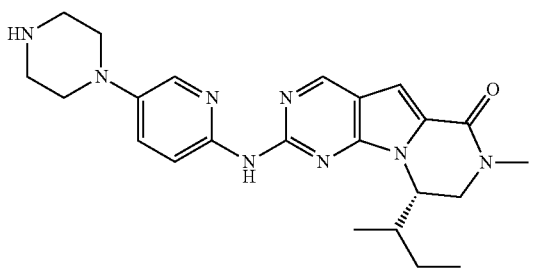 [SMILES: CCC(C)[C@H]1CN(C)C(=O)c2cc3cnc(Nc4ccc(N5CCNCC5)cn4)nc3n21]

The compound was synthesized in a similar manner to that described for compound 78 followed by the deblocking step described for compound 65 and was converted to an HCl salt. $^1$HNMR (600 MHz, DMSO-d$_6$) δ ppm 0.78 (t, J=7.32 Hz, 3H) 0.85 (d, J=6.73 Hz, 3H) 1.10-1.27 (m, 2H) 1.82-1.99 (m, 1H) 3.04 (s, 3H) 3.28-3.77 (m, 8H) 3.97 (dd, J=13.91, 4.54 Hz, 2H) 4.62-4.75 (m, 1H) 7.07-7.24 (m, 1H) 7.62-7.75 (m, 1H) 7.94 (d, J=2.34 Hz, 1H) 7.97-8.08 (m, 1H) 9.05 (s, 1H) 9.29 (s, 2H). LCMS (ESI) 435 (M+H).

Example 82

Synthesis of Compound 82

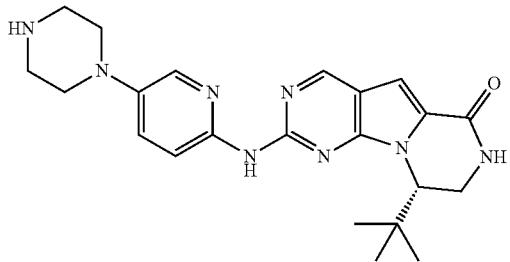 [SMILES: CC(C)(C)[C@H]1CNC(=O)c2cc3cnc(Nc4ccc(N5CCNCC5)cn4)nc3n21]

The compound was synthesized in a similar manner to that described for compound 78 followed by the deblocking step described for compound 65 and was converted to an HCl salt. $^1$HNMR (600 MHz, DMSO-d$_6$) δ ppm 0.96 (s, 9H) 3.15-3.87 (m, 10H) 4.42-4.53 (m, 1H) 6.99 (s, 1H) 7.24 (s, 1H) 8.06 (s, 1H) 8.11-8.21 (m, 1H) 8.79-8.98 (m, 2H) 9.25 (s, 2H) 9.88 (s, 1H). LCMS (ESI) 421 (M+H).

Example 83

Synthesis of Compound 83

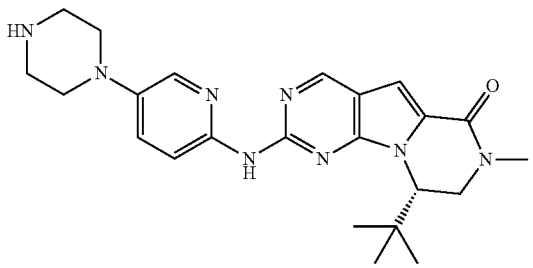 [SMILES: CN1C[C@H](C(C)(C)C)n2c(cc3cnc(Nc4ccc(N5CCNCC5)cn4)nc32)C1=O]

Compound 83 was synthesized in a similar manner to that described for compound 78 followed by the deblocking step described for compound 65 and was converted to an HCl salt. $^1$HNMR (600 MHz, DMSO-d$_6$) δ ppm 0.95 (s, 9H) 2.79 (d, J=4.10 Hz, 3H) 3.06-3.86 (m, 10H) 4.56-4.67 (m, 1H) 7.17 (s, 1H) 7.70 (s, 1H) 7.96 (d, J=2.63 Hz, 1H) 7.99-8.08 (m, 1H) 8.26 (s, 1H) 9.06 (s, 1H) 10.80 (s, 1H). LCMS (ESI) 435 (M+H).

Example 84

Synthesis of Compound 84

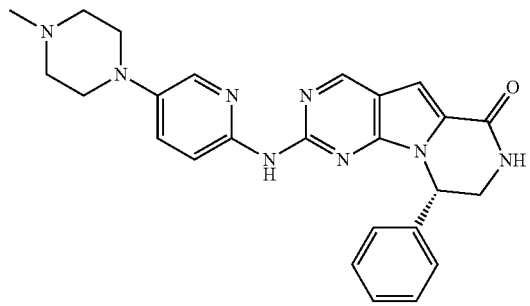 [SMILES: CN1CCN(c2ccc(Nc3ncc4cc5n(c4n3)[C@@H](c3ccccc3)CNC5=O)nc2)CC1]

Compound 84 was synthesized in a similar manner to that described for compound 78 and was converted to an HCl salt. $^1$HNMR (600 MHz, DMSO-d$_6$) δ ppm 2.75-2.81 (m, 3H) 3.12-3.16 (m, 2H) 3.46-3.54 (m, 4H) 3.60-3.69 (m, 2H) 3.72-3.79 (m, 1H) 4.07-4.18 (m, 2H) 6.06-6.09 (m, 1H) 6.90 (d, J=7.61 Hz, 2H) 7.20-7.31 (m, 3H) 7.33 (s, 1H) 7.49-7.55 (m, 1H) 7.62-7.70 (m, 1H) 7.92 (d, J=2.93 Hz, 1H) 8.22 (s, 1H) 9.14 (s, 1H). LCMS (ESI) 455 (M+H).

Example 85

Synthesis of Compound 85

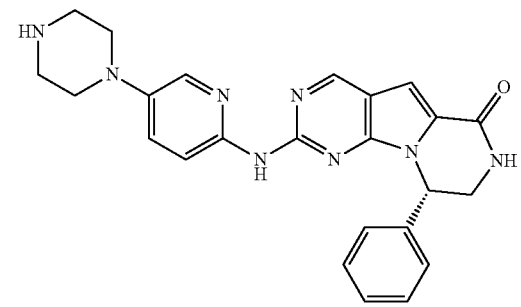 [SMILES: O=C1NC[C@H](c2ccccc2)n2c1cc1cnc(Nc3ccc(N4CCNCC4)cn3)nc12]

Compound 85 was synthesized in a similar manner to that described for compound 78 followed by the deblocking step described for compound 65 and was converted to an HCl salt. $^1$HNMR (600 MHz, DMSO-d$_6$) δ ppm 3.21 (s, 4H) 3.35-3.67 (m, 5H) 4.07-4.20 (m, 2H) 6.13 (s, 1H) 6.90 (d, J=7.32 Hz, 2H) 7.22-7.31 (m, 3H) 7.36 (s, 1H) 7.48 (d, J=9.37 Hz, 1H) 7.93 (d, J=2.34 Hz, 1H) 8.04-8.11 (m, 1H) 8.25 (d, J=4.98 Hz, 1H) 9.17 (s, 1H) 11.77 (br, s., 1H). LCMS (ESI) 441 (M+H).

Example 86

Synthesis of Compound 86

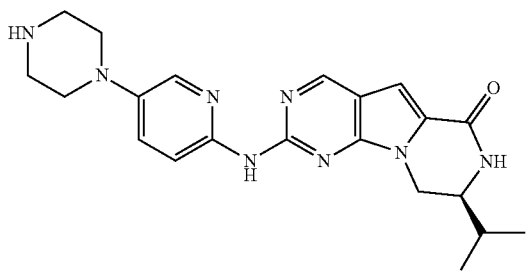 [SMILES: CC(C)[C@H]1Cn2c(cc3cnc(Nc4ccc(N5CCNCC5)cn4)nc32)C(=O)N1]

Compound 86 was synthesized in a similar manner to that described for compound 78 followed by the deblocking step described for compound 65 and was converted to an HCl salt. $^1$HNMR (600 MHz, DMSO-d$_6$) δ ppm 0.90 (d, J=6.15 Hz, 6H) 1.72-1.89 (m, 1H) 3.15-3.92 (m, 9H) 4.10-4.46 (m, 2H) 7.18 (s, 1H) 7.59 (d, J=8.78 Hz, 1H) 8.00 (s, 1H) 8.13 (d, J=9.37 Hz, 1H) 8.55 (s, 1H) 9.09 (s, 1H) 9.67 (s, 2H) 11.91 (s, 1H). LCMS (ESI) 407 (ESI).

Example 87

Synthesis of Compound 87

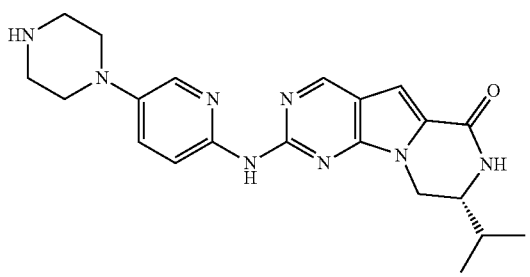 [SMILES: CC(C)[C@@H]1Cn2c(cc3cnc(Nc4ccc(N5CCNCC5)cn4)nc32)C(=O)N1]

Compound 87 was synthesized in a manner similar to compound 86 and was converted to an HCl salt. The characterization data (NMR and LCMS) was similar to that obtained for the antipode compound 86.

Example 88

Synthesis of Compound 88

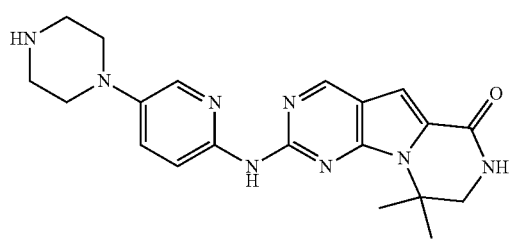 [SMILES: CC1(C)CNC(=O)c2cc3cnc(Nc4ccc(N5CCNCC5)cn4)nc3n21]

Compound 88 was synthesized in a similar manner to that described for compound 78 followed by the deblocking step described for compound 65 and was converted to an HCl salt. $^1$HNMR (600 MHz, DMSO-d$_6$) δ ppm 1.78 (s, 6H) 3.40-3.53 (m, 6H) 3.64-3.73 (m, 4H) 7.27 (s, 1H) 7.66 (d, J=9.37 Hz, 1H) 7.98 (d, J=2.34 Hz, 1H) 8.12 (br. s., 1H) 8.47 (br. s., 1H) 9.11 (s, 1H) 9.45 (br. s., 2H) 11.62 (br. s., 1H). LCMS (ESI) 393 (M+H).

Example 89

Synthesis of Compound 89 (Also Referred to as Compound T)

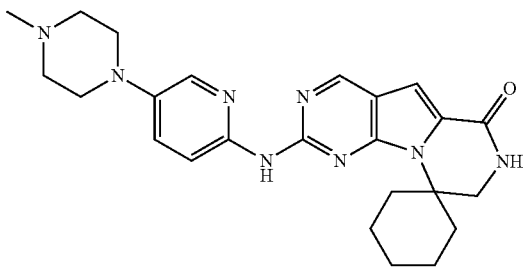 [SMILES: CN1CCN(c2ccc(Nc3ncc4cc5n(c4n3)C3(CCCCC3)CNC5=O)nc2)CC1]

Compound 89 was synthesized in a similar manner to that described for compound 78 and was converted to an HCl salt. $^1$HNMR (600 MHz, DMSO-d$_6$) δ ppm 1.47 (br. s., 6H) 1.72 (br. s., 2H) 1.92 (br. s., 2H) 2.77 (br. s., 3H) 3.18 (br. s., 2H) 3.46 (br. s., 2H) 3.63 (br. s., 2H) 3.66 (d, J=6.15 Hz, 2H) 3.80 (br. s., 2H) 7.25 (s, 1H) 7.63 (br. s., 2H) 7.94 (br. s., 1H) 8.10 (br. s., 1H) 8.39 (br. s., 1H) 9.08 (br. s., 1H) 11.59 (br. s., 1H). LCMS (ESI) 447 (M+H).

Example 90

Synthesis of Compound 90 (Also Referred to as Compound Q)

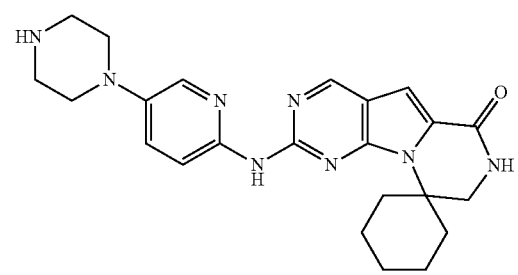 [SMILES: O=C1NCC2(CCCCC2)n2c1cc1cnc(Nc3ccc(N4CCNCC4)cn3)nc12]

Compound 90 was synthesized in a similar manner to that described for compound 78 followed by the deblocking step described for compound 65 and was converted to an HCl salt. $^1$HNMR (600 MHz, DMSO-d$_6$) δ ppm 1.27-1.64 (m, 6H) 1.71 (br. s., 2H) 1.91 (br. s., 2H) 2.80 (br. s., 1H) 3.17-3.24 (m, 2H) 3.41 (br. s., 4H) 3.65 (br. s., 4H) 7.26 (br. s., 1H) 7.63 (br. s., 1 H) 7.94 (br. s., 1H) 8.13 (br. s., 1H) 8.40 (br. s., 1H) 9.09 (br. s., 1H) 9.62 (br. s., 1H) 11.71 (br. s., 1H). LCMS (ESI) 433 (M+H).

Example 91

Synthesis of Compound 91 (Also Referred to as Compound ZZ)

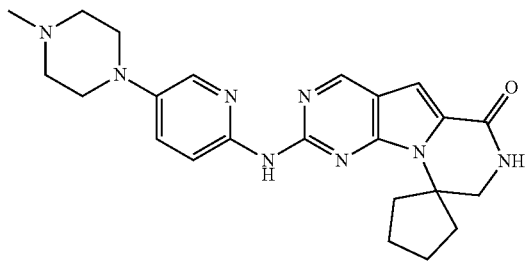 [SMILES: CN1CCN(c2ccc(Nc3ncc4cc5n(c4n3)C3(CCCC3)CNC5=O)nc2)CC1]

Compound 91 was synthesized using similar conditions to those described for compound 78 and was converted to an HCl salt. $^1$HNMR (600 MHz, DMSO-$d_6$) δ ppm 1.64-1.75 (m, 2H) 1.83-1.92 (m, 2H) 1.96-2.06 (m, 2H) 2.49-2.58 (m, 2H) 2.79 (d, J=3.81 Hz, 3H) 3.06-3.18 (m, 4H) 3.59-3.69 (m, 2H) 3.73-3.83 (m, 2H) 4.04-4.12 (m, 2H) 7.17 (br. s., 1H) 7.60-7.70 (m, 2H) 7.70-7.92 (m, 2H) 7.96 (br. s., 1H) 8.41 (br. s., 1H) 8.98 (br. s., 1H) 10.77 (br. s., 1H). LCMS (ESI) 433 (M+H).

Example 92

Synthesis of Compound 92

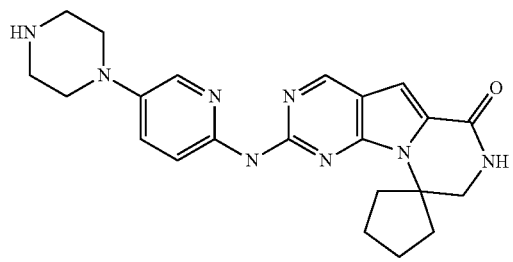 [SMILES: O=C1NCC2(CCCC2)n2c1cc1cnc(Nc3ccc(N4CCNCC4)cn3)nc12]

Compound 92 was synthesized in a similar manner to that described for compound 78 followed by the deblocking step described for compound 65 and was converted to an HCl salt. $^1$HNMR (600 MHz, DMSO-$d_6$) δ ppm 1.64-1.75 (m, 2H) 1.84-1.92 (m, 2H) 1.96-2.05 (m, 2H) 2.48-2.56 (m, 2H) 3.22 (br. s., 4H) 3.42-3.48 (m, 4H) 3.60-3.69 (m, 2H) 4.05-4.13 (m, 1H) 7.18 (s, 1H) 7.65 (d, J=13.47 Hz, 1H) 7.70-7.77 (m, 1H) 7.94 (d, J=1.76 Hz, 1H) 8.42 (br. s., 1H) 9.00 (s, 1H) 9.15 (br. s., 2H). LCMS (ESI) 419 (M+H).

Example 93

Synthesis of Compound 93

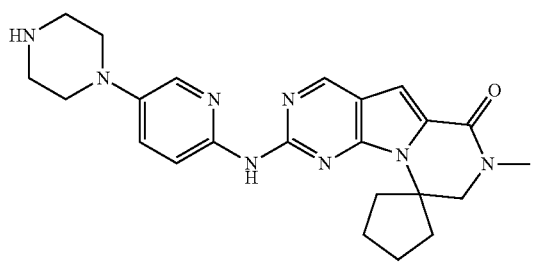 [SMILES: CN1CC2(CCCC2)n2c(cc3cnc(Nc4ccc(N5CCNCC5)cn4)nc32)C1=O]

Compound 93 was synthesized in a similar manner to that described for compound 78 followed by the deblocking step described for compound 65 and was converted to an HCl salt. $^1$HNMR (600 MHz, DMSO-$d_6$) δ ppm 1.76 (br. s., 2H) 1.89 (br. s., 2H) 2.03 (br. s., 2H) 2.47-2.58 (m, 2H) 3.04 (s, 3H) 3.22 (br. s., 4H) 3.39 (br. s., 4H) 3.66 (s, 2H) 7.21 (s, 1H) 7.67 (d, J=9.37 Hz, 1H) 7.93 (br. s., 1H) 7.98-8.09 (m, 1H) 9.04 (s, 1H) 9.34 (br. s., 2H) 11.31 (br. s., 1H). LCMS (ESI) 433 (M+H).

Example 94

Synthesis of Compound 94

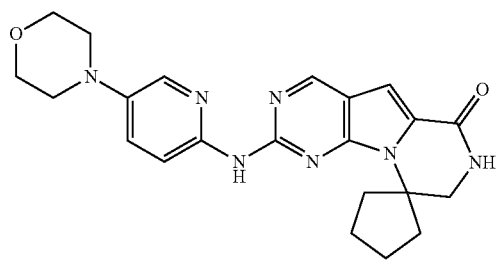

Compound 94 was synthesized using similar conditions to that described for compound 78 and was converted to an HCl salt. $^1$HNMR (600 MHz, DMSO-$d_6$) δ ppm 1.66-1.77 (m, 2H) 1.84-1.94 (m, 2H) 1.96-2.08 (m, 2H) 2.48-2.57 (m, 2H) 3.36-3.52 (m, 4H) 3.60-3.80 (m, 6H) 7.21 (s, 1H) 7.53-7.74 (m, 2H) 7.86 (s, 1H) 8.02 (s, 1H) 8.45 (s, 1H) 9.03 (s, 1H) 11.19 (br. s., 1H). LCMS (ESI) 420 (M+H).

Example 95

Synthesis of Compound 95

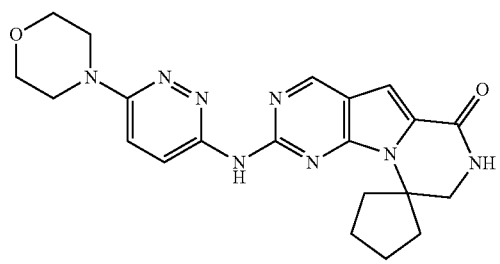 [SMILES: O=C1NCC2(CCCC2)n2c1cc1cnc(Nc3ccc(N4CCOCC4)nn3)nc12]

Compound 95 was synthesized using similar conditions to that described for compound 78 and was converted to an HCl salt. $^1$HNMR (600 MHz, DMSO-$d_6$) δ ppm 1.65-1.79 (m, 2H) 1.85-1.95 (m, 2H) 1.97-2.08 (m, 2H) 2.47-2.54 (m, 2H) 3.40-3.58 (m, 5H) 3.65 (dd, J=21.67, 5.56 Hz, 1H) 3.69-3.78 (m, 4H) 7.24 (s, 1H) 7.97-8.17 (m, 2H) 8.48 (s, 1H) 9.08 (s, 1H) 11.81 (s, 1H). LCMS (ESI) 421 (M+H).

Example 96

Synthesis of Compound 96

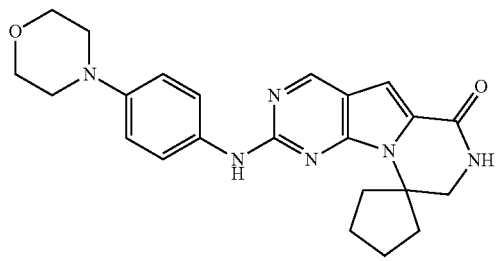 [SMILES: O=C1NCC2(CCCC2)n2c1cc1cnc(Nc3ccc(N4CCOCC4)cc3)nc12]

Compound 96 was synthesized using similar conditions to that described for compound 78 and was converted to an HCl salt. ¹HNMR (600 MHz, DMSO-$d_6$) δ ppm 1.55-1.74 (m, 2H) 1.80-1.98 (m, 4H) 2.48-2.60 (m, 2H) 3.40-3.50 (m, 4H) 3.57-3.72 (m, 2H) 3.90-4.20 (m, 4H) 7.08 (s, 1H) 7.37-7.57 (m, 2H) 7.70 (m, 2H) 8.32 (s, 1H) 8.88 (s, 1H) 9.98 (s, 1H). LCMS (ESI) 419 (M+H).

Example 97

Synthesis of Compound 97 (Also Referred to as Compound III)

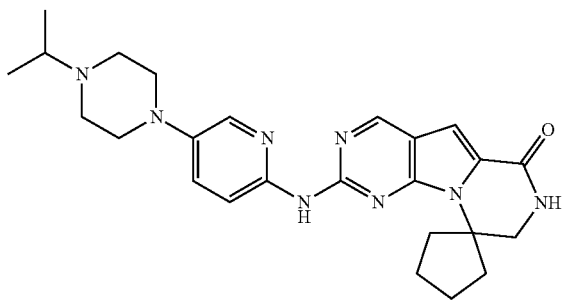 [SMILES: CC(C)N1CCN(c2ccc(Nc3ncc4cc5n(c4n3)C3(CCCC3)CNC5=O)nc2)CC1]

Compound 97 was synthesized using similar conditions to that described for compound 78 and was converted to an HCl salt. ¹HNMR (600 MHz, DMSO-$d_6$) δ ppm 1.30 (d, J=5.27 Hz, 6H) 1.65-1.78 (m, 2H) 1.83-1.95 (m, 2H) 1.97-2.10 (m, 2H) 2.45-2.55 (m, 2H) 3.25-3.36 (m, 1H) 3.39-3.48 (m, 4H) 3.60-3.70 (m, 4H) 3.75-4.15 (m, 2H) 7.24 (s, 1H) 7.54-7.75 (m, 2H) 7.95 (s, 1H) 8.10 (s, 1H) 8.49 (s, 1H) 9.07 (s, 1H) 11.25 (s, 1H) 11.48 (s, 1H). LCMS (ESI) 461 (M+H).

Example 98

Synthesis of Compound 98

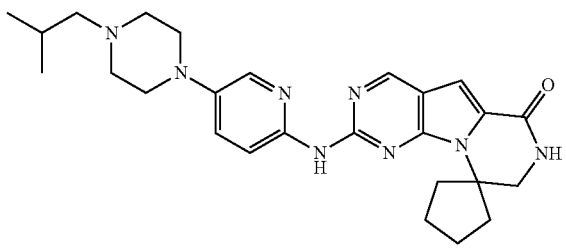 [SMILES: CC(C)CN1CCN(c2ccc(Nc3ncc4cc5n(c4n3)C3(CCCC3)CNC5=O)nc2)CC1]

Compound 98 was synthesized using similar conditions to that described for compound 78 and was converted to an HCl salt. ¹H NMR (600 MHz, DMSO-$d_6$) δ ppm 0.99 (d, J=6.15 Hz, 6H) 1.65-1.78 (m, 2H) 1.90 (m, 2H) 1.97-2.08 (m, 2H) 2.08-2.17 (m, 1H) 2.45-2.55 (m, 2H) 2.88-3.02 (m, 2H) 3.33-3.48 (m, 4H) 3.50-3.90 (m, 6H) 7.24 (s, 1H) 7.67 (s, 2H) 7.94 (s, 1H) 8.12 (s, 1H) 8.49 (s, 1H) 9.07 (s, 1H) 10.77 (s, 1H) 11.51 (s, 1H). LCMS (ESI) 475 (M+H).

Example 99

Synthesis of Compound 99

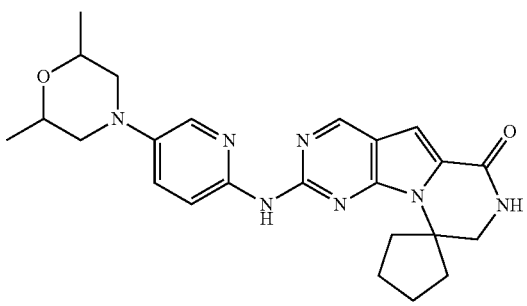 [SMILES: CC1CN(c2ccc(Nc3ncc4cc5n(c4n3)C3(CCCC3)CNC5=O)nc2)CC(C)O1]

Compound 99 was synthesized using similar conditions to those described for compound 78 and was converted to an HCl salt. ¹HNMR (600 MHz, DMSO-$d_6$) δ ppm 1.13 (d, J=5.86 Hz, 6H) 1.66-1.77 (m, 2H) 1.84-1.94 (m, 2H) 1.97-2.09 (m, 2H) 2.40-2.53 (m, 2H) 3.37-3.49 (m, 2H) 3.50-3.59 (m, 2H) 3.59-3.73 (m, 4H) 7.23 (s, 1H) 7.64 (m, 3H) 7.85 (s, 1H) 8.11 (s, 1H) 8.47 (s, 1H) 9.05 (s, 1H). 11.35 (br s., 1H). LCMS (ESI) 448 (M+H).

Example 100

Synthesis of Compound 100

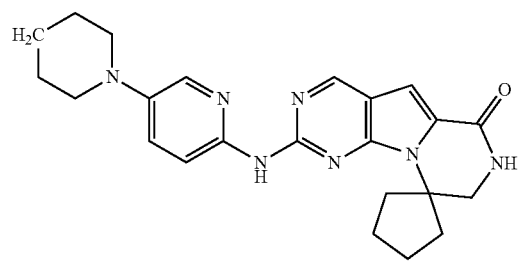 [SMILES: O=C1NCC2(CCCC2)n2c1cc1cnc(Nc3ccc(N4CCCCC4)cn3)nc12]

Compound 100 was synthesized using similar conditions to that described for compound 78 and was converted to an HCl salt. ¹HNMR (600 MHz, DMSO-$d_6$) δ ppm 1.50-1.57 (m, 2H) 1.62-1.68 (m, 3H) 1.68-1.75 (m, 2H) 1.84-1.92 (m, 2H) 1.97-2.08 (m, 2H) 2.48-2.53 (m, 2H) 3.14-3.23 (m, 4H) 3.43-3.47 (m, 2H) 3.58-3.70 (m, 2H) 7.22 (s, 1H) 7.58-7.70 (m, 2H) 7.85-8.00 (m, 1H) 8.16 (d, 1H) 8.46 (s, 1H) 9.04 (s, 1H) 11.37 (br s., 1H). LCMS (ESI) 418 (M+H).

Example 101

Synthesis of Compound 101 (Also Referred to as Compound WW)

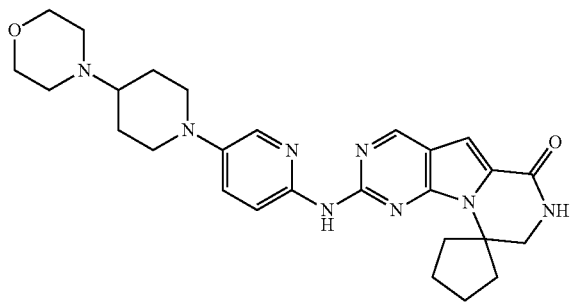 [SMILES: O=C1NCC2(CCCC2)n2c1cc1cnc(Nc3ccc(N4CCC(N5CCOCC5)CC4)cn3)nc12]

Compound 101 was synthesized using similar conditions to those described for compound 78 and was converted to an HCl salt. $^1$HNMR (600 MHz, DMSO-d$_6$) δ ppm 1.72 (s, 2H) 1.90 (s, 4H) 2.03 (s, 2H) 2.21 (s, 2H) 2.48-2.54 (m, 2H) 2.73 (s, 2H) 3.03 (s, 2H) 3.25-3.35 (m, 1H) 3.38-3.48 (m, 4H) 3.65-3.99 (m, 5H) 7.23 (s, 1H) 7.63 (d, J=9.66 Hz, 1H) 7.90 (s, 1H) 8.13 (s, 1H) 8.47 (s, 1H) 9.06 (s, 1H) 10.50 (br s., 1H). LCMS (ESI) 503 (M+H).

Example 102

Synthesis of Compound 102 (Also Referred to as Compound HHH)

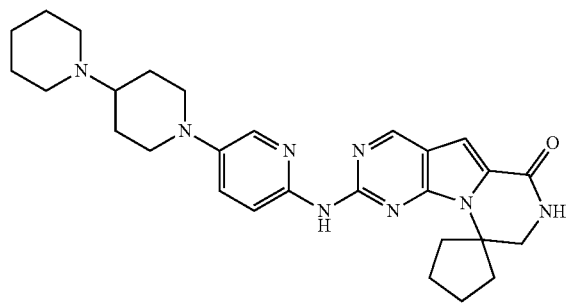

Compound 102 was synthesized using similar conditions to those described for compound 78 and was converted to an HCl salt. $^1$HNMR (600 MHz, DMSO-d$_6$) δ ppm 1.63-1.85 (m, 6H) 1.87-1.92 (m, 2H) 1.99-2.06 (m, 2H) 2.15-2.23 (m, 2H) 2.47-2.53 (m, 1H) 2.69-2.79 (m, 2H) 2.81-2.91 (m, 2H) 2.98-3.08 (m, 2H) 3.32-3.48 (m, 4H) 3.57-3.72 (m, 4H) 3.77-3.85 (m, 2H) 7.22 (s, 1H) 7.60-7.68 (m, 2H) 7.90 (s, 1H) 8.07 (s, 1H) 8.46 (s, 1H) 9.04 (s, 1H). 11.41 (br s., 1H). LCMS (ESI) 501 (M+H).

Example 103

Synthesis of Compound 103

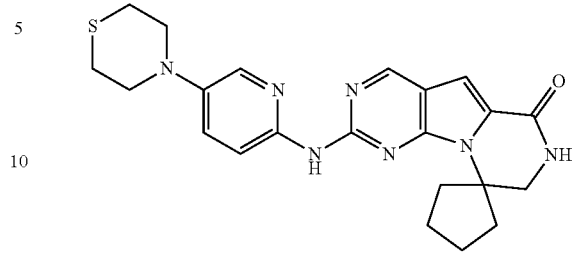

Compound 103 was synthesized using similar conditions to those described for compound 78 and was converted to an HCl salt. $^1$HNMR (600 MHz, DMSO-d$_6$) δ ppm 1.64-1.76 (m, 2H) 1.87-1.93 (m, 2H) 2.00-2.07 (m, 2H) 2.48-2.53 (m, 2H) 2.67-2.72 (m, 4H) 3.44-3.47 (m, 2H) 3.50-3.55 (m, 4H) 7.24 (s, 1H) 7.61 (d, J=9.37 Hz, 2H) 7.86 (d, J=2.63 Hz, 1H) 8.09 (d, J=12.88 Hz, 1H) 8.48 (s, 1H) 9.06 (s, 1H) 11.41 (br s., 1H). LCMS (ESI) 436 (M+H).

Example 104

Synthesis of Compound 104

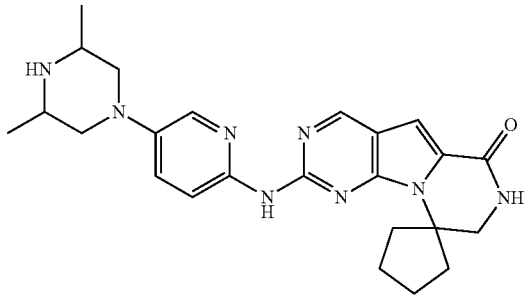 [SMILES: CC1CN(c2ccc(Nc3ncc4cc5n(c4n3)C3(CCCC3)CNC5=O)nc2)CC(C)N1]

Compound 104 was synthesized using similar conditions to those described for compound 78 and was converted to an HCl salt. $^1$HNMR (600 MHz, DMSO-d$_6$) δ ppm 1.29 (d, J=6.73 Hz, 6H) 1.66-1.79 (m, 2H) 1.84-1.95 (m, 2H) 1.98-2.09 (m, 2H) 2.46-2.55 (m, 2H) 3.29-3.39 (m, 2H) 3.58-3.70 (m, 4H) 3.77-3.86 (m, 4H) 7.24 (s, 1H) 7.66 (d, J=9.37 Hz, 1H) 7.96 (d, J=2.93 Hz, 1H) 8.08 (s, 1H) 8.48 (s, 1H) 9.06 (s, 1H) 9.28 (s, 1H) 9.67 (s, 1H) 11.36 (s, 1H). LCMS (ESI) 447 (M+H).

Example 105

Synthesis of Compound 105

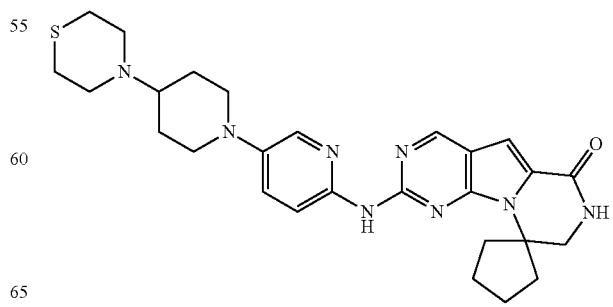

Compound 105 was synthesized using similar conditions to those described for compound 78 and was converted to an HCl salt. ¹HNMR (600 MHz, DMSO-d$_6$) δ ppm 1.73 (s, 2H) 1.76-1.85 (m, 2H) 1.85-1.94 (m, 2H) 1.98-2.07 (m, 2H) 2.19-2.26 (m, 2H) 2.48-2.52 (m, 1H) 2.70-2.81 (m, 4H) 3.13-3.20 (m, 1H) 3.30-3.48 (m, 3H) 3.58-3.71 (m, 4H) 3.78-3.84 (m, 4H) 7.24 (s, 1H) 7.62 (d, J=9.37 Hz, 2H) 7.89 (d, J=1.17 Hz, 1H) 8.09-8.18 (m, 1H) 8.48 (s, 1H) 9.06 (s, 1H) 11.46 (br s., 1H). LCMS (ESI) 519 (M+H).

Example 106

Synthesis of Compound 106

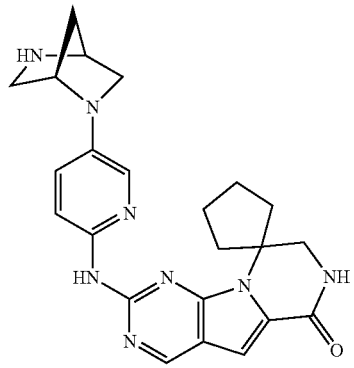 [SMILES: O=C1NCC2(CCCC2)n2c1cc1cnc(Nc3ccc(N4CC5C[C@@H]4CN5)cn3)nc12]

Compound 106 was synthesized using similar conditions to those described for compound 78 followed by the deblocking step described for compound 65 and was converted to an HCl salt. ¹HNMR (600 MHz, DMSO-d$_6$) δ ppm 1.65-1.75 (m, 2H) 1.85-1.93 (m, 2H) 1.93-1.99 (m, 1H) 2.00-2.06 (m, 2H) 2.08-2.14 (m, 1H) 2.47-2.55 (m, 2H) 3.07-3.25 (m, 2H) 3.25-3.69 (m, 5H) 4.46 (s, 1H) 4.67 (s, 1H) 7.22 (s, 1H) 7.58-7.69 (m, 2H) 8.46 (s, 1H) 9.02 (s, 1H) 9.34 (s, 1H) 9.65 (s, 1H). LCMS (ESI) 431 (M+H).

Example 107

Synthesis of Compound 107 (Also Referred to as Compound YY)

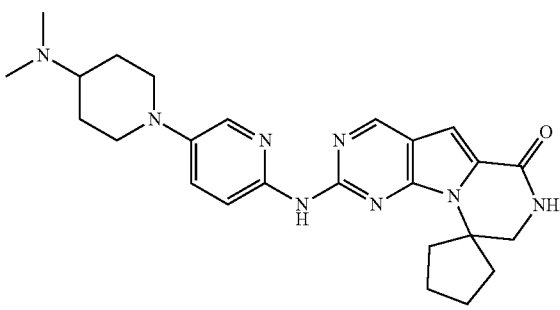 [SMILES: CN(C)C1CCN(c2ccc(Nc3ncc4cc5n(c4n3)C3(CCCC3)CNC5=O)nc2)CC1]

Compound 107 was synthesized using similar conditions to those described for compound 78 and was converted to an HCl salt. ¹HNMR (600 MHz, DMSO-d$_6$) δ ppm 1.65-1.82 (m, 3H) 1.89 (br. s., 2H) 1.98-2.08 (m, 2H) 2.13 (br. s., 2H) 2.47-2.55 (m, 2H) 2.68 (d, J=4.98 Hz, 6H) 2.71-2.80 (m, 2H) 3.29-3.71 (m, 10H) 7.16-7.26 (m, 1H) 7.67 (d, J=9.66 Hz, 2H) 7.91 (d, J=2.05 Hz, 1H) 8.14 (br. s., 1H) 8.48 (br. s., 1H) 9.05 (s, 1H) 11.14 (br. s., 1H) 11.43 (br. s., 1H). LCMS (ESI) 461 (M+H).

Example 108

Synthesis of Compound 108

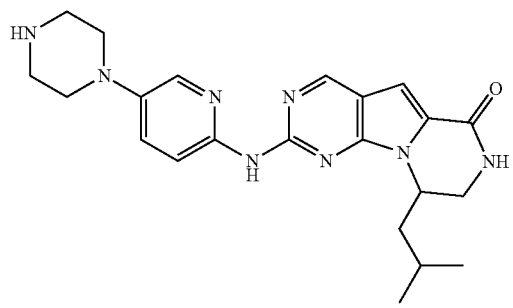

Compound 108 was synthesized in a manner similar to that described for compounds 64 and 65 and was recovered as an HCl salt. The analytical data was consistent with that described for the antipode compound 75.

Example 109

Synthesis of Compound 109

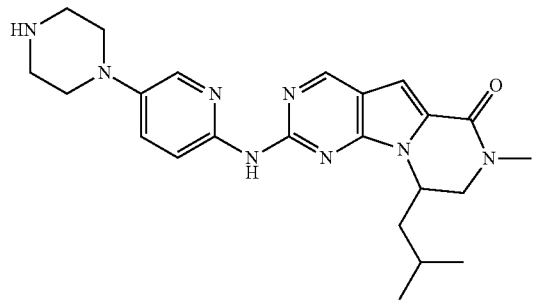

Compound 109 was synthesized in a manner similar to that described for compounds 64 and 65 and was recovered as an HCl salt. The analytical data was consistent with that described for the antipode compound 75.

Example 110

Synthesis of Compound 110

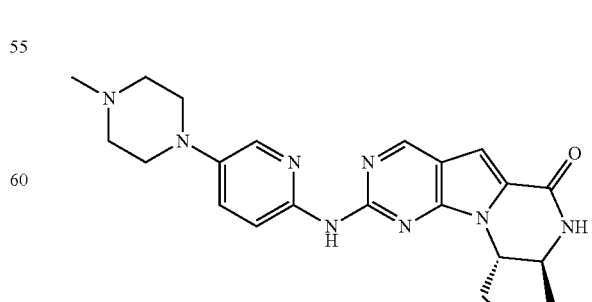

Compound 110 was synthesized in a similar manner to that described for compound 78 and then converted to its hydrochloride salt. ¹HNMR (600 MHz, DMSO-d₆) δ ppm 1.50-1.65 (m, 1H) 1.92-2.02 (m, 3H) 2.06-2.15 (m, 1H) 2.78 (d, J=3.81 Hz, 4H) 3.10-3.20 (m, 4H) 3.47-3.51 (m, 2H) 3.64-3.71 (m, 1H) 3.76-3.83 (m, 2H) 3.98-4.14 (m, 1H) 7.20 (s, 2H) 7.77 (s, 1H) 7.97 (s, 2H) 8.81 (s, 1H) 9.03 (s, 1H) 10.97 (br s., 1H). LCMS (ESI) 419 (M+H).

Example 111

Synthesis of Compound 111

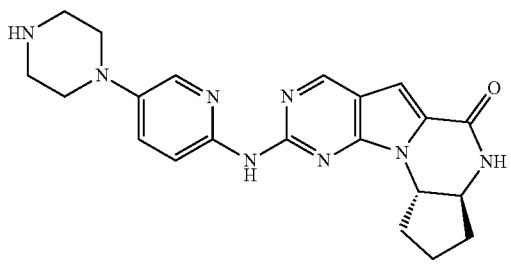 [SMILES: O=C1N[C@H]2CCC[C@@H]2n2c1cc1cnc(Nc3ccc(N4CCNCC4)cn3)nc12]

Compound 111 was synthesized in a similar manner to that described for compound 78 and then converted to its hydrochloride salt. ¹HNMR (600 MHz, DMSO-d₆) δ ppm 1.54-1.59 (m, 1H) 1.92-2.01 (m, 3H) 2.06-2.15 (m, 1H) 2.76-2.84 (m, 1H) 3.17-3.24 (m, 6H) 3.64-3.71 (m, 2H) 4.02-4.11 (m, 2H) 7.22 (s, 2H) 7.64 (s, 1H) 7.97 (s, 2H) 8.75 (s, 1H) 8.97 (s, 1H) 9.21 (s, 1H). LCMS (ESI) 405 (M+H).

Example 112

Synthesis of Compound 112

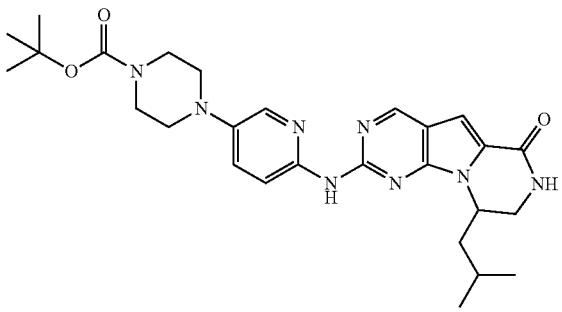 [SMILES: CC(C)CC1CNC(=O)c2cc3cnc(Nc4ccc(N5CCN(C(=O)OC(C)(C)C)CC5)cn4)nc3n21]

Compound 112 was synthesized using similar experimental conditions to that described for compound 64, Example 113

Synthesis of tert-butyl N-[2-[(5-bromo-2-chloro-pyrimidin-4-yl)amino]ethyl]carbamate, Compound 113

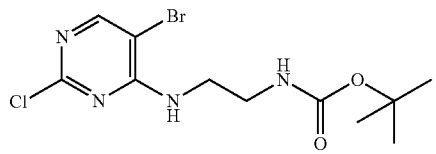 [SMILES: CC(C)(C)OC(=O)NCCNc1nc(Cl)ncc1Br]

To a solution of 5-bromo-2,4-dichloropyrimidine (12.80 g, 0.054 mole) in ethanol (250 mL) was added Hunig's base (12.0 mL) followed by the addition of a solution of N-(tert-butoxycarbonyl)-1,2-diaminoethane (10 g, 0.0624 mole) in ethanol (80 mL). The contents were stirred overnight for 20 hrs. The solvent was evaporated under vacuum. Ethyl acetate (800 mL) and water (300 mL) were added and the layers separated. The organic layer was dried with magnesium sulfate and then concentrated under vacuum. Column chromatography on silica gel using hexane/ethyl acetate (0-60%) afforded tert-butyl N-[2-[(5-bromo-2-chloro-pyrimidin-4-yl)amino]ethyl]carbamate. LCMS (ESI) 351 (M+H).

Example 114

Synthesis of tert-butyl N-[2-[[2-chloro-5-(3,3-diethoxyprop-1-ynyl)pyrimidin-4 yl]amino]ethyl]carbamate, Compound 114

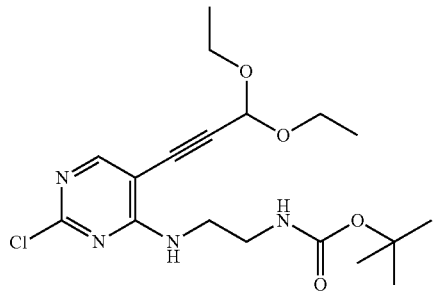 [SMILES: CCOC(C#Cc1cnc(Cl)nc1NCCNC(=O)OC(C)(C)C)OCC]

To tert-butyl N-[2-[(5-bromo-2-chloro-pyrimidin-4-yl)amino]ethyl]carbamate (5 g, 14.23 mmole) in toluene (42 mL) and triethylamine (8.33 mL) under nitrogen was added triphenyl arsine (4.39 g), 3,3-diethoxyprop-1-yne (3.24 mL) and Pddba (1.27 g). The contents were heated at 70 degrees for 24 hrs. After filtration through CELITE®, the crude reaction was columned using hexane/ethyl acetate (0-20%) to afford the desired product 3.9 g). Column chromatography of the resulting residue using hexane/ethyl acetate (0-30%) afforded tert-butyl N-[2-[[2-chloro-5-(3,3-diethoxyprop-1-ynyl)pyrimidin-4-yl]amino]ethyl]carbamate. LCMS (ESI) 399 (M+H).

Example 115

Synthesis of tert-butyl N-[2-[2-chloro-6-(diethoxymethyl)pyrrolo[2,3-d]pyrimidin-7-yl]ethyl]carbamate, Compound 115

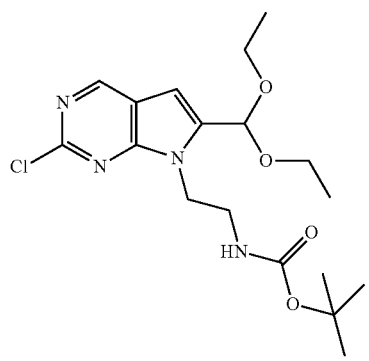 [SMILES: CCOC(OCC)c1cc2cnc(Cl)nc2n1CCNC(=O)OC(C)(C)C]

To a solution of Compound 114 (3.9 g, 0.00976 mole) in THF (60 mL) was added TBAF (68.3 mL, 7 eq). The contents were heated to 45 degrees for 2 hrs. Concentration followed by column chromatography using ethyl acetate/hexane (0-50%) afforded tert-butyl N-[2-[2-chloro-6-(diethoxymethyl)pyrrolo[2,3-d]pyrimidin-7-yl]ethyl]carbamate as a pale brown liquid (1.1 g). $^1$HNMR (d6-DMSO) δ ppm 8.88 (s, 1H), 6.95 (brs, 1H), 6.69 (s, 1H), 5.79 (s, 1H), 4.29 (m, 2H), 3.59 (m, 4H), 3.34 (m, 1H), 3.18 (m, 1H), 1.19 (m, 9H), 1.17 (m, 6H). LCMS (ESI) 399 (M+H).

Example 116

Synthesis of tert-butyl N-[2-[2-chloro-6-(diethoxymethyl)-5-iodo-pyrrolo[2,3-d]pyrimidin-7-yl]ethyl]carbamate, Compound 116

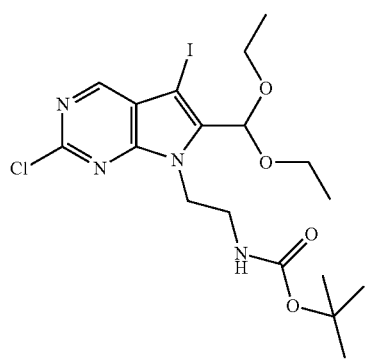 [SMILES: CCOC(OCC)c1c(I)c2cnc(Cl)nc2n1CCNC(=O)OC(C)(C)C]

To tert-butyl N-[2-[2-chloro-6-(diethoxymethyl)pyrrolo[2,3-d]pyrimidin-7-yl]ethyl]carbamate (0.1 g, 0.00025 mol) in acetonitrile (2 mL) was added 1,3-diiodo-5,5-dimethylhydantoin (95 mg, 1 eq), and solid NaHCO$_3$ (63 mg, 3 eq). The reaction was stirred at room temperature for 16 hrs. The reaction was filtered and concentrated in vacuo. The product was purified by silica gel column chromatography using hexane/ethylacetate (0-50%) to afford tert-butyl N-[2-[2-chloro-6-(diethoxymethyl)-5-iodo-pyrrolo[2,3-d]pyrimidin-7-yl]ethyl]carbamate as a pale yellow solid (0.03 g). LCMS (ESI) 525 (M+H).

Example 117

Synthesis of tert-Butyl N-[2-[2-chloro-6-(diethoxymethyl)-5-(o-tolyl)pyrrolo[2,3-d]pyrimidin-7-yl]ethyl]carbamate, Compound 117

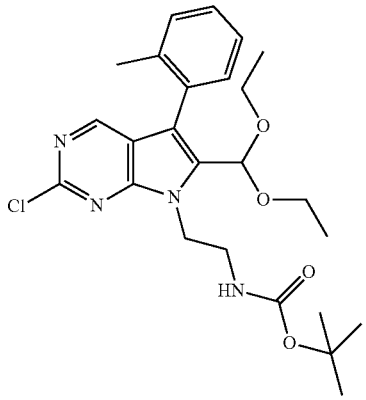 [SMILES: CCOC(OCC)c1c(-c2ccccc2C)c2cnc(Cl)nc2n1CCNC(=O)OC(C)(C)C]

To tert-butyl N-[2-[2-chloro-6-(diethoxymethyl)-5-iodo-pyrrolo[2,3-d]pyrimidin-7-yl]ethyl]carbamate (0.1 g, 0.19 mmole) in dioxane (3 mL) was added 2-methylphenylboronic acid (28 mg), tetrakis(triphenylphosphine)palladium (25 mg) and potassium phosphate (250 mg) in water (0.3 mL). The reaction was heated in a CEM Discovery microwave at 90° C. for 3 hrs. The crude reaction was loaded onto silica gel and columned using hexane/ethyl acetate (0-30%) to afford tert-butyl N-[2-[2-chloro-6-(diethoxymethyl)-5-(o-tolyl)pyrrolo[2,3-d]pyrimidin-7-yl]ethyl]carbamate (0.06 g). LCMS (ESI) 489 (M+H).

Example 118

Synthesis of 7-[2-(tert-butoxycarbonylamino)ethyl]-2-chloro-5-(o-tolyl)pyrrolo[2,3-d]pyrimidine-6-carboxylic Acid, Compound 118

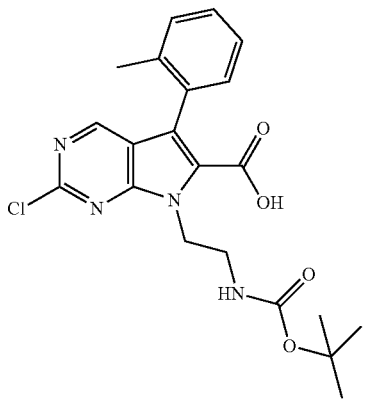 [SMILES: Cc1ccccc1-c1c(C(=O)O)n(CCNC(=O)OC(C)(C)C)c2nc(Cl)ncc12]

To tert-butyl N-[2-[2-chloro-6-(diethoxymethyl)-5-(o-tolyl)pyrrolo[2,3-d]pyrimidin-7-yl]ethyl]carbamate (0.85 g, 1.74 mmole) in AcOH (10 mL) was added water (1.5 mL). The reaction was stirred at room temperature for 16 hrs. The crude reaction was then concentrated under vacuum. After the addition of ethyl acetate (50 mL), the organic layer was washed with satd. NaHCO₃. The organic layer was dried with magnesium sulfate and then concentrated under vacuum to afford the crude intermediate, tert-butyl N-[2-[2-chloro-6-formyl-5-(o-tolyl)pyrrolo[2,3-d]pyrimidin-7-yl]ethyl]carbamate. To this crude intermediate in DMF (5 mL) was added oxone (1.3 g). After stirring for 2.5 hrs, water (20 mL) and ethyl acetate (100 mL) were added. The organic layer was separated, dried and then concentrated under vacuum to afford the crude product which was columned over silica gel using hexane/ethyl acetate (0-50%) to afford 7-[2-(tert-butoxycarbonylamino)ethyl]-2-chloro-5-(o-tolyl)pyrrolo[2,3-d]pyrimidine-6-carboxylic acid (0.112 g). LCMS (ESI) 431 (M+H).

Example 119

Synthesis of Compound 119

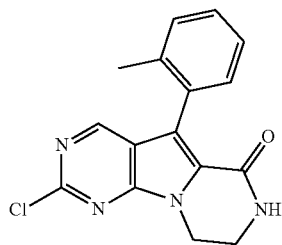 [SMILES: Cc1ccccc1-c1c2n(c3nc(Cl)ncc13)CCNC2=O]

To 7-[2-(tert-butoxycarbonylamino)ethyl]-2-chloro-5-(o-tolyl)pyrrolo[2,3-d]pyrimidine-6-carboxylic acid (0.1 g, 0.261 mmol) in DCM (4.1 mL) was added DMAP (20 mg) followed by the addition of N,N'-diisopropylcarbodiimide (0.081 mL, 2 eq). After stirring for 3 hrs, TFA (0.723 mL) was added. Stirring was then continued for another 30 minutes. The reaction mixture was neutralized with satd. NaHCO₃. DCM (20 mL) was then added and the organic layer separated, dried with magnesium sulfate and then concentrated under vacuum to afford the crude product which was columned using hexane/ethylacetate (0-100%) to afford chloro tricyclic amide Compound 119 (0.65 g). LCMS (ESI) 313 (M+H).

Example 120

Synthesis of Compound 120

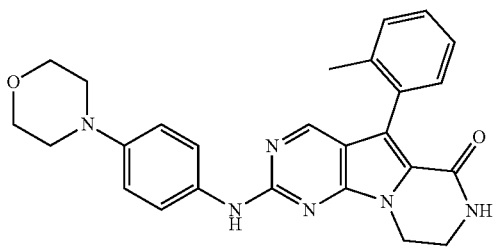 [SMILES: Cc1ccccc1-c1c2n(c3nc(Nc4ccc(N5CCOCC5)cc4)ncc13)CCNC2=O]

To the chloro tricyclic amide (0.040 g, 0.128 mmole) (Compound 119) in dioxane (2.5 mL) under nitrogen was added Pd₂(dba)₃ (12 mg), sodium tert-butoxide (16 mg), BINAP (16 mg) and 4-morpholinoaniline (22.7 mg, 1 eq). The reaction mixture was heated at 90° C. in a CEM Discovery microwave for 3.0 hrs. The crude reaction was loaded onto a silica gel column and the contents eluted with DCM/MeOH (0-6%) to afford the product (10 mg). LCMS (ESI) 455 (M+H). ¹HNMR (600 MHz, DMSO-d₆) δ ppm 2.14 (s, 3H) 3.23-3.50 (m, 2H) 3.57-3.73 (m, 2H) 3.81-3.92 (m, 8H), 7.11-7.31 (m, 4H) 7.31-7.48 (m, 1H) 7.58-7.73 (m, 1H) 7.77-7.95 (m, 2H) 8.05-8.21 (m, 1H) 8.44 (s, 1H) 9.85-10.01 (m, 1H).

Example 121

Synthesis of Compound 121

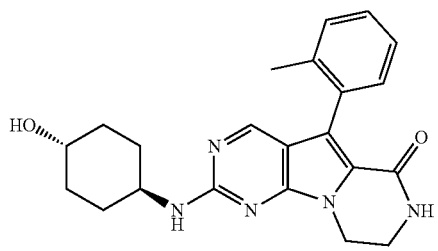 [SMILES: Cc1ccccc1-c1c2n(c3nc(N[C@H]4CC[C@H](O)CC4)ncc13)CCNC2=O]

To the chloro tricyclic amide (0.024 g) (Compound 119) in N-methyl-2-pyrrolidone (NMP) (1.5 mL) was added trans-4-aminocyclohexanol (0.0768 mmol, 26.54 mg, 3 eq) and Hunig's base (0.4 mL). The reaction was heated in a CEM Discovery microwave vessel at 150° C. for 1.2 hrs. The crude reaction was loaded onto a silica gel column and the contents eluted with DCM/MeOH (0-10%) to afford the product (21 mg). LCMS (ESI) 392 (M+H). ¹HNMR (600 MHz, DMSO-d₆) δ ppm 1.23 (d, J=8.78 Hz, 4H) 1.84 (br. s., 4H) 2.11 (s, 3H) 3.34-3.43 (m, 1H) 3.55 (br. s., 2H) 3.72 (br. s., 1H) 4.13 (br. s., 2H) 4.50 (br. s., 1H) 7.03 (br. s., 1H) 7.12-7.28 (m, 4H) 7.96 (br. s., 1H) 8.18 (br. s., 1H).

Example 122

Synthesis of 7-[2-(tert-butoxycarbonylamino)ethyl]-2-chloro-pyrrolo[2,3-d]pyrimidine-6-carboxylic Acid, Compound 122

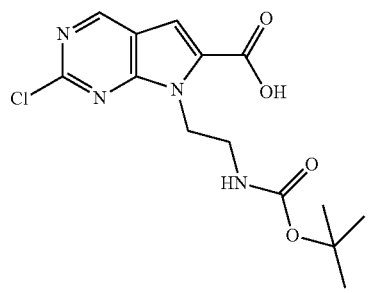 [SMILES: CC(C)(C)OC(=O)NCCn1c(C(=O)O)cc2cnc(Cl)nc21]

7-[2-(tert-butoxycarbonylamino)ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 341 (M+H).

Example 123

Synthesis of Compound 123

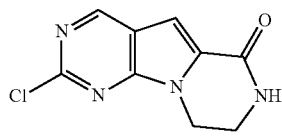 [SMILES: O=C1NCCn2c1cc1cnc(Cl)nc12]

Chloro tricyclic amide, Compound 123, was synthesized using a similar experimental procedure as that described for the synthesis of chloro tricyclic amide (Compound 119). LCMS (ESI) 223 (M+H).

Example 124

Synthesis of Compound 124

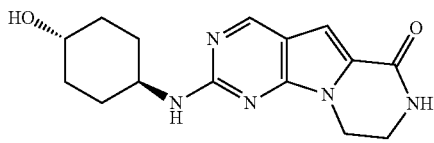 [SMILES: O=C1NCCn2c1cc1cnc(N[C@H]3CC[C@H](O)CC3)nc12]

To the chloro tricyclic amide, Compound 123 (0.035 g, 0.00157 mole) in NMP (1.5 mL) was added Hunig's base (0.3 mL) followed by the addition of the trans-4-aminocyclohexanol (54.2 mg). The reaction mixture was heated at 150° C. for 1.5 hrs. The crude reaction was loaded onto a silica gel column and the column was eluted with DCM/MeOH (0-10%) to afford the product (5 mg). LCMS (ESI) 302 (M+H).

Example 125

Synthesis of tert-butyl N-[2-[(5-bromo-2-chloro-pyrimidin-4-yl)amino]-2-methyl-propyl]carbamate, Compound 125

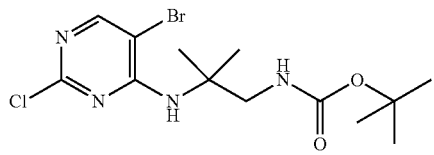 [SMILES: CC(C)(CNC(=O)OC(C)(C)C)Nc1nc(Cl)ncc1Br]

tert-butyl N-[2-[(5-bromo-2-chloro-pyrimidin-4-yl) amino]-2-methyl-propyl]carbamate was synthesized by treating 5-bromo-2,4-dichloropyrimidine with tert-butyl N-(2-amino-2-methyl-propyl)carbamate using similar experimental conditions as described for the synthesis of tert-butyl N-[2-[(5-bromo-2-chloro-pyrimidin-4-yl)amino] ethyl]carbamate. LCMS (ESI) (M+H) 379.

Example 126

Synthesis of tert-butyl N-[2-[[2-chloro-5-(3,3-diethoxyprop-1-ynyl)pyrimidin-4-yl]amino]-2-methyl-propyl]carbamate, Compound 126

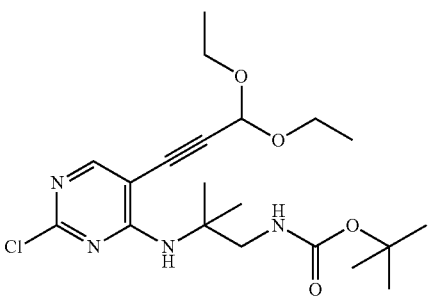 [SMILES: CCOC(C#Cc1cnc(Cl)nc1NC(C)(C)CNC(=O)OC(C)(C)C)OCC]

tert-butyl N-[2-[[2-chloro-5-(3,3-diethoxyprop-1-ynyl) pyrimidin-4-yl]amino]-2-methyl-propyl]carbamate was synthesized by treating tert-butyl N-[2-[(5-bromo-2-chloro-pyrimidin-4-yl)amino]-2-methyl-propyl]carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate LCMS (ESI) (M+H) 427.

Example 127

Synthesis of tert-butyl N-[2-[2-chloro-6-(diethoxymethyl)pyrrolo[2,3-d]pyrimidin-7-yl]-2-methyl-propyl]carbamate, Compound 127

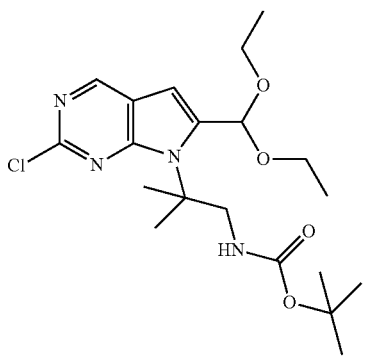 [SMILES: CCOC(OCC)c1cc2cnc(Cl)nc2n1C(C)(C)CNC(=O)OC(C)(C)C]

tert-butyl N-[2-[2-chloro-6-(diethoxymethyl)pyrrolo[2,3-d]pyrimidin-7-yl]-2-methyl-propyl]carbamate was synthesized by treating tert-butyl N-[2-[[2-chloro-5-(3,3-diethoxy-prop-1-ynyl)pyrimidin-4-yl]amino]-2-methyl-propyl] carbamate with TBAF using similar experimental conditions as described for the synthesis tert-butyl N-[2-[2-chloro-6-(diethoxymethyl)pyrrolo[2,3-d]pyrimidin-7-yl]ethyl]carbamate. LCMS (ESI) (M+H) 427.

Example 128

Synthesis of 7-[2-(tert-butoxycarbonylamino)-1,1-dimethyl-ethyl]-2-chloro-pyrrolo[2,3-d]pyrimidine-6-carboxylic Acid, Compound 128

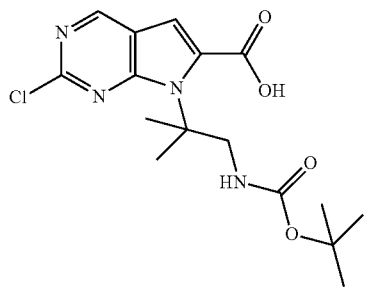 [SMILES: CC(C)(C)OC(=O)NCC(C)(C)n1c(C(=O)O)cc2cnc(Cl)nc21]

7-[2-(tert-butoxycarbonylamino)-1,1-dimethyl-ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 369 (M+H).

Example 129

Synthesis of Compound 129

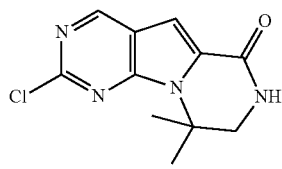 [SMILES: CC1(C)CNC(=O)c2cc3cnc(Cl)nc3n21]

Chloro tricyclic amide, Compound 129, was synthesized using a similar procedure as that described for the synthesis of chloro tricyclic amide, Compound 119. LCMS (ESI) 251 (M+H).

Example 130

Synthesis of Compound 130

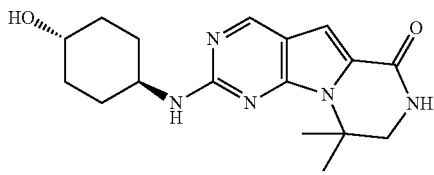 [SMILES: CC1(C)CNC(=O)c2cc3cnc(N[C@H]4CC[C@H](O)CC4)nc3n21]

Compound 130 was synthesized by treating chlorotricyclic amine Compound 129 with trans-4-aminocyclohexanol using similar experimental conditions as for compound 124. LCMS (ESI) 330 (M+H). $^1$HNMR (600 MHz, DMSO-$d_6$) δ ppm 1.07-1.34 (m, 4H) 1.47-2.05 (m, 10H) 3.09 (m, 1H) 3.51 (d, J=2.91 Hz, 2H) 3.57 (m, 1H) 4.50 (br. s., 1H) 6.89 (s, 1H) 6.94-7.05 (m, 1H) 8.04 (br. s., 1H) 8.60 (s, 1H) 9.00 (br. s., 1H).

Example 131

Synthesis of benzyl N-[1-[[(5-bromo-2-chloro-pyrimidin-4-yl)amino]methyl]propyl]carbamate, Compound 131

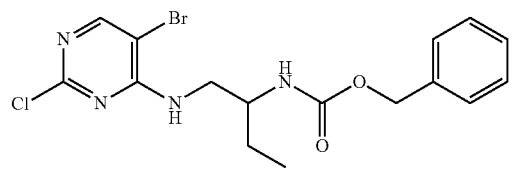 [SMILES: CCC(CNc1nc(Cl)ncc1Br)NC(=O)OCc1ccccc1]

Benzyl N-[1-[[(5-bromo-2-chloro-pyrimidin-4-yl)amino]methyl]propyl]carbamate was synthesized by treating 5-bromo-2,4-dichloropyrimidine with benzyl N-[1-(aminomethyl)propyl]carbamate using similar experimental conditions as described for the synthesis of tert-butyl N-[2-[(5-bromo-2-chloro-pyrimidin-4-yl)amino]ethyl]carbamate. LCMS (ESI) (M+H) 413.

Example 132

Synthesis of benzyl N-[1-[[[2-chloro-5-(3,3-diethoxyprop-1-ynyl)pyrimidin-4-yl]amino]methyl]propyl]carbamate, Compound 132

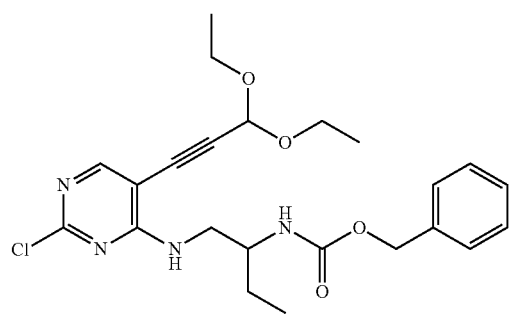 [SMILES: CCOC(C#Cc1cnc(Cl)nc1NCC(CC)NC(=O)OCc1ccccc1)OCC]

Benzyl N-[1-[[[2-chloro-5-(3,3-diethoxyprop-1-ynyl)pyrimidin-4-yl]amino]methyl]propyl]carbamate was prepared by treating benzyl N-[1-[[(5-bromo-2-chloro-pyrimidin-4-yl)amino]methyl]propyl]-carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4-yl]amino]ethyl]carbamate LCMS (ESI) (M+H) 461.

Example 133

Synthesis of benzyl N-[1-[[2-chloro-6-(diethoxymethyl)pyrrolo[2,3-d]pyrimidin-7-yl]methyl]propyl] carbamate, Compound 133

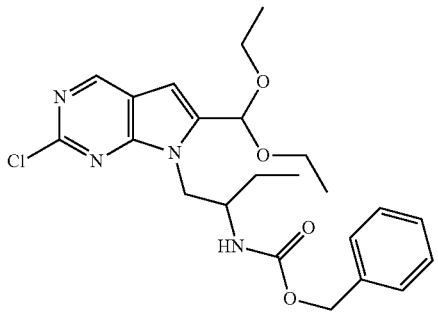 [SMILES: CCOC(OCC)c1cc2cnc(Cl)nc2n1CC(CC)NC(=O)OCc1ccccc1]

Benzyl N-[1-[[2-chloro-6-(diethoxymethyl)pyrrolo[2,3-d]pyrimidin-7-yl]methyl]propyl]carbamate was synthesized by treating benzyl N-[1-[[[2-chloro-5-(3,3-diethoxyprop-1-ynyl)pyrimidin-4-yl]amino]methyl]propyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) (M+H) 461.

Example 134

Synthesis of 7-[2-(benzyloxycarbonylamino)butyl]-2-chloro-pyrrolo[2,3-d]pyrimidine-6-carboxylic Acid, Compound 134

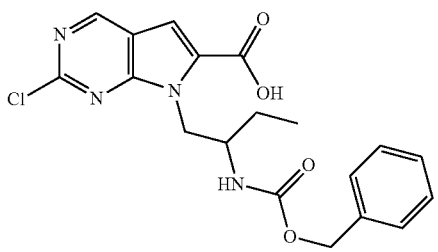 [SMILES: CCC(Cn1c(C(=O)O)cc2cnc(Cl)nc21)NC(=O)OCc1ccccc1]

7-[2-(benzyloxycarbonylamino)butyl]-2-chloro-pyrrolo [2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 403 (M+H).

Example 135

Synthesis of Compound 135

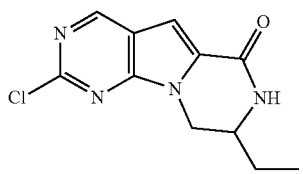 [SMILES: CCC1Cn2c(cc3cnc(Cl)nc32)C(=O)N1]

To a solution of 7-[2-(benzyloxycarbonylamino)butyl]-2-chloro-pyrrolo[2,3-d]pyrimidine-6-carboxylic acid in dichloromethane was added HBr, the reaction was stirred at 45 degrees for 3 hrs. After concentration, 2N NaOH was added to basify (pH=8.0) the reaction followed by the addition of THF (20 mL). Boc$_2$O was then added (1.2 eq) and the reaction was stirred for 16 hrs. To the crude reaction mixture was then added ethyl acetate (100 mL) and water (50 mL) and the organic phase was separated, dried (magnesium sulfate) and then concentrated under vacuum. To the crude product was added dichloromethane (30 mL) followed by DIC and DMAP. After stirring for 2 hrs, TFA was added and the contents stirred for an hour. The solvents were evaporated under vacuum and the residue basified with satd. NaHCO$_3$. Ethyl acetate was then added and the organic layer separated, dried (magnesium sulfate) and then concentrated under vacuum. Column chromatography with hexane/ethyl acetate (0-100%) afforded the desired chlorotricyclic core, Compound 135. LCMS (ESI) 251 (M+H).

Example 136

Synthesis of Compound 136

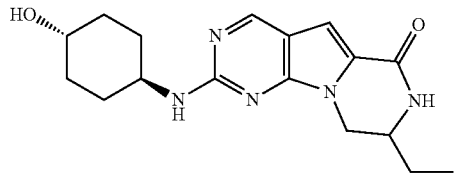 [SMILES: CCC1Cn2c(cc3cnc(N[C@H]4CC[C@H](O)CC4)nc32)C(=O)N1]

Compound 136 was synthesized by treating chlorotricyclic amine, Compound 135, with trans-4-aminocyclohexanol using similar experimental conditions as for compound 124. LCMS (ESI) 330 (M+H). $^1$HNMR (600 MHz, DMSO-d$_6$) δ ppm 0.80-0.95 (m, 3H) 1.35-1.92 (m, 10H) 3.66 (br. m., 3H) 4.17 (br. s., 2H) 4.47 (br. s., 1H) 6.85 (s, 1H) 6.96 (br. s., 1H) 8.15 (br. s., 1H) 8.62 (br. s., 1H).

Example 137

Synthesis of tert-butyl N-[1-[[(5-bromo-2-chloro-pyrimidin-4-yl)amino]methyl]cyclopentyl]carbamate, Compound 137

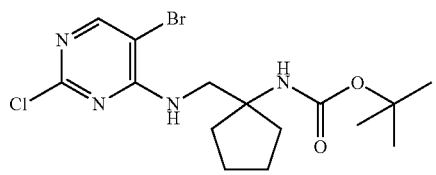 [SMILES: CC(C)(C)OC(=O)NC1(CNc2nc(Cl)ncc2Br)CCCC1]

tert-butyl N-[1-[[(5-bromo-2-chloro-pyrimidin-4-yl)amino]methyl]cyclopentyl]carbamate was synthesized by treating 5-bromo-2,4-dichloropyrimidine with tert-butyl N-[1-(aminomethyl)cyclopentyl]carbamate using similar experimental conditions as described for the synthesis of tert-butyl N-[2-[(5-bromo-2-chloro-pyrimidin-4-yl)amino] ethyl]carbamate. LCMS (ESI) 405 (M+H).

Example 138

Synthesis of tert-butyl N-[1-[[[2-chloro-5-(3,3-diethoxyprop-1-ynyl)pyrimidin-4-yl]amino]methyl]cyclopentyl]carbamate, Compound 138

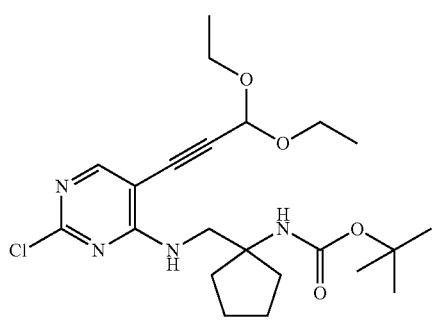 [SMILES: CCOC(C#Cc1cnc(Cl)nc1NCC1(NC(=O)OC(C)(C)C)CCCC1)OCC]

tert-butyl N-[1-[[[2-chloro-5-(3,3-diethoxyprop-1-ynyl)pyrimidin-4-yl]amino]methyl]cyclopentyl]carbamate was synthesized by treating tert-butyl N-[1-[[(5-bromo-2-chloro-pyrimidin-4-yl)amino]methyl]cyclopentyl]carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate LCMS (ESI) 453 (M+H).

Example 139

Synthesis of tert-butyl N-[1-[[2-chloro-6-(diethoxymethyl)pyrrolo[2,3-d]pyrimidin-7-yl]methyl]cyclopentyl]carbamate, Compound 139

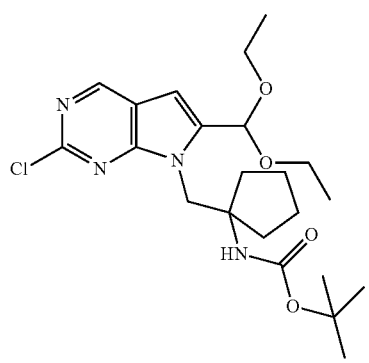 [SMILES: CCOC(OCC)c1cc2cnc(Cl)nc2n1CC1(NC(=O)OC(C)(C)C)CCCC1]

tert-butyl N-[1-[[2-chloro-6-(diethoxymethyl)pyrrolo[2,3-d]pyrimidin-7-yl]methyl]cyclopentyl]carbamate was synthesized by treating tert-butyl N-[2-[[2-chloro-5-(3,3-diethoxyprop-1-ynyl)pyrimidin-4-yl]amino]-2-methyl-propyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) 453 (M+H).

Example 140

Synthesis of 7-[[1-(tert-butoxycarbonylamino)cyclopentyl]methyl]-2-chloro-pyrrolo[2,3-d]pyrimidine-6-carboxylic Acid, Compound 140

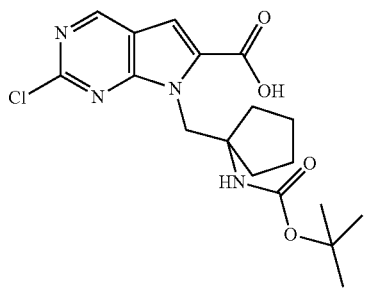 [SMILES: CC(C)(C)OC(=O)NC1(Cn2c(C(=O)O)cc3cnc(Cl)nc32)CCCC1]

7-[[1-(tert-butoxycarbonylamino)cyclopentyl]methyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 395 (M+H).

Example 141

Synthesis of Compound 141

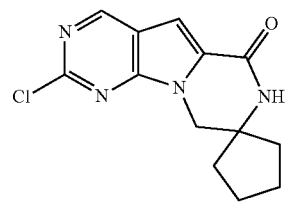 [SMILES: O=C1NC2(CCCC2)Cn2c1cc1cnc(Cl)nc12]

Chlorotricyclic core Compound 141 was synthesized using a similar experimental procedure as that described for the synthesis of chloro tricyclic amide Compound 119. LCMS (ESI) 277 (M+H).

Example 142

Synthesis of Compound 142

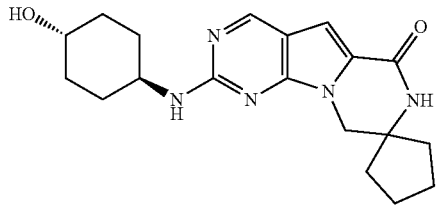 [SMILES: O=C1NC2(CCCC2)Cn2c1cc1cnc(N[C@H]3CC[C@H](O)CC3)nc12]

Compound 142 was synthesized by treating chlorotricyclic amine, Compound 141, with trans-4-aminocyclohexanol using similar experimental conditions as for Compound 124. LCMS (ESI) 356 (M+H). $^1$HNMR (600 MHz, DMSO-$d_6$) δ ppm 1.08-1.32 (m, 8H) 1.60-2.09 (m, 8H) 3.03-3.17

(m, 1H) 3.35 (s, 2H) 3.54-3.62 (m, 1H) 4.51 (d, J=4.39 Hz, 1H) 6.88 (s, 1H) 6.96 (br. s., 1H) 8.07 (br. s., 1H) 8.58 (s, 1H).

Example 143

Synthesis of tert-butyl N-[[1-[(5-bromo-2-chloro-pyrimidin-4-yl)amino]cyclopentyl]methyl]carbamate, Compound 143

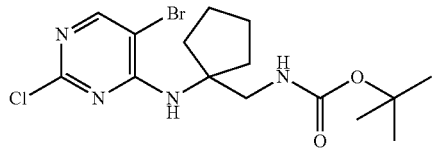 [SMILES: CC(C)(C)OC(=O)NCC1(Nc2nc(Cl)ncc2Br)CCCC1]

tert-butyl N-[[1-[(5-bromo-2-chloro-pyrimidin-4-yl)amino]cyclopentyl]methyl]carbamate was synthesized by treating 5-bromo-2,4-dichloropyrimidine with tert-butyl N-[(1-aminocyclopentyl)methyl]carbamate using similar experimental conditions as described for the synthesis of tert-butyl N-[2-[(5-bromo-2-chloro-pyrimidin-4-yl)amino]ethyl]carbamate. LCMS (ESI) 405 (M+H).

Example 144

Synthesis of tert-butyl N-[2-[[2-chloro-5-(3,3-diethoxyprop-1-ynyl)pyrimidin-4-yl]amino]-2-methyl-propyl]carbamate, Compound 144

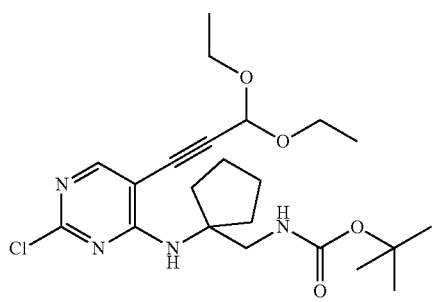 [SMILES: CCOC(C#Cc1cnc(Cl)nc1NC1(CNC(=O)OC(C)(C)C)CCCC1)OCC]

tert-butyl N-[[1-[[2-chloro-5-(3,3-diethoxyprop-1-ynyl)pyrimidin-4-yl]amino]cyclopentyl]methyl]carbamate was synthesized by treating tert-butyl N-[2-[(5-bromo-2-chloro-pyrimidin-4-yl)amino]-2-methyl-propyl]carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate. LCMS (ESI) 453 (M+H).

Example 145

Synthesis of tert-butyl N-[[1-[2-chloro-6-(diethoxymethyl)pyrrolo[2,3-d]pyrimidin-7-yl]cyclopentyl]methyl]carbamate, Compound 145

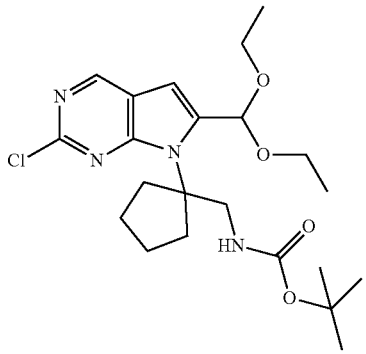 [SMILES: CCOC(OCC)c1cc2cnc(Cl)nc2n1C1(CNC(=O)OC(C)(C)C)CCCC1]

tert-Butyl N-[[1-[2-chloro-6-(diethoxymethyl)pyrrolo[2,3-d]pyrimidin-7-yl]cyclopentyl]methyl]carbamate was synthesized by treating tert-butyl N-[2-[[2-chloro-5-(3,3-diethoxyprop-1-ynyl)pyrimidin-4-yl]amino]-2-methyl-propyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) 4534 (M+H).

Example 146

Synthesis of 7-[2-(tert-butoxycarbonylamino)-1,1-dimethyl-ethyl]-2-chloro-pyrrolo[2,3-d]pyrimidine-6carboxylic Acid, Compound 146

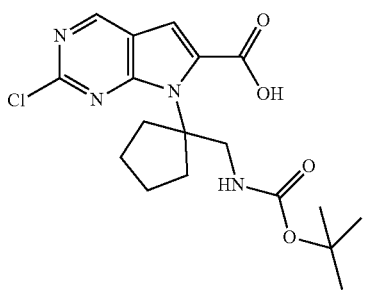 [SMILES: CC(C)(C)OC(=O)NCC1(n2c(C(=O)O)cc3cnc(Cl)nc32)CCCC1]

7-[2-(tert-Butoxycarbonylamino)-1,1-dimethyl-ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 395 (M+H).

Example 147

Synthesis of Compound 147

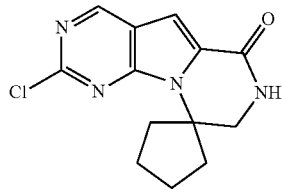 [SMILES: O=C1NCC2(CCCC2)n2c1cc1cnc(Cl)nc12]

Chloro tricyclic amide, Compound 147 was synthesized using a similar experimental procedure as that described for the chloro tricyclic amide, Compound 119. LCMS (ESI) 277 (M+H).

Example 148

Synthesis of Compound 148

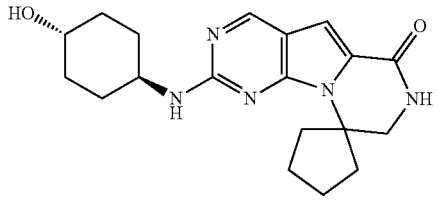 [SMILES: O=C1NCC2(CCCC2)n2c1cc1cnc(N[C@H]3CC[C@H](O)CC3)nc12]

Compound 148 was synthesized by treating chlorotricyclic amine, Compound 147, with trans-4-aminocyclohexanol using similar experimental conditions as for Compound 124. LCMS (ESI) 356 (M+H). $^1$HNMR (600 MHz, DMSO-$d_6$) δ ppm 1.06-1.35 (m, 8H) 1.45-1.95 (m, 8H) 3.10 (m, 1H) 3.58 (br. s., 2H) 3.95 (br. s., 1H) 4.49 (br. s., 1H) 6.84 (s, 1H) 6.85-6.93 (m, 1H) 8.29 (s, 1H) 8.61 (br. s., 1H).

Example 149

Synthesis of Compound 149

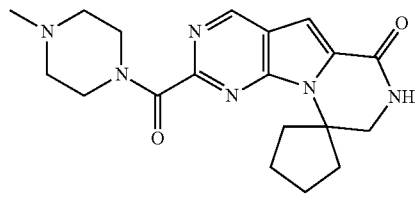 [SMILES: CN1CCN(C(=O)c2ncc3cc4n(c3n2)C2(CCCC2)CNC4=O)CC1]

Step 1: Compound 59 is Boc protected according to the method of A. Sarkar et al. (JOC, 2011, 76, 7132-7140).
Step 2: Boc-protected Compound 59 is treated with 5 mol % NiCl$_2$(Ph$_3$)$_2$, 0.1 eq triphenylphosphine, 3 eq Mn, 0.1 eq tetraethylammonium iodide, in DMI under CO2 (1 atm) at 25° C. for 20 hours to convert the aryl halide derivative into the carboxylic acid.
Step 3: The carboxylic acid from Step 2 is converted to the corresponding acid chloride using standard conditions.
Step 4: The acid chloride from Step 3 is reacted with N-methyl piperazine to generate the corresponding amide.
Step 5: The amide from Step 4 is deprotected using trifluoroacetic acid in methylene chloride to generate the target compound. Compound 149 is purified by silica gel column chromatography eluting with a dichloromethane -methanol gradient to provide Compound 149.

Each of Compounds 119 through 149 and corresponding compounds with various $R^8$, $R^1$ and Z definitions may be reacted with sodium hydride and an alkyl halide or other halide to insert the desired R substitution prior to reaction with an amine, such as described above for the synthesis of Compound 120, to produce the desired product of Formulae I, II, III, IV, or V.

Example 150

CDK4/6 Inhibition In Vitro Assay

Selected compounds disclosed herein were tested in CDK4/cyclinD1, CDK6/CycD3 CDK2/CycA and CDK2/cyclinE kinase assays by Nanosyn (Santa Clara, Calif.) to determine their inhibitory effect on these CDKs. The assays were performed using microfluidic kinase detection technology (Caliper Assay Platform). The compounds were tested in 12-point dose-response format in singlicate at Km for ATP. Phosphoacceptor substrate peptide concentration used was 1 µM for all assays and Staurosporine was used as the reference compound for all assays. Specifics of each assay are as described below:

CDK2/CyclinA: Enzyme concentration: 0.2 nM; ATP concentration: 50 µM; Incubation time: 3 hr.
CDK2/CyclinE: Enzyme concentration: 0.28 nM; ATP concentration: 100 µM; Incubation time: 1 hr.
CDK4/CyclinD1: Enzyme concentration: 1 nM; ATP concentration: 200 µM; Incubation time: 10 hr.
CDK6/CyclinD3: Enzyme concentration: 1 nM; ATP concentration: 300 µM; Incubation time: 3 hr.

The inhibitory IC$_{50}$ values for the compounds in Table 1 for CDK4/CycD1, CDK2/CycE, CDK2/CycA, as well as fold selectivity are presented in Table 2.

TABLE 2

Selective Inhibition of CDK4

| Structure | CDK4/CycD1 IC$_{50}$ [nM] | CDK2/CycE IC$_{50}$ [nM] | Fold Selectivity (CDK2/CycE/CDK4) | CDK2/CycA IC$_{50}$ [nM] | Fold Selectivity (CDK2/CycA/CDK4) |
|---|---|---|---|---|---|
| A | 4.2 | 6350 | 1516 | 3160 | 754 |
| B | 0.4 | 3040 | 6862 | 1890 | 4266 |
| C | 1.4 | 1920 | 1333 | 616 | 428 |
| D | 0.9 | 3480 | 3779 | 1500 | 1629 |
| E | 1 | 695 | 688 | 204 | 202 |
| F | 1.5 | 628 | 419 | 190 | 127 |
| G | 1.5 | 2580 | 1767 | 646 | 442 |
| H | 1.5 | 1520 | 1013 | 377 | 251 |
| I | 2 | 2120 | 1065 | 1130 | 568 |
| J | 0.7 | 5110 | 7707 | 4340 | 6546 |
| K | 1 | 1070 | 1019 | 738 | 703 |
| L | 5.7 | 4530 | 789 | 1490 | 260 |
| M | 2.3 | 2280 | 1004 | 1410 | 621 |
| N | 1 | 1500 | 1500 | ND | ND |
| O | 2.5 | 41410 | 1636 | 3150 | 1245 |
| P | 3.3 | 3560 | 1085 | 1010 | 308 |
| Q | 0.6 | 1080 | 1722 | 3030 | 4833 |
| R | 0.5 | 1920 | 3918 | 1360 | 2776 |
| S | 1.7 | 1250 | 718 | 342 | 197 |
| T | 0.8 | 1660 | 2022 | 1670 | 2034 |

TABLE 2-continued

Selective Inhibition of CDK4

| Structure | CDK4/CycD1 IC$_{50}$ [nM] | CDK2/CycE IC$_{50}$ [nM] | Fold Selectivity (CDK2/CycE/CDK4) | CDK2/CycA IC$_{50}$ [nM] | Fold Selectivity (CDK2/CycA/CDK4) |
|---|---|---|---|---|---|
| U | 0.7 | 1460 | 2229 | 857 | 1308 |
| V | 2.9 | 3500 | 1224 | 2130 | 745 |
| W | 2.7 | 3970 | 1481 | 539 | 201 |
| X | 0.9 | 11600 | 12975 | 1840 | 2058 |
| Y | 2.5 | 124 | 50 | 61 | 25 |
| Z | 3.2 | 3710 | 1174 | 647 | 205 |
| AA | 0.5 | 6100 | 13319 | 4630 | 10109 |
| BB | 0.8 | 1680 | 2017 | 502 | 603 |
| CC | 1.6 | 1250 | 791 | 755 | 478 |
| DD | 1.9 | 9620 | 5200 | 8360 | 4519 |
| EE | 3.8 | 1660 | 432 | 1110 | 289 |
| FF | 1.2 | 4620 | 3949 | 1400 | 1197 |
| GG | 1 | 3580 | 3377 | 1510 | 1425 |
| HH | 1.7 | 1280 | 766 | 265 | 159 |
| II | 2 | 367 | 184 | 239 | 120 |
| JJ | 1.4 | 288 | 204 | ND | ND |
| KK | 2.3 | 1760 | 762 | 915 | 396 |
| LL | 2 | 202 | 103 | 108 | 55 |
| MM | 1.8 | 3390 | 1863 | 597 | 328 |
| NN | 3.7 | 4700 | 1274 | 1560 | 423 |
| OO | 9 | 3980 | 442 | 570 | 63 |
| PP | 3.1 | 3600 | 1146 | 3090 | 984 |
| QQ | 4.1 | 3060 | 746 | 2570 | 627 |
| RR | 1.2 | 1580 | 1374 | 693 | 603 |
| SS | 0.8 | 1460 | 1865 | 1390 | 1775 |
| TT | 0.8 | 1260 | 1550 | 596 | 733 |
| UU | 7.3 | 3960 | 542 | ND | ND |
| VV | 3.3 | 2630 | 809 | 789 | 243 |
| WW | 0.7 | 1350 | 204 | ND | ND |
| XX | 1.3 | 7300 | 5615 | 6290 | 4838 |
| YY | 4.6 | 6900 | 1490 | ND | ND |
| ZZ | 10.5 | 9960 | 949 | ND | ND |
| AAA | 2.3 | 6010 | 2591 | 2130 | 918 |
| BBB | 2.8 | 187 | 68 | 85 | 31 |
| CCC | 2 | 2170 | 1074 | 457 | 226 |
| DDD | 9.5 | 9350 | 986 | ND | ND |
| EEE | 2.3 | 2950 | 1266 | 943 | 405 |
| FFF | 4.7 | 4540 | 966 | 1370 | 291 |
| GGG | 13.7 | 7610 | 555 | ND | ND |
| HHH | 6.8 | 2840 | 419 | ND | ND |
| III | 6 | 3770 | 626 | ND | ND |
| JJJ | 3.2 | 5200 | 1620 | 2830 | 882 |
| KKK | 1.3 | 291 | 231 | 87.3 | 69 |
| LLL | 3.2 | 1620 | 509 | 4530 | 1425 |
| MMM | 3.2 | 1890 | 600 | 990 | 314 |
| NNN | 1.4 | 2930 | 2154 | 1010 | 743 |
| OOO | 2.4 | 393 | 164 | 203 | 85 |
| PPP | 0.8 | 16500 | 21263 | 2640 | 3402 |
| QQQ | 10.5 | 11100 | 1057 | ND | ND |
| RRR | 2.6 | 4500 | 1758 | ND | ND |
| SSS | 2 | 2280 | 1112 | 1880 | 917 |
| TTT | 3.4 | 3030 | 899 | ND | ND |
| UUU | 18 | 16460 | 914 | ND | ND |
| VVV | 7.4 | 4380 | 589 | ND | ND |
| WWW | 18.5 | 2500 | 135 | ND | ND |
| XXX | 11.4 | 6620 | 581 | ND | ND |

To further characterize its kinase activity, Compound T was screened against 456 (395 non-mutant) kinases using DiscoveRx's KINOMEscan™ profiling service. The compound was screened using a single concentration of 1000 nM (>1000 times the IC50 on Cdk4). Results from this screen confirmed the high potency against Cdk4 and high selectivity versus Cdk2. Additionally, the kinome profiling showed that Compound T was relatively selective for Cdk4 and Cdk6 compared to the other kinases tested. Specifically, when using an inhibitory threshold of 65%, 90%, or 99%, Compound T inhibited 92 (23.3%), 31 (7.8%) or 6 (1.5%) of 395 non-mutant kinases respectively.

In addition to CDK4 kinase activity, several compounds were also tested against CDK6 kinase activity. The results of the CDK6/CycD3 kinase assays, along with the CDK4/cyclinD1, CDK2/CycA and CDK2/cyclinE kinase assays, are shown for PD0332991 (Reference) and the compounds T, Q, GG, and U in Table 3. The IC$_{50}$ of 10 nM for CDK4/cyclinD1 and 10 uM for CDK12/CyclinE agrees well with previously published reports for PD0332991 (Fry et al. Molecular Cancer Therapeutics (2004) 3(11)1427-1437; Toogood et al. Journal of Medicinal Chemistry (2005) 48, 2388-2406). Compounds T, Q, GG, and U are more potent (lower IC$_{50}$) with respect to the reference compound (PD0332991) and demonstrate a higher fold selectivity with respect to the reference compound (CDK2/CycE IC$_{50}$ divided by CDK4/CycD1 IC$_{50}$).

TABLE 3

Inhibition of CDK kinases by Compounds T, Q, GG, and U

| Formula | CDK4/CycD1 IC$_{50}$ (nM) | CDK2/CycE IC$_{50}$ (uM) | Fold Selectivity CDK2/CDK4 | CDK2/CycA IC$_{50}$ (uM) | CDK6/CycD3 IC$_{50}$ (nM) |
|---|---|---|---|---|---|
| PD0332991 Reference | 10 | 10 | 1000 | Not determined | Not determined |
| Compound T | 0.821 | 1.66 | 2022 | 1.67 | 5.64 |
| Compound Q | 0.627 | 1.08 | 1722 | 3.03 | 4.38 |
| Compound GG | 1.060 | 3.58 | 3377 | 1.51 | 4.70 |
| Compound U | 0.655 | 1.46 | 2229 | .857 | 5.99 |

Example 151

G1 Arrest (Cellular G1 and S-phase) Assay

For determination of cellular fractions in various stages of the cell cycle following various treatments, HS68 cells (human skin fibroblast cell line (Rb-positive)) were stained with propidium iodide staining solution and run on Dako Cyan Flow Cytometer. The fraction of cells in G0-G1 DNA cell cycle versus the fraction in S-phase DNA cell cycle was determined using FlowJo 7.2.2 analysis.

The compounds listed in Table 1 were tested for their ability to arrest HS68 cells at the G1 phase of the cell cycle. From the results of the cellular G1 arrest assay, the range of the inhibitory EC$_{50}$ values necessary for G1 arrest of HS68 cells was from 22 nM to 1500 nM (see column titled "Cellular G1 Arrest EC$_{50}$" in Table 4).

Example 152

Cell Cycle Arrest by Compound T in Cdk4/6-Dependent Cells

To test the ability of Cdk4/6 inhibitors to induce a clean G1-arrest, a cell based screening method was used consisting of two Cdk4/6-dependent cell lines (tHS68 and WM2664; Rb-positive) and one Cdk4/6-independent (A2058; Rb-negative) cell line. Twenty-four hours after plating, each cell line was treated with Compound T in a dose dependent manner for 24 hours. At the conclusion of the experiment, cells were harvested, fixed, and stained with propidium iodide (a DNA intercalator), which fluoresces strongly red (emission maximum 637 nm) when excited by 488 nm light. Samples were run on Dako Cyan flow cytometer and >10,000 events were collected for each sample. Data were analyzed using FlowJo 2.2 software developed by TreeStar, Inc.

Figure 2A:
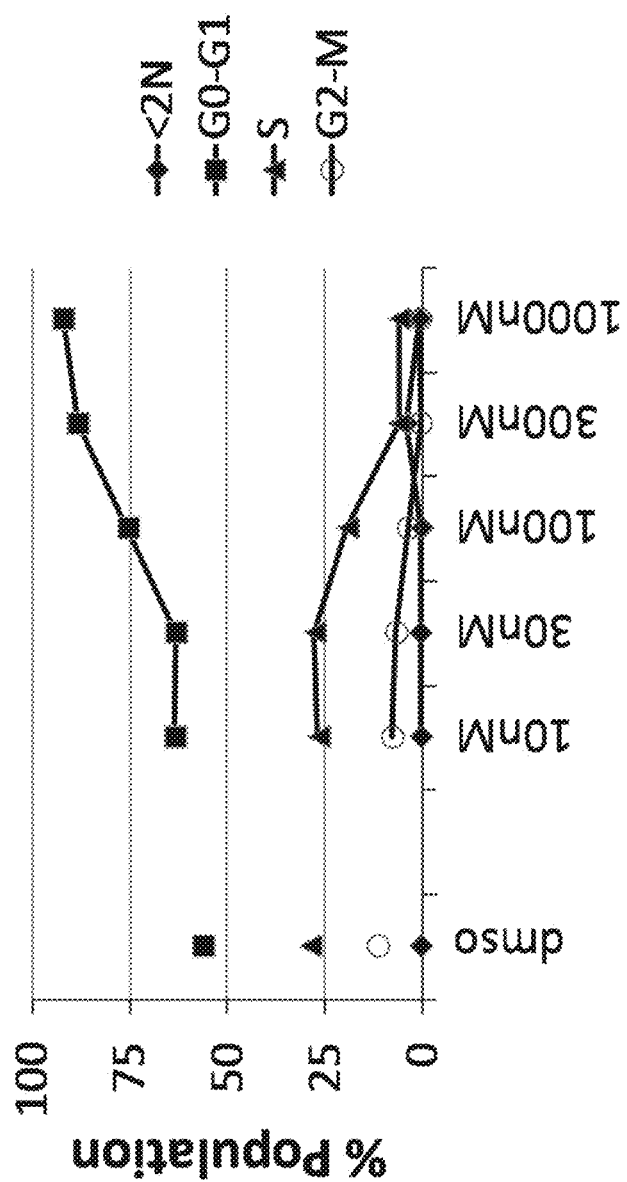
FIG. 2A is a graph of the percentage of cells in G2-M phase (open circles), S phase (triangles), G0-G1 phase (squares), <2N (diamonds) vs. variable concentration (nM) of Compound T in tHS68 cells. The Cdk4/6-dependent cell line (tHS68) was treated with the indicated concentrations of Compound T for 24 hours. Following treatment of Compound T, cells were harvested and analyzed for cell cycle distribution. As described in Example 152, tHS68 cells show a clean G1 arrest accompanied by a corresponding decrease in the number of cells in S-phase.
Figure 2C:
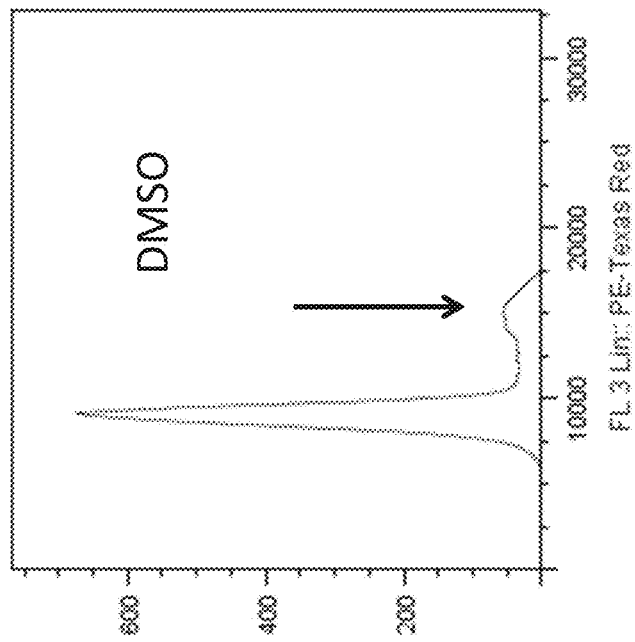
FIG. 2C is a graph of the number of WM2664 cells (CDK4/6-dependent cell line) vs. the DNA content of the cells (as measured by propidium iodide). Cells were treated with DMSO for 24 hours, harvested, and analyzed for cell cycle distribution.
Figure 2B:
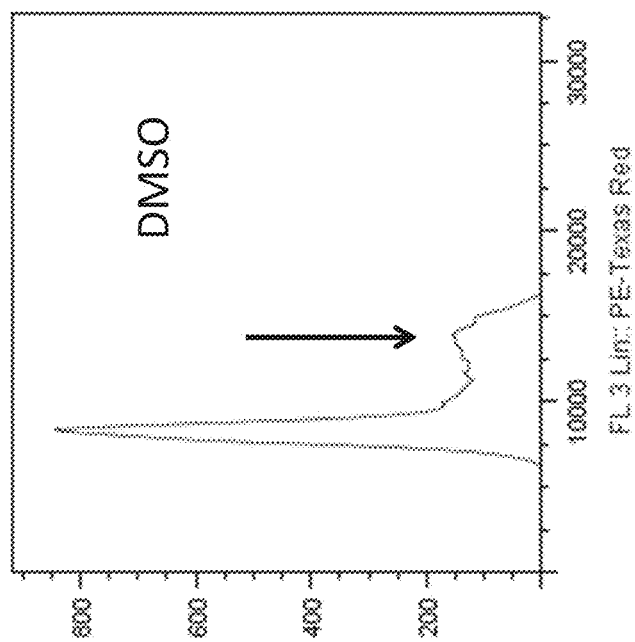
FIG. 2B is a graph of the number of tHS68 cells (CDK4/6-dependent cell line) vs. the DNA content of the cells (as measured by propidium iodide). Cells were treated with DMSO for 24 hours, harvested, and analyzed for cell cycle distribution.

FIG. 2B is a graph of the number of tHS68 cells (CDK4/6-dependent cell line) vs. the DNA content of the cells (as measured by propidium iodide). Cells were treated with DMSO for 24 hours, harvested, and analyzed for cell cycle distribution. FIG. 2C is a graph of the number of WM2664 cells (CDK4/6-dependent cell line) vs. the DNA content of the cells (as measured by propidium iodide). Cells were treated with DMSO for 24 hours, harvested, and analyzed for cell cycle distribution. FIG. 2D is a graph of the number of A2058 cells (CDK4/6-independent cell line) vs. the DNA content of the cells (as measured by propidium iodide). Cells were treated with DMSO for 24 hours, harvested, and analyzed for cell cycle distribution. FIG. 2E is a graph of the number of tHS68 cells (CDK4/6-dependent cell line) vs. the DNA content of the cells (as measured by propidium iodide) after treatment with Compound T. Cells were treated with Compound T (300 nM) for 24 hours, harvested, and analyzed for cell cycle distribution. As described in Example 152, treatment of tHS68 cells with Compound T causes a loss of the S-phase peak (indicated by arrow). FIG. 2F is a graph of the number of WM2664 cells (CDK4/6-dependent cell line) vs. the DNA content of the cells (as measured by propidium iodide) after treatment with Compound T. Cells were treated with Compound T (300 nM) for 24 hours, harvested, and analyzed for cell cycle distribution. As described in Example 152, treatment of WM2664 cells with Compound T causes a loss of the S-phase peak (indicated by arrow). FIG. 2G is a graph of the number of A2058 cells (CDK4/6-independent cell line) vs. the DNA content of the cells (as measured by propidium iodide) after treatment with Compound T. Cells were treated with Compound T (300 nM) for 24 hours, harvested, and analyzed for cell cycle distribution. As described in Example 152, treatment of A2058 cells with Compound T does not cause a loss of the S-phase peak (indicated by arrow).

Example 153

Compound T Inhibits Phosphorylation of RB

Figure 3:
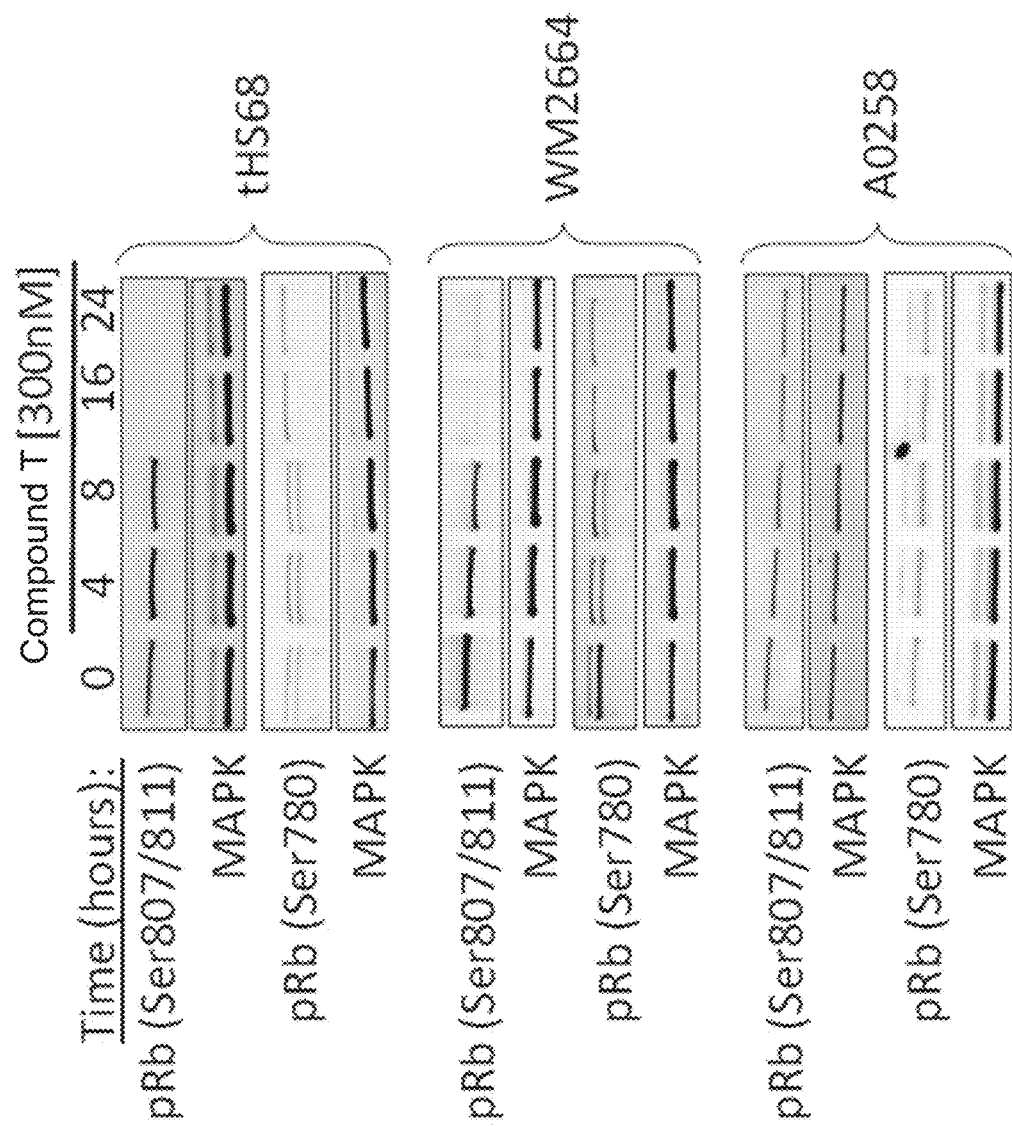
FIG. 3 is a Western blot showing the phosphorylation levels of Rb at Ser807/811 and Ser780 after treatment with Compound T. Cdk4/6-dependent (tHS68 or WM2664) and Cdk4/6-independent cell lines (A2058) were treated with Compound T (300 nM) for the indicated times (0, 4, 8, 16, and 24 hours). MAPK levels are shown as a control for protein levels. Following treatment, cells were harvested and analyzed for Rb-phosphorylation by western blot analysis. As described in Example 153, Compound T treatment resulted in reduced Rb-phosphorylation after treatment in Cdk4/6-dependent cell lines (tHS68 and WM2664), but not in the Cdk4/6-independent cell line (A2058).

The Cdk4/6-cyclin D complex is essential for progression from G1 to the S-phase of the DNA cell cycle. This complex phosphorylates the retinoblastoma tumor suppressor protein (Rb). To demonstrate the impact of Cdk4/6 inhibition on Rb phosphorylation (pRb), Compound T was exposed to three cell lines, two Cdk4/6 dependent (tHS68, WM2664; Rb-positive) and one Cdk4/6 independent (A2058; Rb-negative). Twenty four hours after seeding, cells were treated with Compound T at 300 nM final concentration for 4, 8, 16, and 24 hours. Samples were lysed and protein was assayed by western blot analysis. Rb phosphorylation was measured at two sites targeted by the Cdk4/6-cyclin D complex, Ser780 and Ser807/811 using species specific antibodies. Results demonstrate that Compound T blocks Rb phosphorylation in Rb-dependent cell lines by 16 hours post exposure, while having no effect on Rb-independent cells (FIG. 3).

Example 154

Small Cell Lung Cancer (SCLC) Cells are Resistant to CDK4/6 Inhibitors

The retinoblastoma (RB) tumor suppressor is a major negative cell cycle regulator that is inactivated in approximately 11% of all human cancers. Functional loss of RB is an obligate event in small cell lung cancer (SCLC) development. In RB competent tumors, activated Cdk2/4/6 promote G1 to S phase traversal by phosphorylating and inactivating RB (and related family members). Conversely, cancers with RB deletion or inactivation do not require Cdk4/6 activity for cell cycle progression. Since inactivation of RB is an obligate event in SCLC development, this tumor type is highly resistant to Cdk4/6 inhibitors and co-administration of Cdk4/6 inhibitors with DNA damaging chemotherapeutic agents such as those used in SCLC should not antagonize the efficacy of such agents.

Several compounds (PD0332991, Compound GG, and Compound T) were tested for their ability to block cell proliferation in a panel of SCLC cell lines with known genetic loss of RB. SCLC cells were treated with DMSO or the indicated Cdk4/6 inhibitor for 24 hours. The effect of Cdk4/6 inhibition on proliferation was measured by EdU incorporation. An RB-intact, Cdk4/6-dependent cell line (WM2664 or tHS68) and a panel of RB-negative SCLC cell lines (H69, H82, H209, H345, NCI417, or SHP-77) were analyzed for growth inhibition by the various CDK4/6 inhibitors.

Figure 4A:
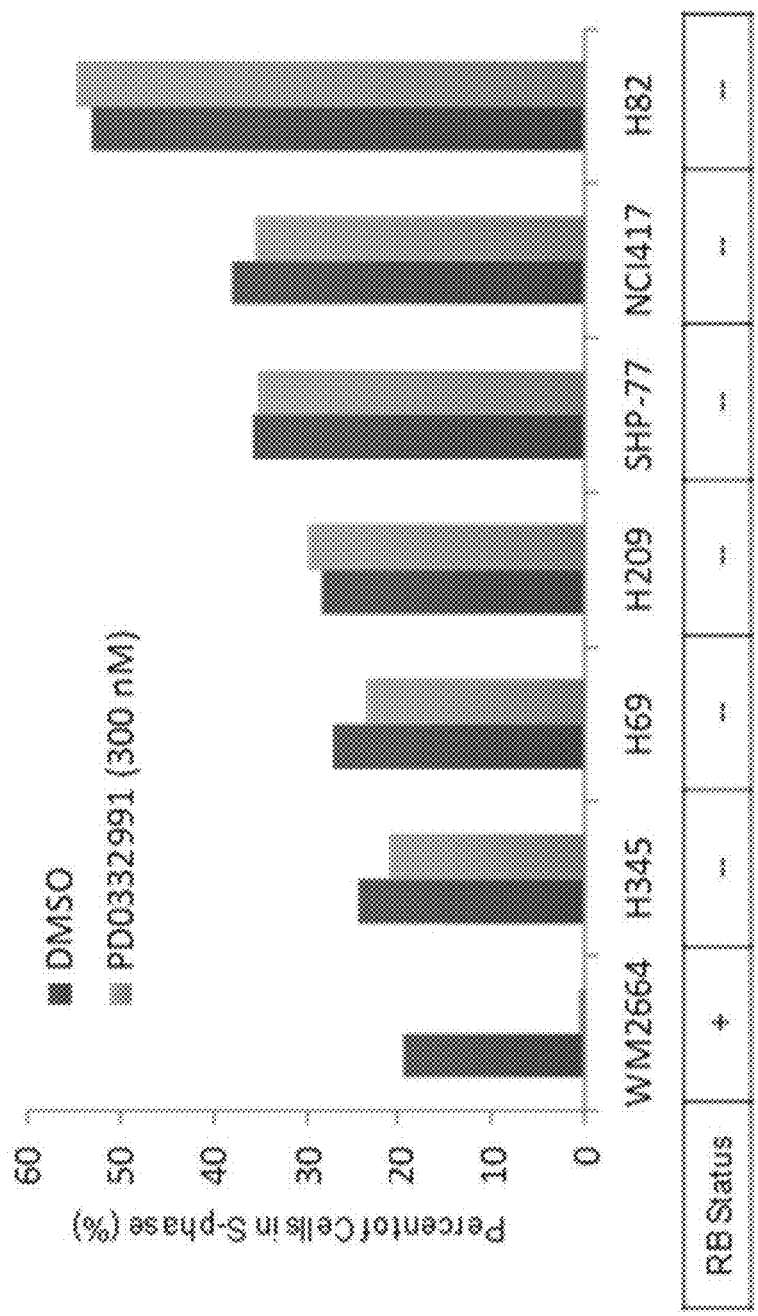
FIG. 4A is a graph of the percentage of cells in S phase in an Rb-positive cell line (WM2664) or in the Rb-negative small cell lung cancer cell lines (H345, H69, H209, SHP-77, NCI417, or H82) after treatment with DMSO (dark bars) or PD0332991 (light bars). Cells were treated with PD0332991 (300 nM) or DMSO control for 24 hours. Cell proliferation was measured by EdU incorporation and flow cytometry. Data represents 100,000 cell events for each cell treatment. As described in Example 154, the RB-null SCLC cell line was resistant to Cdk4/6 inhibition, as no changes in the percent of cells in S-phase were seen upon treatment with PD0332991.
Figure 4B:
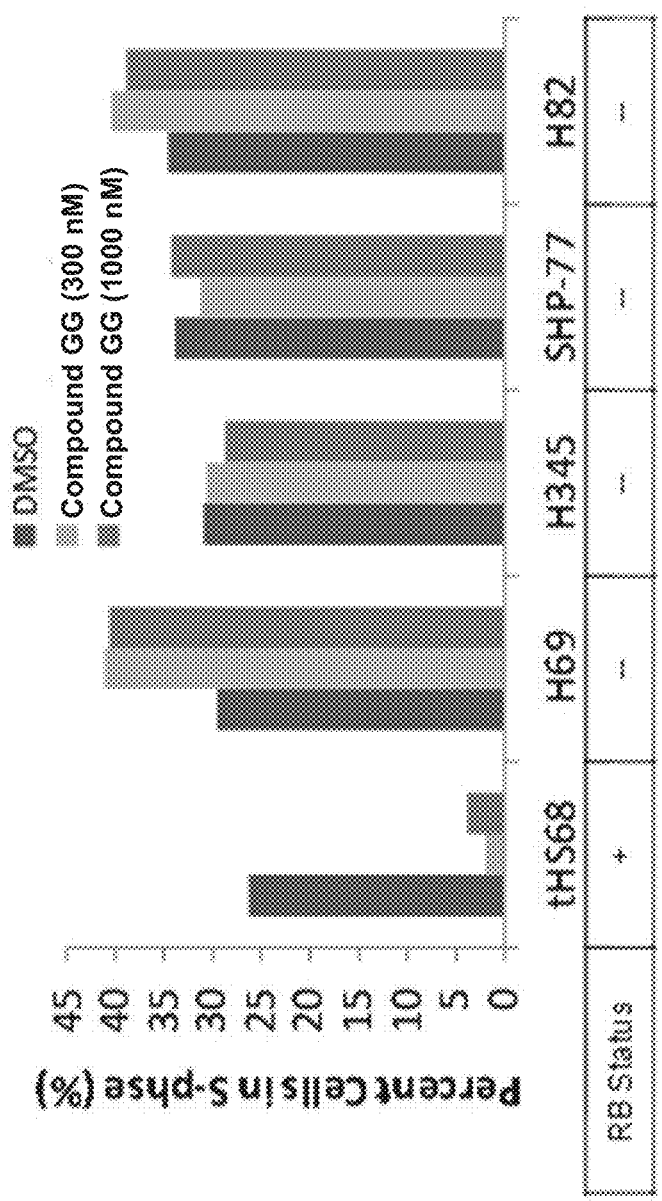
FIG. 4B is a graph of the percentage of cells in S phase in an Rb-positive cell line (tHS68) or in the Rb-negative small cell lung cancer cell lines (H345, H69, SHP-77, or H82) after treatment with DMSO (dark bars) or Compound GG (lighter bars). Cells were treated with Compound GG (300 nM or 1000 nM) or DMSO control for 24 hours. Cell proliferation was measured by EdU incorporation and flow cytometry. Data represents 100,000 cell events for each cell treatment. As described in Example 154, the RB-null SCLC cell line was resistant to Cdk4/6 inhibition, as no changes in the percent of cells in S-phase were seen upon treatment with Compound GG.
Figure 4C:
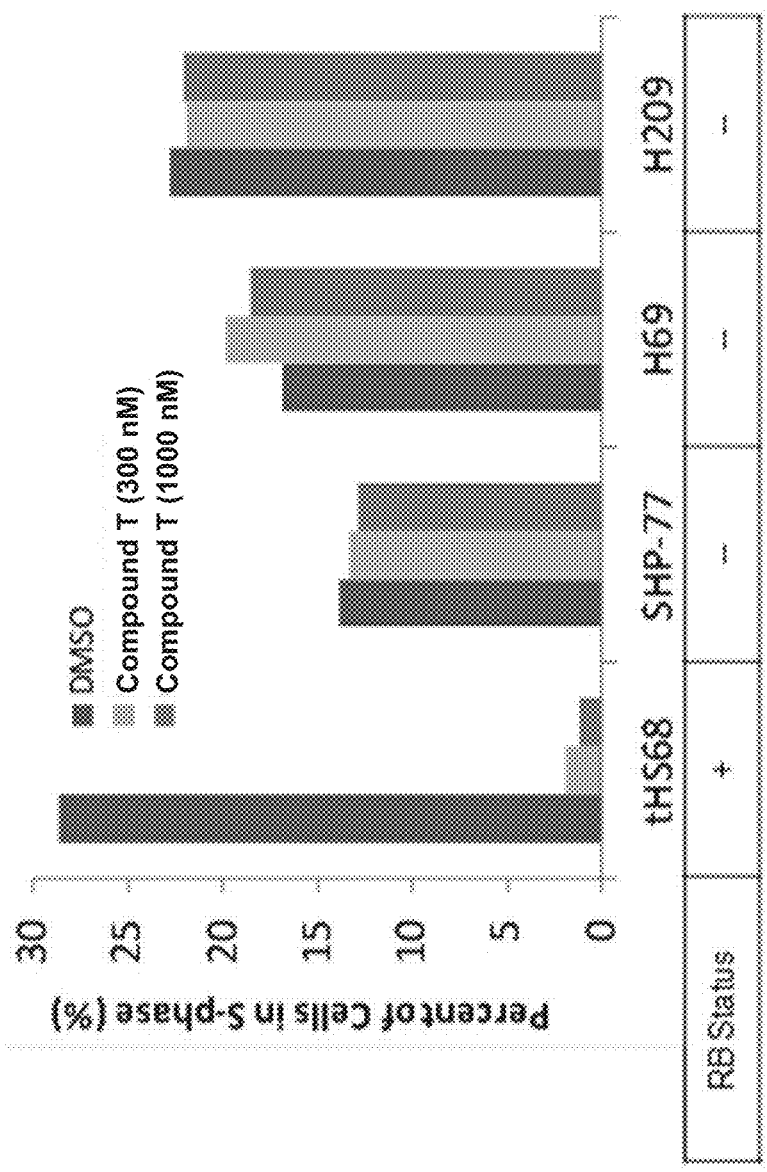
FIG. 4C is a graph of the percentage of cells in S phase in an Rb-positive cell line (tHS68) or in the Rb-negative small cell lung cancer cell lines (H345, H209, or SHP-77) after treatment with DMSO (dark bars) or Compound T (lighter bars). Cells were treated with Compound T (300 nM or 1000 nM) or DMSO control for 24 hours. Cell proliferation was measured by EdU incorporation and flow cytometry. Data represents 100,000 cell events for each cell treatment. As described in Example 154, the RB-null SCLC cell line was resistant to Cdk4/6 inhibition, as no change in the percent of cells in S-phase were seen upon treatment with Compound T.

As shown in FIG. 4, Rb-negative SCLC cells are resistant to Cdk4/6 inhibition. In FIG. 4A, PD0332991 inhibits the Rb-positive cell line (WM2664), but does not affect the growth of the Rb-negative small cell lung cancer cell lines (H345, H69, H209, SHP-77, NCI417, and H82). In FIG. 4B, Compound GG inhibits the Rb-positive cell line (tHS68), but does not affect the growth of the Rb-negative cell lines (H345, H69, SHP-77, and H82). In FIG. 4C, Compound T inhibits the Rb-positive cell line (tHS68), but does not affect the growth of the Rb-negative cell lines (H69, SHP-77, and H209). This analysis demonstrated that RB-null SCLC cell lines were resistant to Cdk4/6 inhibition, as no change in the percent of cells in S-phase were seen upon treatment with any of the Cdk4/6 inhibitors tested, including Compound T and Compound GG, while the RB-proficient cell line in each experiment was highly sensitive to Cdk4/6 inhibition with almost no cells remaining in S-phase after 24 hours of treatment.

Example 155

Rb-Negative Cancer Cells are Resistant to CDK4/6 Inhibitors

Cellular proliferation assays were conducted using the following Rb-negative cancer cell lines: H69 (human small cell lung cancer—Rb-negative) cells or A2058 (human metastatic melanoma cells—Rb-negative). These cells were seeded in Costar (Tewksbury, Mass.) 3093 96 well tissue culture treated white walled/clear bottom plates. Cells were treated with the compounds of Table 1 as nine point dose response dilution series from 10 uM to 1 nM. Cells were exposed to compounds and then cell viability was determined after either four (H69) or six (A2058) days as indicated using the CellTiter-Glo® luminescent cell viability assay (CTG; Promega, Madison, Wis., United States of America) following the manufacturer's recommendations. Plates were read on BioTek (Winooski, Vt.) Syngergy2 multi-mode plate reader. The Relative Light Units (RLU) were plotted as a result of variable molar concentration and data was analyzed using Graphpad (LaJolla, Californaia) Prism 5 statistical software to determine the $EC_{50}$ for each compound.

Select compounds disclosed herein were evaluated against a small cell lung cancer cell line (H69) and a human metastatic melanoma cell line (A2058), two Rb-deficient (Rb-negative) cell lines. The results of these cellular inhibition assays are shown in Table 4. The range of the inhibitory $EC_{50}$ values necessary for inhibition of H69 small cell lung cancer cells was 2040 nM to >3000 nM. The range of the inhibitory $EC_{50}$ values necessary for inhibition of A2058 malignant melanoma cell proliferation was 1313 nM to >3000 nM. In contrast to the significant inhibition seen on Rb-positive cell lines, it was found that the compounds tested were not significantly effective at inhibiting proliferation of the small cell lung cancer or melanoma cells.

TABLE 4

Resistance of Rb-Negative Cancer Cells to CDK4/6 Inhibitors

| Structure | Cellular G1 Arrest $EC_{50}$ (nM) | H69 Cellular $EC_{50}$ [nM] | A2058 Cellular $EC_{50}$ [nM] |
|---|---|---|---|
| A | 110 | >3000 | ND |
| B | 90 | ND | ND |
| C | 95 | ND | ND |
| D | 50 | 2911 | 1670 |
| E | 75 | 2580 | 1371 |
| F | 175 | ND | ND |
| G | 175 | ND | ND |
| H | 85 | 2040 | 1313 |
| I | 80 | 2950 | 1062 |
| J | 110 | >3000 | >3000 |
| K | 28 | >3000 | 1787 |
| L | 65 | 2161 | >3000 |
| M | 100 | ND | ND |
| N | 25 | >3000 | 1444 |
| O | 40 | >3000 | 2668 |
| P | 30 | >3000 | >3000 |
| Q | 100 | >3000 | 2610 |
| R | 70 | >3000 | 2632 |
| S | 150 | >3000 | >3000 |
| T | 100 | >3000 | >3000 |
| U | 25 | >3000 | >3000 |
| V | 70 | >3000 | 1353 |
| W | 160 | >3000 | >3000 |
| X | 65 | >3000 | >3000 |
| Y | 350 | ND | ND |
| Z | 110 | ND | ND |
| AA | 70 | >3000 | ND |
| BB | 75 | 2943 | 1635 |
| CC | 90 | >3000 | >3000 |
| DD | 100 | ND | ND |
| EE | 125 | ND | ND |
| FF | 80 | ND | ND |
| GG | 80 | 2920 | 2691 |
| HH | 110 | ND | ND |
| II | 40 | >3000 | >3000 |
| JJ | 90 | >3000 | >3000 |
| KK | 22 | 2421 | 1379 |
| LL | 125 | >3000 | >3000 |
| MM | 100 | >3000 | >3000 |
| NN | 110 | ND | ND |
| OO | 95 | >3000 | >3000 |
| PP | 100 | ND | ND |
| QQ | 120 | >3000 | >3000 |
| RR | 90 | 2888 | 1617 |
| SS | 80 | 2948 | 1658 |
| TT | 75 | ND | ND |
| UU | 300 | ND | ND |
| VV | 200 | ND | ND |
| WW | 400 | ND | ND |
| XX | 225 | ND | ND |
| YY | 175 | ND | ND |
| ZZ | 500 | ND | ND |
| AAA | 275 | >3000 | >3000 |
| BBB | 230 | >3000 | >3000 |
| CCC | 250 | ND | ND |
| DDD | 350 | ND | ND |
| EEE | 250 | >3000 | >3000 |
| FFF | 650 | ND | ND |
| GGG | 350 | ND | ND |
| HHH | 250 | ND | ND |
| III | 250 | ND | ND |
| JJJ | 240 | ND | ND |
| KKK | 190 | ND | ND |
| LLL | 250 | ND | ND |
| MMM | 200 | >3000 | >3000 |
| NNN | 210 | ND | ND |
| OOO | 200 | >3000 | >3000 |
| PPP | 275 | ND | ND |
| QQQ | 500 | ND | ND |
| RRR | 400 | ND | ND |
| SSS | 1500 | ND | ND |
| TTT | 350 | ND | ND |
| UUU | 300 | ND | ND |
| VVV | 300 | ND | ND |
| WWW | 300 | ND | ND |
| XXX | 300 | ND | ND |

Example 156

HSPC Growth Suppression Studies

Figure 5:
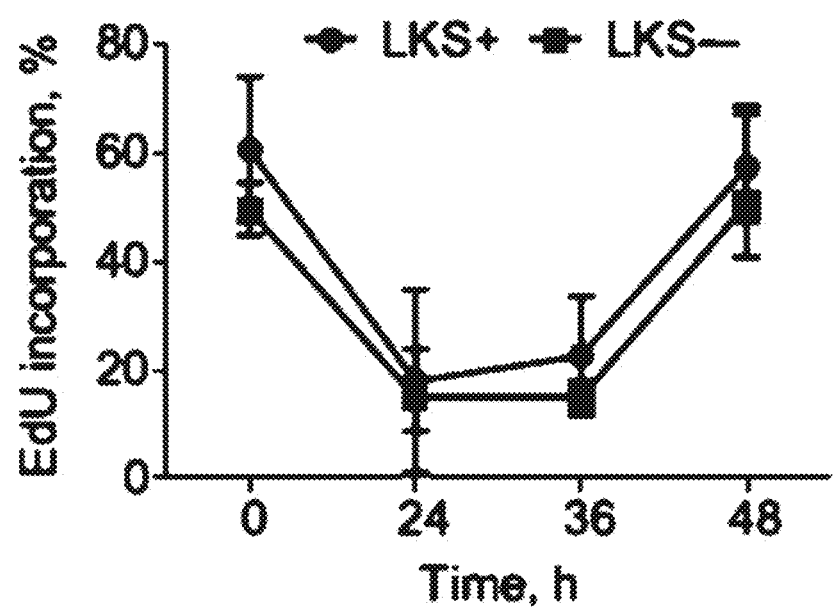
FIG. 5 is a graph of EdU incorporation vs. time after administration (hours) of PD0332991 to healthy mice HSPCs and healthy myeloid progenitor cells. PD0332991 (150 mg/kg) was administered by oral gavage to assess the temporal effect of transient CDK4/6 inhibition on bone marrow arrest as reported in Roberts et al. Multiple Roles of Cyclin-Dependent Kinase 4/6 Inhibitors in Cancer Therapy. JCNI 2012; 104(6):476-487 (FIG. 2A). As described in Example 156, a single oral dose of PD0332991 results in a sustained reduction in HSPC EdU incorporation (circles; LKS+) and myeloid progenitor cells EdU incorporation (squares; LKS−) for greater than 36 hours.

The effect of PD0332991 on HSPCs has been previously demonstrated. FIG. 5 shows the EdU incorporation of mice HSPC and myeloid progenitor cells following a single dose of 150 mg/kg PD0332991 by oral gavage to assess the temporal effect of transient CDK4/6 inhibition on bone marrow arrest as reported in Roberts et al. Multiple Roles of Cyclin-Dependent Kinase 4/6 Inhibitors in Cancer Therapy. JCNI 2012; 104(6):476-487. As can be seen in FIG. 5, a single oral dose of PD0332991 results in a sustained reduction in HSPC (LKS+) and myeloid progenitor cells (LKS−) for greater than 36 hours. Not until 48 hours post oral dosing do HSPC and myeloid progenitor cells return to baseline cell division.

Example 157

Bone Marrow Proliferation as Evaluated Using EdU Incorporation and Flow Cytometry Analysis For HSPC proliferation experiments, young adult female FVB/N mice were treated with a single dose as indicated of compound T, compound Q, compound GG or PD0332991 by oral gavage. Mice were then sacrificed at the indicated times (0, 12, 24, 36, or 48 hours following compound administration), and bone marrow was harvested (n=3 mice per time point), as previously described (Johnson et al. J. Clin. Invest. (2010) 120(7), 2528-2536). Four hours before the bone marrow was harvested, mice were treated with 100 µg of EdU by intraperitoneal injection (Invitrogen). Bone marrow mononuclear cells were harvested and immunophenotyped using previously described methods and percent EdU positive cells were then determined (Johnson et al. J. Clin. Invest. (2010) 120(7), 2528-2536). In brief, HSPCs were identified by expression of lineage markers (Lin−), Sca1 (S+), and c-Kit (K+).

Figure 6A:
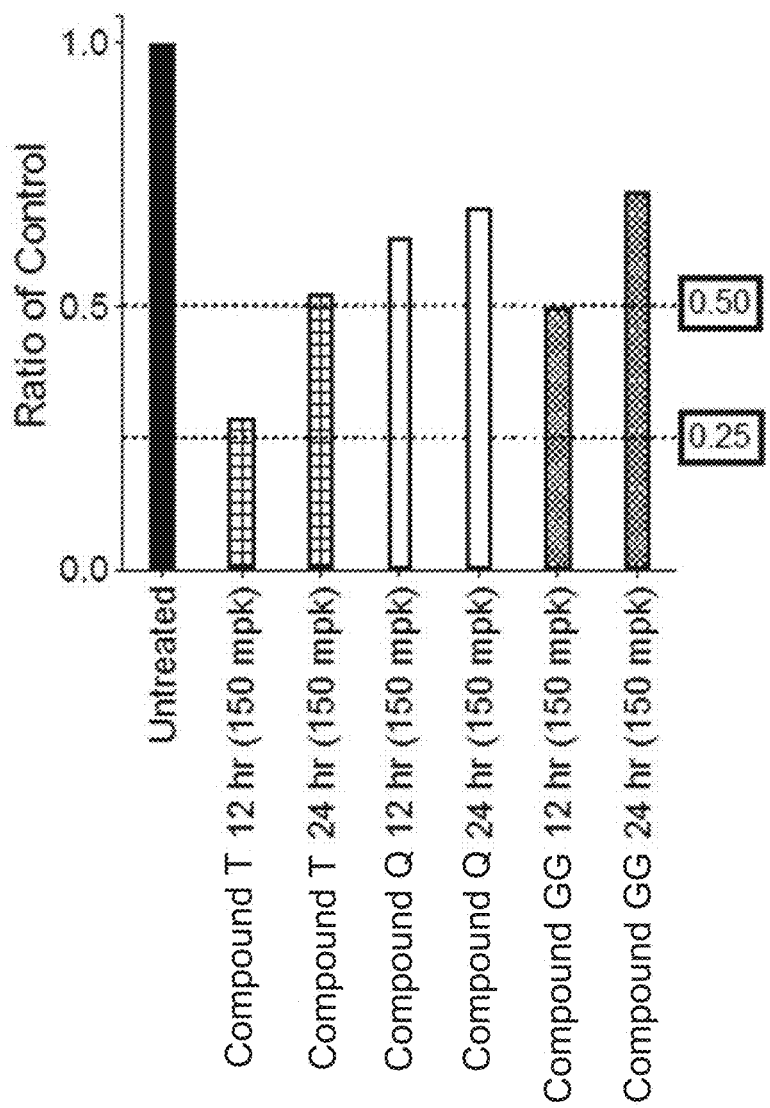
FIG. 6A is a graph of the ratio of EdU incorporation into HSPCs (compared to untreated control mice) following oral gavage of Compounds T, Q, or GG at 150 mg/kg at either 12 or 24 hours post administration.

Analysis in mice determined that Compound T, Compound Q, and Compound GG demonstrated dose dependent, transient, and reversible G1-arrest of bone marrow stem cells (HSPC) (FIG. 6). Six mice per group were dosed by oral gavage at 150 mg/kg of Compound T, Compound Q, Compound GG, or vehicle only. Four hours before animals were sacrificed and the bone marrow was harvested, mice were treated with 100 µg of EdU by intraperitoneal injection. Three mice per group were sacrificed at 12 hours and the remaining three animals per group were sacrificed at 24 hours. Results are shown in FIG. 6A as the ratio of EdU positive cells for treated animals at 12 or 24 hour time points compared to control. Compound T and GG demonstrated a reduction in EdU incorporation at 12 hours which was starting to return to normal at 24 hours. Compound Q also demonstrated some reduction at 12 hours and started to return to baseline at 24 hours despite the fact that oral bioavailability of Compound Q is low.

Figure 6B:
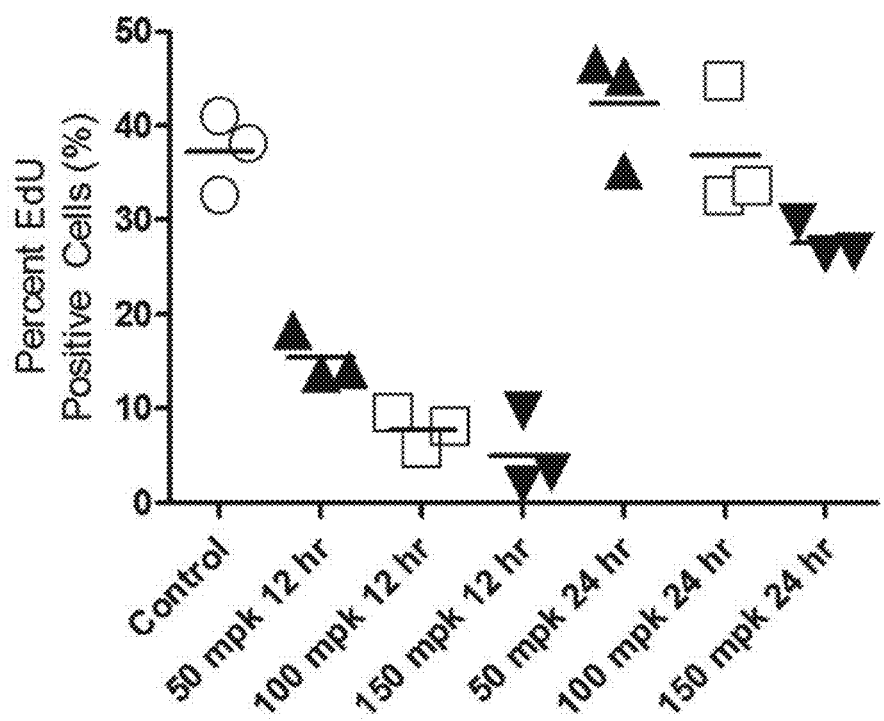
FIG. 6B is a graph of the percentage of EdU positive HSPC cells for mice treated with Compound T at either 12 or 24 hours. Mice were dosed with 50 mg/kg (triangles), 100 mg/kg (squares), or 150 (upside down triangles) mg/kg by oral gavage.

Further experiments were completed with Compound T examining dose response and longer periods of compound treatment. Compound T was dosed by oral gavage at 50, 100 or 150 mg/kg and EdU incorporation into bone marrow was determined at 12 and 24 hours as described above. Alternatively, Compound T was dosed by oral gavage at 150 mg/kg and EdU incorporation into bone marrow was determined at 12, 24, 36 and 48 hours. As can be seen in FIGS. 6B and 5C, and similar to the cellular washout experiments, bone marrow cells, and in particular HSPCs were returning to normal cell division as determined by EdU incorporation in 24 hours following oral gavage at a number of doses. The 150 mg/kg oral dose of Compound T in FIG. 6C can be compared directly to the results of the same dose of PD0332991 shown in FIG. 5 where cells were still non-dividing (as determined by low EdU incorporation) at 24 and 36 hours, only returning to normal values at 48 hours.

Example 158

HSPC Growth Suppression Studies Comparing Compound T and PD0332991

Figure 7:
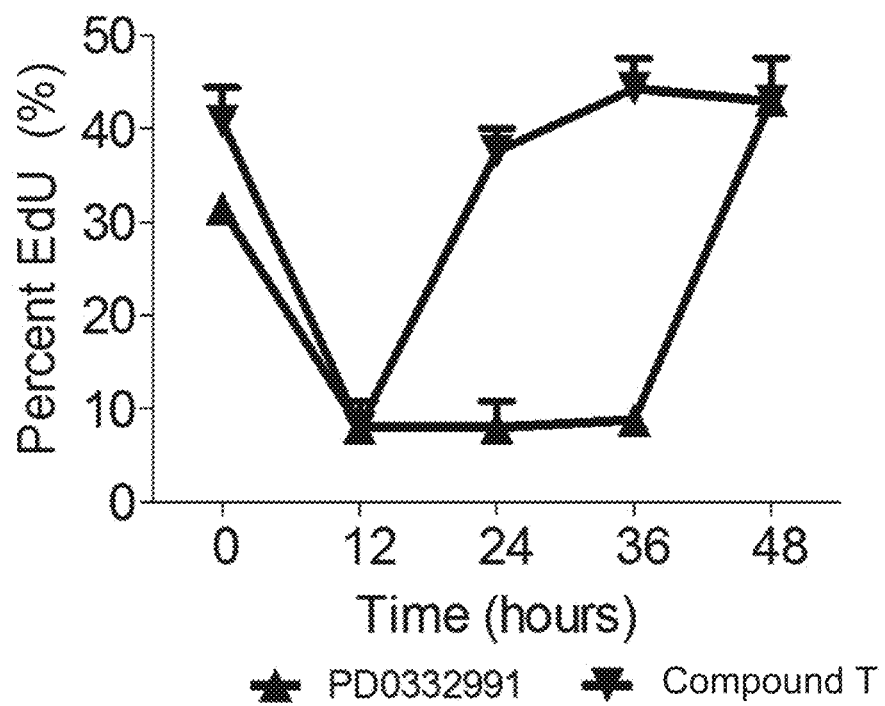
FIG. 7 is a graph of the percentage of EdU positive HSPC cells for mice treated with either PD0332991 (triangles) or Compound T (upside down triangles) v. time after administration (hours) of the compound. Both compounds were administered at 150 mg/kg by oral gavage and the percentage of EdU positive HSPC cells was measured at 12, 24, 36 or 48 hours. As described in Example 158, a single oral dose of PD0332991 results in a sustained reduction of HSPC proliferation for greater than 36 hours. In contrast, a single oral dose of Compound T results in an initial reduction of HSPC proliferation at 12 hours, but proliferation of HSPCs resumes by 24 hours after dosage of Compound T.
Figure 8A:
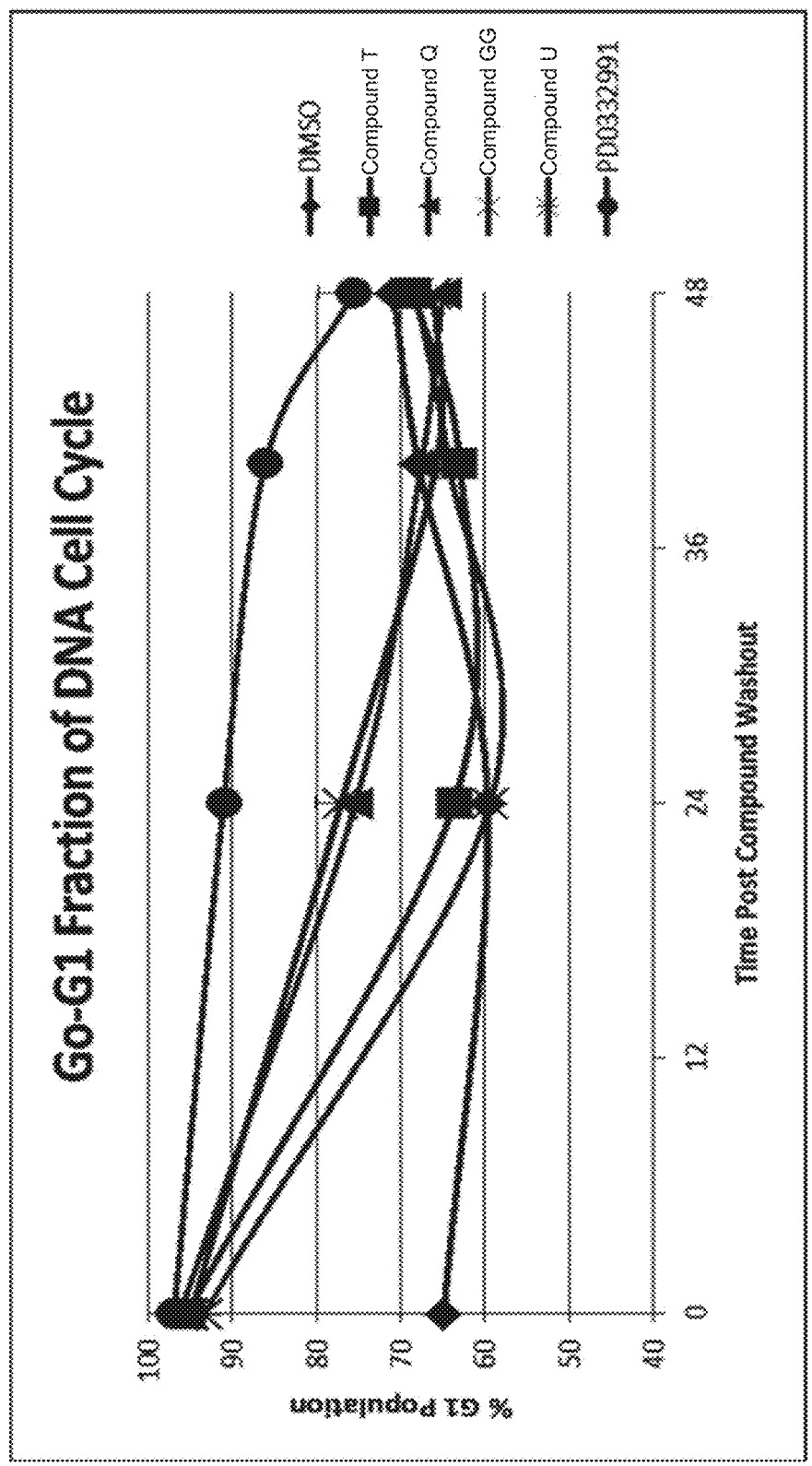
FIG. 8A is a graph of the percentage of cells in the G0-G1 phase of the cell cycle vs. time after washout of the compound (hours) in human fibroblast (Rb-positive) cells.
Figure 8B:
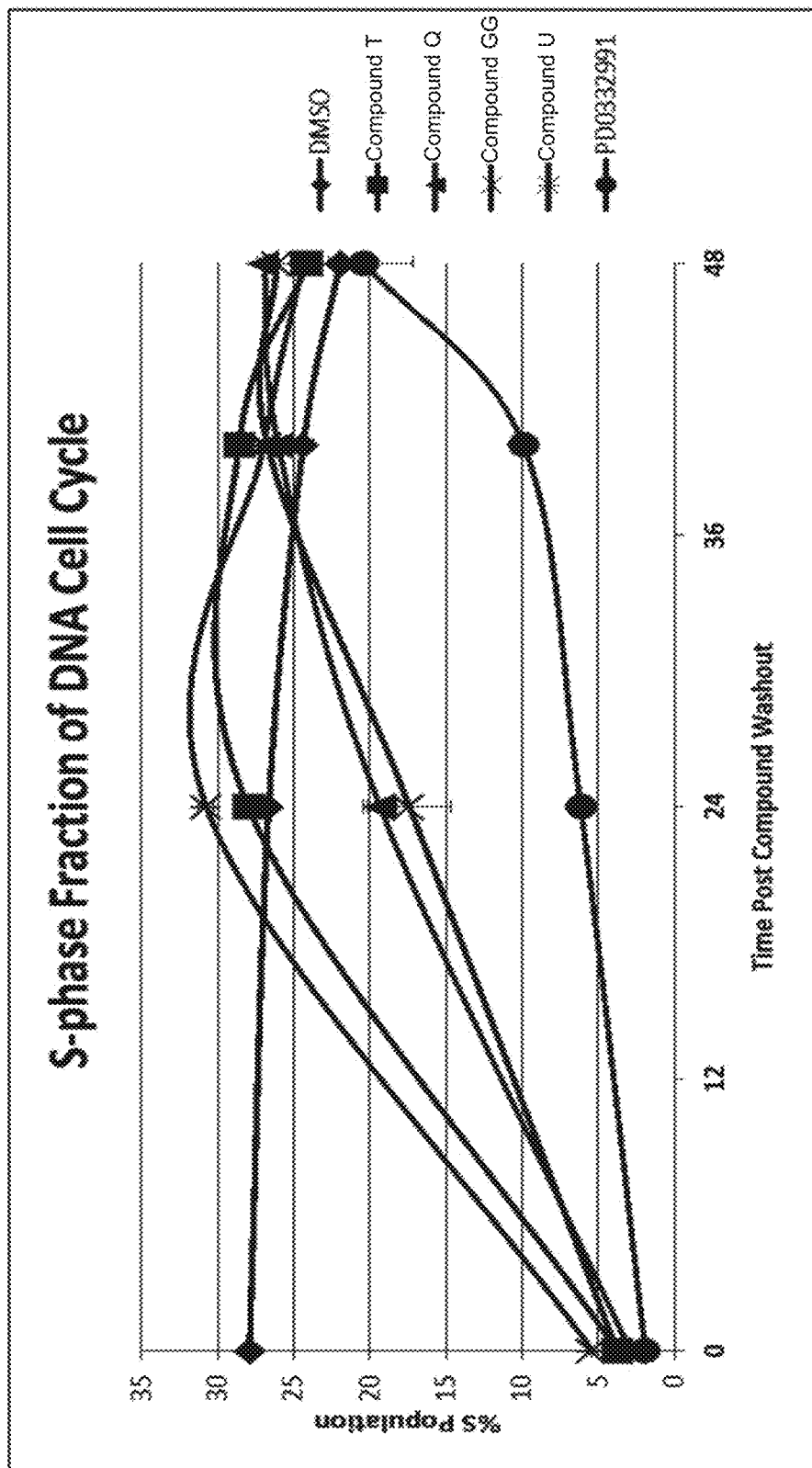
FIG. 8B is a graph of the percentage of cells in the S phase of the cell cycle vs. time after washout of the compound (hours) in human fibroblast (Rb-positive) cells.
Figure 8C:
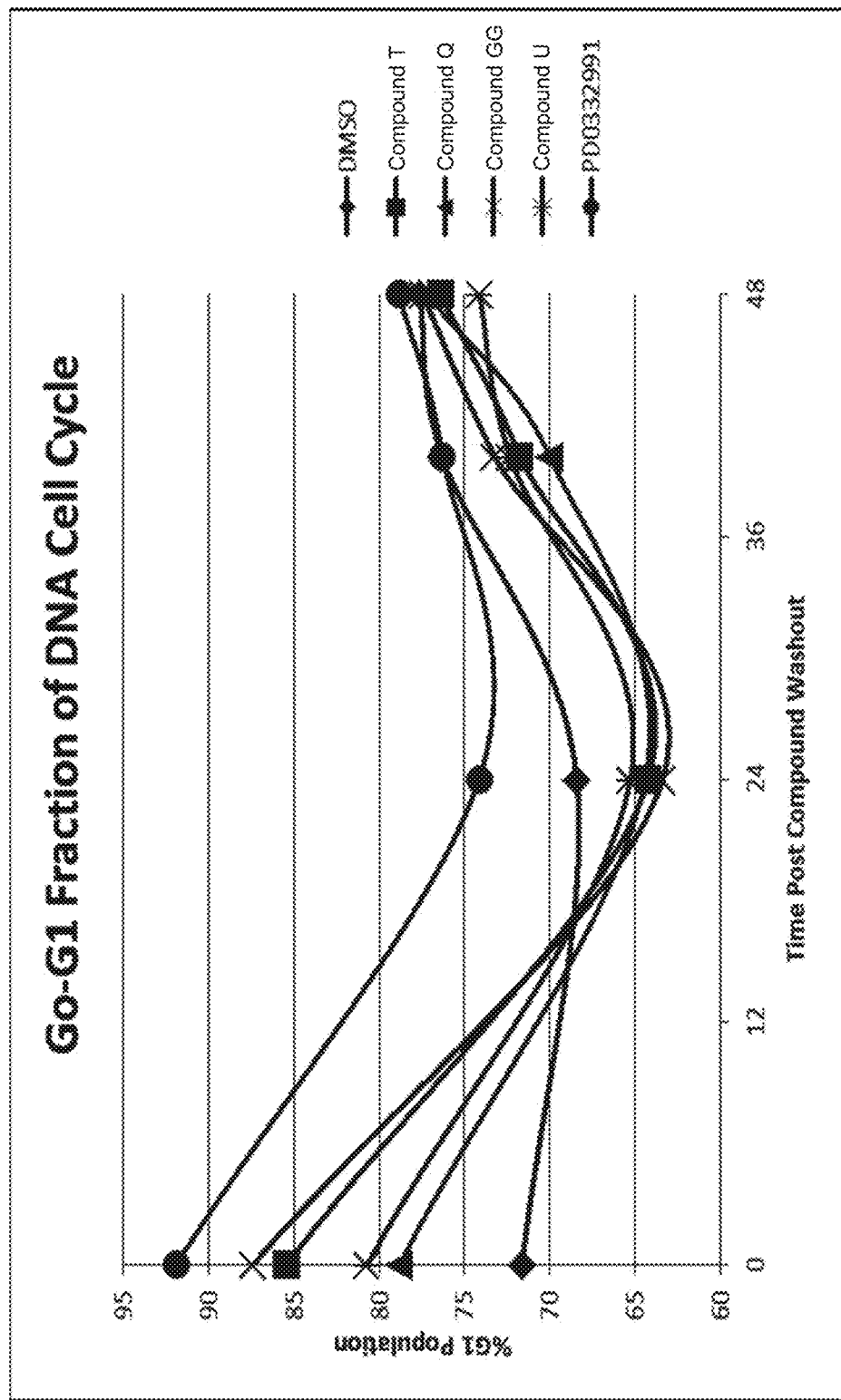
FIG. 8C is a graph of the percentage of cells in the G0-G1 phase of the cell cycle vs. time after washout of the compound (hours) in human renal proximal tubule epithelial (Rb-positive) cells.
Figure 8D:
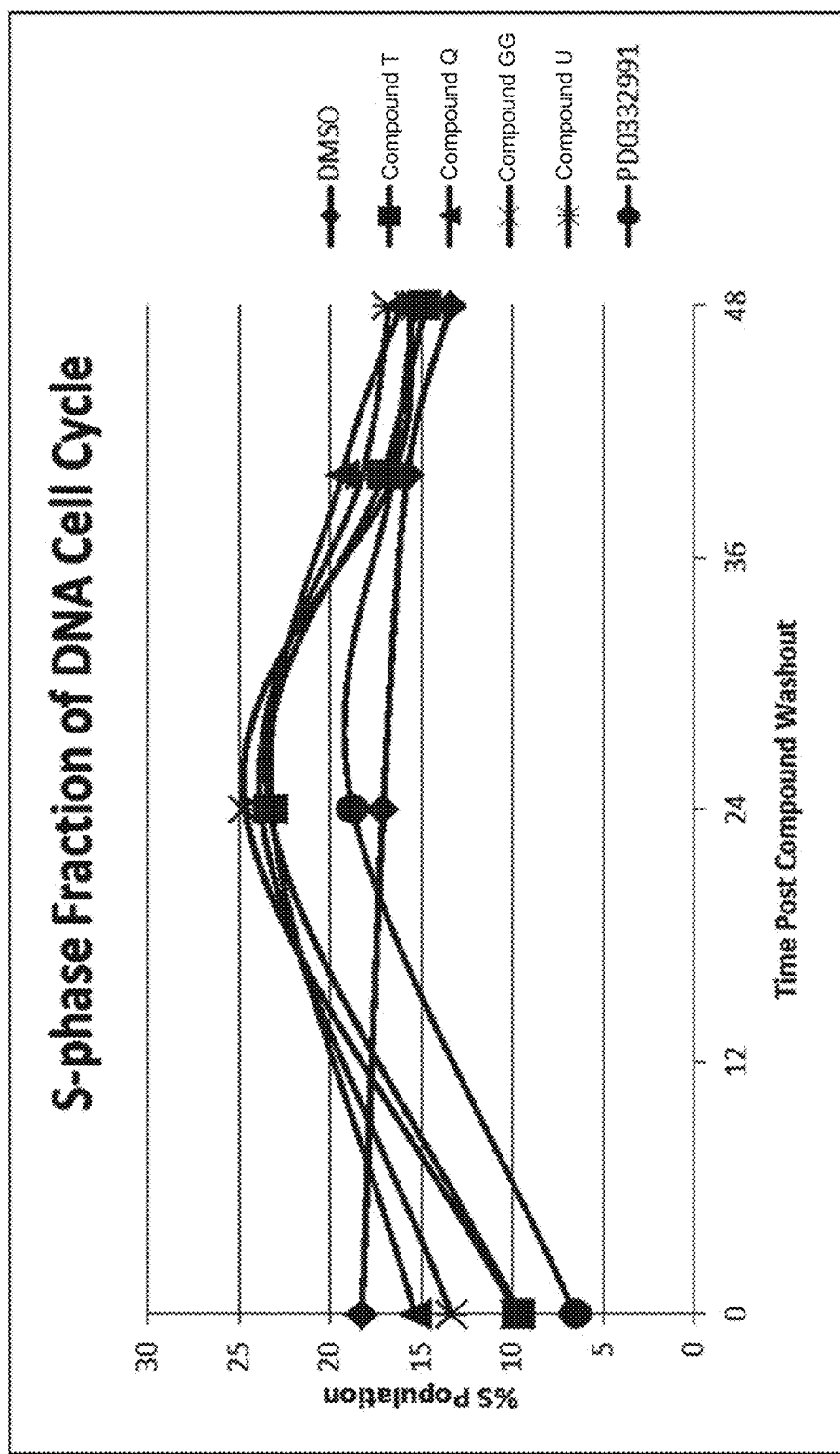
FIG. 8D is a graph of the percentage of cells in the S phase of the cell cycle vs. time after washout of the compound (hours) in human renal proximal tubule epithelial (Rb-positive) cells. These cellular wash out experiments demonstrated that the inhibitor compounds of the present invention have a short, transient G1-arresting effect in different cell types. The effect on the cell cycle following washing out of the compounds was determined at 24, 36, 40, and 48 hours. As described in Example 159, the results show that cells treated with PD0332991 (circles) took significantly longer to reach baseline levels of cell division (see cells treated only with DMSO (diamonds)), than cells treated with Compound T (squares), Compound Q (triangles), Compound GG (X), or Compound U (X with cross).
Figure 9A:
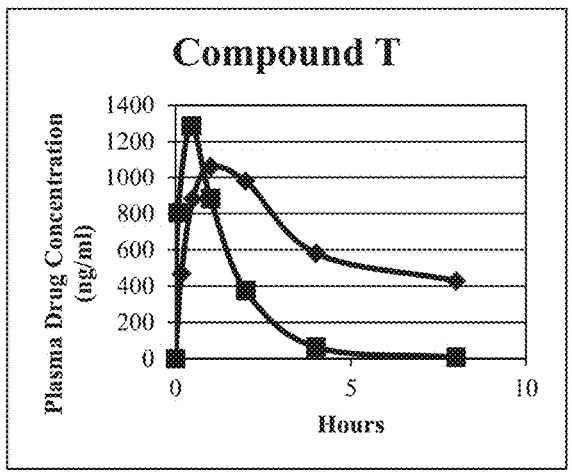
FIG. 9A is a graph of plasma drug concentration (ng/ml) vs. time after administration (hours) of Compound T.
Figure 9B:
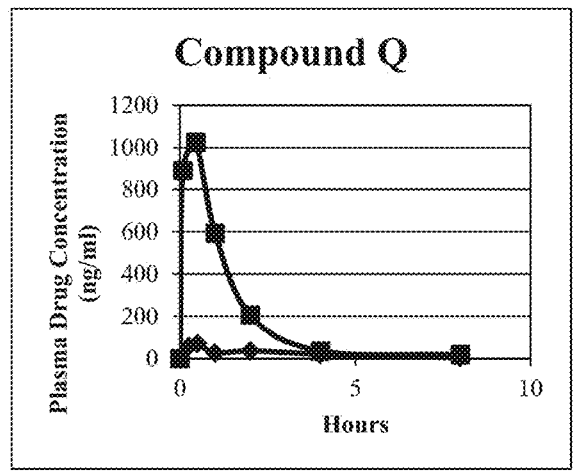
FIG. 9B is a graph of plasma drug concentration (ng/ml) vs. time after administration (hours) of Compound Q.
Figure 9C:
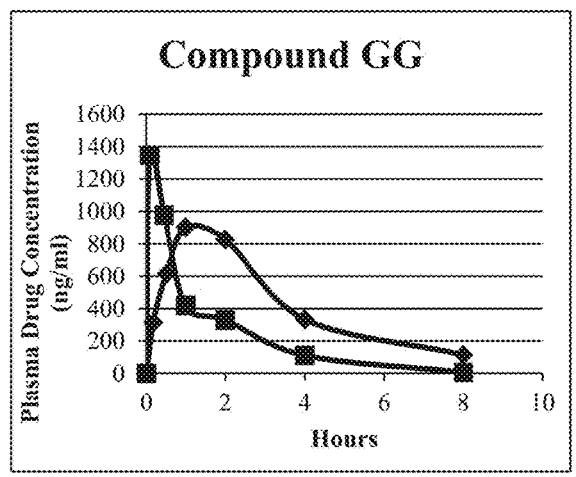
FIG. 9C is a graph of plasma drug concentration (ng/ml) vs. time after administration (hours) of compound GG.
Figure 9D:
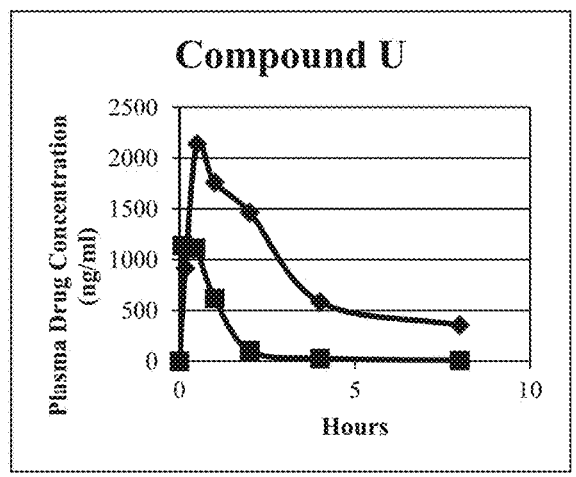
FIG. 9D is a graph of plasma drug concentration (ng/ml) vs. time after administration (hours) of Compound U. Compounds were dosed to mice at 30 mg/kg by oral gavage (diamonds) or 10 mg/kg by intravenous injection (squares). Blood samples were taken at 0, 0.25, 0.5, 1.0, 2.0, 4.0, and 8.0 hours post dosing and the plasma concentrations were determined by HPLC.

FIG. 7 is a graph of the percentage of EdU positive HSPC cells for mice treated with either PD0332991 (triangles) or compound T (upside down triangles) v. time after administration (hours) of the compound. Both compounds were administered at 150 mg/kg by oral gavage. One hour prior to harvesting bone marrow, EdU was IP injected to label cycling cells. Bone marrow was harvested at 12, 24, 36, and 48 hours after compound treatment and the percentage of EdU positive HSPC cells was determined at each time point. As seen in FIG. 7, a single oral dose of PD0332991 results in a sustained reduction in HSPCs for greater than 36 hours. In contrast, a single oral dose of Compound T results in an initial reduction of HSPC proliferation at 12 hours, but proliferation of HSPCs resumes by 24 hours after dosage of Compound T.

Example 159

Cellular Wash-Out Experiment

HS68 cells were seeded out at 40,000 cells/well in 60 mm dish on day 1 in DMEM containing 10% fetal bovine serum, 100 U/ml penicillin/streptomycin and 1× Glutamax (Invitrogen) as described (Brookes et al. EMBO J, 21(12)2936-2945 (2002) and Ruas et al. Mol Cell Biol, 27(12)4273-4282 (2007)). 24 hrs post seeding, cells are treated with compound T, compound Q, compound GG, compound U, PD0332991, or DMSO vehicle alone at 300 nM final concentration of test compounds. On day 3, one set of treated cell samples were harvested in triplicate (0 Hour sample). Remaining cells were washed two times in PBS-CMF and returned to culture media lacking test compound. Sets of samples were harvested in triplicate at 24, 40, and 48 hours.

Alternatively, the same experiment was done using normal Renal Proximal Tubule Epithelial Cells (Rb-positive) obtained from American Type Culture Collection (ATCC, Manassas, Va.). Cells were grown in an incubator at 37° C. in a humidified atmosphere of 5% CO2 in Renal Epithelial Cell Basal Media (ATCC) supplemented with Renal Epithelial Cell Growth Kit (ATCC) in 37° C. humidified incubator.

Upon harvesting cells, samples were stained with propidium iodide staining solution and samples run on Dako Cyan Flow Cytometer. The fraction of cells in G0-G1 DNA cell cycle versus the fraction in S-phase DNA cell cycle was determined using FlowJo 7.2.2 analysis.

FIG. 8 shows cellular wash-out experiments which demonstrate the inhibitor compounds of the present invention have a short, transient G1-arresting effect in different cell types. Compounds T, Q, GG, and U were compared to PD0332991 in either human fibroblast cells (Rb-positive) (FIGS. 8A & 8B) or human renal proximal tubule epithelial cells (Rb-positive) (FIGS. 8C & 8D) and the effect on cell cycle following washing out of the compounds was determined at 24, 36, 40, and 48 hours.

As shown in FIG. 8 and similar to results in vivo as shown in FIG. 5, PD0332991 required greater than 48 hours post wash out for cells to return to normal baseline cell division. This is seen in FIG. 8A and FIG. 8B as values equivalent to those for the DMSO control for either the G0-G1 fraction or the S-phase of cell division, respectively, were obtained. In contrast, HS68 cells treated with compounds of the present invention returned to normal baseline cell division in as little as 24 hours or 40 hours, distinct from PD0332991 at these same time points. The results using human renal proximal tubule epithelial cells (FIGS. 8C & 8D) also show that PD0332991-treated cells took significantly longer to return to baseline levels of cell division as compared to cells treated with compounds T, Q, GG, or U.

Example 160

Pharmacokinetic and Pharmacodynamic Properties of CDK4/6 Inhibitors

Compounds of the present invention demonstrate good pharmacokinetic and pharmacodynamic properties. Compound T, Q, GG, and U were dosed to mice at 30 mg/kg by oral gavage or 10 mg/kg by intravenous injection. Blood samples were taken at 0, 0.25, 0.5, 1.0, 2.0, 4.0, and 8.0 hours post dosing and the plasma concentration of compound T, Q, GG, or U were determined by HPLC. Compound T, GG, and U were demonstrated to have excellent oral pharmacokinetic and pharmacodynamic properties as shown in Table 5. This includes very high oral bioavailability (F (%)) of 52% to 80% and a plasma half-life of 3 to 5 hours following oral administration. Compound T, Q, GG, and U were demonstrated to have excellent pharmacokinetic and pharmacodynamic properties when delivered by intravenous administration. Representative IV and oral PK curves for all four compounds are shown in FIG. 9.

TABLE 5

Pharmacokinetic and pharmacodynamic properties of CDK4/6 inhibitors

| Mouse PK | Compound T | Compound Q | Compound GG | Compound U |
|---|---|---|---|---|
| CL (mL/min/kg) | 35 | 44 | 82 | 52 |
| Vss (L/kg) | 2.7 | 5.2 | 7.5 | 3.4 |
| $t_{1/2}$ (h) p.o. | 5 | 0.8 | 3.5 | 3 |
| $AUC_{0-inf}$ (uM*h) i.v. | 1.3 | 0.95 | 1.1 | 0.76 |
| AUC (uM*h) p.o. | 2.9 | 0.15 | 1.9 | 3.3 |
| $C_{max}$ (uM) p.o. | 2.5 | 0.16 | 1.9 | 4.2 |
| $T_{max}$ (h) p.o. | 1 | 0.5 | 1 | 0.5 |
| F (%) | 80 | 2 | 52 | 67 |

Example 161

Metabolic Stability

The metabolic stability of Compound T in comparison to PD0332991 was determined in human, dog, rat, monkey, and mouse liver microsomes. Human, mouse, and dog liver microsomes were purchased from Xenotech, and Sprague-Dawley rat liver microsomes were prepared by Absorption Systems. The reaction mixture comprising 0.5 mg/mL of liver microsomes, 100 mM of potassium phosphate, pH 7.4, 5 mM of magnesium chloride, and 1 uM of test compound was prepared. The test compound was added into the reaction mixture at a final concentration of 1 uM. An aliquot of the reaction mixture (without cofactor) was incubated in shaking water bath at 37 deg. C. for 3 minutes. The control compound, testosterone, was run simultaneously with the test compound in a separate reaction. The reaction was initiated by the addition of cofactor (NADPH), and the mixture was then incubated in a shaking water bath at 37 deg. C. Aliquots (100 µL) were withdrawn at 0, 10, 20, 30, and 60 minutes for the test compound and 0, 10, 30, and 60 minutes for testosterone. Test compound samples were immediately combined with 100 µL of ice-cold acetonitrile containing internal standard to terminate the reaction. Testosterone samples were immediately combined with 800 µL of ice cold 50/50 acetonitrile/dH2O containing 0.1% formic acid and internal standard to terminate the reaction. The samples were assayed using a validated LC-MS/MS method. Test compound samples were analyzed using the Orbitrap high resolution mass spectrometer to quantify the disappearance of parent test compound and detect the appearance of metabolites. The peak area response ration (PARR) to internal standard was compared to the PARR at time 0 to determine the percent of test compound or positive control remaining at time-point. Half-lives were calculated using GraphPad software, fitting to a single-phase exponential decay equation.

Half-life was calculated based on t1/2=0.693k, where k is the elimination rate constant based on the slope plot of natural logarithm percent remaining versus incubation time. When calculated half-life was longer than the duration of the experiment, the half-life was expressed as >the longest incubation time. The calculated half-life is also listed in parentheses. If the calculated half-life is >2× the duration of the experiment, no half-life was reported. The timely resumption of cellular proliferation is necessary for tissue repair, and therefore an overly long period of arrest is undesirable in healthy cells such as HSPCs. The characteristics of a CDK4/6 inhibitor that dictate its arresting duration are its pharmacokinetic (PK) and enzymatic half-lives. Once initiated, a G1-arrest in vivo will be maintained as long as circulating compound remains at an inhibitory level, and as long as the compound engages the enzyme. PD0332991, for example, possesses an overall long PK half-life and a fairly slow enzymatic off-rate. In humans, PD0332991 exhibits a PK half-life of 27 hours (see Schwartz, G K et al. (2011) BJC, 104:1862-1868). In humans, a single administration of PD0332991 produces a cell cycle arrest of HSPC lasting approximately one week. This reflects the 6 days to clear the compound (5 half-lives x 27 hour half-life), as well as an additional 1.5 to 2 days of inhibition of enzymatic CDK4/6 function. This calculation suggests that it takes a total of 7+ days for normal bone marrow function to return, during which time new blood production is reduced. These observations may explain the severe granulocytopenia seen with PD0332991 in the clinic.

Figure 6C:
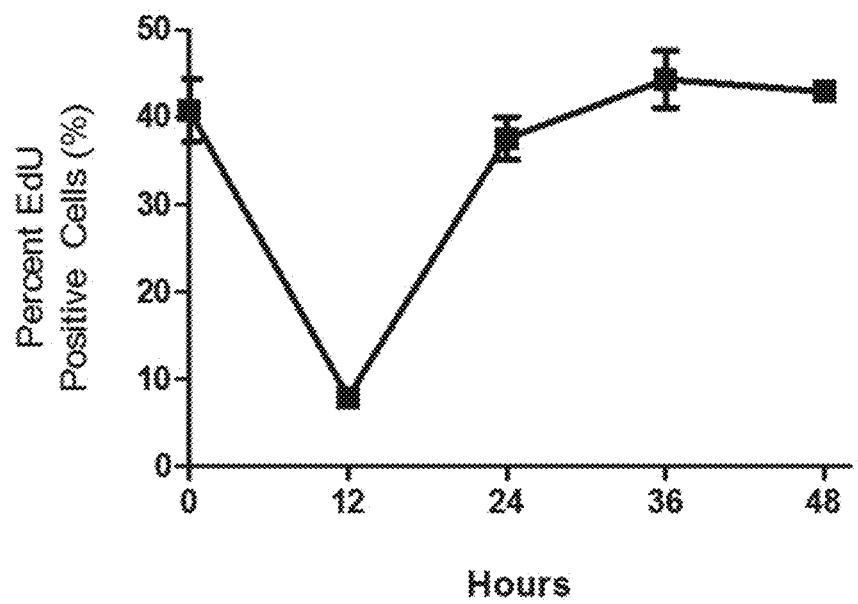
FIG. 6C is a graph of the percentage of EdU positive HSPC cells for mice treated with compound T (150 mg/kg by oral gavage) at either 12, 24, 36 and 48 hours. As described in Example 157, Compound T and GG demonstrated a reduction in EdU incorporation at 12 hours, and started to return to normal levels of cell division by 24 hours.

Further experiments were completed with Compound T and PD0332991 to compare the metabolic stability (half-life) in human, dog, rat, monkey, and mouse liver microsomes. As shown in FIG. 10, when analyzing the stability of the compounds in liver microsomes across species, the determinable half-life of Compound T is shorter in each species compared to that reported for PD0332991. Furthermore, as previously described above and in FIG. 8, it appears that PD0332991 also has an extended enzymatic half-life, as evidenced by the production of a pronounced cell cycle arrest in human cells lasting more than forty hours even after compound is removed from the cell culture media (i.e., in an in vitro wash-out experiment). As further shown in FIG. 8, removal of the compounds described herein from the culture media leads to a rapid resumption of proliferation, consistent with a rapid enzymatic off rate. These differences in enzymatic off rates translate into a marked difference in pharmacodynamic (PD) effect, as shown in FIGS. 5, 6C, and 7. As shown, a single oral dose of PD0332991 produces a 36+ hour growth arrest of hematopoietic stem and progenitor cells (HSPCs) in murine bone marrow, which is greater than would be explained by the 6 hour PK half-life of PD0332991 in mice. In contrast, the effect of Compound T is much shorter, allowing a rapid re-entry into the cell cycle, providing exquisite in vivo control of HSPC proliferation.

Example 162

Compound T Prevents Chemotherapy-Induced Cell Death, DNA Damage, and Caspase Activation In order to demonstrate that pharmacological quiescence induced by Compound T treatment affords resistance to chemotherapeutic agents with differing mechanisms of action, an in vitro model was developed using telomerized human diploid fibroblasts (tHDFs; a human foreskin fibroblast line immortalized with expression of human telomerase). These cells are highly Cdk4/6-dependent for proliferation as demonstrated by their complete G1 arrest following treatment with Cdk4/6 inhibitors (See Roberts P J, et al. Multiple Roles of Cyclin-Dependent Kinase 4/6 Inhibitors in Cancer Therapy. J Natl Cancer Inst 2012; March 21; 104(6): 476-87). Cell survival was determined by Cell TiterGlo assay per manufacturer's recommendations. For both γ-H2AX and caspase 3/7 assays, cells were plated and allowed to become adherent for 24 hours. Cells were then treated with Compound T (at indicated concentrations) or vehicle control for 16 hours, at which time the indicated chemotherapy was added to the pretreated cells. For γ-H2AX, cells were harvested for analysis 8 hours after chemotherapy exposure. For the γ-H2AX assay, cells were fixed, permeabilized, and stained with anti-γ-H2AX as per the γ-H2AX Flow Kit (Millipore) and quantitated by flow cytometry. Data was analyzed using FlowJo 2.2 software developed by TreeStar, Inc. For the in vitro caspase 3/7 assay, cells were harvested 24 hours post chemotherapy treatment. Caspase 3/7 activation was measured using the Caspase-Glo® 3/7 Assay System (Promega) per manufacturer's recommendations.

Figure 11A:
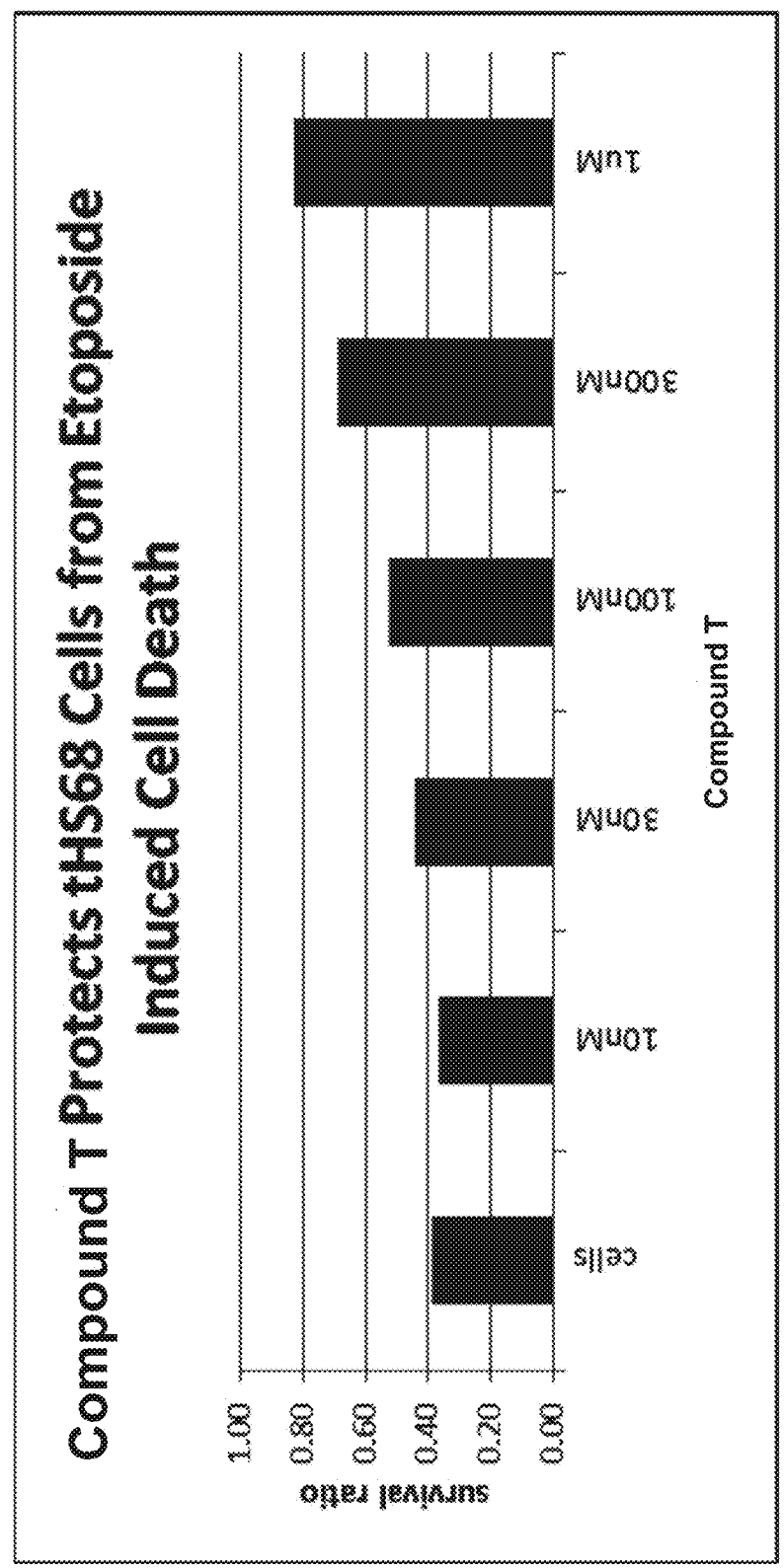
FIG. 11A is a graph of cell survival of cells treated with 5 uM etoposide vs. treatment with the indicated amount of Compound T. Surviving cells were determined at 24 hours post treatment. As described in Example 162, shows that Compound T protects tHS68 cells from chemotherapeutic induced cell death.
Figure 11B:
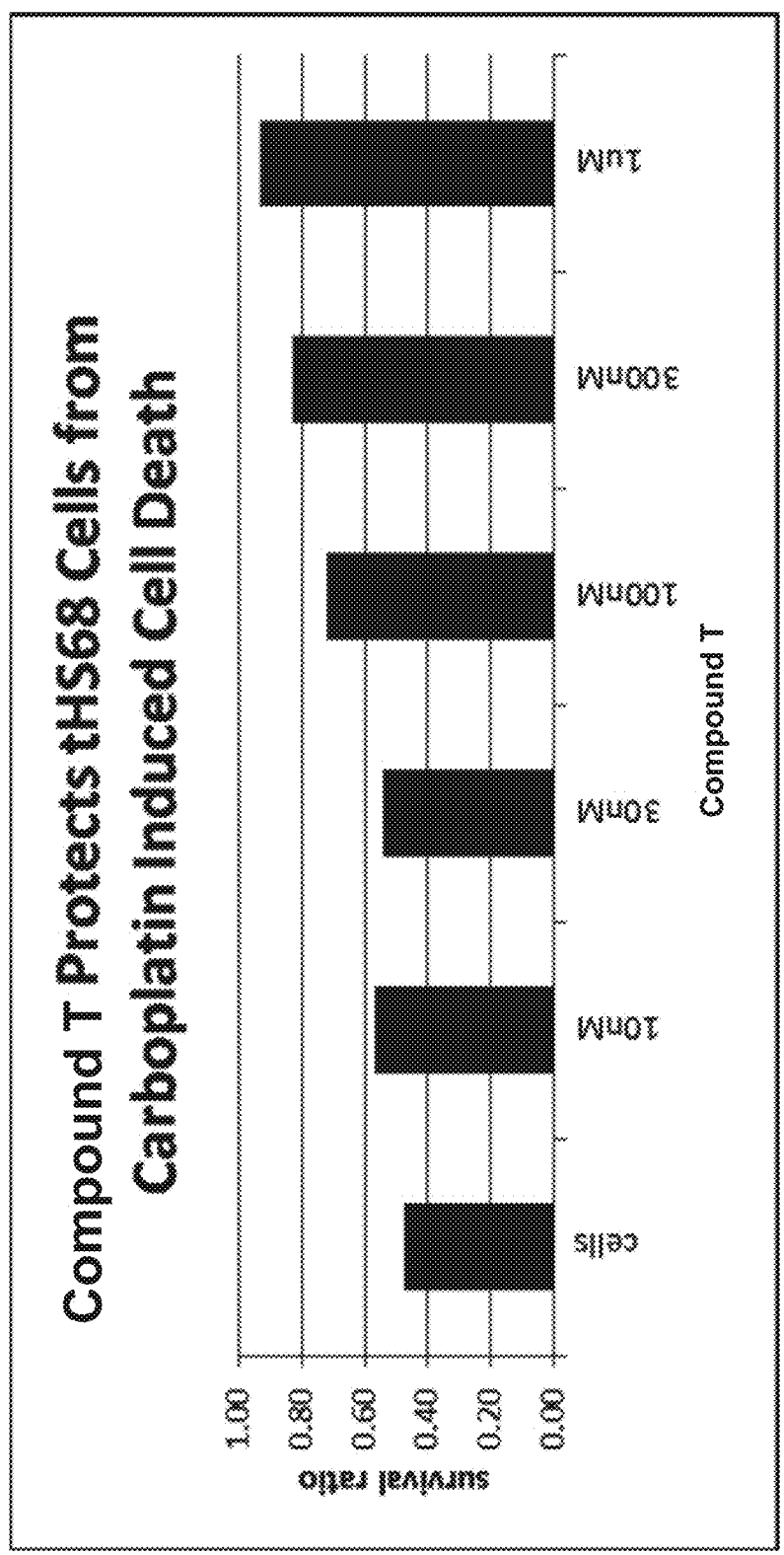
FIG. 11B is a graph of cell survival of cells treated with 100 µM carboplatin vs. treatment with the indicated amount of Compound T. Surviving cells were determined at 24 hours post treatment. As described in Example 162, Compound T protects tHS68 cells from chemotherapeutic induced cell death.

As shown in FIG. 11, Compound T provides selective protection from carboplatin and etoposide-induced cell death. Treatment of tHS68 human fibroblasts with increasing concentrations of Compound T in the presence of etoposide (5 μM; FIG. 11A) or carboplatin (100 μM; FIG. 11B) selectively induces a dose dependent cell survival as determined by Cell TiterGlo.

Figure 12A:
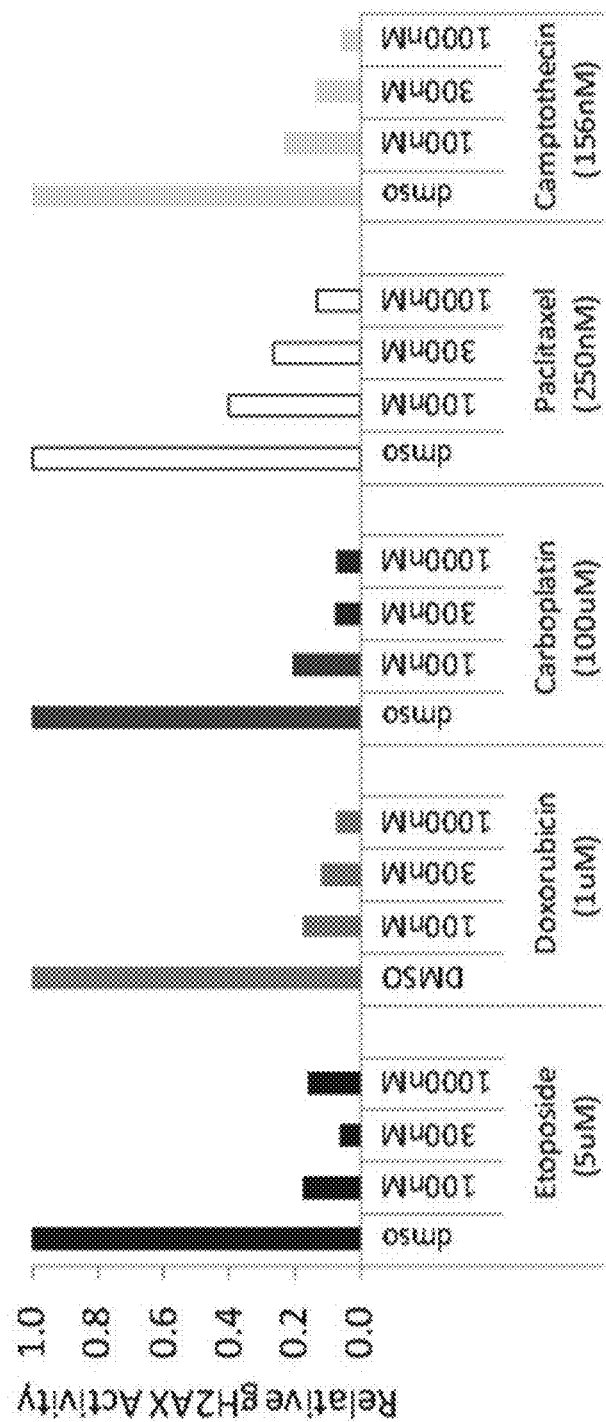
FIG. 12A is a graph of the relative H2AX activity vs. variable concentration of Compound T (nM) in HS68 cells treated with Compound T (100 nM, 300 nM, or 1000 nM) and chemotherapy (etoposide, doxorubicin, carboplatin, paclitaxel, or camptothecin). Cdk4/6-dependent HS68 cells were treated with the indicated doses of Compound T and chemotherapy. H2AX foci formation was measured to evaluate chemotherapy-induced DNA damage. As described in Example 162, cells treated with Compound T and various chemotherapeutic compounds were protected from DNA damage induced by the chemotherapy.
Figure 12B:
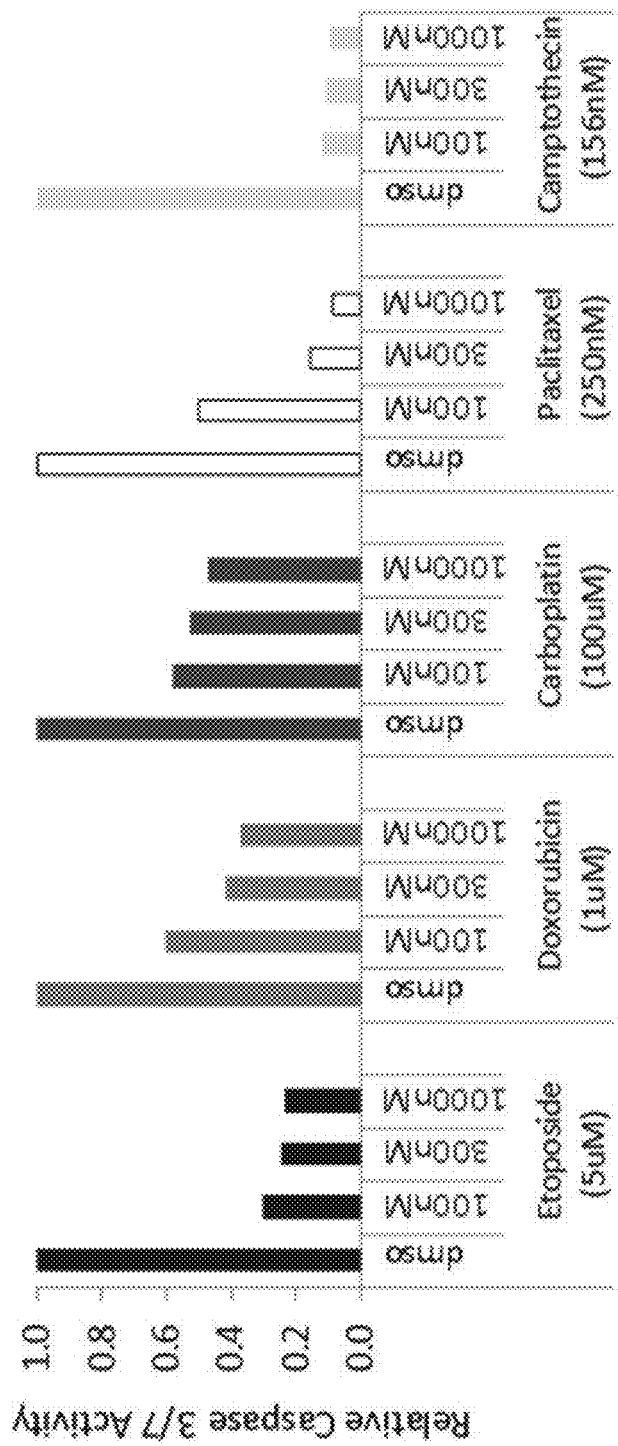
FIG. 12B is a graph of the relative Caspase 3/7 activity vs. variable concentration of Compound T (nM) in HS68 cells treated with Compound T (100 nM, 300 nM, or 1000 nM) and chemotherapy (etoposide, doxorubicin, carboplatin, paclitaxel, or camptothecin). Cdk4/6-dependent HS68 cells were treated with the indicated doses of Compound T and chemotherapy. Caspase 3/7 activity was measured to evaluate chemotherapy-induced apoptosis. As described in Example 162, cells treated with Compound T and various chemotherapeutic compounds were protected from caspase 3/7 activation induced by the chemotherapy.

Treatment with Compound T prior to treatment with several DNA damaging agents (e.g., carboplatin, doxorubicin, etoposide, camptothecin) or an anti-mitotic (paclitaxel) attenuated DNA damage as measured by γ-H2AX formation (FIG. 12A). Additionally, treatment of tHDF cells with Compound T prior to carboplatin, doxorubicin, etoposide, camptothecin, and paclitaxel exposure elicited a robust decrease in caspase 3/7 activation in a dose-dependent manner (FIG. 12B). These data show that a transient cell cycle arrest in G1, induced by Cdk4/6 inhibition, decreases the toxicity of a variety of commonly used cytotoxic chemotherapy agents associated with myelosuppression in Cdk4/6-sensitive cells.

Example 163

Compound T Inhibits Proliferation of Hematopoietic Stem and/or Progenitor Cells (HSPCs)

To characterize the effects of Compound T treatment on proliferation of the different mouse hematopoietic cells, 8-week-old female C57B1/6 mice were given a single dose of vehicle alone (20% Solutol) or Compound T (150 mg/kg) by oral gavage. Ten-hours later, all mice were given a single i.p. injection of 100 mcg EdU (5-ethynyl-2'-deoxyuridine) to label cells in S-phase of the cell cycle. All treated mice were euthanized 2 hours after EdU injection, bone marrow cells were harvested and processed for flow cytometric analysis of EdU-incorporation (FIG. 13).

Figure 13:
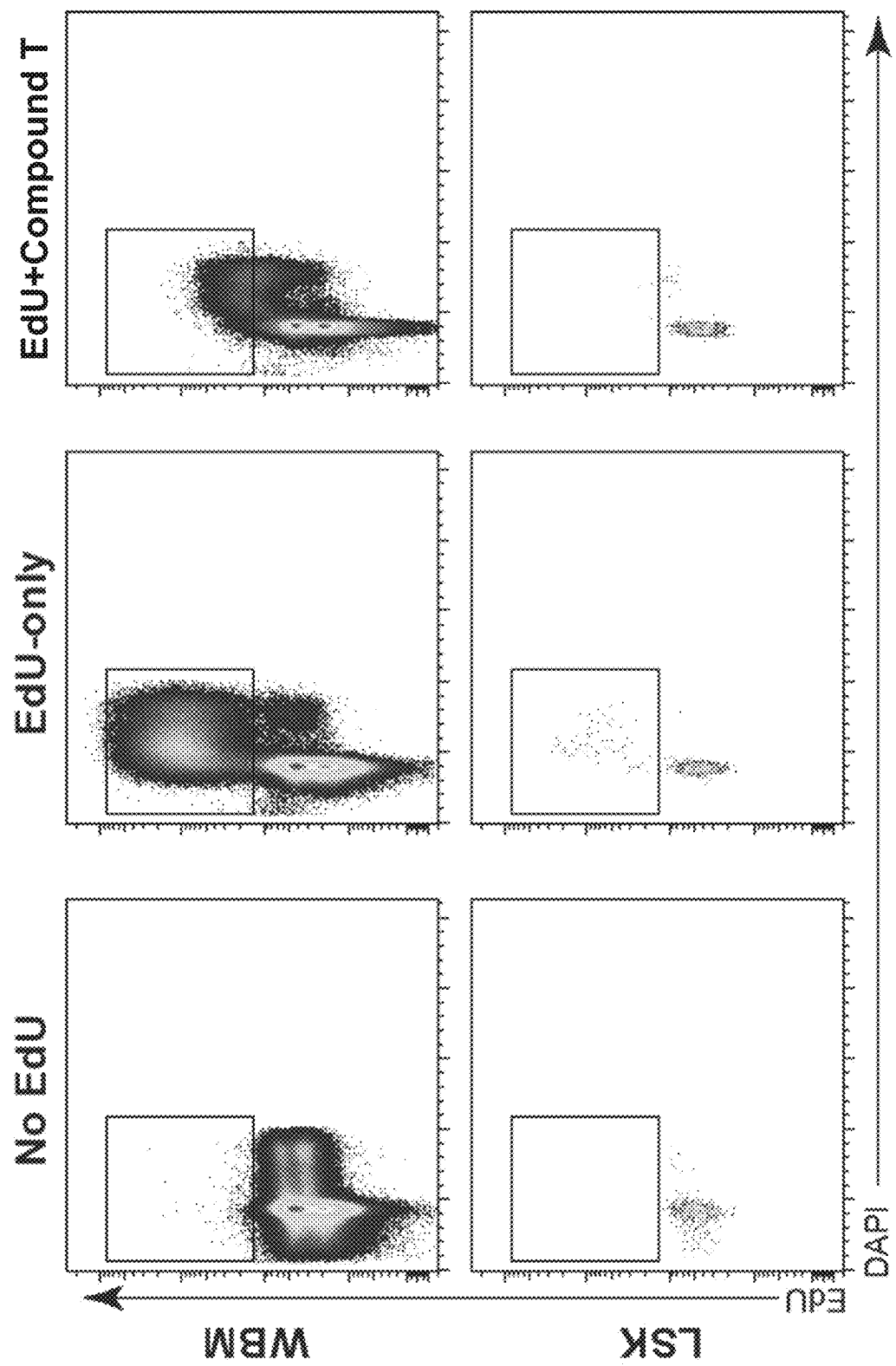
FIG. 13 is a series of contour plots showing proliferation (as measured by EdU incorporation after 12 hours) vs. cellular DNA content (as measured by DAPI staining). Representative contour plots show proliferation in WBM (whole bone marrow; top) and HSPCs (hematopoietic stem and progenitor cells; LSK; bottom), as measured by EdU incorporation after 12 hours of no treatment, EdU treatment only, or EdU plus Compound T treatment. As described in Example 163, Compound T reduces proliferation of whole bone marrow and hematopoietic stem and/or progenitor cells.

In FIG. 13, representative contour plots show proliferation in WBM (whole bone marrow; top) and HSPCs (hematopoietic stem and progenitor cells; LSK; bottom), as measured by EdU incorporation for cells with no treatment, EdU treatment only, or EdU plus Compound T treatment. Compound T was found to reduce proliferation of whole bone marrow and hematopoietic stem and progenitor cells.

Figure 14A:
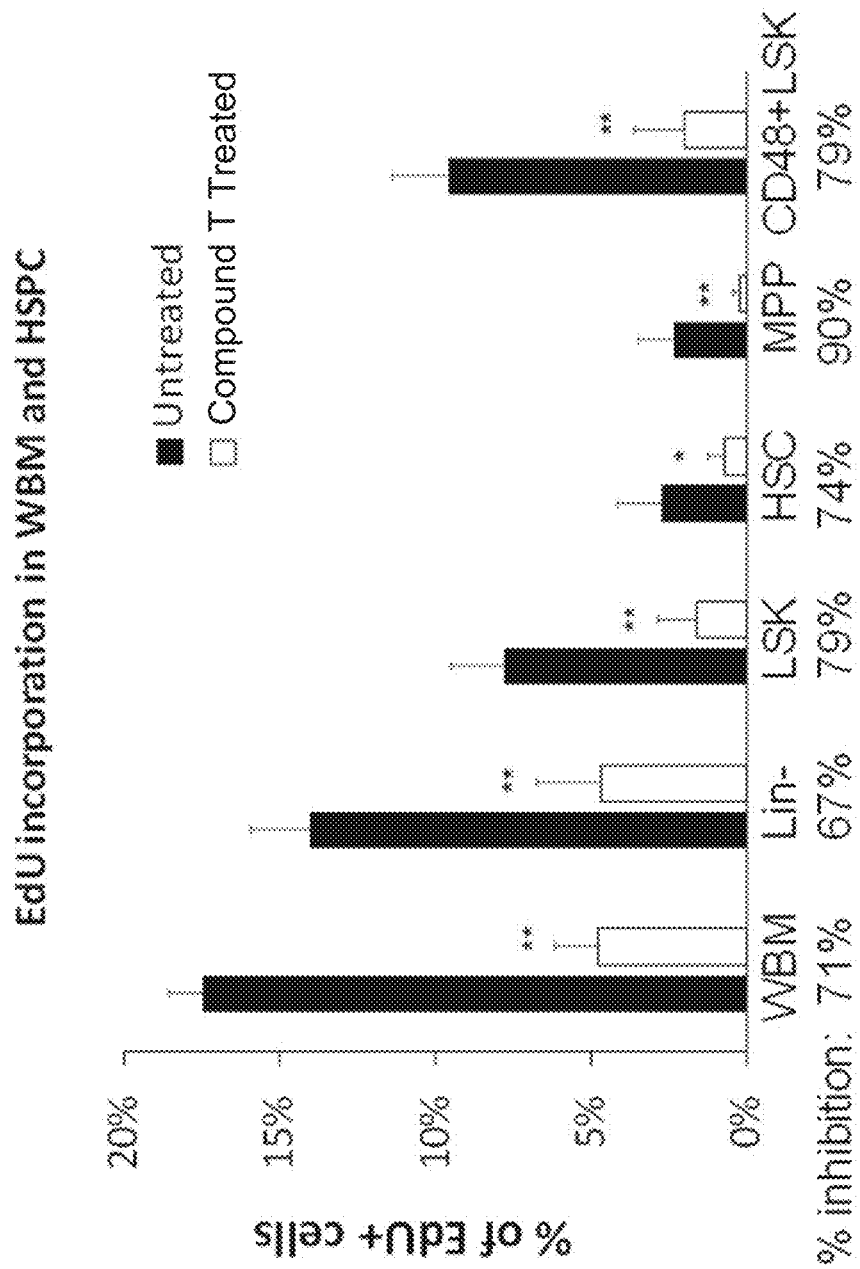
FIG. 14A is a graph of the percentage of EdU-positive cells in whole bone marrow (WBM) and various hematopoietic stem and progenitor cells (Lin−, LSK, HSC, MPP, or CD28+LSK cell lineages) treated with Compound T (open bars) or untreated (solid bars). As described in Example 163, treatment with Compound T inhibits proliferation of WBM and all HSPC lineages tested. *P<0.05, **P<0.01.

Compared to vehicle-treated mice, Compound T treated mice showed significantly less EdU-positive (EdU$^+$) cells in all hematopoietic lineages analyzed. The reduction in EdU$^+$ cell frequency is most likely due to reduced S-phase entry, which is consistent with the fact that Compound T potently inhibits Cdk4/6 activity. Overall, Compound T treatment caused ~70% reduction of EdU$^+$ cell frequency in unfractionated whole bone marrow cells (See FIG. 13 and FIG. 14). In the hematopoietic stem and progenitor cells (HSPC), Compound T treatment resulted in potent cell cycle arrest of hematopoietic stem cells (HSC, 74% inhibition), the most primitive cells in the entire hematopoietic lineage hierarchy, as well as multipotent progenitors (MPP, 90% inhibition), the immediate downstream progeny of HSCs (FIG. 14A).

Figure 14B:
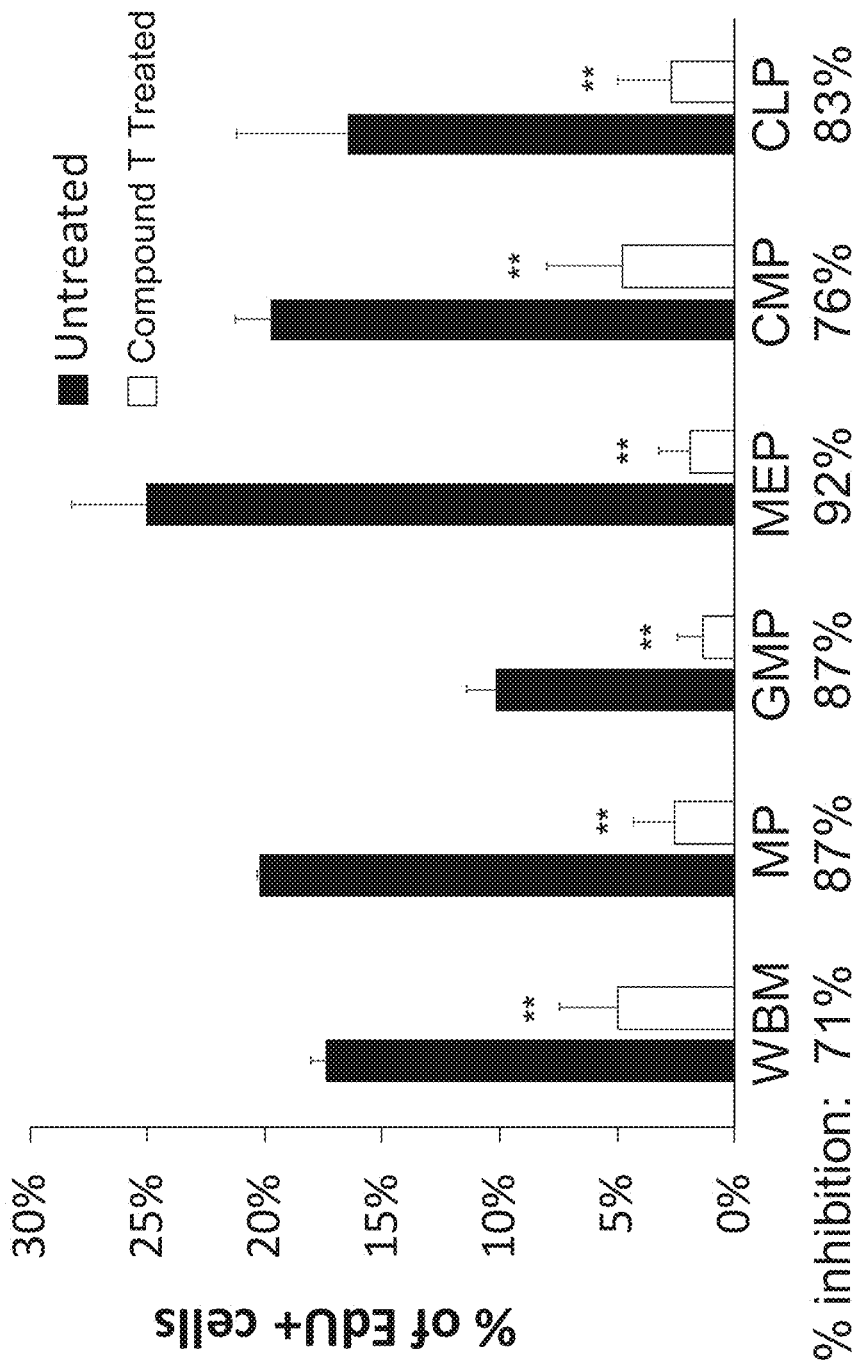
FIG. 14B is a graph of the percentage of EdU-positive cells in whole bone marrow (WBM) and various lineage restricted progenitors (MP, GMP, MEP, CMP, or CLP cell lineages) treated with Compound T (open bars) or untreated (solid bars). As described in Example 163, treatment with Compound T inhibits proliferation of WBM and all lineage restricted progenitors tested. *P<0.05, **P<0.01.

As shown in FIG. 14B, further down the lineage differentiation hierarchy, proliferation of the lineage restricted myeloid (CMP, GMP and MEP) and lymphoid progenitors (CLP) were also significantly inhibited by Compound T, showing between a 76-92% reduction in EdU$^+$ cell frequency.

Example 164

Compound T Inhibits Proliferation of Differentiated Hematopoietic Cells

Figure 15A:
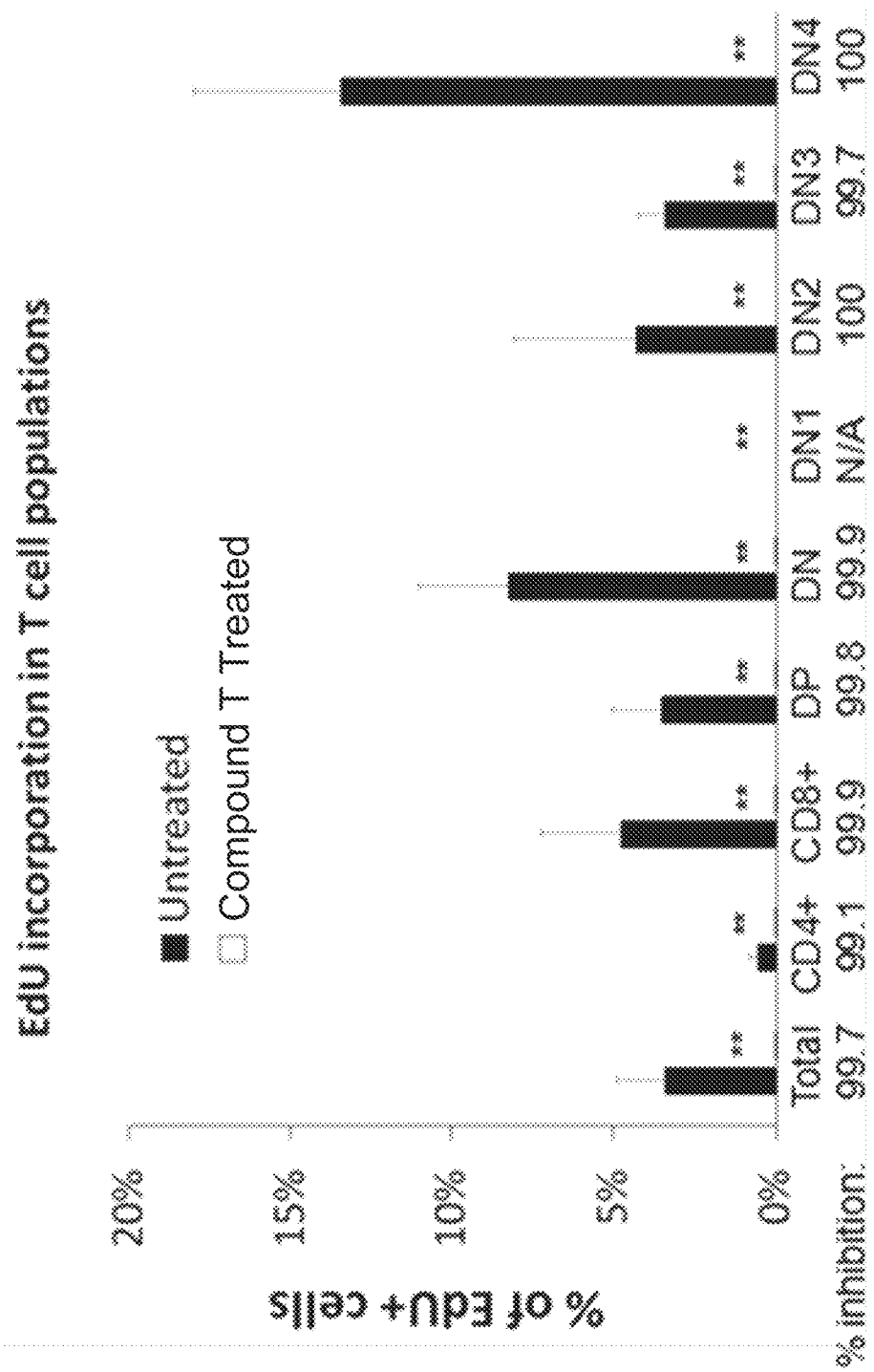
FIG. 15A is a graph of the percentage of EdU-positive cells in T cell populations (Total, CD4+, CD8+, DP, DN, DN1, DN2, DN3, or DN4) treated with Compound T (open bars) or untreated (solid bars). As described in Example 164, treatment with Compound T inhibits proliferation of the CD4+, CD8+, DP, DN, DN1, DN2, DN3, or DN4 T cell populations. *P<0.05, **P<0.01.
Figure 15B:
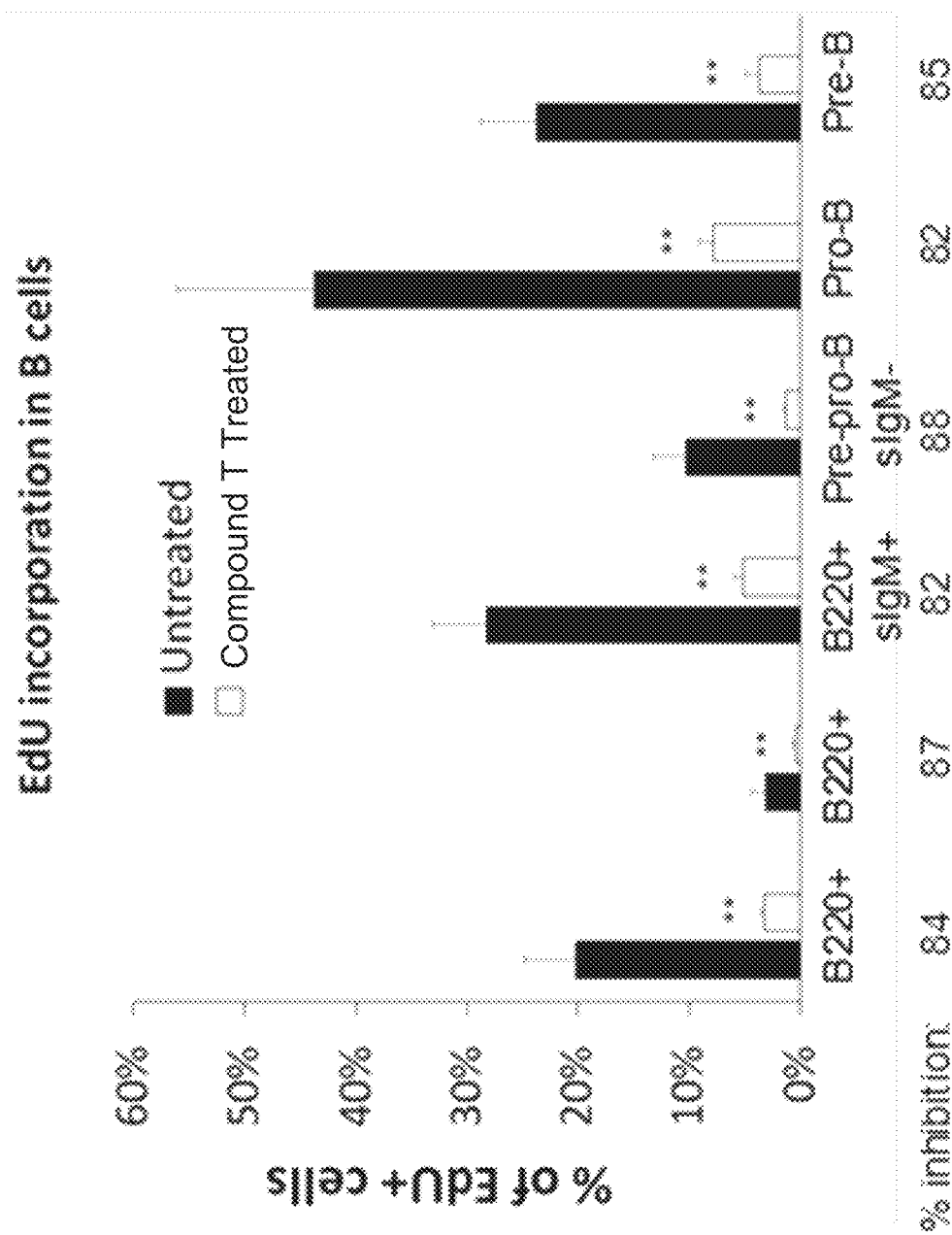
FIG. 15B is a graph of the percentage of EdU-positive cells in B cell populations (B220+, B220+sIgM+, Pre-pro-B sIgM-, Pro-B, Pre-B) treated with Compound T (open bars) or untreated (solid bars). As described in Example 164, treatment with Compound T inhibits proliferation of the various B cell populations (B220+, B220+sIgM+, Pre-pro-B sIgM-, Pro-B, and Pre-B). *P<0.05, **P<0.01.
Figure 15C:
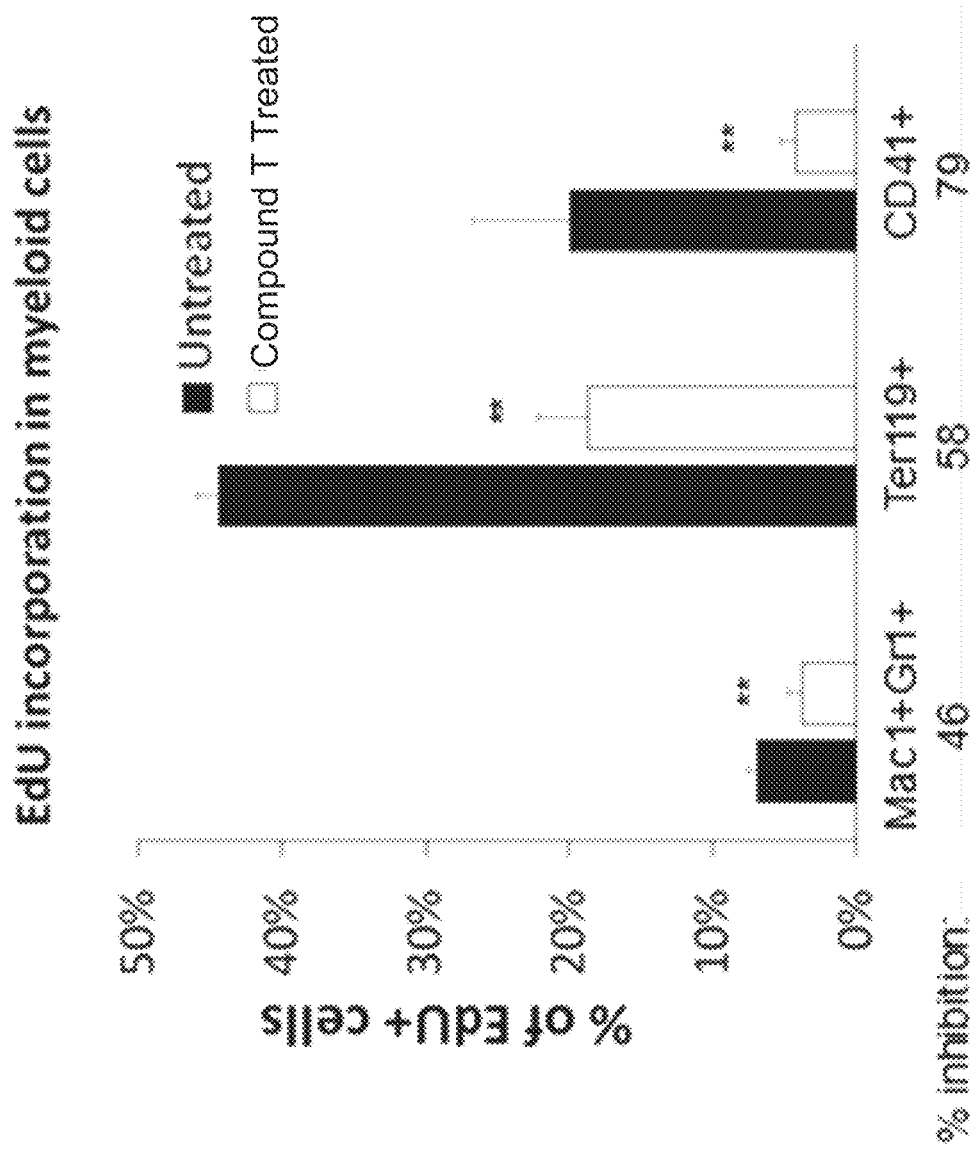
FIG. 15C is a graph of the percentage of EdU-positive cells in myeloid cell populations (Mac1+Gr1+, Ter119+, or CD41+) treated with Compound T (open bars) or untreated (solid bars). As described in Example 164, treatment with Compound T inhibits proliferation of the Mac1+Gr1+, Ter119+, or CD41+ myeloid cell populations. *P<0.05, **P<0.01.

Using the same experimental protocol as discussed in Example X above and shown in FIGS. 13 and 14, the effects of Compound T on the proliferation of differentiated hematopoietic cells was investigated. The resulting effect of Compound T in differentiated hematopoietic cells was more variable than that seen in HSPCs. While T and B cell progenitors are highly sensitive to Compound T (>99% and >80% reduction in EdU$^+$ cell frequencies respectively), proliferation of differentiated myeloerythroid cells are more resistant to Compound T, with Mac1$^+$G1$^+$ myeloid cells showing 46% reduction in EdU$^+$ cell frequency, and Ter119$^+$ erythroid cells showing 58% reduction in EdU$^+$ cell frequency (FIG. 15). Together, these data suggest that while all hematopoietic cells are sensitive to Compound T-induced cell cycle arrest, the degree of inhibition varies among different cell lineages, with myeloid cells showing a smaller effect of Compound T on cell proliferation than seen in the other cell lineages.

Example 165

Compound GG Protects Bone Marrow Progenitors

Figure 16:
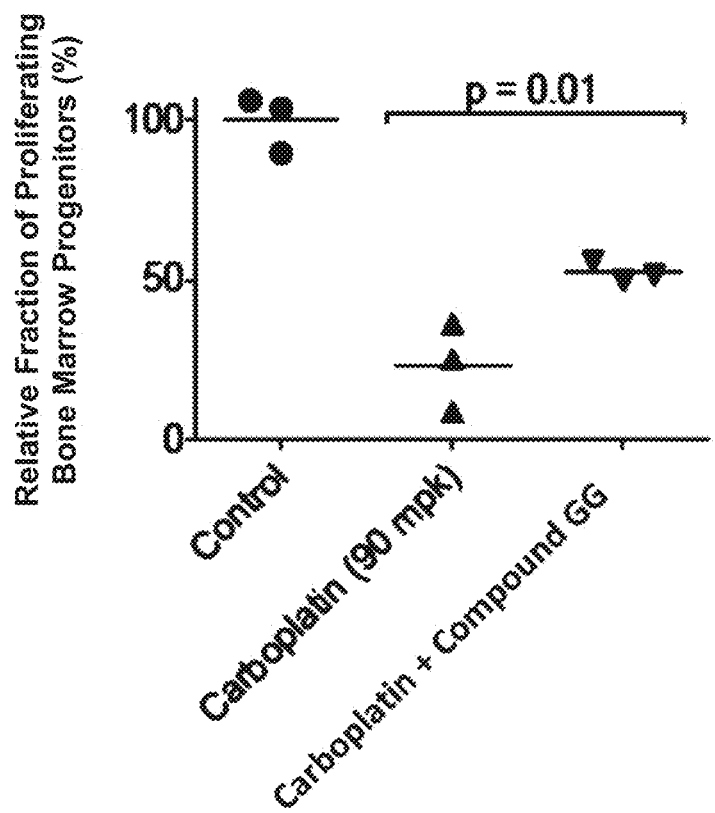
FIG. 16 shows the pharmacodynamic assessment of Compound GG in the bone marrow. To assess the effect of transient CDK4/6 inhibition by Compound GG on carboplatin-induced cytotoxicity in the bone marrow, FVB/n mice (n=3 per group) were treated with vehicle control, 90 mg/kg carboplatin by intraperitoneal injection, or 150 mg/kg Compound GG by oral gavage plus 90 mg/kg carboplatin by intraperitoneal injection. 24 hours after treatment bone marrow was harvested and the percent of cycling bone marrow progenitors was measured by EdU incorporation as explained earlier.

To assess the effect of transient CDK4/6 inhibition by Compound GG on carboplatin-induced cytotoxicity in the bone marrow, FVB/n mice (n=3 per group) were treated with vehicle control, 90 mg/kg carboplatin by intraperitoneal injection, or 150 mg/kg Compound GG by oral gavage plus 90 mg/kg carboplatin by intraperitoneal injection. 24 hours after treatment bone marrow was harvested and the percent of cycling bone marrow progenitors was measured by EdU incorporation as explained earlier. As shown in FIG. 16, administration of Compound GG at the same time as carboplatin administration results in a significant protection of bone marrow progenitors. EdU incorporation in control animals was normalized to 100% and compared to EdU incorporation for bone marrow from carboplatin treated animals or carboplatin and Compound GG treated animals.

Example 166

Compound T Decreases 5FU-Induced Myelosuppression

To determine the ability of Compound T to modulate chemotherapy-induced myelosuppression, a well characterized single-dose 5-fluorouracil (5FU) regimen, known to be highly myelosuppressive in mice, was utilized. FVB/n female mice were given single oral doses of vehicle or Compound T at 150 mg/kg, followed 30 minutes later by a single intraperitoneal dose of 5FU at 150 mg/kg. Complete blood cell counts were measured every two days starting on day six.

Figures 17A, 17B:
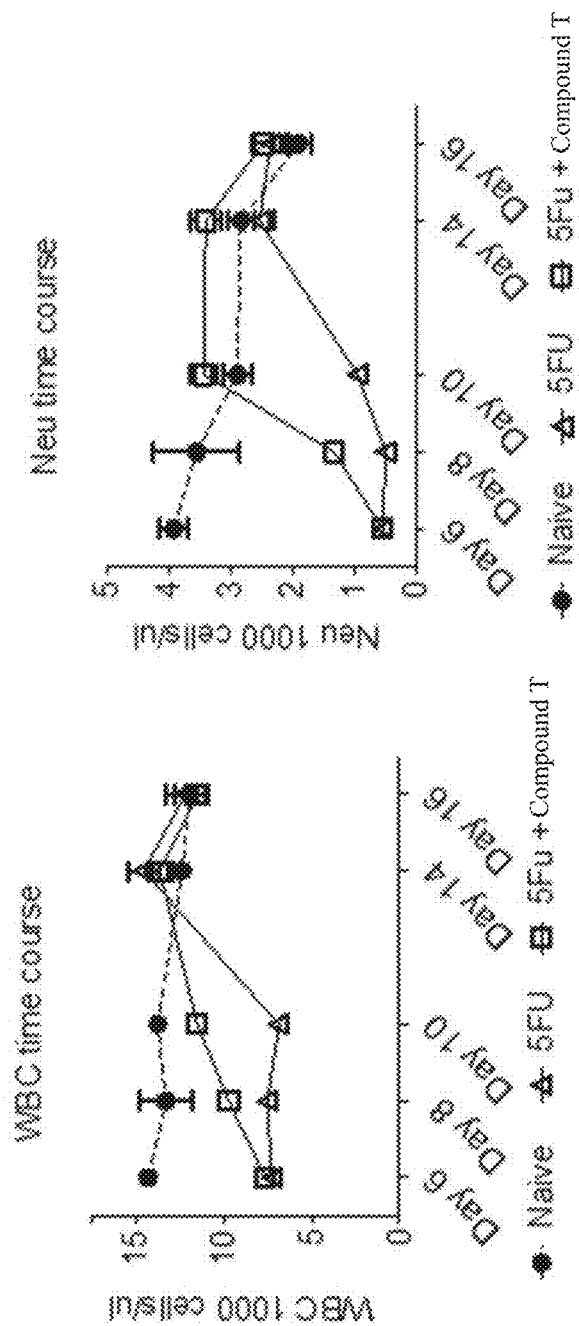
FIG. 17A is a graph of whole blood cell counts vs. time (days) after administration of 5-fluoruracil (5FU) (triangles), 5FU plus Compound T (squares), or untreated control (circles). FVB wild-type mice were treated with Compound T (150 mg/kg) or vehicle control by oral gavage thirty minutes prior to administration of 5-flurouracil (5FU) 150 mg/kg by intraperitoneal injection. Complete blood cell counts were measured every two days starting on day six. As described in Example 166, whole blood cells recover more rapidly from chemotherapy (5FU) when pretreated with Compound T.
FIG. 17B is a graph of neutrophil cell counts vs. time (days) after administration of 5-fluoruracil (5FU) (triangles), 5FU plus Compound T (squares), or untreated control (circles). Experiments were conducted as described in FIG. 17A. As described in Example 166, neutrophils recover more rapidly from chemotherapy (5FU) when pretreated with Compound T.
Figures 17E, 17F:
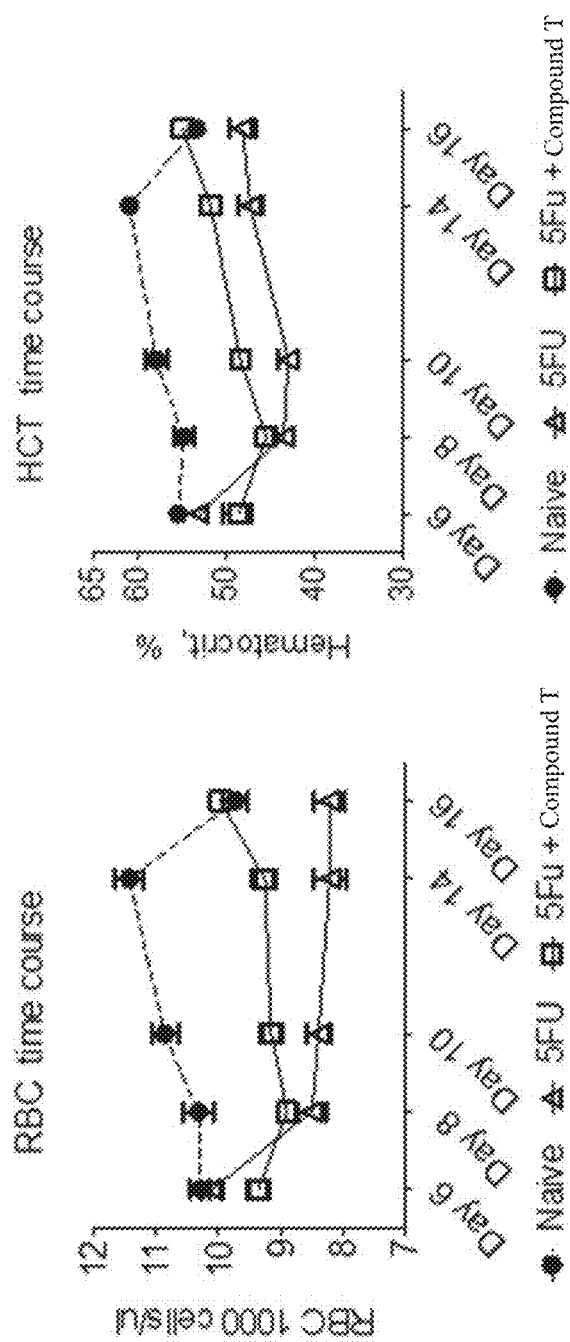
FIG. 17E is a graph of red blood cell counts vs. time (days) after administration of 5-fluoruracil (5FU) (triangles), 5FU plus Compound T (squares), or untreated control (circles). Experiments were conducted as described in FIG. 17A. As described in Example 166, red blood cells recover more rapidly from chemotherapy (5FU) when pretreated with Compound T.
FIG. 17F is a graph of hematocrit (%) vs. time (days) after administration of 5-fluoruracil (5FU) (triangles), 5FU plus Compound T (squares), or untreated control (circles). Experiments were conducted as described in FIG. 17A. As described in Example 166, hematocrit percentage recovers more rapidly from chemotherapy (5FU) when pretreated with Compound T.

Co-administration of Compound T positively impacted recovery of all hematopoietic lineages from 5-FU induced myelosuppression. FIG. 17 demonstrates the time course of recovery of different blood cell types in mice treated with Compound T or vehicle control prior to 5FU administration. It was determined that in each hematopoietic cell lineage tested (whole blood cells, neutrophils, lymphocytes, platelets, and red blood cells), Compound T provided a more rapid recovery of that cells treated only with 5FU. These data show that Compound T treatment likely decreases 5FU-induced DNA damage in HSPCs, leading to accelerated blood count recovery post-chemotherapy.

FIG. 18 shows the data from day 14 of the myelosuppression studies described above and shown in FIG. 17. Complete blood cell counts were analyzed on day 14. FIG. 18 shows the results for white blood cells (FIG. 18A), neutrophils (FIG. 18B), lymphocytes (FIG. 18C), red blood cells (FIG. 18D), and platelets (FIG. 18E). In all cases, Compound T when administered with 5FU resulted in a significant protection of each cell type at Day 14 as compared to the myelosuppressive effect of 5FU treatment alone.

Example 167

Compound T Decreases 5FU-Induced Myelosuppression Through Repeated Cycles of 5FU Treatment To determine the ability of Compound T to modulate chemotherapy-induced myelosuppression, a well characterized 5-fluorouracil (5FU) regimen, known to be highly myelosuppressive in mice was utilized. 8-week-old female C57B1/6 mice were given a single oral dose of vehicle (20% Solutol) or Compound T at 150 mg/kg followed 30 minutes later by an intraperitoneal dose of 5FU at 150 mg/kg. This was repeated every 21 days for 3 cycles. Blood samples were taken for hematology analysis on Day 10 of Cycles 1-3.

Figure 19E:
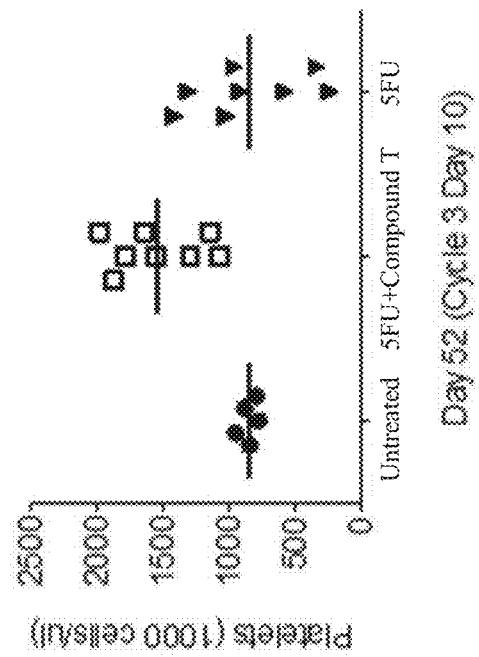
FIG. 19E is a graph of platelets (1000 cells/ul) in untreated mice (circles), 5-fluoruracil (5FU) plus Compound T treated mice (squares), or 5-FU treated mice (triangles) at Cycle 3, Day 10 (Day 52). Experiments were conducted as described in FIG. 19A. As described in Example 167, platelet levels are elevated in recovery from chemotherapy (5FU) when treated with several cycles of Compound T.
Figure 19D:
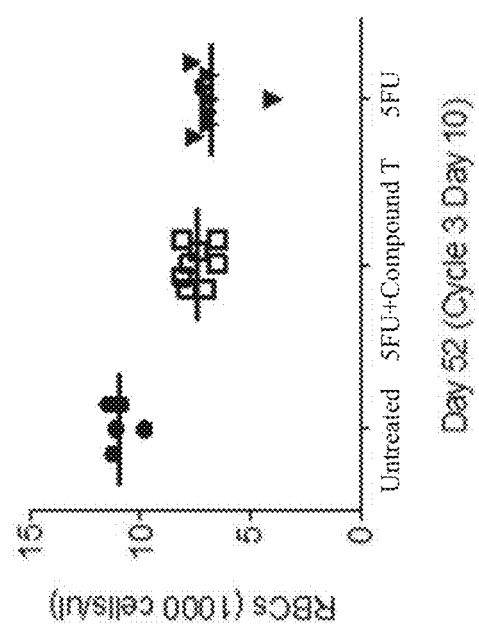
FIG. 19D is a graph of red blood cells (1000 cells/ul) in untreated mice (circles), 5-fluoruracil (5FU) plus Compound T treated mice (squares), or 5-FU treated mice (triangles) at Cycle 3, Day 10 (Day 52). Experiments were conducted as described in FIG. 19A. As described in Example 167, red blood cells show an improved recovery from chemotherapy (5FU) when treated with several cycles of Compound T.

Co-administration of Compound T reduced the myelosuppression on Day 10 of the third cycle (FIG. 19), as well as other cycles (data not shown). In accordance with the single-dose study described above, these data show that Compound T treatment likely decreases 5FU-induced DNA damage in HSPCs, leading to improved hematopoietic blood cell counts.

Example 168

DNA Cell Cycle Analysis in Human Renal Proximal Tubule Cells

Figure 20:
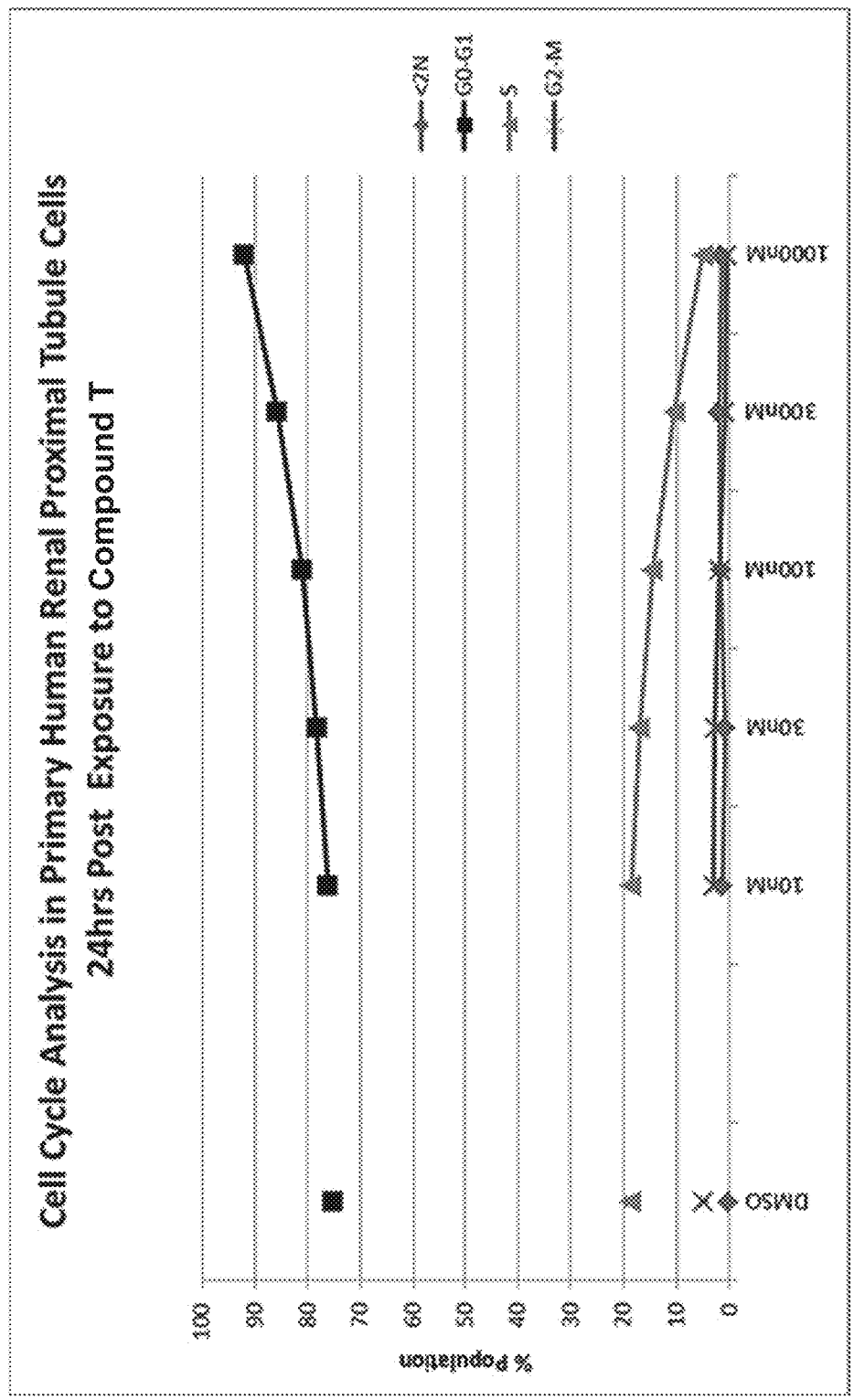
FIG. 20 is a graph of the percentage of cells in G2-M phase (X), S phase (triangles), G0-G1 phase (squares), or <2N (diamonds) vs. variable concentration (nM) of compound T in human renal proximal tubule cells. The cells were treated with the indicated concentrations of Compound T for 24 hours. Following treatment of Compound T, cells were harvested and analyzed for cell cycle distribution. As described in Example 168, human renal proximal tubule cells show a clean G1 arrest accompanied by a corresponding decrease in the number of cells in S-phase.

To test the ability of Cdk4/6 inhibitors to induce a clean G1-arrest in non-hematopoietic cells, G1 arrest was examined in human renal proximal tubule cells. The cells were treated with Compound T in a dose dependent manner for 24 hours. At the conclusion of the experiment, cells were harvested, fixed, and stained with propidium iodide (a DNA intercalator), which fluoresces strongly red (emission maximum 637 nm) when excited by 488 nm light. Samples were run on Dako Cyan flow cytometer. Data were analyzed using FlowJo 2.2 software developed by TreeStar, Inc. Assays were run in triplicate, and error bars were not detectable. As seen in FIG. 20, results show that Compound T induces a robust G1 cell cycle arrest in human renal proximal tubule cells, as nearly all cells are found in the G0-G1 phase upon treatment with increasing amounts of Compound T.

Example 169

Figure 21:
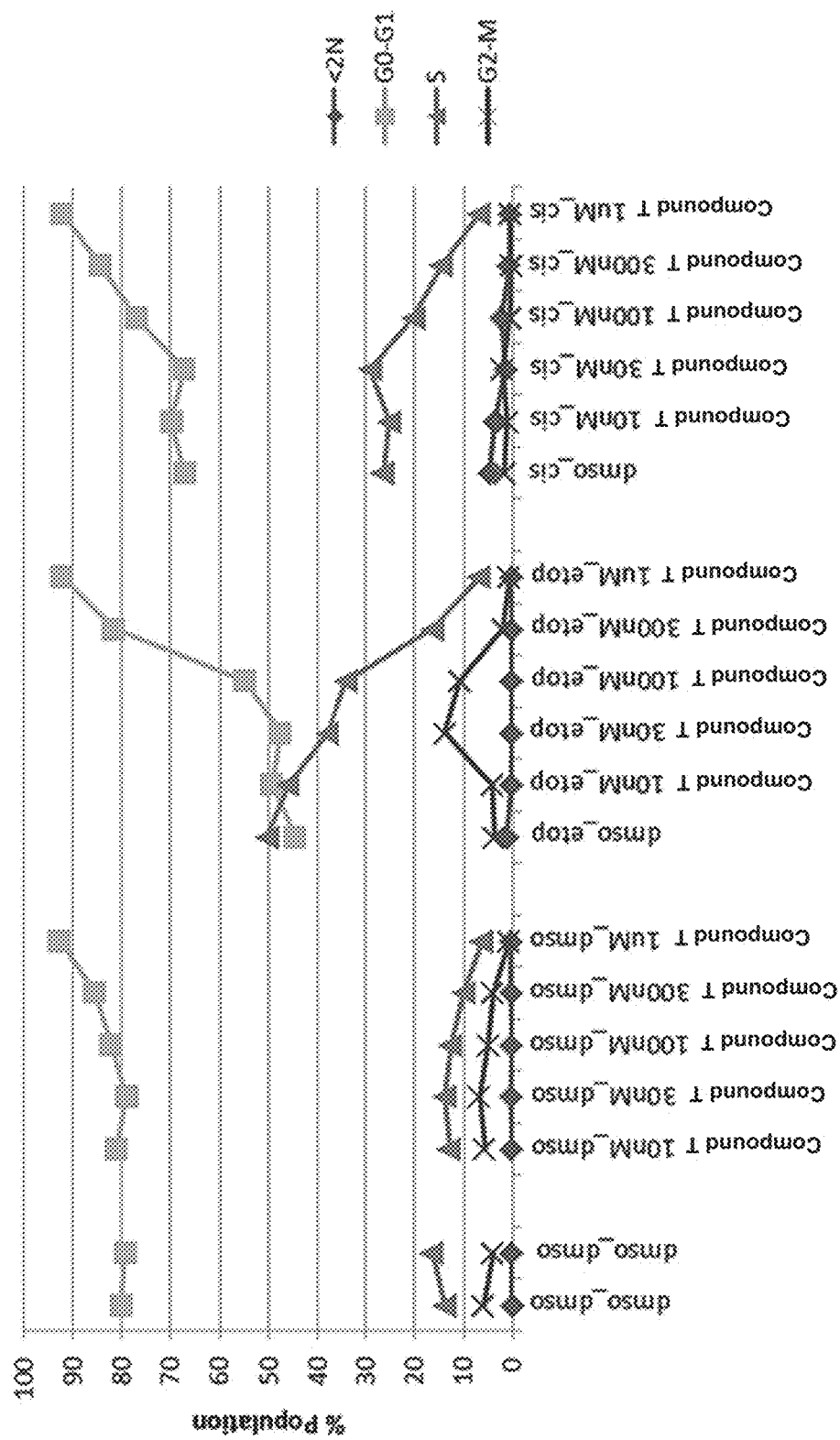
FIG. 21 is a graph of the percentage of cells in G2-M phase (X), S phase (triangles), G0-G1 phase (squares), or <2N (diamonds) vs. variable concentration (nM) of Compound T in human renal proximal tubule cells treated with DMSO, etoposide, or cisplatin. The cells were treated with the indicated concentrations of Compound T for 24 hours in combination with DMSO, etoposide, or cisplatin. Following treatment of Compound T, cells were harvested and analyzed for cell cycle distribution. As described in Example 169, treatment of human renal proximal tubule cells with Compound T protects these cells from chemotherapy induced damage by etoposide and cisplatin.

Compound T Protects Renal Proximal Tubule Epithelial Cells from Chemotherapy-Induced DNA Damage The ability of Cdk4/6 inhibitors to protect human renal proximal tubule cells from chemotherapy induced DNA damage was analyzed using etoposide and cisplatin. The cells were treated with Compound T in a dose dependent manner (10 nM, 30 nM, 100 nM, 300 nM, or 1000 nM). At the conclusion of the experiment, cells were harvested, fixed, and stained with propidium iodide (a DNA intercalator), which fluoresces strongly red (emission maximum 637 nm) when excited by 488 nm light. Samples were run on Dako Cyan flow cytometer. Data were analyzed using FlowJo 2.2 software developed by TreeStar, Inc. As seen in FIG. 21, results show that Compound T protects renal proximal tubule epithelial cells from chemotherapy induced DNA damage, as increasing dosages of Compound T in combination with etoposide or cisplatin cause a decrease in the percentage of S-phase cells, with a corresponding rise in the percentage of cells in the G0-G1 phase.

Example 170

Compound T Prevents Chemotherapy-Induced DNA Damage and Caspase Activation in Human Renal Proximal Tubule Cells In order to demonstrate that pharmacological quiescence induced by CDK4/6 inhibitor treatment affords resistance to chemotherapeutic agents in non-hematopoietic cells, the protective effect of Compound T on human renal proximal tubule cells was analyzed. Normal renal proximal tubule epithelial cells were obtained from American Type Culture Collection (ATCC, Manassas, Va.). Cells were grown in an incubator at 37° C. in a humidified atmosphere of 5% CO2 in Renal Epithelial Cell Basal Media (ATCC) supplemented with Renal Epithelial Cell Growth Kit (ATCC) in 37° C. humidified incubator. Cells were treated with either DMSO or 10 nM, 30 nM, 100 nM, 300 nM or 1 uM Compound T in either the absence or presence of 25 uM cisplatin. For the γ-H2AX assay, cells were fixed, permeabilized, and stained with anti-γ-H2AX as per the γ-H2AX Flow Kit (Millipore) and quantitated by flow cytometry. Data was analyzed using FlowJo 2.2 software developed by TreeStar, Inc. Caspase 3/7 activation was measured using the Caspase-Glo 3/7 Assay System (Promega, Madison, Wis.) by following the manufacturer's instructions.

Figure 22:
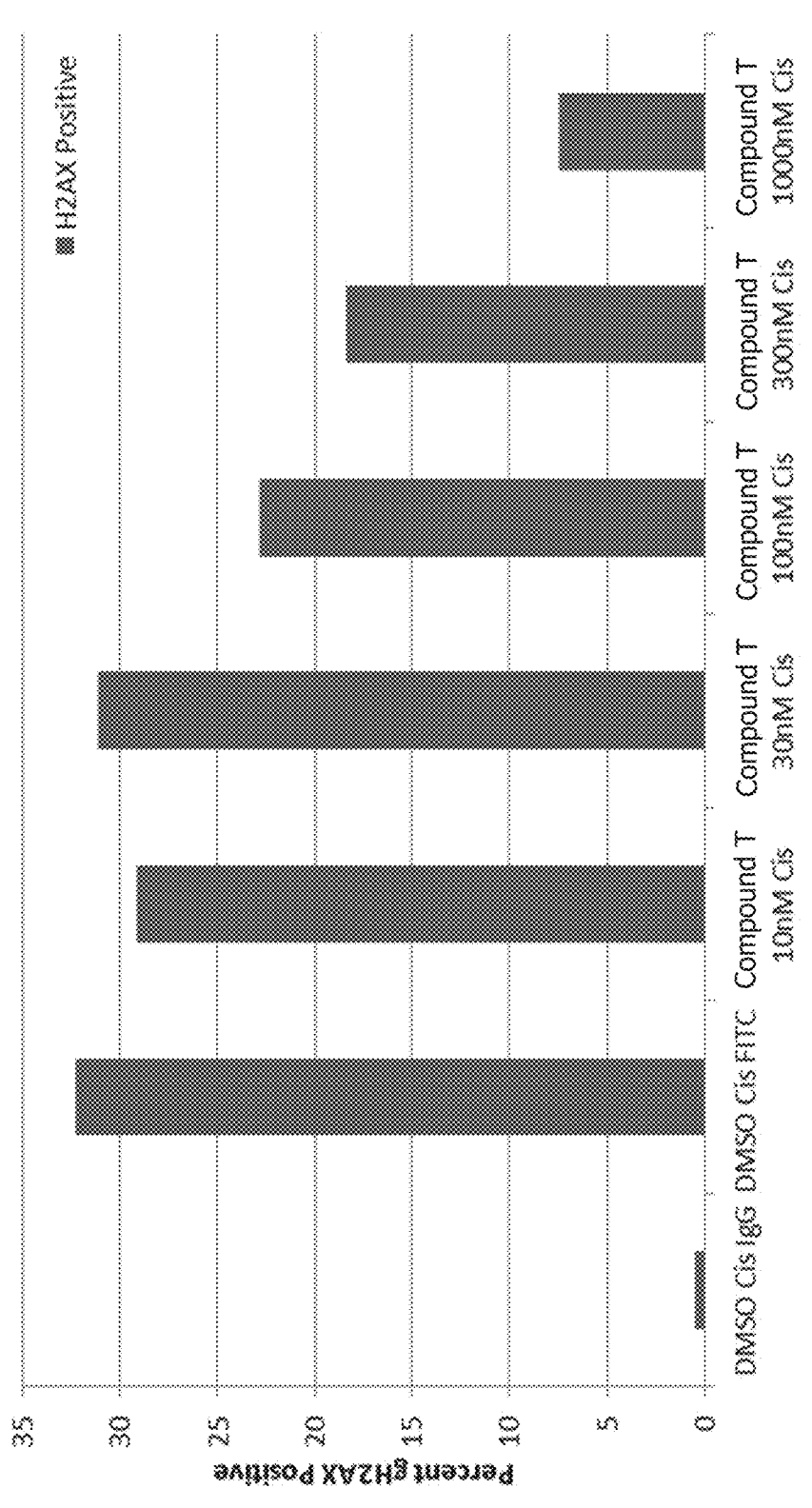
FIG. 22 is a graph of the relative γ-H2AX activity vs. variable concentration of Compound T (nM) in human renal proximal tubule cells treated with Compound T and chemotherapy (cisplatin). Cells were treated with the indicated doses of Compound T (10 nM, 30 nM, 100 nM, 300 nM, or 1000 nM) and chemotherapy (25 uM cisplatin). γ-H2AX foci formation was measured to evaluate chemotherapy-induced DNA damage. As described in Example 170, cells treated with Compound T were protected from DNA damage induced by the chemotherapy (cisplatin).

Treatment of renal proximal tubule cells with Compound T in combination with cisplatin attenuated DNA damage as measured by γ-H2AX formation (FIG. 22). As seen in FIG. 22, DNA damage caused by cisplatin decreased in a dose-dependent manner after treatment with Compound T.

Figure 23:
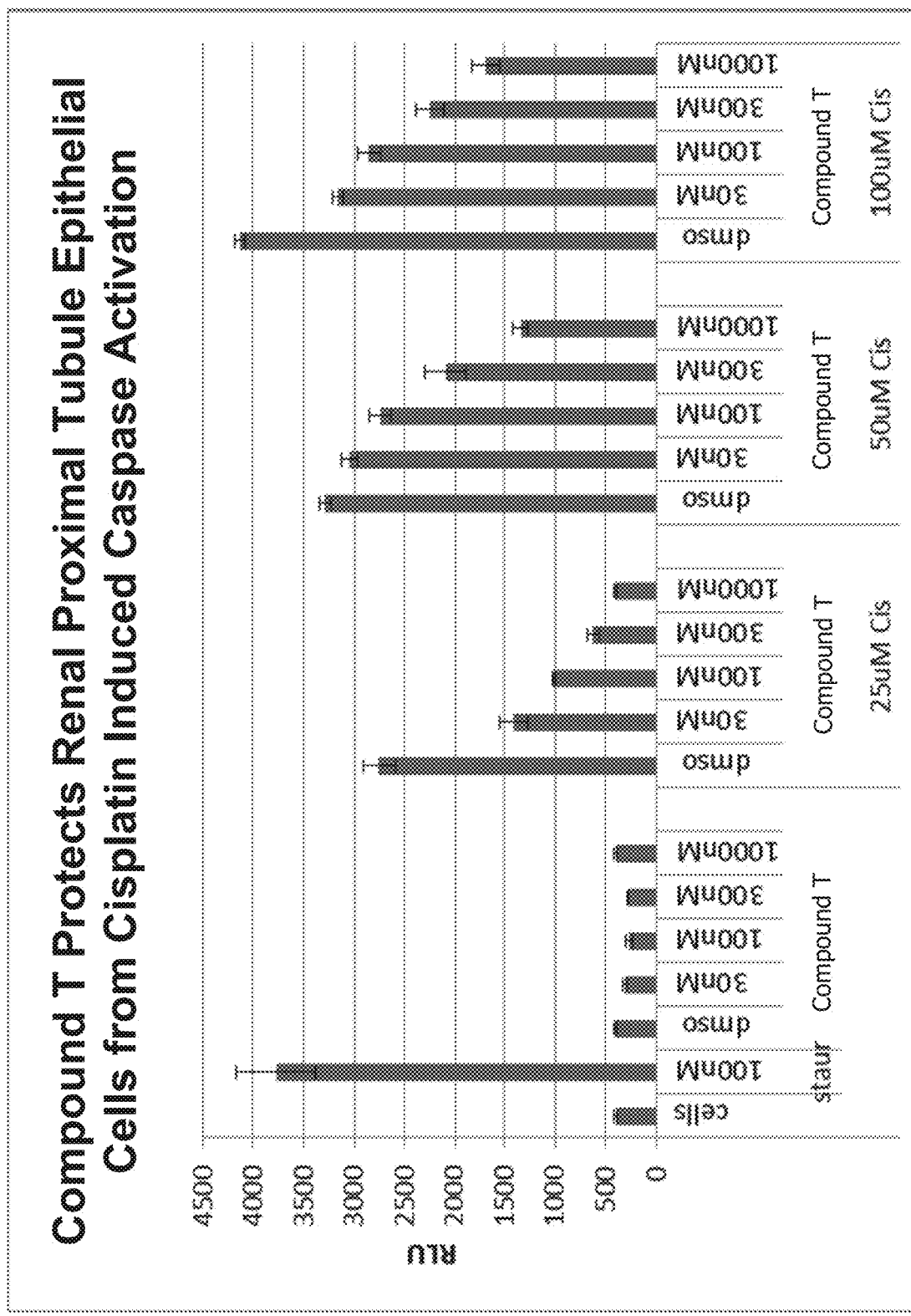
FIG. 23 is a graph of caspase 3/7 activation (as measured by relative light units) in renal tubule epithelial cells treated with the indicated concentrations of Compound T and either DMSO or cisplatin (25 uM, 50 uM, or 100 uM). Normal renal proximal tubule epithelial cells were obtained from American Type Culture Collection (ATCC, Manassas, Va.). Cells were grown in an incubator at 37° C. in a humidified atmosphere of 5% CO2 in Renal Epithelial Cell Basal Media (ATCC) supplemented with Renal Epithelial Cell Growth Kit (ATCC) in 37° C. humidified incubator. Cells were treated with DMSO or 30 nM, 100 nM, 300 nM or 1 uM Compound T in either the absence or presence of 25, 50 uM, or 100 uM cisplatin. Caspase 3/7 activation was measured 24 hours later using the Caspase-Glo 3/7 Assay System (Promega, Madison, Wis.) by following the manufacturer's instructions. As described in Example 170, Compound T demonstrated a dose-dependent reduction in caspase 3/7 activation in these cells.

The ability of Compound T to protect renal proximal tubule epithelial cells against cisplatin induced apoptosis (caspase 3/7 activation) was also investigated. As shown in FIG. 23, Compound T demonstrated a dose-dependent reduction in caspase 3/7 activation in these cells. This reduction in caspase 3/7 activity was seen at all three levels of cisplatin tested (25 uM, 50 uM, or 100 uM). These data show that a transient cell cycle arrest in G1, induced by Cdk4/6 inhibition, can protect renal proximal tubule cells from chemotherapy-induced DNA damage.

Example 171

Preparation of Drug Product

The active compounds of the present invention can be prepared for intravenous administration using the following procedure. The excipients hydroxypropyl-beta-cyclodextrin and dextrose can be added to 90% of the batch volume of USP Sterile Water for Injection or Irrigation with stirring; stir until dissolved. The active compound in the hydrochloride salt form is added and stirred until it is dissolved. The pH is adjusted with 1N NaOH to pH 4.3+0.1 and 1N HCl can be used to back titrate if necessary. USP Sterile Water for Injection or Irrigation can be used to bring the solution to the final batch weight. The pH is next re-checked to ensure that the pH is pH 4.3+0.1. If the pH is outside of the range add 1N HCl or 1N NaOH as appropriate to bring the pH to 4.3+0.1. The solution is next sterile filtered to fill 50 or 100 mL flint glass vials, stopper, and crimped.

This specification has been described with reference to embodiments of the invention. The invention has been described with reference to assorted embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the invention.

We claim:

1. A method of treating a human with cancer comprising:
administering to the human an effective amount of a selective CDK4/6 inhibitor of structure:

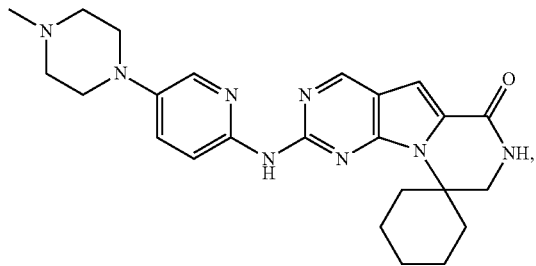 [SMILES: CN1CCN(c2ccc(Nc3ncc4cc5n(c4n3)C3(CCCCC3)CNC5=O)nc2)CC1]

or a pharmaceutically acceptable salt thereof; and,
administering to the human a chemotherapeutic agent;
wherein the selective CDK4/6 inhibitor is administered to the human about 24 hours or less prior to administration of the chemotherapeutic agent.

2. The method of claim 1, wherein the selective CDK4/6 inhibitor is administered to the human about 4 hours or less prior to administration of the chemotherapeutic agent.

3. The method of claim 1, wherein the chemotherapeutic agent is selected from the group consisting of etoposide, carboplatin, gemcitabine, topotecan, paclitaxel, docetaxel, doxorubicin, cisplatin, and fluorouracil, and a combination thereof.

4. The method of claim 1, wherein the cancer is lung cancer.

5. The method of claim 1, wherein the cancer is breast cancer.

6. The method of claim 1, wherein the cancer is human papilloma virus positive head and neck cancer.

7. The method of claim 1, wherein the cancer is cervical cancer.

8. The method of claim 1, wherein the cancer is prostate cancer.

9. The method of claim 1, wherein the cancer is bladder cancer.

10. The method of claim 1, wherein the cancer is colorectal cancer.

11. The method of claim 4, wherein the lung cancer is small cell lung cancer.

12. The method of claim 5, wherein the breast cancer is triple negative breast cancer.

13. The method of claim 3, wherein the chemotherapeutic agent is etoposide.

14. The method of claim 3, wherein the chemotherapeutic agent is carboplatin.

15. The method of claim 3, wherein the chemotherapeutic agent is gemcitabine.

16. The method of claim 3, wherein the chemotherapeutic agent is topotecan.

17. The method of claim 3, wherein the chemotherapeutic agent is paclitaxel.

18. The method of claim 3, wherein the chemotherapeutic agent is docetaxel.

19. A method of treating a human with triple negative breast cancer comprising:
administering to the human an effective amount of a selective CDK4/6 inhibitor of structure:

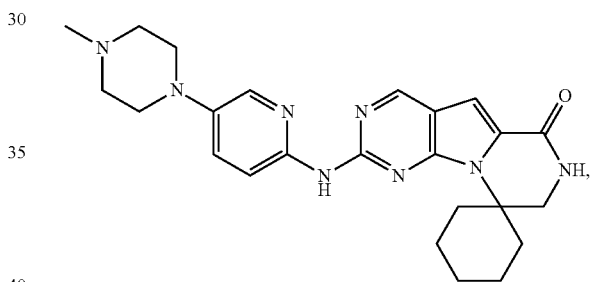

or a pharmaceutically acceptable salt thereof; and,
administering to the human a chemotherapeutic agent;
wherein the selective CDK4/6 inhibitor is administered to the human 24 hours or less prior to administration of the chemotherapeutic agent.

20. The method of claim 19, wherein the selective CDK4/6 inhibitor is administered to the human 4 hours or less prior to administration of the chemotherapeutic agent.

21. The method of claim 19, wherein the selective CDK4/6 inhibitor is administered to the human ½ hour or less prior to administration of the chemotherapeutic agent.

22. The method of claim 19, wherein the chemotherapeutic agent is selected from the group consisting of carboplatin, gemcitabine, paclitaxel, doxorubicin, cyclophosphamide, and a combination thereof.

23. The method of claim 22, wherein the chemotherapeutic agent is carboplatin.

24. The method of claim 22, wherein the chemotherapeutic agent is gemcitabine.

25. The method of claim 22, wherein the chemotherapeutic agent is paclitaxel.

26. The method of claim 22, wherein the chemotherapeutic agent is doxorubicin.

27. The method of claim 1, wherein the selective CDK4/6 inhibitor is administered to the human ½ hour or less prior to administration of the chemotherapeutic agent.

28. The method of claim 3, wherein the chemotherapeutic agent is cisplatin.

29. The method of claim 3, wherein the chemotherapeutic agent is 5-fluorouracil.

30. The method of claim 22, wherein the chemotherapeutic agent is cyclophosphamide.

\* \* \* \* \*